US008389252B2

(12) United States Patent
LaRossa

(10) Patent No.: US 8,389,252 B2
(45) Date of Patent: Mar. 5, 2013

(54) YEAST STRAIN FOR PRODUCTION OF FOUR CARBON ALCOHOLS

(75) Inventor: Robert A. LaRossa, Chadds Ford, PA (US)

(73) Assignee: Butamax(TM) Advanced Biofuels LLC, Wilmington, DE (US)

( * ) Notice: Subject to any disclaimer, the term of this patent is extended or adjusted under 35 U.S.C. 154(b) by 374 days.

(21) Appl. No.: 12/435,530

(22) Filed: May 5, 2009

(65) Prior Publication Data

US 2009/0280546 A1 Nov. 12, 2009

Related U.S. Application Data

(60) Provisional application No. 61/052,286, filed on May 12, 2008, provisional application No. 61/025,289, filed on May 12, 2008.

(51) Int. Cl.

| | |
|---|---|
| ***C12P 7/16*** | (2006.01) |
| ***C12N 1/19*** | (2006.01) |
| ***C12N 9/02*** | (2006.01) |
| ***C12N 9/10*** | (2006.01) |
| ***C07H 21/04*** | (2006.01) |

(52) U.S. Cl. ................ 435/160; 435/254.2; 435/254.21; 435/189; 435/193; 536/23.2

(58) Field of Classification Search .................. 435/160, 435/254.2, 254.21, 189, 193; 536/23.2
See application file for complete search history.

(56) References Cited

U.S. PATENT DOCUMENTS

| | | | |
|---|---|---|---|
| 5,192,673 | A | 3/1993 | Jain et al. |
| 6,358,717 | B1 | 3/2002 | Blaschek et al. |
| 6,960,465 | B1 | 11/2005 | Papoutsakis et al. |
| 2007/0092957 | A1 | 4/2007 | Donaldson et al. |
| 2007/0259410 | A1 | 11/2007 | Donaldson et al. |
| 2007/0259411 | A1 | 11/2007 | Bramucci et al. |
| 2007/0292927 | A1 | 12/2007 | Donaldson et al. |
| 2008/0124774 | A1 | 5/2008 | Bramucci et al. |
| 2008/0138870 | A1 | 6/2008 | Bramucci et al. |
| 2008/0182308 | A1 | 7/2008 | Donaldson et al. |
| 2009/0155870 | A1 | 6/2009 | Donaldson et al. |
| 2009/0162911 | A1 | 6/2009 | LaRossa et al. |
| 2009/0203097 | A1 | 8/2009 | Flint et al. |
| 2009/0203139 | A1 | 8/2009 | LaRossa et al. |
| 2009/0288337 | A1 * | 11/2009 | Picataggio et al. ............. 44/449 |

OTHER PUBLICATIONS

International Preliminary Report on Patentability mailed Nov. 25, 2010 in corresponding PCT/US2009/043275.

Girbal, Laurence et al., Regulation of solvent production in *Clostridium acetobutylicum*, Trends in Biotechnology, 1998, pp. 11-16, vol. 16, Elsevier Science Ltd.

Dickinson, J. Richard et al., An Investigation of the Metabolism of Valine to Isobutyl Alcohol in *Saccharomyces cerevisiae*, The Journal of Biological Chemistry, Oct. 2, 1998, pp. 25751-25756, vol. 273, No. 40, The American Society for Biochemistry and Molecular Biology, Inc.

(Continued)

*Primary Examiner* — Rosanne Kosson

(74) *Attorney, Agent, or Firm* — Christine M. Lhulier; Jenafer Evans

(57) ABSTRACT

Yeast cells with a reduced general control response to amino acid starvation were found to have increased tolerance to butanol in the growth medium. The reduced response was engineered by genetic modification of a gene involved in the response, a GCN gene, to eliminate activity of the encoded protein. Yeast strains with an engineered butanol biosynthetic pathway and a genetic modification in a gene involved in the general control response to amino acid starvation, which have increased butanol tolerance, are useful for production of butanol.

13 Claims, 4 Drawing Sheets

OTHER PUBLICATIONS

Tomas, Christopher A. et al., Overexpression of groESL in *Clostridium acetobutylicum* Results in Increased Solvent Production and Tolerance, Prolonged Metabolism, and Changes in the Cell's Transcriptional Program, Applied and Environmental Microbiology, Aug. 2003, pp. 4951-4965, vol. 69, No. 8, American Society for Microbiology.

Quratulain, S. et al., Development and Characterization of Butanol-Resistant Strain of *Clostridium acetobutylicum* in Molasses Medium, Folia Microbiologica, 1995, pp. 467-471, vol. 40, No. 5.

Soucaille, Philippe et al., Butanol Tolerance and Autobacteriocin Production by *Clostridium aceobutylicum*, Current Microbiology, 1987, pp. 295-299, vol. 14.

Desmond, C. et al., Improved Stress Tolerance of GroESL-Overproducing *Lactococcus lactis* and Probiotic *Lactobacillus paracasei* NFBC 338, Applied and Environmental Microbiology, Oct. 2004, pp. 5929-5936, vol. 70, No. 10, American Society for Microbiology.

Sardessai, Yogita N. et al., Organic solvent-tolerant bacteria in mangrove ecosystem, Current Science, Mar. 25, 2002, pp. 622-623, vol. 82, No. 6.

Bieszkiewicz, Ewa et al., Studies on the Resistance of Activated Sludge Bacteria to High Concentrations of Methanol, Butanol, Glycol, Cyclohexanone and Cyclohexylamine, Acta Microbiologica Polonica, 1987, pp. 259-265, vol. 36, No. 3.

International Search Report of corresponding application No. PCT/US2009/043275 mailed Aug. 3, 2009.

Ashe et al., "A Novel EIF2B-Dependent Mechanism of Translational Control in Yeast as a Response to Fusel Alcohols", The EMBO Journal Nov. 15, 2001, vol. 20., No. 22, pp. 6464-6474.

Hinnebusch, "Mechanisms of Gene Regulation in the General Control of Amino Acid Biosynthesis in *Saccharomyces-cerevisiae*", Microbiological Reviews, vol. 52, No. 2, 1988, pp. 248-273.

Hannig et al., "Molecular Analysis of GCN3 A Translational Activator of GCN4 Evidence for Posttranslational Control of GCN3 Regulatory Function", Molecular and Cellular Biology, vol. 8, No. 11, 1988, pp. 4808-4820.

Winzeler et al., "Functional Characterization of the S. Cerevisiae Genome by Gene Deletion and Paralles Analysis", Science vol. 285, pp. 901-906 (1999).

Paluh et al., "The Cross-Pathway Control Gene of Neurospora Crassa, CPC-1, Encodes a Protein Similar to GCN4 of Yeast and the DNA-Binding Domain of the Oncogene V-Jun-Encoded Protein", Proc. Natl. Acad. Sci., Vol. 85, pp. 3728-3732, USA (1988).

Giaever et al., Functional Profiling of the Saccharomyces Cerevisiae Genome, Nature Publishing Group, vol. 418, pp. 387-391, (2002).

Brachmann et al., "Designer Deletion Strains Derived From Saccharomyces Cerevisiae S288C: A Useful Set of Strains and Plasmids for PCR-Mediated Gene Disruption and Other Applications", John Wiley & Sons, Ltd, vol. 14, pp. 115-132, (1998).

Bode et al., "Occurrence of the General Control of Amino Acid Biosynthesis in Yeast", J. Basic Microbiol, vol. 30, pp. 31-35, (1990).

Hinnebusch, "Translational Regulation of GCN4 and the General Amino Acid Control of Yeast", Annual Review of Microbiology, pp. 407-450, (2005).

Stewart, "A Chemist's Perspective on the Use of Genetically Engineered Microbes As Reagents for Organic Synthesis", Biotechnology and Genetic Reviews, vol. 14, pp. 67-143, (1997).

* cited by examiner

YEAST STRAIN FOR PRODUCTION OF FOUR CARBON ALCOHOLS

This application claims the benefit of U.S. Applications 61/052,286 and 61/052,289, both filed May 12, 2008, both now pending.

FIELD OF INVENTION

The invention relates to the field of microbiology and genetic engineering. More specifically, yeast genes involved in response to butanol were identified. Yeast strains with reduced expression of the identified genes were found to have improved growth yield in the presence of butanol.

BACKGROUND OF INVENTION

Butanol is an important industrial chemical, useful as a fuel additive, as a feedstock chemical in the plastics industry, and as a foodgrade extractant in the food and flavor industry. Each year 10 to 12 billion pounds of butanol are produced by petrochemical means and the need for this commodity chemical will likely increase.

Methods for the chemical synthesis of butanols are known, however these processes use starting materials derived from petrochemicals, are generally expensive, and are not environmentally friendly. Methods of producing butanol by fermentation are also known, where the most popular process produces a mixture of acetone, 1-butanol and ethanol and is referred to as the ABE processes (Blaschek et al., U.S. Pat. No. 6,358,717). Acetone-butanol-ethanol (ABE) fermentation by *Clostridium acetobutylicum* is one of the oldest known industrial fermentations, and the pathways and genes responsible for the production of these solvents have been reported (Girbal et al., *Trends in Biotechnology* 16:11-16 (1998)). Isobutanol is produced biologically as a by-product of yeast fermentation. It is a component of “fusel oil” that forms as a result of incomplete metabolism of amino acids by this group of fungi. Isobutanol is specifically produced from catabolism of L-valine. After the amine group of L-valine is harvested as a nitrogen source, the resulting a-keto acid is decarboxylated and reduced to isobutanol by enzymes of the so-called Ehrlich pathway (Dickinson et al., *J. Biol. Chem.* 273(40):25752-25756 (1998)). Yields of fusel oil and/or its components achieved during beverage fermentation are typically low.

Additionally, recombinant microbial production hosts, expressing a 1-butanol biosynthetic pathway (Donaldson et al., copending and commonly owned U.S. Patent Application Publication No. 20080182308), a 2-butanol biosynthetic pathway (Donaldson et al., copending and commonly owned U.S. Patent Application Publication Nos. US 20070259410A1 and US 2007-0292927), and an isobutanol biosynthetic pathway (Maggio-Hall et al., copending and commonly owned U.S. Patent Application Publication No. US 20070092957) have been described.

Biological production of butanols is believed to be limited by butanol toxicity to the host microorganism used in fermentation for butanol production. Strains of *Clostridium* that are tolerant to 1-butanol have been isolated by chemical mutagenesis (Jain et al. U.S. Pat. No. 5,192,673; and Blaschek et al. U.S. Pat. No. 6,358,717), overexpression of certain classes of genes such as those that express stress response proteins (Papoutsakis et al. U.S. Pat. No. 6,960,465; and Tomas et al., *Appl. Environ. Microbiol.* 69(8):4951-4965 (2003)), and by serial enrichment (Quratulain et al., *Folia Microbiologica* (Prague) 40(5):467-471 (1995); and Soucaille et al., Current Microbiology 14(5):295-299 (1987)). Desmond et al. (*Appl. Environ. Microbiol.* 70(10): 5929-5936 (2004)) report that overexpression of GroESL, two stress responsive proteins, in *Lactococcus lactis* and *Lactobacillus paracasei* produced strains that were able to grow in the presence of 0.5% volume/volume (v/v) [0.4% weight/volume (w/v)] 1-butanol. Additionally, the isolation of 1-butanol tolerant strains from estuary sediment (Sardessai et al., *Current Science* 82(6):622-623 (2002)) and from activated sludge (Bieszkiewicz et al., *Acta Microbiologica Polonica* 36(3):259-265 (1987)) has been described. Butanol tolerant bacterial strains have been isolated from microbial consortia (copending and commonly owned U.S. Patent Publication Nos. 20070259411, 20080124774 and 20080138870) or by mutant screening (copending and commonly owned U.S. patent application Ser. Nos. 12/330,530, 12/330,531, and 12/330,534).

There remains a need for butanol producing yeast strains that are more tolerant to butanols, as well as methods of producing butanols using yeast host strains that are more tolerant to these chemicals and engineered for butanol production.

SUMMARY OF THE INVENTION

The invention provides a recombinant yeast host which produces butanol and comprises a genetic modification that results in reduced response in the general control response to amino acid starvation. Such cells have an increased tolerance to butanol as compared with cells that lack the genetic modification. Reduction in response in the general control response to amino acid starvation may be accomplished via mutation of endogenous genes that impact the response. Host cells of the invention may produce butanol naturally or may be engineered to do so via an engineered pathway.

Accordingly, the invention provides a recombinant yeast host cell producing butanol where the yeast cell comprises at least one genetic modification which reduces the response in the general control response to amino acid starvation.

In one embodiment the yeast cell of the invention comprises a genetic modification in a gene encoding a protein selected from Gcn1p, Gcn2p, Gcn3p, Gcn4p, Gcn5p, and Gcn20p.

In another embodiment the yeast cell comprises a recombinant biosynthetic pathway selected from the group consisting of:

a) a 1-butanol biosynthetic pathway;
b) a 2-butanol biosynthetic pathway; and
c) an isobutanol biosynthetic pathway.

In another embodiment the invention provides a method for the production of butanol comprising the steps of:

(a) providing a recombinant yeast host cell which
  1) produces butanol and
  2) comprises at least one genetic modification which reduces the response in the general control response to amino acid starvation; and
(b) culturing the strain of (a) under conditions wherein butanol is produced.

BRIEF DESCRIPTION OF THE FIGURES AND SEQUENCE DESCRIPTIONS

The various embodiments of the invention can be more fully understood from the following detailed description, the figures, and the accompanying sequence descriptions, which form a part of this application.

Figure 1A:
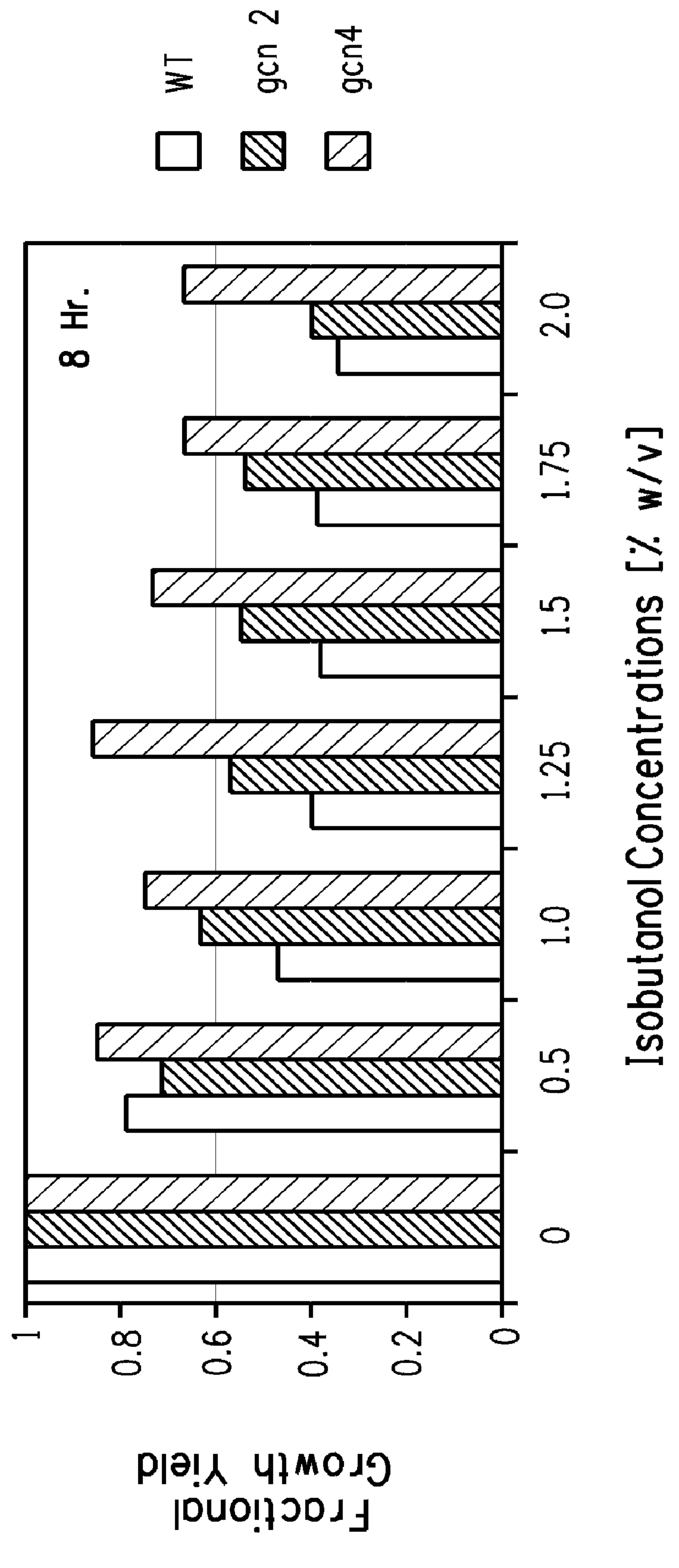
FIG. 1 shows fractional growth yields of wild type, mutant GCN2 and mutant GCN4 strains at 8 hr (A) and 24 hr (B) time points for growth in YVCM containing different concentrations of isobutanol.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Summary of Gene and Protein SEQ ID Numbers for 1-Butanol Biosynthetic Pathway

| Description | SEQ ID NO: Nucleic acid | SEQ ID NO: Peptide |
|---|---|---|
| Acetyl-CoA acetyltransferase thlA from *Clostridium acetobutylicum* ATCC 824 | 1 | 2 |
| Acetyl-CoA acetyltransferase thlB from *Clostridium acetobutylicum* ATCC 824 | 3 | 4 |
| Acetyl-CoA acetyltransferase from *Saccharomyces cerevisiae* | 39 | 40 |
| 3-Hydroxybutyryl-CoA dehydrogenase from Clostridium acetobutylicum ATCC 824 | 5 | 6 |
| Crotonase from *Clostridium acetobutylicum* ATCC 824 | 7 | 8 |
| Putative trans-enoyl CoA reductase from *Clostridium acetobutylicum* ATCC 824 | 9 | 10 |
| Butyraldehyde dehydrogenase from *Clostridium beijerinckii* NRRL B594 | 11 | 12 |
| 1-Butanol dehydrogenase bdhB from *Clostridium acetobutylicum* ATCC 824 | 13 | 14 |
| 1-Butanol dehydrogenase bdhA from *Clostridium acetobutylicum* ATC 824 | 15 | 16 |

TABLE 2

Summary of Gene and Protein SEQ ID Numbers for 2-Butanol Biosynthetic Pathway

| Description | SEQ ID NO: Nucleic acid | SEQ ID NO: Peptide |
|---|---|---|
| budA, acetolactate decarboxylase from *Klebsiella pneumoniae* ATCC 25955 | 17 | 18 |
| budB, acetolactate synthase from *Klebsiella pneumoniae* ATCC 25955 | 19 | 20 |
| budC, butanediol dehydrogenase from *Klebsiella pneumoniae* IAM1063 | 21 | 22 |
| pddA, butanediol dehydratase alpha subunit from *Klebsiella oxytoca* ATCC 8724 | 23 | 24 |
| pddB, butanediol dehydratase beta subunit from *Klebsiella oxytoca* ATCC 8724 | 25 | 26 |
| pddC, butanediol dehydratase gamma subunit from *Klebsiella oxytoca* ATCC 8724 | 27 | 28 |
| sadH, 2-butanol dehydrogenase from *Rhodococcus* ruber 219 | 29 | 30 |

TABLE 3

Summary of Gene and Protein SEQ ID Numbers for Isobutanol Biosynthetic Pathway

| Description | SEQ ID NO: Nucleic acid | SEQ ID NO: Peptide |
|---|---|---|
| *Klebsiella pneumoniae* budB (acetolactate synthase) | 19 | 20 |
| *Bacillus subtilis* alsS (acetolactate synthase) | 41 | 42 |
| *E. coli* ilvC (acetohydroxy acid reductoisomerase) | 31 | 32 |
| *S. cerevisiae* ILV5 (acetohydroxy acid reductoisomerase) | 43 | 44 |
| *B. subtilis* ilvC (acetohydroxy acid reductoisomerase) | 45 | 46 |
| *E. coli* ilvD (acetohydroxy acid dehydratase) | 33 | 34 |
| *S. cerevisiae* ILV3 (Dihydroxyacid dehydratase) | 47 | 48 |
| *Lactococcus lactis* kivD (branched-chain α-keto acid decarboxylase), codon optimized | 35 | 36 |
| *E. coli* yqhD (branched-chain alcohol dehydrogenase) | 37 | 38 |

TABLE 4

Summary of Gene and Protein SEQ ID Numbers for members of general control system for amino acid biosynthesis

| Description | SEQ ID NO: Nucleic acid | SEQ ID NO: Peptide |
|---|---|---|
| GCN1 from *Saccharomyces cerevisiae* | 49 | 50 |
| GCN2 from *Saccharomyces cerevisiae* | 51 | 52 |
| GCN3 from *Saccharomyces cerevisiae* | 53 | 54 |
| GCN4 from *Saccharomyces cerevisiae* | 55 | 56 |
| GCN5 from *Saccharomyces cerevisiae* | 57 | 58 |
| GCN20 from *Saccharomyces cerevisiae* | 59 | 60 |
| GCN1 from *Yarrowia lipolytica* | 61 | 62 |
| GCN2 from *Yarrowia lipolytica* | 63 | 64 |
| GCN3 from *Yarrowia lipolytica* | 65 | 66 |
| GCN5 from *Yarrowia lipolytica* | 67 | 68 |
| GCN2 from *Candida albicans* | 69 | 70 |
| GCN3 from *Candida albicans* | 71 | 72 |
| GCN5 from *Candida albicans* -1 | 73 | 74 |
| GCN5 from *Candida albicans* -2 | 75 | 74* |

*the same amino acid sequence is encoded by both SEQ ID NO: 73 and 75

SEQ ID NO:76 is the nucleotide sequence of the GPD promoter described in Example 2.

SEQ ID NO:77 is the nucleotide sequence of the CYC1 terminator described in Example 2.

SEQ ID NO:78 is the nucleotide sequence of the FBA promoter described in Example 2.

SEQ ID NO:79 is the nucleotide sequence of ADH1 promoter described in Example 2.

SEQ ID NO:80 is the nucleotide sequence of ADH1 terminator described in Example 2.

SEQ ID NO:81 is the nucleotide sequence of GPM promoter described in Example 2.

SEQ ID NOs:82-137 are the nucleotide sequences of oligonucleotide cloning, screening or sequencing primers used in the Examples described herein.

SEQ ID NO:138 is the nucleotide sequence of the "URA3 repeats" fragment.

SEQ ID NOs:139 and 140 are the nucleotide sequences of PCR primers used to amplify a DNA fragment for gcn2 deletion.

SEQ ID NOs:141 and 142 are the nucleotide sequences of PCR primers used to amplify a DNA fragment for gcn4 deletion.

SEQ ID NOs:143 and 144 are primer binding sequences that bound direct repeats flanking $URA3^+$: in the "URA3 repeats" fragment. SEQ ID NOs:145 and 146 are direct repeat sequences that flank the promoter and coding sequence in the "URA3 repeats" fragment.

SEQ ID NO:147 is the promoter sequence in the "URA3 repeats" fragment.

SEQ ID NO:148 is the URA3 coding sequence in the "URA3 repeats" fragment.

DETAILED DESCRIPTION OF THE INVENTION

The present invention provides a recombinant yeast host which produces butanol and comprises a genetic modification that results in a reduced response in the general control response to amino acid starvation. Such cells have an increased tolerance to butanol as compared with cells that lack the genetic modification. A tolerant yeast strain of the invention has at least one genetic modification that causes the reduced general control response to amino acid starvation. This reduced response may be accomplished via mutation of endogenous genes that impact the response. Host cells of the invention may produce butanol naturally or may be engineered to do so via an engineered pathway.

Butanol produced using the present strains may be used as an alternative energy source to fossil fuels. Fermentative production of butanol results in less pollutants than typical petrochemical synthesis.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "butanol" as used herein, refers to 1-butanol, 2-butanol, isobutanol, or mixtures thereof.

The terms "butanol tolerant yeast strain" and "tolerant" when used to describe a modified yeast strain of the invention, refers to a modified yeast that shows better growth in the presence of butanol than the parent strain from which it is derived.

The term "butanol biosynthetic pathway" refers to an enzyme pathway to produce 1-butanol, 2-butanol, or isobutanol.

The term "1-butanol biosynthetic pathway" refers to an enzyme pathway to produce 1-butanol from acetyl-coenzyme A (acetyl-CoA).

The term "2-butanol biosynthetic pathway" refers to an enzyme pathway to produce 2-butanol from pyruvate.

The term "isobutanol biosynthetic pathway" refers to an enzyme pathway to produce isobutanol from pyruvate.

The term "acetyl-CoA acetyltransferase" refers to an enzyme that catalyzes the conversion of two molecules of acetyl-CoA to acetoacetyl-CoA and coenzyme A (CoA). Preferred acetyl-CoA acetyltransferases are acetyl-CoA acetyltransferases with substrate preferences (reaction in the forward direction) for a short chain acyl-CoA and acetyl-CoA and are classified as E.C. 2.3.1.9 [*Enzyme Nomenclature* 1992, Academic Press, San Diego]; although, enzymes with a broader substrate range (E.C. 2.3.1.16) will be functional as well. Acetyl-CoA acetyltransferases are available from a number of sources, for example, *Escherichia coli* (GenBank Nos: NP_416728, NC_000913; NCBI (National Center for Biotechnology Information) amino acid sequence, NCBI nucleotide sequence), *Clostridium acetobutylicum* (GenBank Nos: NP_349476.1 (SEQ ID NO:2), NC_003030; NP_149242 (SEQ ID NO:4), NC_001988), *Bacillus subtilis* (GenBank Nos: NP_390297, NC_000964), and *Saccharomyces cerevisiae* (GenBank Nos: NP_015297, NC_001148 (SEQ ID NO:39)).

The term "3-hydroxybutyryl-CoA dehydrogenase" refers to an enzyme that catalyzes the conversion of acetoacetyl-CoA to 3-hydroxybutyryl-CoA. 3-Hydroxybutyryl-CoA dehydrogenases may be reduced nicotinamide adenine dinucleotide (NADH)-dependent, with a substrate preference for (S)-3-hydroxybutyryl-CoA or (R)-3-hydroxybutyryl-CoA and are classified as E.C. 1.1.1.35 and E.C. 1.1.1.30, respectively. Additionally, 3-hydroxybutyryl-CoA dehydrogenases may be reduced nicotinamide adenine dinucleotide phosphate (NADPH)-dependent, with a substrate preference for (S)-3-hydroxybutyryl-CoA or (R)-3-hydroxybutyryl-CoA and are classified as E.C. 1.1.1.157 and E.C. 1.1.1.36, respectively. 3-Hydroxybutyryl-CoA dehydrogenases are available from a number of sources, for example, *C. acetobutylicum* (GenBank NOs: NP_349314 (SEQ ID NO:6), NC_003030), *B. subtilis* (GenBank NOs: AAB09614, U29084), *Ralstonia eutropha* (GenBank NOs: ZP_0017144, NZ_AADY01000001, *Alcaligenes eutrophus* (GenBank NOs: YP_294481, NC_007347), and *A. eutrophus* (GenBank NOs: P14697, J04987).

The term "crotonase" refers to an enzyme that catalyzes the conversion of 3-hydroxybutyryl-CoA to crotonyl-CoA and $H_2O$. Crotonases may have a substrate preference for (S)-3-hydroxybutyryl-CoA or (R)-3-hydroxybutyryl-CoA and are classified as E.C. 4.2.1.17 and E.C. 4.2.1.55, respectively. Crotonases are available from a number of sources, for example, *E. coli* (GenBank NOs: NP_415911 (SEQ ID NO:8), NC_000913), *C. acetobutylicum* (GenBank NOs:

NP_349318, NC_003030), *B. subtilis* (GenBank NOs: CAB13705, Z99113), and *Aeromonas caviae* (GenBank NOs: BAA21816, D88825).

The term "butyryl-CoA dehydrogenase", also called trans-enoyl CoA reductase, refers to an enzyme that catalyzes the conversion of crotonyl-CoA to butyryl-CoA. Butyryl-CoA dehydrogenases may be NADH-dependent or NADPH-dependent and are classified as E.C. 1.3.1.44 and E.C. 1.3.1.38, respectively. Butyryl-CoA dehydrogenases are available from a number of sources, for example, *C. acetobutylicum* (GenBank NOs: NP_347102 (SEQ ID NO:10), NC_003030), *Euglena gracilis* (GenBank NOs: Q5EU90, AY741582), *Streptomyces collinus* (GenBank NOs: AAA92890, U37135), and *Streptomyces coelicolor* (GenBank NOs: CAA22721, AL939127).

The term "butyraldehyde dehydrogenase" refers to an enzyme that catalyzes the conversion of butyryl-CoA to butyraldehyde, using NADH or NADPH as cofactor. Butyraldehyde dehydrogenases with a preference for NADH are known as E.C. 1.2.1.57 and are available from, for example, *Clostridium beijerinckii* (GenBank NOs: AAD31841 (SEQ ID NO:12), AF157306) and *C. acetobutylicum* (GenBank NOs: NP_149325, NC_001988).

The term "1-butanol dehydrogenase" refers to an enzyme that catalyzes the conversion of butyraldehyde to 1-butanol. 1-butanol dehydrogenases are a subset of the broad family of alcohol dehydrogenases. 1-butanol dehydrogenase may be NADH- or NADPH-dependent. 1-butanol dehydrogenases are available from, for example, *C. acetobutylicum* (GenBank NOs: NP_149325, NC_001988; NP_349891 (SEQ ID NO:14), NC_003030; and NP_349892 (SEQ ID NO:16), NC_003030) and *E. coli* (GenBank NOs: NP_417484, NC_000913).

The term "acetolactate synthase", also known as "acetohydroxy acid synthase", refers to a polypeptide (or polypeptides) having an enzyme activity that catalyzes the conversion of two molecules of pyruvic acid to one molecule of alpha-acetolactate. Acetolactate synthase, known as EC 2.2.1.6 [formerly 4.1.3.18] (*Enzyme Nomenclature* 1992, Academic Press, San Diego) may be dependent on the cofactor thiamin pyrophosphate for its activity. Suitable acetolactate synthase enzymes are available from a number of sources, for example, *Bacillus subtilis* (GenBank Nos: AAA22222 NCBI (National Center for Biotechnology Information) amino acid sequence (SEQ ID NO:42), L04470 NCBI nucleotide sequence (SEQ ID NO:41)), *Klebsiella terrigena* (GenBank Nos: AAA25055, L04507), and *Klebsiella pneumoniae* (GenBank Nos: AAA25079 (SEQ ID NO:20), M73842 (SEQ ID NO:19).

The term "acetolactate decarboxylase" refers to a polypeptide (or polypeptides) having an enzyme activity that catalyzes the conversion of alpha-acetolactate to acetoin. Acetolactate decarboxylases are known as EC 4.1.1.5 and are available, for example, from *Bacillus subtilis* (GenBank Nos: AAA22223, L04470), *Klebsiella terrigena* (GenBank Nos: AAA25054, L04507) and *Klebsiella pneumoniae* (SEQ ID NO:18 (amino acid) SEQ ID NO:17 (nucleotide)).

The term "butanediol dehydrogenase" also known as "acetoin reductase" refers to a polypeptide (or polypeptides) having an enzyme activity that catalyzes the conversion of acetoin to 2,3-butanediol. Butanediol dehydrogenases are a subset of the broad family of alcohol dehydrogenases. Butanediol dehydrogenase enzymes may have specificity for production of R- or S-stereochemistry in the alcohol product. S-specific butanediol dehydrogenases are known as EC 1.1.1.76 and are available, for example, from *Klebsiella pneumoniae* (GenBank Nos: BBA13085 (SEQ ID NO:22), D86412. R-specific butanediol dehydrogenases are known as EC 1.1.1.4 and are available, for example, from *Bacillus cereus* (GenBank Nos. NP_830481, NC_004722; AAP07682, AE017000), and *Lactococcus lactis* (GenBank Nos. AAK04995, AE006323).

The term "butanediol dehydratase", also known as "diol dehydratase" or "propanediol dehydratase" refers to a polypeptide (or polypeptides) having an enzyme activity that catalyzes the conversion of 2,3-butanediol to 2-butanone, also known as methyl ethyl ketone (MEK). Butanediol dehydratase may utilize the cofactor adenosyl cobalamin. Adenosyl cobalamin-dependent enzymes are known as EC 4.2.1.28 and are available, for example, from *Klebsiella oxytoca* (GenBank Nos: BAA08099 (alpha subunit) (SEQ ID NO:24), BAA08100 (beta subunit) (SEQ ID NO:26), and BBA08101 (gamma subunit) (SEQ ID NO:28), (Note all three subunits are required for activity), D45071).

The term "2-butanol dehydrogenase" refers to a polypeptide (or polypeptides) having an enzyme activity that catalyzes the conversion of 2-butanone to 2-butanol. 2-butanol dehydrogenases are a subset of the broad family of alcohol dehydrogenases. 2-butanol dehydrogenase may be NADH- or NADPH-dependent. The NADH-dependent enzymes are known as EC 1.1.1.1 and are available, for example, from *Rhodococcus ruber* (GenBank Nos: CAD36475 (SEQ ID NO:30), AJ491307 (SEQ ID NO:29)). The NADPH-dependent enzymes are known as EC 1.1.1.2 and are available, for example, from *Pyrococcus furiosus* (GenBank Nos: AAC25556, AF013169).

The term "acetohydroxy acid isomeroreductase" or "acetohydroxy acid reductoisomerase" refers to an enzyme that catalyzes the conversion of acetolactate to 2,3-dihydroxyisovalerate using NADPH (reduced nicotinamide adenine dinucleotide phosphate) as an electron donor. Preferred acetohydroxy acid isomeroreductases are known by the EC number 1.1.1.86 and sequences are available from a vast array of microorganisms, including, but not limited to, *Escherichia coli* (GenBank Nos: NP_418222 (SEQ ID NO:32), NC_000913 (SEQ ID NO:31)), *Saccharomyces cerevisiae* (GenBank Nos: NP_013459 (SEQ ID NO:44), NC_001144 (SEQ ID NO:43)), *Methanococcus maripaludis* (GenBank Nos: CAF30210, BX957220), and *Bacillus subtilis* (GenBank Nos: CAB14789 (SEQ ID NO:46), Z99118 (SEQ ID NO:45)).

The term "acetohydroxy acid dehydratase" or "dihydroxy acid dehydratase" refers to an enzyme that catalyzes the conversion of 2,3-dihydroxyisovalerate to α-ketoisovalerate. Preferred acetohydroxy acid dehydratases are known by the EC number 4.2.1.9. These enzymes are available from a vast array of microorganisms, including, but not limited to, *E. coli* (GenBank Nos: YP_026248 (SEQ ID NO:34), NC_000913 (SEQ ID NO:33)), *S. cerevisiae* (GenBank Nos: NP_012550 (SEQ ID NO:48), NC_001142 (SEQ ID NO:47)), *M. maripaludis* (GenBank Nos: CAF29874, BX957219), and *B. subtilis* (GenBank Nos: CAB14105, Z99115).

The term "branched-chain α-keto acid decarboxylase" refers to an enzyme that catalyzes the conversion of α-ketoisovalerate to isobutyraldehyde and $CO_2$. Preferred branched-chain α-keto acid decarboxylases are known by the EC number 4.1.1.72 and are available from a number of sources, including, but not limited to, *Lactococcus lactis* (GenBank Nos: AAS49166, AY548760; CAG34226 (SEQ ID NO:36), AJ746364, *Salmonella typhimurium* (GenBank Nos: NP_461346, NC_003197), and *Clostridium acetobutylicum* (GenBank Nos: NP_149189, NC_001988).

The term "branched-chain alcohol dehydrogenase" refers to an enzyme that catalyzes the conversion of isobutyraldehyde to isobutanol. Preferred branched-chain alcohol dehydrogenases are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donor and are available from a number of sources, including, but not limited to, *S. cerevisiae* (GenBank Nos: NP_010656, NC_001136; NP_014051, NC_001145), *E. coli* (GenBank Nos: NP_417484 (SEQ ID NO:38), NC_000913 (SEQ ID NO:37)), and *C. acetobutylicum* (GenBank Nos: NP_349892, NC_003030).

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

A "carbon substrate" means a carbon contain compound useful as an energy source of a yeast and may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt.

A "cell having a reduced response in the general control response to amino acid starvation" refers herein to a cell that does not sense uncharged tRNA as a signal for induction of transcription of amino acid biosynthetic genes, and/or it does not respond to amino acid starvation by inducing transcription of amino acid biosynthetic genes (Hinnebusch (2005) *Ann. Rev. Microbiol.* 59:407-450).

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. *Molecular Cloning: A Laboratory Manual,* $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humania: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, *CABIOS.* 5:151-153 (1989); Higgins, D. G. et al., *Comput. Appl. Biosci.,* 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, *CABIOS.* 5:151-153 (1989); Higgins, D. G. et al., *Comput. Appl. Biosci.* 8:189-191(1992)) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 70%, 75%, 80%, 85%, 90%, or 95%, or any integer percentage from 70% to 100% may be useful in describing the present invention, such as 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments encode polypeptides with the above identities and typically encode a polypeptide having at least about 250 amino acids, preferably at least 300 amino acids, and most preferably at least about 348 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.,* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res*., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., *J. Mol. Biol.,* 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular alcohol dehydrogenase proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The invention encompasses more than the specific exemplary sequences because it is well known in the art that alterations in an amino acid sequence or in a coding region wherein a chemically equivalent amino acid is substituted at a given site, which does not effect the functional properties of the encoded protein, are common. For the purposes of the present invention substitutions are defined as exchanges within one of the following five groups:

1. Small aliphatic, nonpolar or slightly polar residues: Ala, Ser, Thr (Pro, Gly);

2. Polar, negatively charged residues and their amides: Asp, Asn, Glu, Gln;
3. Polar, positively charged residues: His, Arg, Lys;
4. Large aliphatic, nonpolar residues: Met, Leu, Ile, Val (Cys); and
5. Large aromatic residues: Phe, Tyr, Trp.

Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. In many cases, nucleotide changes which result in alteration of the N-terminal and C-terminal portions of the protein molecule would also not be expected to alter the activity of the protein. Thus coding regions with the described codon variations, and proteins with the described amino acid variations are encompassed in the present invention.

Standard recombinant DNA and molecular cloning techniques used here are well known in the art and are described by Sambrook, J., Fritsch, E. F. and Maniatis, T. *Molecular Cloning: A Laboratory Manual,* $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, New York, 1984; and by Ausubel, F. M. et al., In *Current Protocols in Molecular Biology*, published by Greene Publishing and Wiley-Interscience, 1987. Additional methods used here are in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif.).

General Control Response Target Genes for Engineering Butanol Tolerance in Yeast The invention relates to the discovery that reducing expression of a gene involved in the general control response to amino acid starvation in *Saccharomyces cerevisiae* results in increased tolerance of cells to butanol. The general control response to amino acid starvation in yeast is a complex system that senses the presence of uncharged tRNAs and responds by inducing transcription of amino acid biosynthetic genes. This control system (reviewed in Hinebusch (2005) *Ann. Rev. Microbiol.* 59: 407-450) includes genes that when mutated confer sensitivity to a wide range of amino acid antagonists and analogs; these genes were called general control non-depressible, or GCN, for the mutant phenotype of not responding to amino acid starvation.

For example, GCN2 encodes a protein (Gcn2p) which senses uncharged tRNA and binds to ribosomes via one Gcn2p domain, the carboxy-terminal domain. Uncharged tRNA is sensed by a second internal domain of Gcn2p termed HisRS (for histidyl-tRNA synthetase like). This binding of uncharged tRNA to the HRS domain results in yet another Gcn2p domain (PK) kinasing eukaryotic initiation factor 2 that is associated with GDP (eIF2~GDP) producing eIF2-P~GDP. In turn, eIF2-P~GDP stimulates translation of the GCN4 encoded mRNA and Gcn4p (the GCN4 encoded protein) activates expression of many genes involved in amino acid biosynthesis.

Initiation of translation requires an activated form of an initiation factor, eIF2: eIF2~GTP. This activated form presents the initiating tRNA, fmet-tRNA, to the ribosome. eIF2-fmet-tRNA~GTP normally starts translation by binding to ribosomes where eventually eIF2~GDP is released. This form of the initiation factor is inactive and must be activated by exchange of GTP for GDP producing eIF2-GTP. When Gcn2p's kinase is activated, eIF2~GDP is hijacked yielding eIF2~P. This form, eIF2~P, blocks the Guanine Exchange Factor eIF2B from catalyzing the reaction: eIF2~GDP+GTP→eIF2~GTP+GDP. Thus most translational initiation is retarded while translation of Gcn4p, the transcriptional activator of amino acid biosynthetic genes, is increased.

Additional GCN gene encoded proteins involved in the general control response to amino acid starvation system in *Saccharomyces cerevisiae* include:

Gcn1p: a positive regulator of the Gcn2p kinase activity

Gcn3p: alpha subunit of the translation initiation factor eIF2B, a positive regulator of GCN4 expression Gcn5p: histone acetyltransferase, acetylates N-terminal lysines on histones H2B and H3; catalytic subunit of the ADA and SAGA histone acetyltransferase complexes Gcn6p: positive regulator of GCN4 transcription Gcn7p: positive regulator of GCN4 transcription Gcn8p: role undefined Gcn9p: role undefined Gcn20p: positive regulator of Gcn2p kinase activity, forms a complex with Gcn1p Given in Table 4 are the SEQ ID NOs for the *Saccharomyces cerevisiae* Gcn1-5p and Gcn20p proteins and their coding regions. Also given in Table 4 are representative coding regions and proteins for GCN genes of *Yarrowia lipolytica* and *Candida albicans.*

A mutation that reduces or eliminates expression of a protein involved in the general control response to amino acid starvation in yeast will reduce the response and surprisingly provide an increase in butanol tolerance. Thus the present yeast host has a genetic modification reducing activity of at least one protein involved in the general control response to amino acid starvation. Suitable genes for genetic modification to reduce the general control response to amino acid starvation include genes encoding Gcn1p, Gcn2p, Gcn3p, Gcn4p, Gcn5p, Gcn6p, Gcn7p, Gcn8p, Gcn9p, and Gcn20p. Examples of these proteins are given in Table 4 as SEQ ID NOS:50, 52, 54, 56, 58, 60, 62, 64, 66, 68, 70, 72, and 74. Genes encoding proteins with sequence identities of at least about 80%, 85%, 90%, 95% or more to these proteins and having GCN activity may be targets for genetic modification to reduce the general control response to amino acid starvation. More suitable targets are genes encoding Gcn1p, Gcn2p, Gcn3p, Gcn4p, Gcn5p, and Gcn20p. Most suitable targets are genes encoding Gcn2p and Gcn4p.

Any yeast gene identified as encoding a Gcn1p, Gcn2p, Gcn3p, Gcn4p, Gcn5p, Gcn6p, Gcn7p, Gcn8p, Gcn9p, or Gcn20p protein, or other gene encoding a protein involved in the general control response to amino acid starvation, is a target gene for modification in the corresponding yeast strain to create a strain of the present invention with increased butanol tolerance. Any type of yeast having a GCN system may be engineered for butanol tolerance using the method of the present invention. Yeast genera including *Saccharomyces, Yarrowia, Candida*, and *Hansenula* have GCN systems (Bode et al. (199) *J. Basic. Microbiol.* 30(1):31-5) and examples of GCN genes of *Saccharomyces cerevisiae, Yarrowia lipolytica*, and *Candida albicans* which are targets for modification to provide tolerance are listed in Table 4. Examples of GCN encoded proteins of *Saccharomyces cerevisiae* include SEQ ID NOs:50, 52, 54, 56, 58, and 60. Examples of GCN encoded proteins of *Yarrowia lipolytica* include SEQ ID NOs:62, 64, 66, and 68. Examples of GCN encoded proteins of *Candida albicans* include SEQ ID NOs:70, 72, and 74. In addition, homologs of GCN2 and GCN4 have been found in the mold *Neurospora crassa* (Paluh et al. (1988) *Proc. Natl. Acad. Sci. USA* 85(11):3728-3732).

Other GCN system target genes may be identified in the literature and in bioinformatics databases well known to the skilled person. Additionally, the sequences described herein or those recited in the art may be used to identify other homologs in nature. For example each of the GCN nucleic acid fragments described herein may be used to isolate genes encoding homologous proteins from the same or other yeasts. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci.* USA 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the GCN genes described herein could be isolated directly by using all or a portion of the instant nucleic acid fragments as DNA hybridization probes to screen libraries from any desired yeast using methodology well known to those skilled in the art. Specific oligonucleotide probes based upon the disclosed nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques), or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency. Heterologous genes may also be identified using functional selections as illustrated by complementation selection for GCN function described in Paluh et al. (ibid.).

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotides as specific hybridization probes in the Diagnosis of Genetic Disorders", in *Human Genetic Diseases: A Practical Approach*, K. E. Davis Ed., (1986) pp 33-50, IRL: Herndon, V A; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the described sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the described nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (e.g., BRL, Gaithersburg, Md.), specific 3' or 5' cDNA fragments can be isolated (Ohara et al., *PNAS USA* 86:5673 (1989); Loh et al., *Science* 243:217 (1989)).

Alternatively, the described GCN sequences may be employed as hybridization reagents for the identification of homologs. The basic components of a nucleic acid hybridization test include a probe, a sample suspected of containing the gene or gene fragment of interest, and a specific hybridization method. Probes are typically single-stranded nucleic acid sequences that are complementary to the nucleic acid sequences to be detected. Probes are “hybridizable” to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Alternatively, because GCN sequences are well known, and because sequencing of the genomes of fungi is prevalent (10 are completed, 71 others have been subjected to a whole genome shotgun approach and are being assembled while 42 others are in progress), suitable GCN system target genes may be identified on the basis of sequence similarity using bioinformatics approaches alone, which are well known to one skilled in the art.

Genetic Modification of General Control Response Genes in Yeast for Butanol Tolerance Many methods for genetic modification of target genes are known to one skilled in the art and may be used to create the present yeast strains. Modifications that may be used to reduce or eliminate expression of a target protein are disruptions that include, but are not limited to, deletion of the entire gene or a portion of the gene encoding a Gcnp, inserting a DNA fragment into a GCN gene (in either the promoter or coding region) so that the protein is not expressed or expressed at lower levels, introducing a mutation into a GCn coding region which adds a stop codon or frame shift such that a functional protein is not expressed, and introducing one or more mutations into a GCN coding region to alter amino acids so that a non-functional or a less enzymatically active protein is expressed. In addition, expression of a GCN gene may be blocked by expression of an antisense RNA or an interfering RNA, and constructs may be introduced that result in cosuppression. Moreover, a GCN gene may be synthesized whose expression is low because rare codons are substituted for plentiful ones, and this gene substituted for the endogenous corresponding GCN gene. Such a gene will produce the same polypeptide but at a lower rate. In addition, the synthesis or stability of the transcript may be lessened by mutation. Similarly the efficiency by which a protein is translated from mRNA may be modulated by mutation. All of these methods may be readily practiced by one skilled in the art making use of the known sequences encoding Gcn proteins. Yeast GCN sequences are publicly available, and representative sequences are listed in Table 4. One skilled in the art may choose specific modification strategies to eliminate or lower the expression of a GCN gene as desired to increase butanol tolerance.

DNA sequences surrounding a GCN coding sequence are also useful in some modification procedures and are available for yeasts such as for *Saccharomycse cerevisiae* in the complete genome sequence coordinated by Genome Project ID9518 of Genome Projects coordinated by NCBI (National Center for Biotechnology Information) with identifying GOPID #13838. Additional examples of yeast genomic sequences include that of *Yarrowia lipolytica*, GOPIC #13837, and of *Candida albicans*, which is included in GPID #10771, #10701 and #16373. Other yeast genomic sequences can be readily found by one of skill in the art in publicly available databases.

In particular, DNA sequences surrounding a GCN coding sequence are useful for modification methods using homologous recombination. For example, in this method GCN gene flanking sequences are placed bounding a selectable marker gene to mediate homologous recombination whereby the marker gene replaces the GCN gene. Also partial GCN gene sequences and GCN flanking sequences bounding a selectable marker gene may be used to mediate homologous recombination whereby the marker gene replaces a portion of the target GCN gene. In addition, the selectable marker may be bounded by site-specific recombination sites, so that following expression of the corresponding site-specific recombinase, the resistance gene is excised from the GCN gene without reactivating the latter. The site-specific recombination leaves behind a recombination site which disrupts expression of the Gcn protein. The homologous recombination vector may be constructed to also leave a deletion in the GCN gene following excision of the selectable marker, as is well known to one skilled in the art.

Deletions may be made using mitotic recombination as described in Wach et al. ((1994) Yeast 10:1793-1808). This method involves preparing a DNA fragment that contains a selectable marker between genomic regions that may be as short as 20 bp, and which bound a target DNA sequence. This DNA fragment can be prepared by PCR amplification of the selectable marker gene using as primers oligonucleotides that hybridize to the ends of the marker gene and that include the genomic regions that can recombine with the yeast genome. The linear DNA fragment can be efficiently transformed into yeast and recombined into the genome resulting in gene replacement including with deletion of the target DNA sequence (as described in Methods in Enzymology, v194, pp 281-301 (1991)).

Moreover, promoter replacement methods may be used to exchange the endogenous transcriptional control elements allowing another means to modulate expression such as described in Mnaimneh et al. ((2004) Cell 118(1):31-44).

Butanol Tolerance of the Present Modified Yeast Strain

A yeast strain of the present invention that is genetically modified for reduced response in the general control response for amino acid starvation has improved tolerance to butanol. The tolerance of reduced response strains may be assessed by assaying their growth in concentrations of butanol that are detrimental to growth of the parental (prior to genetic modification) strains. Improved tolerance is to butanol compounds including 1-butanol, isobutanol, and 2-butanol. The amount of tolerance observed will vary depending on the inhibiting chemical and its concentration, growth conditions, growth period, and the specific genetically modified strain. For example, as shown in Example 1 herein, improved tolerance was observed with growth in 1%-2% isobutanol for 8 hours in a medium lacking amino acids other than histidine and leucine. In this medium the cells have more biosynthetic demand than is the case in rich medium, which contains histidine and leucine. Other conditions for demonstration of the improved butanol tolerance of the present yeast strains include conditions where biosynthetic demand is higher than in rich medium conditions, including a lack of any metabolic product, such as other amino acids, nucleotides, or fatty acids. Additionally the presence of inhibitors, osmotic imbalance, or other non-ideal growth conditions may provide conditions for demonstration of improved butanol tolerance.

Butanol Biosynthetic Pathway

In the present invention, a genetic modification conferring increased butanol tolerance, as described above, is engineered in a yeast cell that is engineered to express a butanol biosynthetic pathway. Either genetic modification may take place prior to the other.

The butanol biosynthetic pathway may be a 1-butanol, 2-butanol, or isobutanol biosynthetic pathway. Particularly suitable yeast hosts for the production of butanol and modification of the general control response to amino acid starvation for increased butanol tolerance include, but are not limited to, members of the genera *Saccharomyces, Candida, Hansenula* and *Yarowia*. Preferred hosts include *Saccharomyces cerevesiae, Candida albicans* and *Yarowia lipolytica.*

1-Butanol Biosynthetic Pathway

A biosynthetic pathway for the production of 1-butanol is described by Donaldson et al. in co-pending and commonly owned U.S. Patent Application Publication No. 0080182308, incorporated herein by reference. This biosynthetic pathway comprises the following substrate to product conversions:

a) acetyl-CoA to acetoacetyl-CoA, as catalyzed for example by acetyl-CoA acetyltransferase with protein sequence such as SEQ ID NO:2, 4 or 40 encoded by the genes given as SEQ ID NO:1, 3 or 39;
b) acetoacetyl-CoA to 3-hydroxybutyryl-CoA, as catalyzed for example by 3-hydroxybutyryl-CoA dehydrogenase with protein sequence such as SEQ ID NO:6 encoded by the gene given as SEQ ID NO:5;
c) 3-hydroxybutyryl-CoA to crotonyl-CoA, as catalyzed for example by crotonase with protein sequence such as SEQ ID NO:8 encoded by the gene given as SEQ ID NO:7;
d) crotonyl-CoA to butyryl-CoA, as catalyzed for example by butyryl-CoA dehydrogenase with protein sequence such as SEQ ID NO:10 encoded by the gene given as SEQ ID NO:9;
e) butyryl-CoA to butyraldehyde, as catalyzed for example by butyraldehyde dehydrogenase with protein sequence such as SEQ ID NO:12 encoded by the gene given as SEQ ID NO:11; and
f) butyraldehyde to 1-butanol, as catalyzed for example by 1-butanol dehydrogenase with protein sequence such as SEQ ID NO:14 or 16 encoded by the genes given as SEQ ID NO:13 or 15.

The pathway requires no ATP and generates $NAD^+$ and/or $NADP^+$, thus, it balances with the central, metabolic routes that generate acetyl-CoA.

2-Butanol Biosynthetic Pathway

Biosynthetic pathways for the production of 2-butanol are described by Donaldson et al. in co-pending and commonly owned U.S. Patent Application Publication Nos. 20070259410 and 20070292927, each incorporated herein by reference. One 2-butanol biosynthetic pathway comprises the following substrate to product conversions:

a) pyruvate to alpha-acetolactate, as catalyzed for example by acetolactate synthase with protein sequence such as SEQ ID NO:20 encoded by the gene given as SEQ ID NO:19;
b) alpha-acetolactate to acetoin, as catalyzed for example by acetolactate decarboxylase with protein sequence such as SEQ ID NO:18 encoded by the gene given as SEQ ID NO:17;
c) acetoin to 2,3-butanediol, as catalyzed for example by butanediol dehydrogenase with protein sequence such as SEQ ID NO:22 encoded by the gene given as SEQ ID NO:21;
d) 2,3-butanediol to 2-butanone, catalyzed for example by butanediol dehydratase with protein sequence such as SEQ ID NO:24, 26, or 28 encoded by genes given as SEQ ID NO:23, 25, or 27; and e) 2-butanone to 2-butanol, as catalyzed for example by 2-butanol dehydrogenase with protein sequence such as SEQ ID NO:30 encoded by the gene given as SEQ ID NO:29.

Isobutanol Biosynthetic Pathway

Biosynthetic pathways for the production of isobutanol are described by Maggio-Hall et al. in copending and commonly owned U.S. Patent Application Publication No. 20070092957, incorporated herein by reference. One isobutanol biosynthetic pathway comprises the following substrate to product conversions:

a) pyruvate to acetolactate, as catalyzed for example by acetolactate synthase with protein sequence such as SEQ ID NO:20 or 42 encoded by genes given as SEQ ID NO:19 or 41;

b) acetolactate to 2,3-dihydroxyisovalerate, as catalyzed for example by acetohydroxy acid isomeroreductase with protein sequence such as SEQ ID NO:32, 44 or 46 encoded by genes given as SEQ ID NO:31, 43 or 45;

c) 2,3-dihydroxyisovalerate to α-ketoisovalerate, as catalyzed for example by acetohydroxy acid dehydratase with protein sequence such as SEQ ID NO:34 encoded by the gene given as SEQ ID NO:33; or dihydroxyacid dehydratase with protein sequence such as SEQ ID NO:48 encoded by the gene given as SEQ ID NO:47;

d) α-ketoisovalerate to isobutyraldehyde, as catalyzed for example by a branched-chain keto acid decarboxylase with protein sequence such as SEQ ID NO:36 encoded by the gene given as SEQ ID NO:35; and e) isobutyraldehyde to isobutanol, as catalyzed for example by a branched-chain alcohol dehydrogenase with protein sequence such as SEQ ID NO:38 encoded by the gene given as SEQ ID NO:37.

Construction of Yeast Strains for Butanol Production

Any yeast strain that is genetically modified for butanol tolerance as described herein is additionally genetically modified (before or after modification to tolerance) to incorporate a butanol biosynthetic pathway by methods well known to one skilled in the art. Genes encoding the enzyme activities described above, or homologs that may be identified and obtained by commonly used methods, such as those described above, that are well known to one skilled in the art, are introduced into a yeast host. Representative coding and amino acid sequences for pathway enzymes that may be used are given in Tables 1, 2, and 3, with SEQ ID NOs:1-48.

Methods for gene expression in yeasts are known in the art; specifically, basic yeast molecular biology protocols including transformation, cell growth, gene expression, gap repair recombination, etc. are described in *Methods in Enzymology*, Volume 194, *Guide to Yeast Genetics and Molecular and Cell Biology* (Part A, 2004, Christine Guthrie and Gerald R. Fink (Eds.), Elsevier Academic Press, San Diego, Calif. Expression of a gene in yeast typically requires a promoter, followed by the coding region of interest, and a transcriptional terminator, all of which are operably linked to provide expression cassettes. A number of yeast promoters can be used in constructing expression cassettes for genes encoding a butanol biosynthetic pathway, including, but not limited to constitutive promoters FBA, GPD, and GPM, and the inducible promoters GAL1, GAL10, and CUP1. Suitable transcriptional terminators include, but are not limited to FBAt, GPDt, GPMt, ERG10t, and GAL1t. For example, suitable promoters, transcriptional terminators, and the genes of a 1-butanol or isobutanol biosynthetic pathway may be cloned into *E. coli*-yeast shuttle vectors, as described in Example 2.

Typically used plasmids in yeast are shuttle vectors pRS423, pRS424, pRS425, and pRS426 (American Type Culture Collection, Rockville, Md.), which contain an *E. coli* replication origin (e.g., pMB1), a yeast 2μ origin of replication, and a marker for nutritional selection. The selection markers for these four vectors are His3 (vector pRS423), Trp1 (vector pRS424), Leu2 (vector pRS425) and Ura3 (vector pRS426). These vectors allow strain propagation in both *E. coli* and yeast strains. Typical hosts for gene cloning and expression include a yeast haploid strain BY4741 (MATa his3Δ1 leu2Δ0 met15Δ0 ura3Δ0) (Research Genetics, Huntsville, Ala., also available from ATCC 201388) and a diploid strain BY4743 (MATa/alpha his3Δ0/his3Δ1 leu2Δ0/leu2Δ0 lys2Δ0/LYS2 MET15/met15Δ0 ura3Δ0/ura3Δ0) (Research Genetics, Huntsville, Ala., also available from ATCC 201390). Construction of expression vectors for genes encoding butanol biosynthetic pathway enzymes may be performed by either standard molecular cloning techniques in *E. coli* or by the gap repair recombination method in yeast.

The gap repair cloning approach takes advantage of the highly efficient homologous recombination in yeast. Typically, a yeast vector DNA is digested (e.g., in its multiple cloning site) to create a "gap" in its sequence. A number of insert DNAs of interest are generated that contain a ≧21 bp sequence at both the 5' and the 3' ends that sequentially overlap with each other, and with the 5' and 3' terminus of the vector DNA. For example, to construct a yeast expression vector for "Gene X', a yeast promoter and a yeast terminator are selected for the expression cassette. The promoter and terminator are amplified from the yeast genomic DNA, and Gene X is either PCR amplified from its source organism or obtained from a cloning vector comprising Gene X sequence. There is at least a 21 bp overlapping sequence between the 5' end of the linearized vector and the promoter sequence, between the promoter and Gene X, between Gene X and the terminator sequence, and between the terminator and the 3' end of the linearized vector. The "gapped" vector and the insert DNAs are then co-transformed into a yeast strain and plated on the medium containing the appropriate compound mixtures that allow complementation of the nutritional selection markers on the plasmids. The presence of correct insert combinations can be confirmed by PCR mapping using plasmid DNA prepared from the selected cells. The plasmid DNA isolated from yeast (usually low in concentration) can then be transformed into an *E. coli* strain, e.g. TOP10, followed by mini preps and restriction mapping to further verify the plasmid construct. Finally the construct can be verified by sequence analysis. Yeast transformants of positive plasmids are grown for performing enzyme assays to characterize the activities of the enzymes expressed by the genes of interest.

Fermentation Media

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415-32.

Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485-489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, and sucrose.

In addition to an appropriate carbon source, fermentation media must contain suitable minerals, salts, cofactors, buffers and other components, known to those skilled in the art, suitable for the growth of the cultures and promotion of the enzymatic pathway necessary for butanol production.

Culture Conditions

Typically cells are grown at a temperature in the range of about 20° C. to about 37° C. in an appropriate medium. Suitable growth media in the present invention are common commercially prepared media such as broth that includes yeast nitrogen base, ammonium sulfate, and dextrose as the carbon/energy source) or YPD Medium, a blend of peptone, yeast extract, and dextrose in optimal proportions for growing most *Saccharomyces cerevisiae* strains. Other defined or synthetic growth media may also be used and the appropriate medium for growth of the particular microorganism will be known by one skilled in the art of microbiology or fermentation science.

Suitable pH ranges for the fermentation are between pH 3.0 to pH 7.5, where pH 4.5.0 to pH 6.5 is preferred as the initial condition.

Fermentations may be performed under aerobic or anaerobic conditions, where anaerobic or microaerobic conditions are preferred.

The amount of butanol produced in the fermentation medium can be determined using a number of methods known in the art, for example, high performance liquid chromatography (HPLC) or gas chromatography (GC).

Methods for Butanol Isolation from the Fermentation Medium

The bioproduced butanol may be isolated from the fermentation medium using methods known in the art. For example, solids may be removed from the fermentation medium by centrifugation, filtration, decantation, or the like. Then, the butanol may be isolated from the fermentation medium, which has been treated to remove solids as described above, using methods such as distillation, liquid-liquid extraction, or membrane-based separation. Because butanol forms a low boiling point, azeotropic mixture with water, distillation can only be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol may be isolated using azeotropic distillation using an entrainer (see for example Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden et al. *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo et al., *J. Membr. Sci.* 245, 199-210 (2004)).

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified.

Microbial strains were obtained from The American Type Culture Collection (ATCC), Manassas, Va., unless otherwise noted.

Methods for Determining Isobutanol Concentration in Culture Media

The concentration of isobutanol in the culture media can be determined by a number of methods known in the art. For example, a specific high performance liquid chromatography (HPLC) method utilizes a Shodex SH-1011 column with a Shodex SH-G guard column, both purchased from Waters Corporation (Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol has a retention time of 46.6 min under the conditions described. Alternatively, gas chromatography (GC) methods are available. For example, a specific GC method utilizes an HP-INNOWax column (30 m×0.53 mm id, 1 μm film thickness, Agilent Technologies, Wilmington, Del.), with a flame ionization detector (FID). The carrier gas is helium at a flow rate of 4.5 mL/min, measured at 150° C. with constant head pressure; injector split is 1:25 at 200° C.; oven temperature is 45° C. for 1 min, 45 to 220° C. at 10° C./min, and 220° C. for 5 min; and FID detection is employed at 240° C. with 26 mL/min helium makeup gas. The retention time of isobutanol is 4.5 min.

The meaning of abbreviations is as follows: "s" means second(s), "min" means minute(s), "h" means hour(s), "psi" means pounds per square inch, "nm" means nanometers, "d" means day(s), "μL" means microliter(s), "mL" means milliliter(s), "L" means liter(s), "mm" means millimeter(s), "nm" means nanometers, "mM" means millimolar, "μM" means micromolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "HPLC" means high performance liquid chromatography, and "GC" means gas chromatography. The term "molar selectivity" is the number of moles of product produced per mole of sugar substrate consumed and is reported as a percent.

Example 1

Butanol Tolerance in qcn2 and qcn4 Mutants

GCN2 gene and GCN4 gene deletion mutants of the diploid a/α *Saccharomyces cerevisiae* strain BY4743 (Brachmann et al. (Yeast 14:115-132 (1998)) are available in a nearly complete, ordered deletion strain collection (Giaever et al. Nature 418, 387-391 (2002); *Saccharomyces* Genome Deletion Project). Cells of the GCN2 gene and GCN4 gene deletion mutants were grown overnight from a single colony on a YPD plate in either YPD or YVCM medium (recipes below) in a 14 ml Falcon tube at 30° C. with shaking at 250 rpm. Overnight cultures were diluted 1:100 (2 ml to 200 ml) in the same medium and growth was monitored every 60 minutes until 1 doubling had occurred. At that point the cultures were split into 25 ml samples that were dispensed to separate 125 ml plastic flasks. Challenging concentrations of isobutanol ranging between 0.5% and 2% w/v were added to all but one flask of each culture that served as the positive control. Control and challenge cultures were incubated with shaking in a 30° C. water bath and absorbance was monitored on about an hourly basis.

The two media used were a rich medium, YPD, which contains per liter: 10 g yeast extract, 20 g peptone, 20 g dextrose; and a defined, synthetic medium, YVCM, which contains per liter: 6.67 g yeast nitrogen base without amino acids but with ammonium sulfate, 20 g dextrose, 20 mg L-histidine, 30 mg L-leucine, 20 mg uracil.

Figure 1B:
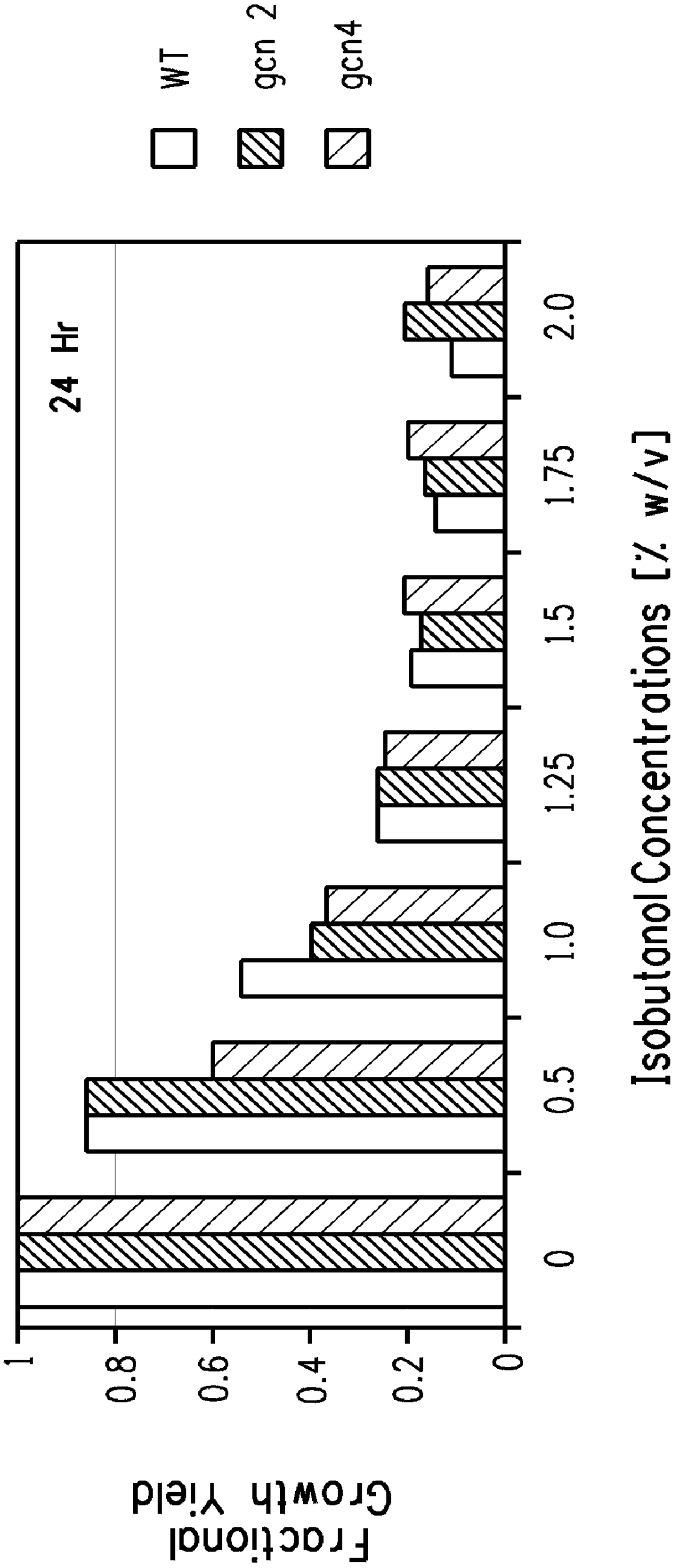

Using 8 and 24 hr time points for growth in YVCM containing isobutanol, fractional growth yields were determined and results are given in FIG. 1. Both GCN2 and GCN4 deletion lines that were grown in the synthetic medium were substantially more tolerant to an 8 hr isobutanol challenge than the parental strain. The accrued advantage disappeared after overnight incubation. The increased tolerance was seen over a 1-2% isobutanol concentration range.

Figure 2A:
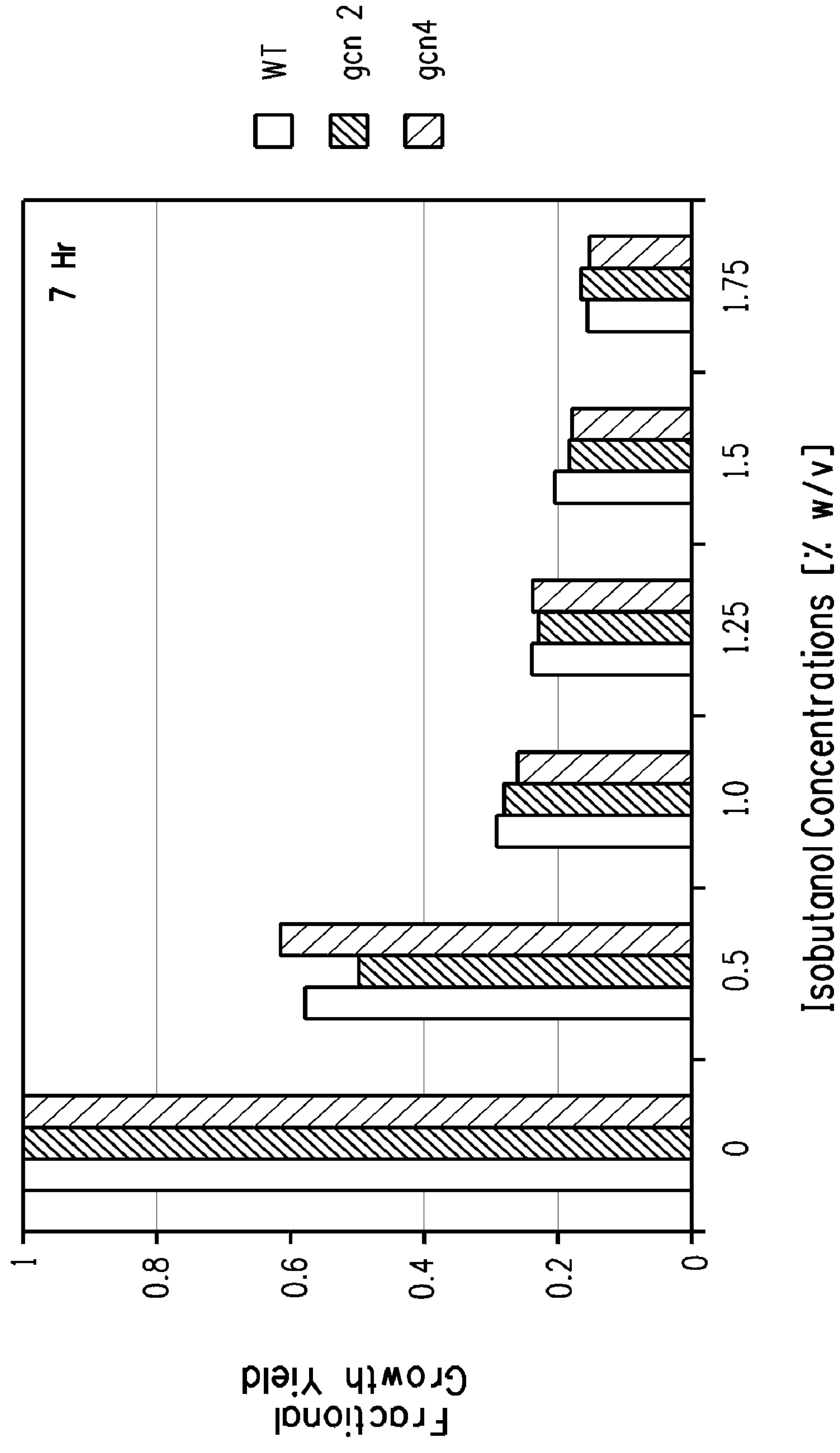
FIG. 2 shows fractional growth yields of wild type, mutant GCN2 and mutant GCN4 strains at 7 hr (A) and 23 hr (B) time points for growth in YPD containing different concentrations of isobutanol.
Figure 2B:
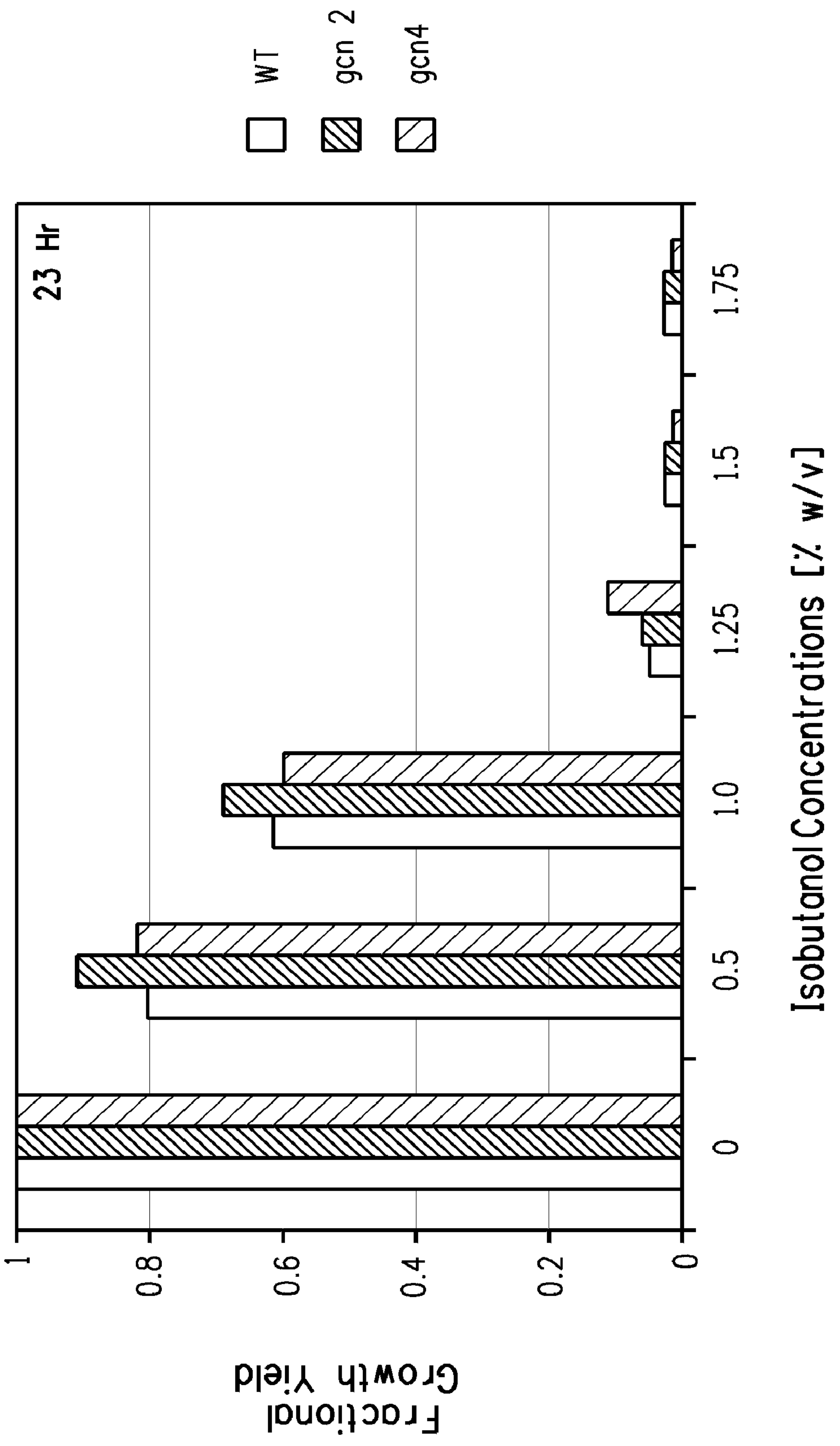

Using 7 and 23 hr time points for growth in YPD containing isobutanol, fractional growth yields were determined and results are given in FIG. 2. In these conditions improved tolerance was not observed at the short time point, and minimal improvement was seen with the GCN2 and GCN4 mutations in different isobutanol concentrations.

Example 2

Expression of Isobutanol Pathway Genes in *Saccharomyces cerevisiae*

To express isobutanol pathway genes in *Saccharomyces cerevisiae*, a number of *E. coli*-yeast shuttle vectors were constructed. A PCR approach (Yu, et al. *Fungal Genet. Biol.* 41:973-981(2004)) was used to fuse genes with yeast promoters and terminators. Specifically, the GPD promoter (SEQ ID NO:76) and CYC1 terminator (SEQ ID NO:77) were fused to the alsS gene from *Bacillus subtilis* (SEQ ID NO:41), the FBA promoter (SEQ ID NO:78) and CYC1 terminator were fused to the ILV5 gene from *S. cerevisiae* (SEQ ID NO:43), the ADH1 promoter (SEQ ID NO:79) and ADH1 terminator (SEQ ID NO:80) were fused to the ILV3 gene from *S. cerevisiae* (SEQ ID NO:47), and the GPM promoter (SEQ ID NO:81) and ADH1 terminator were fused to the kivD gene from *Lactococcus lactis* (SEQ ID NO:35). The primers, given in Table 5, were designed to include restriction sites for cloning promoter/gene/terminator products into *E. coli*-yeast shuttle vectors from the pRS400 series (Christianson et al. *Gene* 110:119-122 (1992)) and for exchanging promoters between constructs. Primers for the 5' ends of ILV5 and ILV3 (N138 and N155, respectively, given as SEQ ID NOs: 92 and 104, respectively) generated new start codons to eliminate mitochondrial targeting of these enzymes.

All fused PCR products were first cloned into pCR4-Blunt by TOPO cloning reaction (Invitrogen) and the sequences were confirmed (using M13 forward and reverse primers (Invitrogen) and the sequencing primers provided in Table 5. Two additional promoters (CUP1 and GAL1) were cloned by TOPO reaction into pCR4-Blunt and confirmed by sequencing; primer sequences are indicated in Table 5. The plasmids that were constructed are described in Table 6. The plasmids were transformed into either *Saccharomyces cerevisiae* BY4743 (ATCC 201390) or YJR148w (ATCC 4036939) to assess enzyme specific activities. For the determination of enzyme activities, cultures were grown to an $OD_{600}$ of 1.0 in synthetic complete medium (*Methods in Yeast Genetics,* 2005, Cold Spring Harbor Laboratory Press, Cold Spring Harbor, N.Y., pp. 201-202) lacking any metabolite(s) necessary for selection of the expression plasmid(s), harvested by centrifugation (2600×g for 8 min at 4° C.), washed with buffer, centrifuged again, and frozen at −80° C. The cells were thawed, resuspended in 20 mM Tris-HCl, pH 8.0 to a final volume of 2 mL, and then disrupted using a bead beater with 1.2 g of glass beads (0.5 mm size). Each sample was processed on high speed for 3 minutes total (with incubation on ice after each minute of beating). Extracts were cleared of cell debris by centrifugation (20,000×g for 10 min at 4° C.).

Acetolactate synthase activity in the cell free extracts is measured using the method described by Bauerle et al. (*Biochim. Biophys. Acta* 92(1):142-149 (1964)). Acetohydroxy acid reductoisomerase activity in the cell free extracts is measured using the method described by Arfin and Umbarger (*J. Biol. Chem.* 244(5):1118-1127 (1969)). Acetohydroxy acid dehydratase activity in the cell free extracts is measured using the method described by Flint et al. (*J. Biol. Chem.* 268(20): 14732-14742 (1993)). Branched-chain keto acid decarboxylase activity in the cell free extracts is measured using the method described by Smit et al. (*Appl. Microbiol. Biotechnol.* 64:396-402 (2003)), except that Purpald® reagent (Aldrich, Catalog No. 162892) is used to detect and quantify the aldehyde reaction products.

TABLE 5

Primer Sequences for Cloning and Sequencing of *S. cerevisiae* Expression Vectors

| Name | Sequence | Description | SEQ ID NO: |
|---|---|---|---|
| N98SeqF1 | CGTGTTAGTCACATCAGGAC | *B. subtilis* alsS sequencing primer | 82 |
| N98SeqF2 | GGCCATAGCAAAAATCCAAACA GC | *B. subtilis* alsS sequencing primer | 83 |
| N98SeqF3 | CCACGATCAATCATATCGAACACG | *B. subtilis* alsS sequencing primer | 84 |
| N98SeqF4 | GGTTTCTGTCTCTGGTGACG | *B. subtilis* alsS sequencing primer | 85 |
| N99SeqR1 | GTCTGGTGATTCTACGCGCAAG | *B. subtilis* alsS sequencing primer | 86 |
| N99SeqR2 | CATCGACTGCATTACGCAACTC | *B. subtilis* alsS sequencing primer | 87 |
| N99SeqR3 | CGATCGTCAGAACAACATCTGC | *B. subtilis* alsS sequencing primer | 88 |
| N99SeqR4 | CCTTCAGTGTTCGCTGTCAG | *B. subtilis* alsS sequencing primer | 89 |
| N136 | CCGCGGATAGATCTGAAATGAA TAACAATACTGACA | FBA promoter forward primer with SacII/BgIII sites | 90 |
| N137 | TACCACCGAAGTTGATTTGCTTC AACATCCTCAGCTCTAGATTTGA ATATGTATTACTTGGTTAT | FBA promoter reverse primer with BbvCI site and ILV5-annealing region | 91 |
| N138 | ATGTTGAAGCAAATCAACTTCGG TGGTA | ILV5 forward primer (creates alternate start codon) | 92 |
| N139 | TTATTGGTTTTCTGGTCTCAAC | ILV5 reverse primer | 93 |
| N140 | AAGTTGAGACCAGAAAACCAAT AATTAATTAATCATGTAATTAGTT ATGTCACGCTT | CYC terminator forward primer with PacI site and ILV5-annealing region | 94 |
| N141 | GCGGCCGCCCGCAAATTAAAGC CTTCGAGC | CYC terminator reverse primer with NotI site | 95 |
| N142 | GGATCCGCATGCTTGCATTTAG TCGTGC | GPM promoter forward primer with BamHI site | 96 |
| N143 | CAGGTAATCCCCCACAGTATAC ATCCTCAGCTATTGTAATATGTG TGTTTGTTTGG | GPM promoter reverse primer with BbvCI site and kivD-annealing region | 97 |

TABLE 5-continued

Primer Sequences for Cloning and Sequencing of *S. cerevisiae* Expression Vectors

| Name | Sequence | Description | SEQ ID NO: |
|---|---|---|---|
| N144 | ATGTATACTGTGGGGGATTACC | kivD forward primer | 98 |
| N145 | TTAGCTTTTATTTTGCTCCGCA | kivD reverse primer | 99 |
| N146 | TTTGCGGAGCAAAATAAAAGCTA ATTAATTAAGAGTAAGCGAATTT CTTATGATTTA | ADH terminator forward primer with PacI site and kivD-annealing region | 100 |
| N147 | ACTAGTACCACAGGTGTTGTCC TCTGAG | ADH terminator reverse primer with SpeI site | 101 |
| N151 | CTAGAGAGCTTTCGTTTTCATG | alsS reverse primer | 102 |
| N152 | CTCATGAAAACGAAAGCTCTCTA GTTAATTAATCATGTAATTAGTTA TGTCACGCTT | CYC terminator forward primer with PacI site and alsS-annealing region | 103 |
| N155 | ATGGCAAAGAAGCTCAACAAGT ACT | ILV3 forward primer (alternate start) codon) | 104 |
| N156 | TCAAGCATCTAAAACACAACCG | ILV3 reverse primer | 105 |
| N157 | AACGGTTGTGTTTTAGATGCTTG ATTAATTAAGAGTAAGCGAATTT CTTATGATTTA | ADH terminator forward primer with PacI site and ILV3-annealing region | 106 |
| N158 | GGATCCTTTTCTGGCAACCAAA CCCATA | ADH promoter forward primer with BamHI site | 107 |
| N159 | CGAGTACTTGTTGAGCTTCTTTG CCATCCTCAGCGAGATAGTTGA TTGTATGCTTG | ADH promoter reverse primer with BbvCI site and ILV3-annealing region | 108 |
| N160SeqF1 | GAAAACGTGGCATCCTCTC | FBA::ILV5::CYC sequencing primer | 109 |
| N160SeqF2 | GCTGACTGGCCAAGAGAAA | FBA::ILV5::CYC sequencing primer | 110 |
| N160SeqF3 | TGTACTTCTCCCACGGTTTC | FBA::ILV5::CYC sequencing primer | 111 |
| N160SeqF4 | AGCTACCCAATCTCTATACCCA | FBA::ILV5::CYC sequencing primer | 112 |
| N160SeqF5 | CCTGAAGTCTAGGTCCCTATTT | FBA::ILV5::CYC sequencing primer | 113 |
| N160SeqR1 | GCGTGAATGTAAGCGTGAC | FBA::ILV5::CYC sequencing primer | 114 |
| N160SeqR2 | CGTCGTATTGAGCCAAGAAC | FBA::ILV5::CYC sequencing primer | 115 |
| N160SeqR3 | GCATCGGACAACAAGTTCAT | FBA::ILV5::CYC sequencing primer | 116 |
| N160SeqR4 | TCGTTCTTGAAGTAGTCCAACA | FBA::ILV5::CYC sequencing primer | 117 |

TABLE 5-continued

Primer Sequences for Cloning and Sequencing of *S. cerevisiae* Expression Vectors

| Name | Sequence | Description | SEQ ID NO: |
|---|---|---|---|
| N160SeqR5 | TGAGCCCGAAAGAGAGGAT | FBA::ILV5::CYC sequencing primer | 118 |
| N161SeqF1 | ACGGTATACGGCCTTCCTT | ADH::ILV3::ADH sequencing primer | 119 |
| N161SeqF2 | GGGTTTGAAAGCTATGCAGT | ADH::ILV3::ADH sequencing primer | 120 |
| N161SeqF3 | GGTGGTATGTATACTGCCAACA | ADH::ILV3::ADH sequencing primer | 121 |
| N161SeqF4 | GGTGGTACCCAATCTGTGATTA | ADH::ILV3::ADH sequencing primer | 122 |
| N161SeqF5 | CGGTTTGGGTAAAGATGTTG | ADH::ILV3::ADH sequencing primer | 123 |
| N161SeqF6 | AAACGAAAATTCTTATTCTTGA | ADH::ILV3::ADH sequencing primer | 124 |
| N161SeqR1 | TCGTTTTAAAACCTAAGAGTCA | ADH::ILV3::ADH sequencing primer | 125 |
| N161SeqR2 | CCAAACCGTAACCCATCAG | ADH::ILV3::ADH sequencing primer | 126 |
| N161SeqR3 | CACAGATTGGGTACCACCA | ADH::ILV3::ADH sequencing primer | 127 |
| N161SeqR4 | ACCACAAGAACCAGGACCTG | ADH::ILV3::ADH sequencing primer | 128 |
| N161SeqR5 | CATAGCTTTCAAACCCGCT | ADH::ILV3::ADH sequencing primer | 129 |
| N161SeqR6 | CGTATACCGTTGCTCATTAGAG | ADH::ILV3::ADH sequencing primer | 130 |
| N162 | ATGTTGACAAAAGCAACAAAAGA | alsS forward primer | 131 |
| N189 | ATCCGCGGATAGATCTAGTTCG AGTTTATCATTATCAA | GPD forward primer with SacII/Bg/II sites | 132 |
| N190.1 | TTCTTTTGTTGCTTTTGTCAACAT CCTCAGCGTTTATGTGTGTTTAT TCGAAA | GPD promoter reverse primer with BbvCI site and alsS-annealing region | 133 |
| N176 | ATCCGCGGATAGATCTATTAGAA GCCGCCGAGCGGGCG | GAL1 promoter forward primer with SacII/Bg/II sites | 134 |
| N177 | ATCCTCAGCTTTTCTCCTTGACG TTAAAGTA | GAL1 promoter reverse with BbvCI site | 135 |
| N191 | ATCCGCGGATAGATCTCCCATT ACCGACATTTGGGCGC | CUP1 promoter forward primer with SacII/BgIII sites | 136 |
| N192 | ATCCTCAGCGATGATTGATTGAT TGATTGTA | CUP1 promoter reverse with BbvCI site | 137 |

TABLE 6

*E. coli*-Yeast Shuttle Vectors Carrying Isobutanol Pathway Genes

| Plasmid Name | Construction |
|---|---|
| pRS426 [ATCC No. 77107], URA3 selection | — |
| pRS426::GPD::alsS::CYC | GPD::alsS::CYC PCR product digested with SacII/NotI cloned into pRS426 digested with same |
| pRS426::FBA::ILV5::CYC | FBA::ILV5::CYC PCR product digested with SacII/NotI cloned into pRS426 digested with same |
| pRS425 [ATCC No. 77106], LEU2 selection | — |
| pRS425::ADH::ILV3::ADH | ADH::ILV3::ADH PCR product digested with BamHI/SpeI cloned into pRS425 digested with same |
| pRS425::GPM::kivD::ADH | GPM::kivD::ADH PCR product digested with BamHI/SpeI cloned into pRS425 digested with same |
| pRS426::CUP1::alsS | 7.7 kbp SacII/BbvCI fragment from pRS426::GPD::alsS::CYC ligated with SacII/BbvCI CUP1 fragment |
| pRS426::GAL1::ILV5 | 7 kbp SacII/BbvCI fragment from pRS426::FBA::ILV5::CYC ligated with SacII/BbvCI GAL1 fragment |
| pRS425::FBA::ILV3 | 8.9 kbp BamHI/BbvCI fragment from pRS425::ADH::ILV3::ADH ligated with 0.65 kbp BglII/ BbvCI FBA fragment from pRS426::FBA::ILV5::CYC |
| pRS425::CUP1-alsS + FBA-ILV | 2.4 kbp SacII/NotI fragment from pRS426::CUP1::alsS cloned into pRS425::FBA::ILV3 cut with SacII/ NotI |
| pRS426::FBA-ILV5 + GPM-kivD | 2.7 kbp BamHI/SpeI fragment from pRS425::GPM::kivD::ADH cloned into pRS426::FBA::ILV5::CYC cut with BamHI/SpeI |
| pRS426::GAL1-FBA + GPM-kiv | 8.5 kbp SacII/NotI fragment from pRS426:: FBA-ILV5 + GPM-kivD ligated with 1.8 kbp SacII/NotI fragment from pRS426::GAL1:: ILV5 |
| pRS423 [ATCC No. 77104], HIS3 selection | — |
| pRS423::CUP1-alsS + FBA-ILV | 5.2 kbp SacI/Sa/I fragment from pRS425::CUP1-alsS + FBA-ILV3 ligated into pRS423 cut with SacI/ Sa/I |
| pHR81 [ATCC No. 87541], URA3 and leu2-d selection | — |
| pHR81::FBA-ILV5 + GPM-kivD | 4.7 kbp SacI/BamHI fragment from pRS426::FBA-ILV5 + GPM-kivD ligated into pHR81 cut with SacI/ BamHI |

Example 3

Prophetic

Production of Isobutanol Using Tolerant *Saccharomyces cerevisiae* Strain

The starting strain for this work is BY4741 (Brachmann, et al. *Yeast.* 14: 115-132 (1998)) and its Δbat2 derivative, YJR148W BY4741, mating type a (6939) available from the ATCC (#406939) with the genotype MATa his3delta1 leu2delta0 met15delta0 ura3delta0 deltaTWT2. bat2 encodes the cytosolic branched-chain amino acid aminotransferase, The deletion of bat2 in combination with the URA3 deletion allows growth in the absence of uracil to be used as a selection for the presence of a URA3 insertion.

First ΔGCN2 and ΔGCN4 derivatives are made using the ATCC strain #406939. This is accomplished by a gene replacement strategy commonly used in yeast in which a URA3$^+$ allele is used as a selectable marker for a GCN insertion-deletion allele in which URA3$^+$ is integrated in the genome along with flanking direct repeat sequences replacing the sequence targeted for deletion. Subsequently a recombination event between the direct repeats is selected by demanding fluoro-orotic acid (FOA) resistance which selects against URA3$^+$ function.

The DNA fragment including a gene for URA3 expression and flanking direct repeats ("URA3 repeats" fragment; SEQ ID NO:138) includes the following (position numbers refer to position in the "URA3 repeats" fragment of SEQ ID NO:138):

1) primer binding sequences that bound the direct repeats flanking URA3$^+$: gcattgcggattacgtattctaatg (position 1-25; SEQ ID NO:143) and gatgatacaacgagttagccaaggtg (position 1449-1474 of SEQ ID NO:144);
2) the direct repeat sequences that flank the promoter and coding sequence:

(position 26-100 of SEQ ID NO: 145)
ttcagcccgcggaacgcoagcaaatcaccacccatgcgcatgatactgag
tcttgtacacgctgggcttccagtg
and (position 1375-1449 of SEQ ID NO: 146)
ttcagcccgcggaacgccagcaaatcaccacccatgcgcatgatactgag
tcttgtacacgctgggcttccagtg 3) the promoter sequence:

(position 149-348 of SEQ ID NO: 147)
tttttattctttttttgatttcggtttctttgaaatttttttgattcg gtaatctccgaacagaaggaagaacgaaggaaggagcacagacttagatt ggtatatatacgcatatgtagtgttgaagaaacatgaaattgcccagtat tcttaacccaactgcacagaacaaaaacctgcaggaaacgaagataaatc
and 4) the coding region:

(position 349-1152 of SEQ ID NO: 148)
atgtcgaaagctacatataaggaacgtgctgctactcatcctagtcctgt tgctgccaagctatttaatatcatgcacgaaaagcaaacaaacttgtgtg cttcattggatgttcgtaccaccaaggaattactggagttagttgaagca ttaggtcccaaaatttgtttactaaaaacacatgtggatatcttgactga tttttccatggagggcacagttaagccgctaaaggcattatccgccaagt acaatttttttactcttcgaagacagaaaatttgctgacattggtaataca gtcaaattgcagtactctgcgggtgtatacagaatagcagaatgggcaga cattacgaatgcacacggtgtggtgggcccaggtattgttagcggtttga agcaggcggcagaagaagtaacaaaggaacctagaggccttttgatgtta gcagaattgtcatgcaagggctccctatctactggagaatatactaaggg tactgttgacattgcgaagagcgacaaagattttgttatcggctttattg ctcaaagagacatgggtggaagagatgaaggttacgattggttgattatg acacccggtgtgggtttagatgacaagggagacgcattgggtcaacagta tagaaccgtggatgatgtggtctctacaggatctgacattattattgttg gaagaggactatttgcaaagggaagggatgctaaggtagagggtgaacgt tacagaaaagcaggctgggaagcatatttgagaagatgcggccagcaaaa ctaa.

A DNA fragment containing a 50 bp sequence that is 100 bp upstream of the GCN2 coding region, the URA3 repeats fragment described above, and a 50 bp sequence that is 100 bp downstream of the GCN2 coding region is prepared using PCR. The 5' primer is a chimeric sequence containing 50 bp of sequence upstream of GCN2 and the position 1-25 primer binding sequence above in (1): 50 (GCN2 5' flanking)+5'ura3 primer (I) (SEQ ID NO:139). The 3' primer is a chimeric sequence containing the complement of 50 bp of sequence downstream of GCN2 and the position 1449-1474 primer binding sequence complement: 50 (reverse compl of GCN2 3' flanking)+3'ura3 primer (reverse compl) (II) (SEQ ID NO:: 140).

The PCR reaction is a 50 μl reaction mixture of 1 μl of template DNA (50 ng total), 1 μl of each primer at 20 μM, 25 μl of 2× TaKaRa Ex Taq premix, 22 μl water. The template is pUC19-URA3 repeat, a pUC19 (Yanisch-Perron et al. (1985) *Gene,* 33:103-119) derivative into which the "URA3 repeat" has been inserted at the multi-cloning site. The PCR condition used is:

94° C. 1 min, then 30 cycles of 94° C. 20 sec, 55° C. 20 sec and 72° C. 2 min followed by 7 min at 72° C. The extension time is 1 min per kb.

The resulting PCR product, a ΔGCN2::URA3$^+$ fragment, is purified using a Qiagen PCR purification kit.

A similar DNA fragment is prepared as above but using primers containing sequences upstream and downstream of the GCN4 coding region: 50 (GCN4 5' flanking)+5'ura3 primer (III) (SEQ ID NO:141) and 50 (reverse compl. of GCN4 3' flanking)+3'ura3 primer (reverse compl) (GCN4) (IV) (SEQ ID NO:142).

The resulting PCR product, a ΔGCN4::URA3$^+$ fragment, is purified using a Qiagen PCR purification kit.

The PCR products are used to transform the strain ATCC #406939. Integrants are selected for growth in the absence of uracil. Integrant strains with insertion of "URA3 repeats" and deletion of GCN2 or GCN4 are called, respectively:

DYW1: MATa his3delta1 leu2delta0 met15delta0 ura3delta0 deltaTWT2 Δgcn2::URA3$^+$ and DYW2: MATa his3delta1 leu2delta0 met15delta0 ura3delta0 deltaTWT2 Δgcn4::URA3$^+$.

Using 5-FOA selection to select for elimination of the URA3$^+$ allele, strains with recombination between the direct repeats are obtained and called:

DYW3: MATa his3delta1 leu2delta0 met15delta0 ura3delta0 deltaTWT2 Δgcn2 and

DYW4: MATa his3delta1 leu2delta0 met15delta0 ura3delta0 deltaTWT2 Δgcn4

Plasmids pRS423::CUP1-alsS+FBA-ILV3 and pHR81::FBA-ILV5+GPM-kivD (described in Example 2) are transformed into *Saccharomyces cerevisiae* DYW3 and DYW4 to produce strains DYW3 (Δgcn2)/pRS423::CUP1-alsS+FBA-ILV3/pHR81::FBA-ILV5+GPM-kivD and DYW4 (Δgcn4)/pRS423::CUP1-alsS+FBA-ILV3/pHR81::FBA-ILV5+GPM-kivD. A control strain is prepared by transforming vectors pRS423 and pHR81 (described in Example 2) into *Saccharomyces cerevisiae* (ATCC strain #406939) [strain 406939 (GCN2$^+$ GCN4$^+$)/pRS423/pHR81]. Strains are maintained on standard *S. cerevisiae* synthetic complete medium (*Methods in Yeast Genetics,* 2005, Cold Spring Harbor Laboratory Press, Cold Spring Harbor, N.Y., pp. 201-202) containing either 2% glucose or sucrose but lacking uracil and histidine to ensure maintenance of plasmids.

For isobutanol production, cells are transferred to synthetic complete medium lacking uracil, histidine and leucine. Removal of leucine from the medium is intended to trigger an increase in copy number of the pHR81-based plasmid due to poor transcription of the leu2-d allele (Erhart and Hollenberg, *J. Bacteriol.* 156:625-635 (1983)). Aerobic cultures are grown in 175 mL capacity flasks containing 50 mL of medium in an Innova4000 incubator (New Brunswick Scientific, Edison, N.J.) at 30° C. and 200 rpm. Low oxygen cultures are prepared by adding 45 mL of medium to 60 mL serum vials that are sealed with crimped caps after inoculation and kept at 30° C. Sterile syringes are used for sampling and addition of inducer, as needed. Approximately 24 h after inoculation, the inducer $CuSO_4$ is added to a final concentration of 0.03 mM. Control cultures for each strain without $CuSO_4$ addition are also prepared. Culture supernatants are analyzed 18 or 19 h and 35 h after $CuSO_4$ addition by both HPLC (Shodex Sugar SH1011 column (Showa Denko America, Inc. NY) with refractive index (RI) detection) and GC (Varian CP-WAX 58(FFAP) CB, 0.25 mm×0.2 μm×25 m (Varian, Inc., Palo Alto, Calif.) with flame ionization detection (FID)) for isobutanol content, as described in the General Methods section. Production of isobutanol is enhanced by the presence of the mutant gcn alleles. In general, higher levels of isobutanol per optical density unit are produced by the GCN mutants.

What is claimed is:

1. A recombinant yeast host cell having the following characteristics:

a) the yeast host cell produces a butanol when grown in a medium containing a carbon substrate;

b) the yeast host cell comprises at least one genetic modification which reduces the response in the general control response to amino acid starvation, wherein the target for said genetic modification is a gene encoding the General Control Nonderepressible (Gcn) protein Gcn4p; and c) the yeast host cell comprises a recombinant biosynthetic pathway selected from the group consisting of:

a) a 1-butanol biosynthetic pathway;

b) a 2-butanol biosynthetic pathway; and c) an isobutanol biosynthetic pathway.

2. The yeast cell of claim 1 wherein the at least one genetic modification reduces production of Gcn4p.

3. The yeast cell of claim 2 wherein the at least one genetic modification is a disruption in an endogenous gene encoding.

4. The yeast cell of claim 1 wherein the cell is a member of a the genus *Saccharomyces.*

5. The yeast of claim 1 where the cell is *Saccharomyces cerevisiae* comprising a disruption in an endogenous gene encoding Gcn4p.

6. The recombinant yeast cell of claim 1, wherein the host cell comprises an isobutanol biosynthetic pathway comprising:

a) at least one gene encoding an acetolactate synthase;

b) at least one gene encoding acetohydroxy acid isomeroreductase;

c) at least one gene encoding acetohydroxy acid dehydratase;

d) at least one gene encoding branched-chain keto acid decarboxylase; and e) at least one gene encoding branched-chain alcohol dehydrogenase.

7. A process for production of a butanol from a recombinant yeast cell comprising:

(a) providing the recombinant yeast host cell of claim 1

(b) culturing the strain of (a) under conditions wherein the butanol is produced.

8. The process of claim 7 wherein the host cell comprises an isobutanol biosynthetic pathway comprising:

a) at least one gene encoding an acetolactate synthase;

b) at least one gene encoding acetohydroxy acid isomeroreductase;

c) at least one gene encoding acetohydroxy acid dehydratase;

d) at least one gene encoding branched-chain keto acid decarboxylase; and e) at least one gene encoding branched-chain alcohol dehydrogenase.

9. The process of claim 7 wherein the at least one genetic modification reduces production of Gcn4p.

10. The recombinant yeast cell of claim 1 wherein the yeast host cell comprises a 1-butanol biosynthetic pathway comprising:

a) at least one gene encoding an acetyl-CoA acetyltransferase;

b) at least one gene encoding a 3-hydroxybutyryl-CoA dehydrogenase;

c) at least one gene encoding a crotonase;

d) at least one gene encoding a butyryl-CoA dehydrogenase;

e) at least one gene encoding a butyraldehyde dehydrogenase; and f) at least one gene encoding a 1-butanol dehydrogenase.

11. The recombinant yeast cell of claim 1 wherein the yeast host cell comprises a 2-butanol biosynthetic pathway comprising:

a) at least one gene encoding an acetolactate synthase;

b) at least one gene encoding an acetolactate decarboxylase;

c) at least one gene encoding a butanediol dehydrogenase;

d) at least one gene encoding a butanediol dehydratase; and e) at least one gene encoding a 2-butanol dehydrogenase.

12. The process of claim 7 wherein the yeast host cell comprises a 1-butanol biosynthetic pathway comprising:

a) at least one gene encoding an acetyl-CoA acetyltransferase;

b) at least one gene encoding a 3-hydroxybutyryl-CoA dehydrogenase;

c) at least one gene encoding a crotonase;

d) at least one gene encoding a butyryl-CoA dehydrogenase;

e) at least one gene encoding a butyraldehyde dehydrogenase; and f) at least one gene encoding a 1-butanol dehydrogenase.

13. The process of claim 7 wherein the yeast host cell comprises a 2-butanol biosynthetic pathway comprising:

a) at least one gene encoding an acetolactate synthase;

b) at least one gene encoding an acetolactate decarboxylase;

c) at least one gene encoding a butanediol dehydrogenase;

d) at least one gene encoding a butanediol dehydratase; and e) at least one gene encoding a 2-butanol dehydrogenase.

* * * * *

SEQUENCE LISTING

```
<160> NUMBER OF SEQ ID NOS: 148

<210> SEQ ID NO 1
<211> LENGTH: 1179
<212> TYPE: DNA
<213> ORGANISM: Clostridium acetobutylicum

<400> SEQUENCE: 1

atgaaagaag ttgtaatagc tagtgcagta agaacagcga ttggatctta tggaaagtct      60

cttaaggatg taccagcagt agatttagga gctacagcta taaaggaagc agttaaaaaa     120

gcaggaataa aaccagagga tgttaatgaa gtcattttag gaaatgttct tcaagcaggt     180

ttaggacaga atccagcaag acaggcatct tttaaagcag gattaccagt tgaaattcca     240

gctatgacta ttaataaggt ttgtggttca ggacttagaa cagttagctt agcagcacaa     300

attataaaag caggagatgc tgacgtaata atagcaggtg gtatggaaaa tatgtctaga     360
```

-continued

```
gctccttact tagcgaataa cgctagatgg ggatatagaa tgggaaacgc taaatttgtt    420

gatgaaatga tcactgacgg attgtgggat gcatttaatg attaccacat gggaataaca    480

gcagaaaaca tagctgagag atggaacatt tcaagagaag aacaagatga gtttgctctt    540

gcatcacaaa aaaaagctga agaagctata aaatcaggtc aatttaaaga tgaaatagtt    600

cctgtagtaa ttaaaggcag aaagggagaa actgtagttg atacagatga gcaccctaga    660

tttggatcaa ctatagaagg acttgcaaaa ttaaaacctg ccttcaaaaa agatggaaca    720

gttacagctg gtaatgcatc aggattaaat gactgtgcag cagtacttgt aatcatgagt    780

gcagaaaaag ctaaagagct tggagtaaaa ccacttgcta agatagtttc ttatggttca    840

gcaggagttg acccagcaat aatgggatat ggacctttct atgcaacaaa agcagctatt    900

gaaaaagcag gttggacagt tgatgaatta gatttaatag aatcaaatga agcttttgca    960

gctcaaagtt tagcagtagc aaaagattta aaatttgata tgaataaagt aaatgtaaat   1020

ggaggagcta ttgcccttgg tcatccaatt ggagcatcag gtgcaagaat actcgttact   1080

cttgtacacg caatgcaaaa aagagatgca aaaaaaggct tagcaacttt atgtataggt   1140

ggcggacaag gaacagcaat attgctagaa aagtgctag                          1179
```

<210> SEQ ID NO 2
<211> LENGTH: 392
<212> TYPE: PRT
<213> ORGANISM: Clostridium acetobutylicum

<400> SEQUENCE: 2

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
                85                  90                  95

Leu Ala Ala Gln Ile Ile Lys Ala Gly Asp Ala Asp Val Ile Ile Ala
            100                 105                 110

Gly Gly Met Glu Asn Met Ser Arg Ala Pro Tyr Leu Ala Asn Asn Ala
        115                 120                 125

Arg Trp Gly Tyr Arg Met Gly Asn Ala Lys Phe Val Asp Glu Met Ile
    130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Glu Ala Ile Lys Ser
            180                 185                 190

Gly Gln Phe Lys Asp Glu Ile Val Pro Val Val Ile Lys Gly Arg Lys
        195                 200                 205

Gly Glu Thr Val Val Asp Thr Asp Glu His Pro Arg Phe Gly Ser Thr
    210                 215                 220

Ile Glu Gly Leu Ala Lys Leu Lys Pro Ala Phe Lys Lys Asp Gly Thr
```

-continued

```
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
    290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
    370                 375                 380

Thr Ala Ile Leu Leu Glu Lys Cys
385                 390


<210> SEQ ID NO 3
<211> LENGTH: 1179
<212> TYPE: DNA
<213> ORGANISM: Clostridium acetobutylicum

<400> SEQUENCE: 3

atgagagatg tagtaatagt aagtgctgta agaactgcaa taggagcata tggaaaaaca      60

ttaaaggatg tacctgcaac agagttagga gctatagtaa taaaggaagc tgtaagaaga     120

gctaatataa atccaaatga gattaatgaa gttatttttg gaaatgtact tcaagctgga     180

ttaggccaaa acccagcaag acaagcagca gtaaaagcag gattaccttt agaaacacct     240

gcgtttacaa tcaataaggt ttgtggttca ggtttaagat ctataagttt agcagctcaa     300

attataaaag ctggagatgc tgataccatt gtagtaggtg gtatggaaaa tatgtctaga     360

tcaccatatt tgattaacaa tcagagatgg ggtcaaagaa tgggagatag tgaattagtt     420

gatgaaatga taaaggatgg tttgtgggat gcatttaatg gatatcatat gggagtaact     480

gcagaaaata ttgcagaaca atggaatata acaagagaag agcaagatga attttcactt     540

atgtcacaac aaaaagctga aaaagccatt aaaaatggag aatttaagga tgaaatagtt     600

cctgtattaa taaagactaa aaaaggtgaa atagtctttg atcaagatga atttcctaga     660

ttcggaaaca ctattgaagc attaagaaaa cttaaaccta ttttcaagga aaatggtact     720

gttacagcag gtaatgcatc cggattaaat gatggagctg cagcactagt aataatgagc     780

gctgataaag ctaacgctct cggaataaaa ccacttgcta agattacttc ttacggatca     840

tatggggtag atccatcaat aatgggatat ggagcttttt atgcaactaa agctgcctta     900

gataaaatta atttaaaacc tgaagactta gatttaattg aagctaacga ggcatatgct     960

tctcaaagta tagcagtaac tagagattta aatttagata tgagtaaagt taatgttaat    1020

ggtggagcta tagcacttgg acatccaata ggtgcatctg gtgcacgtat tttagtaaca    1080

ttactatacg ctatgcaaaa aagagattca aaaaaaggtc ttgctactct atgtattggt    1140

ggaggtcagg gaacagctct cgtagttgaa agagactaa                           1179
```

<210> SEQ ID NO 4
<211> LENGTH: 392
<212> TYPE: PRT
<213> ORGANISM: Clostridium acetobutylicum

<400> SEQUENCE: 4

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380
```

```
Thr Ala Leu Val Val Glu Arg Asp
385                 390

<210> SEQ ID NO 5
<211> LENGTH: 849
<212> TYPE: DNA
<213> ORGANISM: Clostridium acetobutylicum

<400> SEQUENCE: 5

atgaaaaagg tatgtgttat aggtgcaggt actatgggtt caggaattgc tcaggcattt      60

gcagctaaag gatttgaagt agtattaaga gatattaaag atgaatttgt tgatagagga     120

ttagatttta tcaataaaaa tctttctaaa ttagttaaaa aaggaaagat agaagaagct     180

actaaagttg aaatcttaac tagaatttcc ggaacagttg accttaatat ggcagctgat     240

tgcgatttag ttatagaagc agctgttgaa agaatggata ttaaaaagca gatttttgct     300

gacttagaca atatatgcaa gccagaaaca attcttgcat caaatacatc atcactttca     360

ataacagaag tggcatcagc aactaaaaga cctgataagg ttataggtat gcatttcttt     420

aatccagctc ctgttatgaa gcttgtagag gtaataagag gaatagctac atcacaagaa     480

acttttgatg cagttaaaga gacatctata gcaataggaa aagatcctgt agaagtagca     540

gaagcaccag gatttgttgt aaatagaata ttaataccaa tgattaatga agcagttggt     600

atattagcag aaggaatagc ttcagtagaa gacatagata aagctatgaa acttggagct     660

aatcacccaa tgggaccatt agaattaggt gattttatag gtcttgatat atgtcttgct     720

ataatggatg ttttatactc agaaactgga gattctaagt atagaccaca tacattactt     780

aagaagtatg taagagcagg atggcttgga agaaaatcag gaaaaggttt ctacgattat     840

tcaaaataa                                                             849

<210> SEQ ID NO 6
<211> LENGTH: 282
<212> TYPE: PRT
<213> ORGANISM: Clostridium acetobutylicum

<400> SEQUENCE: 6

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
```

```
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270

Ser Gly Lys Gly Phe Tyr Asp Tyr Ser Lys
        275                 280


<210> SEQ ID NO 7
<211> LENGTH: 786
<212> TYPE: DNA
<213> ORGANISM: Clostridium acetobutylicum

<400> SEQUENCE: 7

atggaactaa acaatgtcat ccttgaaaag gaaggtaaag ttgctgtagt taccattaac      60

agacctaaag cattaaatgc gttaaatagt gatacactaa aagaaatgga ttatgttata     120

ggtgaaattg aaaatgatag cgaagtactt gcagtaattt taactggagc aggagaaaaa     180

tcatttgtag caggagcaga tatttctgag atgaaggaaa tgaataccat tgaaggtaga     240

aaattcggga tacttggaaa taaagtgttt agaagattag aacttcttga aaagcctgta     300

atagcagctg ttaatggttt tgctttagga ggcggatgcg aaatagctat gtcttgtgat     360

ataagaatag cttcaagcaa cgcaagattt ggtcaaccag aagtaggtct cggaataaca     420

cctggttttg gtggtacaca aagactttca agattagttg gaatgggcat ggcaaagcag     480

cttatattta ctgcacaaaa tataaaggca gatgaagcat taagaatcgg acttgtaaat     540

aaggtagtag aacctagtga attaatgaat acagcaaaag aaattgcaaa caaaattgtg     600

agcaatgctc cagtagctgt taagttaagc aaacaggcta ttaatagagg aatgcagtgt     660

gatattgata ctgctttagc atttgaatca gaagcatttg gagaatgctt ttcaacagag     720

gatcaaaagg atgcaatgac agctttcata gagaaaagaa aaattgaagg cttcaaaaat     780

agatag                                                                786


<210> SEQ ID NO 8
<211> LENGTH: 261
<212> TYPE: PRT
<213> ORGANISM: Clostridium acetobutylicum

<400> SEQUENCE: 8

Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
```

-continued

```
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160

Leu Ile Phe Thr Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Gln Ala Ile Asn Arg Gly Met Gln Cys Asp Ile Asp Thr
    210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260


<210> SEQ ID NO 9
<211> LENGTH: 1197
<212> TYPE: DNA
<213> ORGANISM: Clostridium acetobutylicum

<400> SEQUENCE: 9

atgatagtaa aagcaaagtt tgtaaaagga tttatcagag atgtacatcc ttatggttgc     60

agaagggaag tactaaatca aatagattat tgtaagaagg ctattgggtt taggggacca    120

aagaaggttt taattgttgg agcctcatct gggtttggtc ttgctactag aatttcagtt    180

gcatttggag gtccagaagc tcacacaatt ggagtatcct atgaaacagg agctacagat    240

agaagaatag gaacagcggg atggtataat aacatatttt ttaaagaatt tgctaaaaaa    300

aaaggattag ttgcaaaaaa cttcattgag gatgcctttt ctaatgaaac caaagataaa    360

gttattaagt atataaagga tgaatttggt aaaatagatt tatttgttta tagtttagct    420

gcgcctagga gaaaggacta taaaactgga aatgtttata cttcaagaat aaaaacaatt    480

ttaggagatt ttgagggacc gactattgat gttgaaagag acgagattac tttaaaaaag    540

gttagtagtg ctagcattga agaaattgaa gaaactagaa aggtaatggg tggagaggat    600

tggcaagagt ggtgtgaaga gctgctttat gaagattgtt tttcggataa agcaactacc    660

atagcatact cgtatatagg atccccaaga acctacaaga tatatagaga aggtactata    720

ggaatagcta aaaaggatct tgaagataag gctaagctta taaatgaaaa acttaacaga    780

gttataggtg gtagagcctt tgtgtctgtg aataaagcat tagttacaaa agcaagtgca    840

tatattccaa cttttcctct ttatgcagct attttatata aggtcatgaa agaaaaaaat    900

attcatgaaa attgtattat gcaaattgag agaatgtttt ctgaaaaaat atattcaaat    960

gaaaaaatac aatttgatga caagggaaga ttaaggatgg acgatttaga gcttagaaaa   1020
```

-continued

```
gacgttcaag acgaagttga tagaatatgg agtaatatta ctcctgaaaa ttttaaggaa   1080

ttatctgatt ataagggata caaaaaagaa ttcatgaact taaacggttt tgatctagat   1140

ggggttgatt atagtaaaga cctggatata gaattattaa gaaaattaga accttaa      1197


<210> SEQ ID NO 10
<211> LENGTH: 398
<212> TYPE: PRT
<213> ORGANISM: Clostridium acetobutylicum

<400> SEQUENCE: 10

Met Ile Val Lys Ala Lys Phe Val Lys Gly Phe Ile Arg Asp Val His
1               5                   10                  15

Pro Tyr Gly Cys Arg Arg Glu Val Leu Asn Gln Ile Asp Tyr Cys Lys
            20                  25                  30

Lys Ala Ile Gly Phe Arg Gly Pro Lys Lys Val Leu Ile Val Gly Ala
        35                  40                  45

Ser Ser Gly Phe Gly Leu Ala Thr Arg Ile Ser Val Ala Phe Gly Gly
    50                  55                  60

Pro Glu Ala His Thr Ile Gly Val Ser Tyr Glu Thr Gly Ala Thr Asp
65                  70                  75                  80

Arg Arg Ile Gly Thr Ala Gly Trp Tyr Asn Asn Ile Phe Phe Lys Glu
                85                  90                  95

Phe Ala Lys Lys Lys Gly Leu Val Ala Lys Asn Phe Ile Glu Asp Ala
            100                 105                 110

Phe Ser Asn Glu Thr Lys Asp Lys Val Ile Lys Tyr Ile Lys Asp Glu
        115                 120                 125

Phe Gly Lys Ile Asp Leu Phe Val Tyr Ser Leu Ala Ala Pro Arg Arg
    130                 135                 140

Lys Asp Tyr Lys Thr Gly Asn Val Tyr Thr Ser Arg Ile Lys Thr Ile
145                 150                 155                 160

Leu Gly Asp Phe Glu Gly Pro Thr Ile Asp Val Glu Arg Asp Glu Ile
                165                 170                 175

Thr Leu Lys Lys Val Ser Ser Ala Ser Ile Glu Glu Ile Glu Glu Thr
            180                 185                 190

Arg Lys Val Met Gly Gly Glu Asp Trp Gln Glu Trp Cys Glu Glu Leu
        195                 200                 205

Leu Tyr Glu Asp Cys Phe Ser Asp Lys Ala Thr Thr Ile Ala Tyr Ser
    210                 215                 220

Tyr Ile Gly Ser Pro Arg Thr Tyr Lys Ile Tyr Arg Glu Gly Thr Ile
225                 230                 235                 240

Gly Ile Ala Lys Lys Asp Leu Glu Asp Lys Ala Lys Leu Ile Asn Glu
                245                 250                 255

Lys Leu Asn Arg Val Ile Gly Gly Arg Ala Phe Val Ser Val Asn Lys
            260                 265                 270

Ala Leu Val Thr Lys Ala Ser Ala Tyr Ile Pro Thr Phe Pro Leu Tyr
        275                 280                 285

Ala Ala Ile Leu Tyr Lys Val Met Lys Glu Lys Asn Ile His Glu Asn
    290                 295                 300

Cys Ile Met Gln Ile Glu Arg Met Phe Ser Glu Lys Ile Tyr Ser Asn
305                 310                 315                 320

Glu Lys Ile Gln Phe Asp Asp Lys Gly Arg Leu Arg Met Asp Asp Leu
                325                 330                 335

Glu Leu Arg Lys Asp Val Gln Asp Glu Val Asp Arg Ile Trp Ser Asn
            340                 345                 350
```

Ile Thr Pro Glu Asn Phe Lys Glu Leu Ser Asp Tyr Lys Gly Tyr Lys
355 360 365

Lys Glu Phe Met Asn Leu Asn Gly Phe Asp Leu Asp Gly Val Asp Tyr
370 375 380

Ser Lys Asp Leu Asp Ile Glu Leu Leu Arg Lys Leu Glu Pro
385 390 395

<210> SEQ ID NO 11
<211> LENGTH: 1407
<212> TYPE: DNA
<213> ORGANISM: Clostridium beijerinckii

<400> SEQUENCE: 11
atgaataaag acacactaat acctacaact aaagatttaa aagtaaaaac aaatggtgaa 60
aacattaatt taaagaacta caaggataat tcttcatgtt tcggagtatt cgaaaatgtt 120
gaaaatgcta taagcagcgc tgtacacgca caaaagatat tatcccttca ttatacaaaa 180
gagcaaagag aaaaaatcat aactgagata agaaaggccg cattacaaaa taaagaggtc 240
ttggctacaa tgattctaga agaaacacat atgggaagat atgaggataa aatattaaaa 300
catgaattgg tagctaaata tactcctggt acagaagatt taactactac tgcttggtca 360
ggtgataatg gtcttacagt tgtagaaatg tctccatatg gtgttatagg tgcaataact 420
ccttctacga atccaactga aactgtaata tgtaatagca taggcatgat agctgctgga 480
aatgctgtag tatttaacgg acacccatgc gctaaaaaat gtgttgcctt tgctgttgaa 540
atgataaata aggcaattat ttcatgtggc ggtcctgaaa atctagtaac aactataaaa 600
aatccaacta tggagtctct agatgcaatt attaagcatc cttcaataaa acttctttgc 660
ggaactgggg gtccaggaat ggtaaaaacc ctcttaaatt ctggtaagaa agctataggt 720
gctggtgctg gaaatccacc agttattgta gatgatactg ctgatataga aaaggctggt 780
aggagcatca ttgaaggctg ttcttttgat aataatttac cttgtattgc agaaaaagaa 840
gtatttgttt ttgagaatgt tgcagatgat ttaatatcta acatgctaaa aaataatgct 900
gtaattataa atgaagatca agtatcaaaa ttaatagatt tagtattaca aaaaaataat 960
gaaactcaag aatactttat aaacaaaaaa tgggtaggaa aagatgcaaa attattctta 1020
gatgaaatag atgttgagtc tccttcaaat gttaaatgca taatctgcga agtaaatgca 1080
aatcatccat ttgttatgac agaactcatg atgccaatat tgccaattgt aagagttaaa 1140
gatatagatg aagctattaa atatgcaaag atagcagaac aaaatagaaa acatagtgcc 1200
tatatttatt ctaaaaatat agacaaccta aatagatttg aaagagaaat agatactact 1260
atttttgtaa agaatgctaa atcttttgct ggtgttggtt atgaagcaga aggatttaca 1320
actttcacta ttgctggatc tactggtgag ggaataacct ctgcaaggaa ttttacaaga 1380
caaagaagat gtgtacttgc cggctaa 1407

<210> SEQ ID NO 12
<211> LENGTH: 468
<212> TYPE: PRT
<213> ORGANISM: Clostridium beijerinckii

<400> SEQUENCE: 12

Met Asn Lys Asp Thr Leu Ile Pro Thr Thr Lys Asp Leu Lys Val Lys
1 5 10 15

Thr Asn Gly Glu Asn Ile Asn Leu Lys Asn Tyr Lys Asp Asn Ser Ser
20 25 30

Cys Phe Gly Val Phe Glu Asn Val Glu Asn Ala Ile Ser Ser Ala Val

-continued

```
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Gln Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Cys Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Arg Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Phe Ile Asn Lys Lys Trp Val Gly Lys Asp Ala
                325                 330                 335

Lys Leu Phe Leu Asp Glu Ile Asp Val Glu Ser Pro Ser Asn Val Lys
            340                 345                 350

Cys Ile Ile Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Ile Lys Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460
```

Val Leu Ala Gly
465

<210> SEQ ID NO 13
<211> LENGTH: 1215
<212> TYPE: DNA
<213> ORGANISM: Clostridium acetobutylicum

<400> SEQUENCE: 13
atggttgatt tcgaatattc aataccaact agaatttttt tcggtaaaga taagataaat 60
gtacttggaa gagagcttaa aaaatatggt tctaaagtgc ttatagttta tggtggagga 120
agtataaaga gaaatggaat atatgataaa gctgtaagta tacttgaaaa aaacagtatt 180
aaattttatg aacttgcagg agtagagcca aatccaagag taactacagt tgaaaaagga 240
gttaaaatat gtagagaaaa tggagttgaa gtagtactag ctataggtgg aggaagtgca 300
atagattgcg caaaggttat agcagcagca tgtgaatatg atggaaatcc atgggatatt 360
gtgttagatg gctcaaaaat aaaaagggtg cttcctatag ctagtatatt aaccattgct 420
gcaacaggat cagaaatgga tacgtgggca gtaataaata atatggatac aaacgaaaaa 480
ctaattgcgg cacatccaga tatggctcct aagttttcta tattagatcc aacgtatacg 540
tataccgtac ctaccaatca aacagcagca ggaacagctg atattatgag tcatatattt 600
gaggtgtatt ttagtaatac aaaaacagca tatttgcagg atagaatggc agaagcgtta 660
ttaagaactt gtattaaata tggaggaata gctcttgaga agccggatga ttatgaggca 720
agagccaatc taatgtgggc ttcaagtctt gcgataaatg gacttttaac atatggtaaa 780
gacactaatt ggagtgtaca cttaatggaa catgaattaa gtgcttatta cgacataaca 840
cacggcgtag ggcttgcaat tttaacacct aattggatgg agtatatttt aaataatgat 900
acagtgtaca agtttgttga atatggtgta aatgtttggg gaatagacaa agaaaaaaat 960
cactatgaca tagcacatca agcaatacaa aaaacaagag attactttgt aaatgtacta 1020
ggtttaccat ctagactgag agatgttgga attgaagaag aaaaattgga cataatggca 1080
aaggaatcag taaagcttac aggaggaacc ataggaaacc taagaccagt aaacgcctcc 1140
gaagtcctac aaatattcaa aaaatctgtg taaaacgcct ccgaagtcct acaaatattc 1200
aaaaaatctg tgtaa 1215

<210> SEQ ID NO 14
<211> LENGTH: 390
<212> TYPE: PRT
<213> ORGANISM: Clostridium acetobutylicum

<400> SEQUENCE: 14

Met Val Asp Phe Glu Tyr Ser Ile Pro Thr Arg Ile Phe Phe Gly Lys
1 5 10 15

Asp Lys Ile Asn Val Leu Gly Arg Glu Leu Lys Lys Tyr Gly Ser Lys
20 25 30

Val Leu Ile Val Tyr Gly Gly Gly Ser Ile Lys Arg Asn Gly Ile Tyr
35 40 45

Asp Lys Ala Val Ser Ile Leu Glu Lys Asn Ser Ile Lys Phe Tyr Glu
50 55 60

Leu Ala Gly Val Glu Pro Asn Pro Arg Val Thr Thr Val Glu Lys Gly
65 70 75 80

Val Lys Ile Cys Arg Glu Asn Gly Val Glu Val Val Leu Ala Ile Gly
85 90 95

Gly Gly Ser Ala Ile Asp Cys Ala Lys Val Ile Ala Ala Ala Cys Glu

```
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390


<210> SEQ ID NO 15
<211> LENGTH: 1170
<212> TYPE: DNA
<213> ORGANISM: Clostridium acetobutylicum

<400> SEQUENCE: 15

atgctaagtt ttgattattc aataccaact aaagtttttt ttggaaaagg aaaaatagac      60

gtaattggag aagaaattaa gaaatatggc tcaagagtgc ttatagttta tggcggagga     120

agtataaaaa ggaacggtat atatgataga gcaacagcta tattaaaaga aaacaatata     180

gctttctatg aactttcagg agtagagcca aatcctagga taacaacagt aaaaaaaggc     240

atagaaatat gtagagaaaa taatgtggat ttagtattag caatagggggg aggaagtgca     300

atagactgtt ctaaggtaat tgcagctgga gtttattatg atggcgatac atgggacatg     360

gttaaagatc catctaaaat aactaaagtt cttccaattg caagtatact tactctttca     420

gcaacagggt ctgaaatgga tcaaattgca gtaatttcaa atatggagac taatgaaaag     480
```

```
cttggagtag gacatgatga tatgagacct aaattttcag tgttagatcc tacatatact    540

tttacagtac ctaaaaatca aacagcagcg ggaacagctg acattatgag tcacaccttt    600

gaatcttact ttagtggtgt tgaaggtgct tatgtgcagg acggtatagc agaagcaatc    660

ttaagaacat gtataaagta tggaaaaata gcaatggaga agactgatga ttacgaggct    720

agagctaatt tgatgtgggc ttcaagttta gctataaatg gtctattatc acttggtaag    780

gatagaaaat ggagttgtca tcctatggaa cacgagttaa gtgcatatta tgatataaca    840

catggtgtag gacttgcaat tttaacacct aattggatgg aatatattct aaatgacgat    900

acacttcata aatttgtttc ttatggaata aatgtttggg gaatagacaa gaacaaagat    960

aactatgaaa tagcacgaga ggctattaaa aatacgagag aatactttaa ttcattgggt   1020

attccttcaa agcttagaga agttggaata ggaaaagata aactagaact aatggcaaag   1080

caagctgtta gaaattctgg aggaacaata ggaagtttaa gaccaataaa tgcagaggat   1140

gttcttgaga tatttaaaaa atcttattaa                                    1170
```

```
<210> SEQ ID NO 16
<211> LENGTH: 389
<212> TYPE: PRT
<213> ORGANISM: Clostridium acetobutylicum

<400> SEQUENCE: 16

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255
```

```
Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asp Asp Thr Leu His Lys
    290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385
```

<210> SEQ ID NO 17
<211> LENGTH: 780
<212> TYPE: DNA
<213> ORGANISM: Klebsiella pneumoniae

<400> SEQUENCE: 17

```
atgaatcatt ctgctgaatg cacctgcgaa gagagtctat gcgaaaccct gcgggcgttt     60

tccgcgcagc atcccgagag cgtgctctat cagacatcgc tcatgagcgc cctgctgagc    120

ggggtttacg aaggcagcac caccatcgcg gacctgctga aacacggcga tttcggcctc    180

ggcaccttta atgagctgga cggggagctg atcgccttca gcagtcaggt ctatcagctg    240

cgcgccgacg gcagcgcgcg caaagcccag ccggagcaga aaacgccgtt cgcggtgatg    300

acctggttcc agccgcagta ccggaaaacc tttgaccatc cggtgagccg ccagcagctg    360

cacgaggtga tcgaccagca aatcccctct gacaacctgt tctgcgccct gcgcatcgac    420

ggccatttcc gccatgccca tacccgcacc gtgccgcgcc agacgccgcc gtaccgggcg    480

atgaccgacg tcctcgacga tcagccggtg ttccgcttta accagcgcga aggggtgctg    540

gtcggcttcc ggaccccgca gcatatgcag gggatcaacg tcgccgggta tcacgagcac    600

tttattaccg atgaccgcaa aggcggcggt cacctgctgg attaccagct cgaccatggg    660

gtgctgacct tcggcgaaat tcacaagctg atgatcgacc tgcccgccga cagcgcgttc    720

ctgcaggcta atctgcatcc cgataatctc gatgccgcca tccgttccgt agaaagttaa    780
```

<210> SEQ ID NO 18
<211> LENGTH: 259
<212> TYPE: PRT
<213> ORGANISM: Klebsiella pneumoniae

<400> SEQUENCE: 18

```
Met Asn His Ser Ala Glu Cys Thr Cys Glu Glu Ser Leu Cys Glu Thr
1               5                   10                  15

Leu Arg Ala Phe Ser Ala Gln His Pro Glu Ser Val Leu Tyr Gln Thr
            20                  25                  30

Ser Leu Met Ser Ala Leu Leu Ser Gly Val Tyr Glu Gly Ser Thr Thr
        35                  40                  45

Ile Ala Asp Leu Leu Lys His Gly Asp Phe Gly Leu Gly Thr Phe Asn
    50                  55                  60
```

```
Glu Leu Asp Gly Glu Leu Ile Ala Phe Ser Ser Gln Val Tyr Gln Leu
65                  70                  75                  80

Arg Ala Asp Gly Ser Ala Arg Lys Ala Gln Pro Glu Gln Lys Thr Pro
                85                  90                  95

Phe Ala Val Met Thr Trp Phe Gln Pro Gln Tyr Arg Lys Thr Phe Asp
            100                 105                 110

His Pro Val Ser Arg Gln Gln Leu His Glu Val Ile Asp Gln Gln Ile
        115                 120                 125

Pro Ser Asp Asn Leu Phe Cys Ala Leu Arg Ile Asp Gly His Phe Arg
    130                 135                 140

His Ala His Thr Arg Thr Val Pro Arg Gln Thr Pro Pro Tyr Arg Ala
145                 150                 155                 160

Met Thr Asp Val Leu Asp Asp Gln Pro Val Phe Arg Phe Asn Gln Arg
                165                 170                 175

Glu Gly Val Leu Val Gly Phe Arg Thr Pro Gln His Met Gln Gly Ile
            180                 185                 190

Asn Val Ala Gly Tyr His Glu His Phe Ile Thr Asp Asp Arg Lys Gly
        195                 200                 205

Gly Gly His Leu Leu Asp Tyr Gln Leu Asp His Gly Val Leu Thr Phe
    210                 215                 220

Gly Glu Ile His Lys Leu Met Ile Asp Leu Pro Ala Asp Ser Ala Phe
225                 230                 235                 240

Leu Gln Ala Asn Leu His Pro Asp Asn Leu Asp Ala Ala Ile Arg Ser
                245                 250                 255

Val Glu Ser
```

<210> SEQ ID NO 19
<211> LENGTH: 1680
<212> TYPE: DNA
<213> ORGANISM: Klebsiella pneumoniae

<400> SEQUENCE: 19

```
atggacaaac agtatccggt acgccagtgg gcgcacggcg ccgatctcgt cgtcagtcag     60

ctggaagctc agggagtacg ccaggtgttc ggcatccccg gcgccaaaat tgacaaggtc    120

ttcgactcac tgctggattc ctcgattcgc attattccgg tacgccacga agccaacgcc    180

gcgtttatgg ccgccgccgt cggacgcatt accggcaaag cgggcgtggc gctggtcacc    240

tccggtccgg gctgttccaa cctgatcacc ggcatggcca ccgcgaacag cgaaggcgac    300

ccggtggtgg ccctgggcgg cgcggtaaaa cgcgccgata aagcgaagca ggtccaccag    360

agtatggata cggtggcgat gttcagcccg gtcaccaaat acgccgtcga ggtgacggcg    420

ccggatgcgc tggcggaagt ggtctccaac gccttccgcg ccgccgagca gggccggccg    480

ggcagcgcgt tcgttagcct gccgcaggat gtggtcgatg gcccggtcag cggcaaagtg    540

ctgccggcca gcggggcccc gcagatgggc gccgcgccgg atgatgccat cgaccaggtg    600

gcgaagctta tcgcccaggc gaagaacccg atcttcctgc tcggcctgat ggccagccag    660

ccggaaaaca gcaaggcgct gcgccgtttg ctggagacca gccatattcc agtcaccagc    720

acctatcagg ccgccggagc ggtgaatcag gataacttct ctcgcttcgc cggccgggtt    780

gggctgttta acaaccaggc cggggaccgt ctgctgcagc tcgccgacct ggtgatctgc    840

atcggctaca gcccggtgga atacgaaccg gcgatgtgga acagcggcaa cgcgacgctg    900

gtgcacatcg acgtgctgcc cgcctatgaa gagcgcaact acaccccgga tgtcgagctg    960

gtgggcgata tcgccggcac tctcaacaag ctggcgcaaa atatcgatca tcggctggtg   1020
```

-continued

```
ctctccccgc aggcggcgga gatcctccgc gaccgccagc accagcgcga gctgctggac   1080

cgccgcggcg cgcagctgaa ccagtttgcc ctgcatccgc tgcgcatcgt tcgcgccatg   1140

caggacatcg tcaacagcga cgtcacgttg accgtggaca tgggcagctt ccatatctgg   1200

attgcccgct acctgtacag cttccgcgcc cgtcaggtga tgatctccaa cggccagcag   1260

accatgggcg tcgccctgcc ctgggctatc ggcgcctggc tggtcaatcc tgagcgaaaa   1320

gtggtctccg tctccggcga cggcggcttc ctgcagtcga gcatggagct ggagaccgcc   1380

gtccgcctga aagccaacgt actgcacctg atctgggtcg ataacggcta caacatggtg   1440

gccattcagg aagagaaaaa ataccagcgc ctgtccggcg tcgagttcgg gccgatggat   1500

tttaaagcct atgccgaatc cttcggcgcg aaagggtttg ccgtggaaag cgccgaggcg   1560

ctggagccga ccctgcacgc ggcgatggac gtcgacggcc cggcggtggt ggccattccg   1620

gtggattatc gcgataaccc gctgctgatg ggccagctgc atctgagtca gattctgtaa   1680


<210> SEQ ID NO 20
<211> LENGTH: 559
<212> TYPE: PRT
<213> ORGANISM: Klebsiella pneumoniae

<400> SEQUENCE: 20

Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110

Asp Lys Ala Lys Gln Val His Gln Ser Met Asp Thr Val Ala Met Phe
        115                 120                 125

Ser Pro Val Thr Lys Tyr Ala Val Glu Val Thr Ala Pro Asp Ala Leu
    130                 135                 140

Ala Glu Val Val Ser Asn Ala Phe Arg Ala Ala Glu Gln Gly Arg Pro
145                 150                 155                 160

Gly Ser Ala Phe Val Ser Leu Pro Gln Asp Val Val Asp Gly Pro Val
                165                 170                 175

Ser Gly Lys Val Leu Pro Ala Ser Gly Ala Pro Gln Met Gly Ala Ala
            180                 185                 190

Pro Asp Asp Ala Ile Asp Gln Val Ala Lys Leu Ile Ala Gln Ala Lys
        195                 200                 205

Asn Pro Ile Phe Leu Leu Gly Leu Met Ala Ser Gln Pro Glu Asn Ser
    210                 215                 220

Lys Ala Leu Arg Arg Leu Leu Glu Thr Ser His Ile Pro Val Thr Ser
225                 230                 235                 240

Thr Tyr Gln Ala Ala Gly Ala Val Asn Gln Asp Asn Phe Ser Arg Phe
                245                 250                 255

Ala Gly Arg Val Gly Leu Phe Asn Asn Gln Ala Gly Asp Arg Leu Leu
```

-continued

```
        260                 265                 270

Gln Leu Ala Asp Leu Val Ile Cys Ile Gly Tyr Ser Pro Val Glu Tyr
    275                 280                 285

Glu Pro Ala Met Trp Asn Ser Gly Asn Ala Thr Leu Val His Ile Asp
    290                 295                 300

Val Leu Pro Ala Tyr Glu Glu Arg Asn Tyr Thr Pro Asp Val Glu Leu
305                 310                 315                 320

Val Gly Asp Ile Ala Gly Thr Leu Asn Lys Leu Ala Gln Asn Ile Asp
                325                 330                 335

His Arg Leu Val Leu Ser Pro Gln Ala Ala Glu Ile Leu Arg Asp Arg
            340                 345                 350

Gln His Gln Arg Glu Leu Leu Asp Arg Arg Gly Ala Gln Leu Asn Gln
        355                 360                 365

Phe Ala Leu His Pro Leu Arg Ile Val Arg Ala Met Gln Asp Ile Val
    370                 375                 380

Asn Ser Asp Val Thr Leu Thr Val Asp Met Gly Ser Phe His Ile Trp
385                 390                 395                 400

Ile Ala Arg Tyr Leu Tyr Ser Phe Arg Ala Arg Gln Val Met Ile Ser
                405                 410                 415

Asn Gly Gln Gln Thr Met Gly Val Ala Leu Pro Trp Ala Ile Gly Ala
            420                 425                 430

Trp Leu Val Asn Pro Glu Arg Lys Val Val Ser Val Ser Gly Asp Gly
        435                 440                 445

Gly Phe Leu Gln Ser Ser Met Glu Leu Glu Thr Ala Val Arg Leu Lys
    450                 455                 460

Ala Asn Val Leu His Leu Ile Trp Val Asp Asn Gly Tyr Asn Met Val
465                 470                 475                 480

Ala Ile Gln Glu Glu Lys Lys Tyr Gln Arg Leu Ser Gly Val Glu Phe
                485                 490                 495

Gly Pro Met Asp Phe Lys Ala Tyr Ala Glu Ser Phe Gly Ala Lys Gly
            500                 505                 510

Phe Ala Val Glu Ser Ala Glu Ala Leu Glu Pro Thr Leu His Ala Ala
        515                 520                 525

Met Asp Val Asp Gly Pro Ala Val Val Ala Ile Pro Val Asp Tyr Arg
    530                 535                 540

Asp Asn Pro Leu Leu Met Gly Gln Leu His Leu Ser Gln Ile Leu
545                 550                 555


<210> SEQ ID NO 21
<211> LENGTH: 771
<212> TYPE: DNA
<213> ORGANISM: Klebsiella pneumoniae

<400> SEQUENCE: 21

atgaaaaaag tcgcacttgt taccggcgcc ggccagggga ttggtaaagc tatcgccctt      60

cgtctggtga aggatggatt tgccgtggcc attgccgatt ataacgacgc caccgccaaa     120

gcggtcgcct cggaaatcaa ccaggccggc ggacacgccg tggcggtgaa agtggatgtc     180

tccgaccgcg atcaggtatt tgccgccgtt gaacaggcgc gcaaaacgct gggcggcttc     240

gacgtcatcg tcaataacgc cggtgtggca ccgtctacgc cgatcgagtc cattaccccg     300

gagattgtcg acaaagtcta caacatcaac gtcaaagggg tgatctgggg tattcaggcg     360

gcggtcgagg cctttaagaa agaggggcac ggcgggaaaa tcatcaacgc ctgttcccag     420

gccggccacg tcggcaaccc ggagctggcg gtgtatagct ccagtaaatt cgcggtacgc     480
```

-continued

```
ggcttaaccc agaccgccgc tcgcgacctc gcgccgctgg gcatcacggt caacggctac    540

tgcccgggga ttgtcaaaac gccaatgtgg gccgaaattg accgccaggt gtccgaagcc    600

gccggtaaac cgctgggcta cggtaccgcc gagttcgcca aacgcatcac tctcggtcgt    660

ctgtccgagc cggaagatgt cgccgcctgc gtctcctatc ttgccagccc ggattctgat    720

tacatgaccg gtcagtcgtt gctgatcgac ggcgggatgg tatttaacta a             771


<210> SEQ ID NO 22
<211> LENGTH: 256
<212> TYPE: PRT
<213> ORGANISM: Klebsiella pneumoniae

<400> SEQUENCE: 22

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly His Ala Val Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220

Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255


<210> SEQ ID NO 23
<211> LENGTH: 1665
<212> TYPE: DNA
<213> ORGANISM: Klebsiella oxytoca

<400> SEQUENCE: 23

atgagatcga aaagatttga agcactggcg aaacgccctg tgaatcagga cggcttcgtt     60

aaggagtgga tcgaagaagg ctttatcgcg atggaaagcc cgaacgaccc aaaaccgtcg    120

attaaaatcg ttaacggcgc ggtgaccgag ctggacggga aaccggtaag cgattttgac    180
```

-continued

```
ctgatcgacc actttatcgc ccgctacggt atcaacctga accgcgccga agaagtgatg    240

gcgatggatt cggtcaagct ggccaacatg ctgtgcgatc cgaacgttaa acgcagcgaa    300

atcgtcccgc tgaccaccgc gatgacgccg gcgaaaattg tcgaagtggt ttcgcatatg    360

aacgtcgtcg agatgatgat ggcgatgcag aaaatgcgcg cccgccgcac cccgtcccag    420

caggcgcacg tcaccaacgt caaagataac ccggtacaga ttgccgccga cgccgccgaa    480

ggggcatggc gcggatttga cgaacaggaa accaccgttg cggtagcgcg ctatgcgccg    540

ttcaacgcca tcgcgctgct ggtgggctcg caggtaggcc gtccgggcgt gctgacgcag    600

tgctcgctgg aagaagccac cgagctgaag ctcggcatgc tgggccacac ctgctacgcc    660

gaaaccatct ccgtctacgg caccgagccg gtctttaccg acggcgacga cacgccgtgg    720

tcgaagggct tcctcgcctc gtcctacgcc tctcgcgggc tgaaaatgcg ctttacctcc    780

ggctccggct cggaagtgca gatgggctac gccgaaggca aatccatgct ttatctggaa    840

gcgcgctgca tctacatcac caaagccgcg ggcgtacagg gtctgcaaaa cggttccgta    900

agctgcatcg gcgtgccgtc tgcggtgcct tccggcattc gcgcggtgct ggcggaaaac    960

ctgatctgtt cgtcgctgga tctggagtgc gcctccagca acgaccagac cttcacccac   1020

tccgatatgc gtcgtaccgc gcgcctgctg atgcagttcc tgccgggcac cgactttatc   1080

tcctccggtt attccgcggt gccgaactac gacaacatgt tcgccggctc caacgaagat   1140

gccgaagact ttgacgacta caacgtcatc cagcgcgacc tgaaggtgga cggcggtttg   1200

cgtccggttc gcgaagagga cgtcatcgcc atccgtaaca aagccgcccg cgcgctgcag   1260

gccgtgtttg ccggaatggg gctgccgccg attaccgatg aagaagttga agccgcgacc   1320

tacgcccacg gttcgaaaga tatgccggag cgcaacatcg tcgaagacat caagttcgcc   1380

caggaaatca tcaataaaaa ccgcaacggt ctggaagtgg tgaaagcgct ggcgcagggc   1440

ggattcaccg acgtggccca ggacatgctc aacatccaga aagctaagct gaccggggac   1500

tacctgcata cctccgcgat tatcgtcggc gacgggcagg tgctgtcagc cgtcaacgac   1560

gtcaacgact atgccggtcc ggcaacgggc tatcgcctgc agggcgaacg ctgggaagag   1620

attaaaaaca tccctggcgc tcttgatccc aacgagattg attaa                   1665
```

<210> SEQ ID NO 24
<211> LENGTH: 554
<212> TYPE: PRT
<213> ORGANISM: Klebsiella oxytoca

<400> SEQUENCE: 24

```
Met Arg Ser Lys Arg Phe Glu Ala Leu Ala Lys Arg Pro Val Asn Gln
1               5                   10                  15

Asp Gly Phe Val Lys Glu Trp Ile Glu Glu Gly Phe Ile Ala Met Glu
            20                  25                  30

Ser Pro Asn Asp Pro Lys Pro Ser Ile Lys Ile Val Asn Gly Ala Val
        35                  40                  45

Thr Glu Leu Asp Gly Lys Pro Val Ser Asp Phe Asp Leu Ile Asp His
    50                  55                  60

Phe Ile Ala Arg Tyr Gly Ile Asn Leu Asn Arg Ala Glu Glu Val Met
65                  70                  75                  80

Ala Met Asp Ser Val Lys Leu Ala Asn Met Leu Cys Asp Pro Asn Val
                85                  90                  95

Lys Arg Ser Glu Ile Val Pro Leu Thr Thr Ala Met Thr Pro Ala Lys
            100                 105                 110

Ile Val Glu Val Val Ser His Met Asn Val Val Glu Met Met Met Ala
```

```
        115                 120                 125

Met Gln Lys Met Arg Ala Arg Arg Thr Pro Ser Gln Gln Ala His Val
    130                 135                 140

Thr Asn Val Lys Asp Asn Pro Val Gln Ile Ala Ala Asp Ala Ala Glu
145                 150                 155                 160

Gly Ala Trp Arg Gly Phe Asp Glu Gln Glu Thr Thr Val Ala Val Ala
                165                 170                 175

Arg Tyr Ala Pro Phe Asn Ala Ile Ala Leu Leu Val Gly Ser Gln Val
            180                 185                 190

Gly Arg Pro Gly Val Leu Thr Gln Cys Ser Leu Glu Glu Ala Thr Glu
        195                 200                 205

Leu Lys Leu Gly Met Leu Gly His Thr Cys Tyr Ala Glu Thr Ile Ser
    210                 215                 220

Val Tyr Gly Thr Glu Pro Val Phe Thr Asp Gly Asp Asp Thr Pro Trp
225                 230                 235                 240

Ser Lys Gly Phe Leu Ala Ser Ser Tyr Ala Ser Arg Gly Leu Lys Met
                245                 250                 255

Arg Phe Thr Ser Gly Ser Gly Ser Glu Val Gln Met Gly Tyr Ala Glu
            260                 265                 270

Gly Lys Ser Met Leu Tyr Leu Glu Ala Arg Cys Ile Tyr Ile Thr Lys
        275                 280                 285

Ala Ala Gly Val Gln Gly Leu Gln Asn Gly Ser Val Ser Cys Ile Gly
    290                 295                 300

Val Pro Ser Ala Val Pro Ser Gly Ile Arg Ala Val Leu Ala Glu Asn
305                 310                 315                 320

Leu Ile Cys Ser Ser Leu Asp Leu Glu Cys Ala Ser Ser Asn Asp Gln
                325                 330                 335

Thr Phe Thr His Ser Asp Met Arg Arg Thr Ala Arg Leu Leu Met Gln
            340                 345                 350

Phe Leu Pro Gly Thr Asp Phe Ile Ser Ser Gly Tyr Ser Ala Val Pro
        355                 360                 365

Asn Tyr Asp Asn Met Phe Ala Gly Ser Asn Glu Asp Ala Glu Asp Phe
    370                 375                 380

Asp Asp Tyr Asn Val Ile Gln Arg Asp Leu Lys Val Asp Gly Gly Leu
385                 390                 395                 400

Arg Pro Val Arg Glu Glu Asp Val Ile Ala Ile Arg Asn Lys Ala Ala
                405                 410                 415

Arg Ala Leu Gln Ala Val Phe Ala Gly Met Gly Leu Pro Pro Ile Thr
            420                 425                 430

Asp Glu Glu Val Glu Ala Ala Thr Tyr Ala His Gly Ser Lys Asp Met
        435                 440                 445

Pro Glu Arg Asn Ile Val Glu Asp Ile Lys Phe Ala Gln Glu Ile Ile
    450                 455                 460

Asn Lys Asn Arg Asn Gly Leu Glu Val Val Lys Ala Leu Ala Gln Gly
465                 470                 475                 480

Gly Phe Thr Asp Val Ala Gln Asp Met Leu Asn Ile Gln Lys Ala Lys
                485                 490                 495

Leu Thr Gly Asp Tyr Leu His Thr Ser Ala Ile Ile Val Gly Asp Gly
            500                 505                 510

Gln Val Leu Ser Ala Val Asn Asp Val Asn Asp Tyr Ala Gly Pro Ala
        515                 520                 525

Thr Gly Tyr Arg Leu Gln Gly Glu Arg Trp Glu Glu Ile Lys Asn Ile
    530                 535                 540
```

Pro Gly Ala Leu Asp Pro Asn Glu Ile Asp
545 550

<210> SEQ ID NO 25
<211> LENGTH: 675
<212> TYPE: DNA
<213> ORGANISM: Klebsiella oxytoca

<400> SEQUENCE: 25
atggaaatta atgaaaaatt gctgcgccag ataattgaag acgtgctcag cgagatgaag 60
ggcagcgata aaccggtctc gtttaatgcg ccggcggcct ccgcggcgcc ccaggccacg 120
ccgcccgccg gcgacggctt cctgacggaa gtgggcgaag cgcgtcaggg aacccagcag 180
gacgaagtga ttatcgccgt cggcccggct ttcggcctgg cgcagaccgt caatatcgtc 240
ggcatcccgc ataagagcat tttgcgcgaa gtcattgccg gtattgaaga agaaggcatt 300
aaggcgcgcg tgattcgctg ctttaaatcc tccgacgtgg ccttcgtcgc cgttgaaggt 360
aatcgcctga gcggctccgg catctctatc ggcatccagt cgaaaggcac cacggtgatc 420
caccagcagg ggctgccgcc gctctctaac ctggagctgt tcccgcaggc gccgctgctg 480
accctggaaa cctatcgcca gatcggcaaa aacgccgccc gctatgcgaa acgcgaatcg 540
ccgcagccgg tcccgacgct gaatgaccag atggcgcggc cgaagtacca ggcgaaatcg 600
gccattttgc acattaaaga gaccaagtac gtggtgacgg gcaaaaaccc gcaggaactg 660
cgcgtggcgc tttga 675

<210> SEQ ID NO 26
<211> LENGTH: 224
<212> TYPE: PRT
<213> ORGANISM: Klebsiella oxytoca

<400> SEQUENCE: 26

Met Glu Ile Asn Glu Lys Leu Leu Arg Gln Ile Ile Glu Asp Val Leu
1 5 10 15

Ser Glu Met Lys Gly Ser Asp Lys Pro Val Ser Phe Asn Ala Pro Ala
20 25 30

Ala Ser Ala Ala Pro Gln Ala Thr Pro Pro Ala Gly Asp Gly Phe Leu
35 40 45

Thr Glu Val Gly Glu Ala Arg Gln Gly Thr Gln Gln Asp Glu Val Ile
50 55 60

Ile Ala Val Gly Pro Ala Phe Gly Leu Ala Gln Thr Val Asn Ile Val
65 70 75 80

Gly Ile Pro His Lys Ser Ile Leu Arg Glu Val Ile Ala Gly Ile Glu
85 90 95

Glu Glu Gly Ile Lys Ala Arg Val Ile Arg Cys Phe Lys Ser Ser Asp
100 105 110

Val Ala Phe Val Ala Val Glu Gly Asn Arg Leu Ser Gly Ser Gly Ile
115 120 125

Ser Ile Gly Ile Gln Ser Lys Gly Thr Thr Val Ile His Gln Gln Gly
130 135 140

Leu Pro Pro Leu Ser Asn Leu Glu Leu Phe Pro Gln Ala Pro Leu Leu
145 150 155 160

Thr Leu Glu Thr Tyr Arg Gln Ile Gly Lys Asn Ala Ala Arg Tyr Ala
165 170 175

Lys Arg Glu Ser Pro Gln Pro Val Pro Thr Leu Asn Asp Gln Met Ala
180 185 190

Arg Pro Lys Tyr Gln Ala Lys Ser Ala Ile Leu His Ile Lys Glu Thr

```
        195                 200                 205

Lys Tyr Val Val Thr Gly Lys Asn Pro Gln Glu Leu Arg Val Ala Leu
    210                 215                 220
```

<210> SEQ ID NO 27
<211> LENGTH: 522
<212> TYPE: DNA
<213> ORGANISM: Klebsiella oxytoca

<400> SEQUENCE: 27

```
atgaataccg acgcaattga atcgatggta cgcgacgtat tgagccgcat gaacagcctg      60

cagggcgagg cgcctgcggc ggctccggcg gctggcggcg cgtcccgtag cgccagggtc     120

agcgactacc cgctggcgaa caagcacccg gaatgggtga aaaccgccac caataaaacg     180

ctggacgact ttacgctgga aaacgtgctg agcaataaag tcaccgccca ggatatgcgt     240

attaccccgg aaaccctgcg cttacaggct tctattgcca aagacgcggg ccgcgaccgg     300

ctggcgatga acttcgagcg cgccgccgag ctgaccgcgg taccggacga tcgcattctt     360

gaaatctaca acgccctccg cccctatcgc tcgacgaaag aggagctgct ggcgatcgcc     420

gacgatctcg aaagccgcta tcaggcgaag atttgcgccg ctttcgttcg cgaagcggcc     480

acgctgtacg tcgagcgtaa aaaactcaaa ggcgacgatt aa                        522
```

<210> SEQ ID NO 28
<211> LENGTH: 173
<212> TYPE: PRT
<213> ORGANISM: Klebsiella oxytoca

<400> SEQUENCE: 28

```
Met Asn Thr Asp Ala Ile Glu Ser Met Val Arg Asp Val Leu Ser Arg
1               5                   10                  15

Met Asn Ser Leu Gln Gly Glu Ala Pro Ala Ala Ala Pro Ala Ala Gly
            20                  25                  30

Gly Ala Ser Arg Ser Ala Arg Val Ser Asp Tyr Pro Leu Ala Asn Lys
        35                  40                  45

His Pro Glu Trp Val Lys Thr Ala Thr Asn Lys Thr Leu Asp Asp Phe
    50                  55                  60

Thr Leu Glu Asn Val Leu Ser Asn Lys Val Thr Ala Gln Asp Met Arg
65                  70                  75                  80

Ile Thr Pro Glu Thr Leu Arg Leu Gln Ala Ser Ile Ala Lys Asp Ala
                85                  90                  95

Gly Arg Asp Arg Leu Ala Met Asn Phe Glu Arg Ala Ala Glu Leu Thr
            100                 105                 110

Ala Val Pro Asp Asp Arg Ile Leu Glu Ile Tyr Asn Ala Leu Arg Pro
        115                 120                 125

Tyr Arg Ser Thr Lys Glu Glu Leu Leu Ala Ile Ala Asp Asp Leu Glu
    130                 135                 140

Ser Arg Tyr Gln Ala Lys Ile Cys Ala Ala Phe Val Arg Glu Ala Ala
145                 150                 155                 160

Thr Leu Tyr Val Glu Arg Lys Lys Leu Lys Gly Asp Asp
                165                 170
```

<210> SEQ ID NO 29
<211> LENGTH: 1041
<212> TYPE: DNA
<213> ORGANISM: Rhodococcus ruber

<400> SEQUENCE: 29

-continued

```
atgaaagccc tccagtacac cgagatcggc tccgagccgg tcgtcgtcga cgtccccacc     60
ccggcgcccg ggccgggtga gatcctgctg aaggtcaccg cggccggctt gtgccactcg    120
gacatcttcg tgatggacat gccggcagag cagtacatct acggtcttcc cctcaccctc    180
ggccacgagg gcgtcggcac cgtcgccgaa ctcggcgccg gcgtcaccgg attcgagacg    240
ggggacgccg tcgccgtgta cggccgtgg gggtgcggtg cgtgccacgc gtgcgcgcgc    300
ggccgggaga actactgcac ccgcgccgcc gagctgggca tcaccccgcc cggtctcggc    360
tcgcccgggt cgatggccga gtacatgatc gtcgactcgg cgcgccacct cgtcccgatc    420
ggggacctcg accccgtcgc ggcggttccg ctcaccgacg cgggcctgac gccgtaccac    480
gcgatctcgc gggtcctgcc cctgctggga cccggctcga ccgcggtcgt catcggggtc    540
ggcggactcg ggcacgtcgg catccagatc ctgcgcgccg tcagcgcggc ccgcgtgatc    600
gccgtcgatc tcgacgacga ccgactcgcg ctcgcccgcg aggtcggcgc cgacgcggcg    660
gtgaagtcgg gcgccggggc ggcggacgcg atccgggagc tgaccggcgg tgagggcgcg    720
acggcggtgt tcgacttcgt cggcgcccag tcgacgatcg acacggcgca gcaggtggtc    780
gcgatcgacg ggcacatctc ggtggtcggc atccatgccg gcgcccacgc caaggtcggc    840
ttcttcatga tcccgttcgg cgcgtccgtc gtgacgccgt actggggcac gcggtccgag    900
ctgatggacg tcgtggacct ggcccgtgcc ggccggctcg acatccacac cgagacgttc    960
accctcgacg agggacccac ggcctaccgg cggctacgcg agggcagcat ccgcggccgc   1020
ggggtggtcg tcccgggctg a                                              1041
```

<210> SEQ ID NO 30
<211> LENGTH: 346
<212> TYPE: PRT
<213> ORGANISM: Rhodococcus ruber

<400> SEQUENCE: 30

```
Met Lys Ala Leu Gln Tyr Thr Glu Ile Gly Ser Glu Pro Val Val Val
1               5                   10                  15

Asp Val Pro Thr Pro Ala Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Glu Gln Tyr Ile Tyr Gly Leu Pro Leu Thr Leu Gly His Glu Gly
    50                  55                  60

Val Gly Thr Val Ala Glu Leu Gly Ala Gly Val Thr Gly Phe Glu Thr
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Glu Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Val Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190
```

```
Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220

Ala Gly Ala Ala Asp Ala Ile Arg Glu Leu Thr Gly Gly Glu Gly Ala
225                 230                 235                 240

Thr Ala Val Phe Asp Phe Val Gly Ala Gln Ser Thr Ile Asp Thr Ala
                245                 250                 255

Gln Gln Val Val Ala Ile Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Asp Val
    290                 295                 300

Val Asp Leu Ala Arg Ala Gly Arg Leu Asp Ile His Thr Glu Thr Phe
305                 310                 315                 320

Thr Leu Asp Glu Gly Pro Thr Ala Tyr Arg Arg Leu Arg Glu Gly Ser
                325                 330                 335

Ile Arg Gly Arg Gly Val Val Val Pro Gly
            340                 345
```

<210> SEQ ID NO 31
<211> LENGTH: 1476
<212> TYPE: DNA
<213> ORGANISM: Escherichia coli

<400> SEQUENCE: 31

```
atggctaact acttcaatac actgaatctg cgccagcagc tggcacagct gggcaaatgt     60

cgctttatgg gccgcgatga attcgccgat ggcgcgagct accttcaggg taaaaaagta    120

gtcatcgtcg gctgtggcgc acagggtctg aaccagggcc tgaacatgcg tgattctggt    180

ctcgatatct cctacgctct gcgtaaagaa gcgattgccg agaagcgcgc gtcctggcgt    240

aaagcgaccg aaaatggttt taaagtgggt acttacgaag aactgatccc acaggcggat    300

ctggtgatta acctgacgcc ggacaagcag cactctgatg tagtgcgcac cgtacagcca    360

ctgatgaaag acggcgcggc gctgggctac tcgcacggtt tcaacatcgt cgaagtgggc    420

gagcagatcc gtaaagatat caccgtagtg atggttgcgc cgaaatgccc aggcaccgaa    480

gtgcgtgaag agtacaaacg tgggttcggc gtaccgacgc tgattgccgt tcacccggaa    540

aacgatccga aaggcgaagg catggcgatt gccaaagcct gggcggctgc aaccggtggt    600

caccgtgcgg gtgtgctgga atcgtccttc gttgcggaag tgaaatctga cctgatgggc    660

gagcaaacca tcctgtgcgg tatgttgcag gctggctctc tgctgtgctt cgacaagctg    720

gtggaagaag gtaccgatcc agcatacgca gaaaaactga ttcagttcgg ttgggaaacc    780

atcaccgaag cactgaaaca gggcggcatc accctgatga tggaccgtct ctctaacccg    840

gcgaaactgc gtgcttatgc gctttctgaa cagctgaaag agatcatggc acccctgttc    900

cagaaacata tggacgacat catctccggc gaattctctt ccggtatgat ggcggactgg    960

gccaacgatg ataagaaact gctgacctgg cgtgaagaga ccggcaaaac cgcgtttgaa   1020

accgcgccgc agtatgaagg caaaatcggc gagcaggagt acttcgataa aggcgtactg   1080

atgattgcga tggtgaaagc gggcgttgaa ctggcgttcg aaaccatggt cgattccggc   1140

atcattgaag agtctgcata ttatgaatca ctgcacgagc tgccgctgat tgccaacacc   1200

atcgcccgta agcgtctgta cgaaatgaac gtggttatct ctgataccgc tgagtacggt   1260
```

```
aactatctgt tctcttacgc ttgtgtgccg ttgctgaaac cgtttatggc agagctgcaa   1320

ccgggcgacc tgggtaaagc tattccggaa ggcgcggtag ataacgggca actgcgtgat   1380

gtgaacgaag cgattcgcag ccatgcgatt gagcaggtag gtaagaaact gcgcggctat   1440

atgacagata tgaaacgtat tgctgttgcg ggttaa                             1476


<210> SEQ ID NO 32
<211> LENGTH: 491
<212> TYPE: PRT
<213> ORGANISM: Escherichia coli

<400> SEQUENCE: 32

Met Ala Asn Tyr Phe Asn Thr Leu Asn Leu Arg Gln Gln Leu Ala Gln
1               5                   10                  15

Leu Gly Lys Cys Arg Phe Met Gly Arg Asp Glu Phe Ala Asp Gly Ala
            20                  25                  30

Ser Tyr Leu Gln Gly Lys Lys Val Val Ile Val Gly Cys Gly Ala Gln
        35                  40                  45

Gly Leu Asn Gln Gly Leu Asn Met Arg Asp Ser Gly Leu Asp Ile Ser
    50                  55                  60

Tyr Ala Leu Arg Lys Glu Ala Ile Ala Glu Lys Arg Ala Ser Trp Arg
65                  70                  75                  80

Lys Ala Thr Glu Asn Gly Phe Lys Val Gly Thr Tyr Glu Glu Leu Ile
                85                  90                  95

Pro Gln Ala Asp Leu Val Ile Asn Leu Thr Pro Asp Lys Gln His Ser
            100                 105                 110

Asp Val Val Arg Thr Val Gln Pro Leu Met Lys Asp Gly Ala Ala Leu
        115                 120                 125

Gly Tyr Ser His Gly Phe Asn Ile Val Glu Val Gly Glu Gln Ile Arg
    130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
            180                 185                 190

Ala Trp Ala Ala Ala Thr Gly Gly His Arg Ala Gly Val Leu Glu Ser
        195                 200                 205

Ser Phe Val Ala Glu Val Lys Ser Asp Leu Met Gly Glu Gln Thr Ile
    210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
            260                 265                 270

Met Met Asp Arg Leu Ser Asn Pro Ala Lys Leu Arg Ala Tyr Ala Leu
        275                 280                 285

Ser Glu Gln Leu Lys Glu Ile Met Ala Pro Leu Phe Gln Lys His Met
    290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335

Thr Ala Phe Glu Thr Ala Pro Gln Tyr Glu Gly Lys Ile Gly Glu Gln
```

```
            340                 345                 350

Glu Tyr Phe Asp Lys Gly Val Leu Met Ile Ala Met Val Lys Ala Gly
        355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
            420                 425                 430

Lys Pro Phe Met Ala Glu Leu Gln Pro Gly Asp Leu Gly Lys Ala Ile
        435                 440                 445

Pro Glu Gly Ala Val Asp Asn Gly Gln Leu Arg Asp Val Asn Glu Ala
    450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490


<210> SEQ ID NO 33
<211> LENGTH: 1851
<212> TYPE: DNA
<213> ORGANISM: Escherichia coli

<400> SEQUENCE: 33

atgcctaagt accgttccgc caccaccact catggtcgta atatggcggg tgctcgtgcg     60

ctgtggcgcg ccaccggaat gaccgacgcc gatttcggta agccgattat cgcggttgtg    120

aactcgttca cccaatttgt accgggtcac gtccatctgc gcgatctcgg taaactggtc    180

gccgaacaaa ttgaagcggc tggcggcgtt gccaaagagt tcaacaccat tgcggtggat    240

gatgggattg ccatgggcca cggggggatg ctttattcac tgccatctcg cgaactgatc    300

gctgattccg ttgagtatat ggtcaacgcc cactgcgccg acgccatggt ctgcatctct    360

aactgcgaca aaatcacccc ggggatgctg atggcttccc tgcgcctgaa tattccggtg    420

atctttgttt ccggcggccc gatggaggcc gggaaaacca aactttccga tcagatcatc    480

aagctcgatc tggttgatgc gatgatccag ggcgcagacc cgaaagtatc tgactcccag    540

agcgatcagg ttgaacgttc cgcgtgtccg acctgcggtt cctgctccgg gatgtttacc    600

gctaactcaa tgaactgcct gaccgaagcg ctgggcctgt cgcagccggg caacggctcg    660

ctgctggcaa cccacgccga ccgtaagcag ctgttcctta atgctggtaa acgcattgtt    720

gaattgacca aacgttatta cgagcaaaac gacgaaagtg cactgccgcg taatatcgcc    780

agtaaggcgg cgtttgaaaa cgccatgacg ctggatatcg cgatgggtgg atcgactaac    840

accgtacttc acctgctggc ggcggcgcag gaagcggaaa tcgacttcac catgagtgat    900

atcgataagc tttcccgcaa ggttccacag ctgtgtaaag ttgcgccgag cacccagaaa    960

taccatatgg aagatgttca ccgtgctggt ggtgttatcg gtattctcgg cgaactggat   1020

cgcgcggggt tactgaaccg tgatgtgaaa aacgtacttg gcctgacgtt gccgcaaacg   1080

ctggaacaat acgacgttat gctgacccag gatgacgcgg taaaaaatat gttccgcgca   1140

ggtcctgcag gcattcgtac cacacaggca ttctcgcaag attgccgttg ggatacgctg   1200

gacgacgatc gcgccaatgg ctgtatccgc tcgctggaac acgcctacag caaagacggc   1260

ggcctggcgg tgctctacgg taactttgcg gaaaacggct gcatcgtgaa aacggcaggc   1320
```

```
gtcgatgaca gcatcctcaa attcaccggc ccggcgaaag tgtacgaaag ccaggacgat   1380

gcggtagaag cgattctcgg cggtaaagtt gtcgccggag atgtggtagt aattcgctat   1440

gaaggcccga aaggcggtcc ggggatgcag gaaatgctct acccaaccag cttcctgaaa   1500

tcaatgggtc tcggcaaagc ctgtgcgctg atcaccgacg gtcgtttctc tggtggcacc   1560

tctggtcttt ccatcggcca cgtctcaccg gaagcggcaa gcggcggcag cattggcctg   1620

attgaagatg gtgacctgat cgctatcgac atcccgaacc gtggcattca gttacaggta   1680

agcgatgccg aactggcggc gcgtcgtgaa gcgcaggacg ctcgaggtga caaagcctgg   1740

acgccgaaaa atcgtgaacg tcaggtctcc tttgccctgc gtgcttatgc cagcctggca   1800

accagcgccg acaaaggcgc ggtgcgcgat aaatcgaaac tgggggggtta a             1851


<210> SEQ ID NO 34
<211> LENGTH: 616
<212> TYPE: PRT
<213> ORGANISM: Escherichia coli

<400> SEQUENCE: 34

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
            100                 105                 110

Ala Asp Ala Met Val Cys Ile Ser Asn Cys Asp Lys Ile Thr Pro Gly
        115                 120                 125

Met Leu Met Ala Ser Leu Arg Leu Asn Ile Pro Val Ile Phe Val Ser
    130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
            180                 185                 190

Gly Ser Cys Ser Gly Met Phe Thr Ala Asn Ser Met Asn Cys Leu Thr
        195                 200                 205

Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285
```

-continued

```
Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
    370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
    610                 615
```

<210> SEQ ID NO 35
<211> LENGTH: 1662
<212> TYPE: DNA
<213> ORGANISM: Lactococcus lactis

<400> SEQUENCE: 35

```
tctagacata tgtatactgt gggggattac ctgctggatc gcctgcacga actggggatt      60

gaagaaattt tcggtgtgcc aggcgattat aacctgcagt tcctggacca gattatctcg     120

cacaaagata tgaagtgggt cggtaacgcc aacgaactga acgcgagcta tatggcagat     180

ggttatgccc gtaccaaaaa agctgctgcg tttctgacga cctttggcgt tggcgaactg     240
```

```
agcgccgtca acggactggc aggaagctac gccgagaacc tgccagttgt cgaaattgtt    300

gggtcgccta cttctaaggt tcagaatgaa ggcaaatttg tgcaccatac tctggctgat    360

ggggatttta aacattttat gaaaatgcat gaaccggtta ctgcggcccg cacgctgctg    420

acagcagaga atgctacggt tgagatcgac cgcgtcctgt ctgcgctgct gaaagagcgc    480

aagccggtat atatcaatct gcctgtcgat gttgccgcag cgaaagccga aaagccgtcg    540

ctgccactga aaaaagaaaa cagcacctcc aatacatcgg accaggaaat tctgaataaa    600

atccaggaat cactgaagaa tgcgaagaaa ccgatcgtca tcaccggaca tgagatcatc    660

tcttttggcc tggaaaaaac ggtcacgcag ttcatttcta agaccaaact gcctatcacc    720

accctgaact tcggcaaatc tagcgtcgat gaagcgctgc cgagttttct gggtatctat    780

aatggtaccc tgtccgaacc gaacctgaaa gaattcgtcg aaagcgcgga ctttatcctg    840

atgctgggcg tgaaactgac ggatagctcc acaggcgcat ttacccacca tctgaacgag    900

aataaaatga tttccctgaa tatcgacgaa ggcaaaatct ttaacgagcg catccagaac    960

ttcgattttg aatctctgat tagttcgctg ctggatctgt ccgaaattga gtataaaggt   1020

aaatatattg ataaaaaaca ggaggatttt gtgccgtcta atgcgctgct gagtcaggat   1080

cgtctgtggc aagccgtaga aaacctgaca cagtctaatg aaacgattgt tgcggaacag   1140

ggaacttcat ttttcggcgc ctcatccatt tttctgaaat ccaaaagcca tttcattggc   1200

caaccgctgt gggggagtat tggttatacc tttccggcgg cgctgggttc acagattgca   1260

gataaggaat cacgccatct gctgtttatt ggtgacggca gcctgcagct gactgtccag   1320

gaactggggc tggcgatccg tgaaaaaatc aatccgattt gctttatcat caataacgac   1380

ggctacaccg tcgaacgcga aattcatgga ccgaatcaaa gttacaatga catcccgatg   1440

tggaactata gcaaactgcc ggaatccttt ggcgcgacag aggatcgcgt ggtgagtaaa   1500

attgtgcgta cggaaaacga atttgtgtcg gttatgaaag aagcgcaggc tgacccgaat   1560

cgcatgtatt ggattgaact gatcctggca aaagaaggcg caccgaaagt tctgaaaaag   1620

atggggaaac tgtttgcgga gcaaaataaa agctaaggat cc                      1662
```

<210> SEQ ID NO 36
<211> LENGTH: 548
<212> TYPE: PRT
<213> ORGANISM: Lactococcus lactis

<400> SEQUENCE: 36

```
Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125
```

-continued

```
Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 37
<211> LENGTH: 1164
<212> TYPE: DNA
<213> ORGANISM: Escherichia coli

<400> SEQUENCE: 37
atgaacaact ttaatctgca caccccaacc cgcattctgt ttggtaaagg cgcaatcgct 60
ggtttacgcg aacaaattcc tcacgatgct cgcgtattga ttacctacgg cggcggcagc 120
gtgaaaaaaa ccggcgttct cgatcaagtt ctggatgccc tgaaaggcat ggacgtgctg 180
gaatttggcg gtattgagcc aaacccggct tatgaaacgc tgatgaacgc cgtgaaactg 240
gttcgcgaac agaaagtgac tttcctgctg gcggttggcg gcggttctgt actggacggc 300
accaaattta tcgccgcagc ggctaactat ccggaaaata tcgatccgtg gcacattctg 360
caaacgggcg gtaaagagat taaaagcgcc atcccgatgg gctgtgtgct gacgctgcca 420
gcaaccggtt cagaatccaa cgcaggcgcg gtgatctccc gtaaaaccac aggcgacaag 480
caggcgttcc attctgccca tgttcagccg gtatttgccg tgctcgatcc ggtttatacc 540
tacaccctgc cgccgcgtca ggtggctaac ggcgtagtgg acgcctttgt acacaccgtg 600
gaacagtatg ttaccaaacc ggttgatgcc aaaattcagg accgtttcgc agaaggcatt 660
ttgctgacgc taatcgaaga tggtccgaaa gccctgaaag agccagaaaa ctacgatgtg 720
cgcgccaacg tcatgtgggc ggcgactcag gcgctgaacg gtttgattgg cgctggcgta 780
ccgcaggact gggcaacgca tatgctgggc cacgaactga ctgcgatgca cggtctggat 840
cacgcgcaaa cactggctat cgtcctgcct gcactgtgga atgaaaaacg cgataccaag 900
cgcgctaagc tgctgcaata tgctgaacgc gtctggaaca tcactgaagg ttccgatgat 960
gagcgtattg acgccgcgat tgccgcaacc cgcaatttct ttgagcaatt aggcgtgccg 1020
acccacctct ccgactacgg tctggacggc agctccatcc cggctttgct gaaaaaactg 1080
gaagagcacg gcatgaccca actgggcgaa aatcatgaca ttacgttgga tgtcagccgc 1140
cgtatatacg aagccgcccg ctaa 1164

<210> SEQ ID NO 38
<211> LENGTH: 387
<212> TYPE: PRT
<213> ORGANISM: Escherichia coli

<400> SEQUENCE: 38

Met Asn Asn Phe Asn Leu His Thr Pro Thr Arg Ile Leu Phe Gly Lys
1 5 10 15

Gly Ala Ile Ala Gly Leu Arg Glu Gln Ile Pro His Asp Ala Arg Val
20 25 30

Leu Ile Thr Tyr Gly Gly Gly Ser Val Lys Lys Thr Gly Val Leu Asp
35 40 45

Gln Val Leu Asp Ala Leu Lys Gly Met Asp Val Leu Glu Phe Gly Gly
50 55 60

Ile Glu Pro Asn Pro Ala Tyr Glu Thr Leu Met Asn Ala Val Lys Leu
65 70 75 80

Val Arg Glu Gln Lys Val Thr Phe Leu Leu Ala Val Gly Gly Gly Ser
85 90 95

Val Leu Asp Gly Thr Lys Phe Ile Ala Ala Ala Ala Asn Tyr Pro Glu
100 105 110

Asn Ile Asp Pro Trp His Ile Leu Gln Thr Gly Gly Lys Glu Ile Lys
115 120 125

```
Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385
```

<210> SEQ ID NO 39
<211> LENGTH: 1197
<212> TYPE: DNA
<213> ORGANISM: Saccharomyces cerevisiae

<400> SEQUENCE: 39

```
atgtctcaga acgtttacat tgtatcgact gccagaaccc caattggttc attccagggt     60

tctctatcct ccaagacagc agtggaattg ggtgctgttg ctttaaaagg cgccttggct    120

aaggttccag aattggatgc atccaaggat tttgacgaaa ttatttttgg taacgttctt    180

tctgccaatt tgggccaagc tccggccaga caagttgctt tggctgccgg tttgagtaat    240

catatcgttg caagcacagt taacaaggtc tgtgcatccg ctatgaaggc aatcattttg    300

ggtgctcaat ccatcaaatg tggtaatgct gatgttgtcg tagctggtgg ttgtgaatct    360

atgactaacg caccatacta catgccagca gcccgtgcgg gtgccaaatt tggccaaact    420

gttcttgttg atggtgtcga aagagatggg ttgaacgatg cgtacgatgg tctagccatg    480

ggtgtacacg cagaaaagtg tgcccgtgat tgggatatta ctagagaaca acaagacaat    540

tttgccatcg aatcctacca aaaatctcaa aaatctcaaa aggaaggtaa attcgacaat    600
```

```
gaaattgtac ctgttaccat taagggattt agaggtaagc ctgatactca agtcacgaag    660

gacgaggaac ctgctagatt acacgttgaa aaattgagat ctgcaaggac tgttttccaa    720

aaagaaaacg gtactgttac tgccgctaac gcttctccaa tcaacgatgg tgctgcagcc    780

gtcatcttgg tttccgaaaa agttttgaag gaaaagaatt tgaagccttt ggctattatc    840

aaaggttggg gtgaggccgc tcatcaacca gctgatttta catgggctcc atctcttgca    900

gttccaaagg ctttgaaaca tgctggcatc gaagacatca attctgttga ttactttgaa    960

ttcaatgaag ccttttcggt tgtcggtttg gtgaacacta agattttgaa gctagaccca   1020

tctaaggtta atgtatatgg tggtgctgtt gctctaggtc acccattggg ttgttctggt   1080

gctagagtgg ttgttacact gctatccatc ttacagcaag aaggaggtaa gatcggtgtt   1140

gccgccattt gtaatggtgg tggtggtgct tcctctattg tcattgaaaa gatatga      1197


<210> SEQ ID NO 40
<211> LENGTH: 398
<212> TYPE: PRT
<213> ORGANISM: Saccharomyces cerevisiae

<400> SEQUENCE: 40

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205

Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
```

```
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395
```

<210> SEQ ID NO 41
<211> LENGTH: 1716
<212> TYPE: DNA
<213> ORGANISM: Bacillus subtilis

<400> SEQUENCE: 41

```
atgttgacaa aagcaacaaa agaacaaaaa tcccttgtga aaaacagagg ggcggagctt     60

gttgttgatt gcttagtgga gcaaggtgtc acacatgtat ttggcattcc aggtgcaaaa    120

attgatgcgg tatttgacgc tttacaagat aaaggacctg aaattatcgt tgcccggcac    180

gaacaaaacg cagcattcat ggcccaagca gtcggccgtt taactggaaa accgggagtc    240

gtgttagtca catcaggacc gggtgcctct aacttggcaa caggcctgct gacagcgaac    300

actgaaggag accctgtcgt tgcgcttgct ggaaacgtga tccgtgcaga tcgtttaaaa    360

cggacacatc aatctttgga taatgcggcg ctattccagc cgattacaaa atacagtgta    420

gaagttcaag atgtaaaaaa tataccggaa gctgttacaa atgcatttag gatagcgtca    480

gcagggcagg ctggggccgc ttttgtgagc tttccgcaag atgttgtgaa tgaagtcaca    540

aatacgaaaa acgtgcgtgc tgttgcagcg ccaaaactcg gtcctgcagc agatgatgca    600

atcagtgcgg ccatagcaaa aatccaaaca gcaaaacttc ctgtcgtttt ggtcggcatg    660

aaaggcggaa gaccggaagc aattaaagcg gttcgcaagc ttttgaaaaa ggttcagctt    720

ccatttgttg aaacatatca agctgccggt accctttcta gagatttaga ggatcaatat    780

tttggccgta tcggtttgtt ccgcaaccag cctggcgatt tactgctaga gcaggcagat    840

gttgttctga cgatcggcta tgacccgatt gaatatgatc cgaaattctg gaatatcaat    900

ggagaccgga caattatcca tttagacgag attatcgctg acattgatca tgcttaccag    960

cctgatcttg aattgatcgg tgacattccg tccacgatca atcatatcga acacgatgct   1020

gtgaaagtgg aatttgcaga gcgtgagcag aaaatccttt ctgatttaaa acaatatatg   1080

catgaaggtg agcaggtgcc tgcagattgg aaatcagaca gagcgcaccc tcttgaaatc   1140

gttaaagagt tgcgtaatgc agtcgatgat catgttacag taacttgcga tatcggttcg   1200

cacgccattt ggatgtcacg ttatttccgc agctacgagc cgttaacatt aatgatcagt   1260

aacggtatgc aaacactcgg cgttgcgctt ccttgggcaa tcggcgcttc attggtgaaa   1320

ccgggagaaa aagtggtttc tgtctctggt gacggcggtt tcttattctc agcaatggaa   1380

ttagagacag cagttcgact aaaagcacca attgtacaca ttgtatggaa cgacagcaca   1440

tatgacatgg ttgcattcca gcaattgaaa aaatataacc gtacatctgc ggtcgatttc   1500
```

```
ggaaatatcg atatcgtgaa atatgcggaa agcttcggag caactggctt gcgcgtagaa   1560

tcaccagacc agctggcaga tgttctgcgt caaggcatga acgctgaagg tcctgtcatc   1620

atcgatgtcc cggttgacta cagtgataac attaatttag caagtgacaa gcttccgaaa   1680

gaattcgggg aactcatgaa aacgaaagct ctctag                             1716


<210> SEQ ID NO 42
<211> LENGTH: 571
<212> TYPE: PRT
<213> ORGANISM: Bacillus subtilis

<400> SEQUENCE: 42

Met Leu Thr Lys Ala Thr Lys Glu Gln Lys Ser Leu Val Lys Asn Arg
1               5                   10                  15

Gly Ala Glu Leu Val Val Asp Cys Leu Val Glu Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335
```

-continued

```
Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570
```

<210> SEQ ID NO 43
<211> LENGTH: 1188
<212> TYPE: DNA
<213> ORGANISM: Saccharomyces cerevisiae

<400> SEQUENCE: 43

```
atgttgagaa ctcaagccgc cagattgatc tgcaactccc gtgtcatcac tgctaagaga     60

acctttgctt tggccacccg tgctgctgct tacagcagac cagctgcccg tttcgttaag    120

ccaatgatca ctacccgtgg tttgaagcaa atcaacttcg gtggtactgt tgaaaccgtc    180

tacgaaagag ctgactggcc aagagaaaag ttgttggact acttcaagaa cgacactttt    240

gctttgatcg gttacggttc ccaaggttac ggtcaaggtt tgaacttgag agacaacggt    300

ttgaacgtta tcattggtgt ccgtaaagat ggtgcttctt ggaaggctgc catcgaagac    360

ggttgggttc caggcaagaa cttgttcact gttgaagatg ctatcaagag aggtagttac    420

gttatgaact tgttgtccga tgccgctcaa tcagaaacct ggcctgctat caagccattg    480

ttgaccaagg gtaagacttt gtacttctcc cacggtttct ccccagtctt caaggacttg    540

actcacgttg aaccaccaaa ggacttagat gttatcttgg ttgctccaaa gggttccggt    600

agaactgtca gatctttgtt caaggaaggt cgtggtatta actcttctta cgccgtctgg    660

aacgatgtca ccggtaaggc tcacgaaaag gcccaagctt tggccgttgc cattggttcc    720

ggttacgttt accaaaccac tttcgaaaga gaagtcaact ctgacttgta cggtgaaaga    780

ggttgtttaa tgggtggtat ccacggtatg ttcttggctc aatacgacgt cttgagagaa    840
```

```
aacggtcact ccccatctga agctttcaac gaaaccgtcg aagaagctac ccaatctcta    900

tacccattga tcggtaagta cggtatggat tacatgtacg atgcttgttc caccaccgcc    960

agaagaggtg ctttggactg gtacccaatc ttcaagaatg ctttgaagcc tgttttccaa   1020

gacttgtacg aatctaccaa gaacggtacc gaaaccaaga gatctttgga attcaactct   1080

caacctgact acagagaaaa gctagaaaag gaattagaca ccatcagaaa catggaaatc   1140

tggaaggttg gtaaggaagt cagaaagttg agaccagaaa accaataa                1188


<210> SEQ ID NO 44
<211> LENGTH: 395
<212> TYPE: PRT
<213> ORGANISM: Saccharomyces cerevisiae

<400> SEQUENCE: 44

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
305                 310                 315                 320
```

```
Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
    370                 375                 380

Lys Glu Val Arg Lys Leu Arg Pro Glu Asn Gln
385                 390                 395


<210> SEQ ID NO 45
<211> LENGTH: 1476
<212> TYPE: DNA
<213> ORGANISM: Bacillus subtilis

<400> SEQUENCE: 45

atggctaact acttcaatac actgaatctg cgccagcagc tggcacagct gggcaaatgt      60

cgctttatgg gccgcgatga attcgccgat ggcgcgagct accttcaggg taaaaaagta     120

gtcatcgtcg gctgtggcgc acagggtctg aaccagggcc tgaacatgcg tgattctggt     180

ctcgatatct cctacgctct gcgtaaagaa gcgattgccg agaagcgcgc gtcctggcgt     240

aaagcgaccg aaaatggttt taaagtgggt acttacgaag aactgatccc acaggcggat     300

ctggtgatta acctgacgcc ggacaagcag cactctgatg tagtgcgcac cgtacagcca     360

ctgatgaaag acggcgcggc gctgggctac tcgcacggtt tcaacatcgt cgaagtgggc     420

gagcagatcc gtaaagatat caccgtagtg atggttgcgc cgaaatgccc aggcaccgaa     480

gtgcgtgaag agtacaaacg tgggttcggc gtaccgacgc tgattgccgt tcacccggaa     540

aacgatccga aaggcgaagg catggcgatt gccaaagcct gggcggctgc aaccggtggt     600

caccgtgcgg gtgtgctgga atcgtccttc gttgcggaag tgaaatctga cctgatgggc     660

gagcaaacca tcctgtgcgg tatgttgcag gctggctctc tgctgtgctt cgacaagctg     720

gtggaagaag gtaccgatcc agcatacgca gaaaaactga ttcagttcgg ttgggaaacc     780

atcaccgaag cactgaaaca gggcggcatc accctgatga tggaccgtct ctctaacccg     840

gcgaaactgc gtgcttatgc gctttctgaa cagctgaaag agatcatggc acccctgttc     900

cagaaacata tggacgacat catctccggc gaattctctt ccggtatgat ggcggactgg     960

gccaacgatg ataagaaact gctgacctgg cgtgaagaga ccggcaaaac cgcgtttgaa    1020

accgcgccgc agtatgaagg caaaatcggc gagcaggagt acttcgataa aggcgtactg    1080

atgattgcga tggtgaaagc gggcgttgaa ctggcgttcg aaaccatggt cgattccggc    1140

atcattgaag agtctgcata ttatgaatca ctgcacgagc tgccgctgat tgccaacacc    1200

atcgcccgta agcgtctgta cgaaatgaac gtggttatct ctgataccgc tgagtacggt    1260

aactatctgt tctcttacgc ttgtgtgccg ttgctgaaac cgtttatggc agagctgcaa    1320

ccgggcgacc tgggtaaagc tattccggaa ggcgcggtag ataacgggca actgcgtgat    1380

gtgaacgaag cgattcgcag ccatgcgatt gagcaggtag gtaagaaact gcgcggctat    1440

atgacagata tgaaacgtat tgctgttgcg ggttaa                              1476


<210> SEQ ID NO 46
<211> LENGTH: 342
<212> TYPE: PRT
<213> ORGANISM: Bacillus subtilis
```

<400> SEQUENCE: 46

```
Met Val Lys Val Tyr Tyr Asn Gly Asp Ile Lys Glu Asn Val Leu Ala
1               5                   10                  15

Gly Lys Thr Val Ala Val Ile Gly Tyr Gly Ser Gln Gly His Ala His
            20                  25                  30

Ala Leu Asn Leu Lys Glu Ser Gly Val Asp Val Ile Val Gly Val Arg
        35                  40                  45

Gln Gly Lys Ser Phe Thr Gln Ala Gln Glu Asp Gly His Lys Val Phe
    50                  55                  60

Ser Val Lys Glu Ala Ala Ala Gln Ala Glu Ile Ile Met Val Leu Leu
65                  70                  75                  80

Pro Asp Glu Gln Gln Gln Lys Val Tyr Glu Ala Glu Ile Lys Asp Glu
                85                  90                  95

Leu Thr Ala Gly Lys Ser Leu Val Phe Ala His Gly Phe Asn Val His
            100                 105                 110

Phe His Gln Ile Val Pro Pro Ala Asp Val Asp Val Phe Leu Val Ala
        115                 120                 125

Pro Lys Gly Pro Gly His Leu Val Arg Arg Thr Tyr Glu Gln Gly Ala
    130                 135                 140

Gly Val Pro Ala Leu Phe Ala Ile Tyr Gln Asp Val Thr Gly Glu Ala
145                 150                 155                 160

Arg Asp Lys Ala Leu Ala Tyr Ala Lys Gly Ile Gly Gly Ala Arg Ala
                165                 170                 175

Gly Val Leu Glu Thr Thr Phe Lys Glu Glu Thr Glu Thr Asp Leu Phe
            180                 185                 190

Gly Glu Gln Ala Val Leu Cys Gly Gly Leu Ser Ala Leu Val Lys Ala
        195                 200                 205

Gly Phe Glu Thr Leu Thr Glu Ala Gly Tyr Gln Pro Glu Leu Ala Tyr
    210                 215                 220

Phe Glu Cys Leu His Glu Leu Lys Leu Ile Val Asp Leu Met Tyr Glu
225                 230                 235                 240

Glu Gly Leu Ala Gly Met Arg Tyr Ser Ile Ser Asp Thr Ala Gln Trp
                245                 250                 255

Gly Asp Phe Val Ser Gly Pro Arg Val Val Asp Ala Lys Val Lys Glu
            260                 265                 270

Ser Met Lys Glu Val Leu Lys Asp Ile Gln Asn Gly Thr Phe Ala Lys
        275                 280                 285

Glu Trp Ile Val Glu Asn Gln Val Asn Arg Pro Arg Phe Asn Ala Ile
    290                 295                 300

Asn Ala Ser Glu Asn Glu His Gln Ile Glu Val Val Gly Arg Lys Leu
305                 310                 315                 320

Arg Glu Met Met Pro Phe Val Lys Gln Gly Lys Lys Lys Glu Ala Val
                325                 330                 335

Val Ser Val Ala Gln Asn
            340
```

<210> SEQ ID NO 47
<211> LENGTH: 1758
<212> TYPE: DNA
<213> ORGANISM: Saccharomyces cerevisiae

<400> SEQUENCE: 47

```
atgggcttgt taacgaaagt tgctacatct agacaattct ctacaacgag atgcgttgca     60

aagaagctca acaagtactc gtatatcatc actgaaccta agggccaagg tgcgtcccag    120
```

```
gccatgcttt atgccaccgg tttcaagaag gaagatttca agaagcctca agtcggggtt    180

ggttcctgtt ggtggtccgg taacccatgt aacatgcatc tattggactt gaataacaga    240

tgttctcaat ccattgaaaa agcgggtttg aaagctatgc agttcaacac catcggtgtt    300

tcagacggta tctctatggg tactaaaggt atgagatact cgttacaaag tagagaaatc    360

attgcagact cctttgaaac catcatgatg gcacaacact acgatgctaa catcgccatc    420

ccatcatgtg acaaaaacat gcccggtgtc atgatggcca tgggtagaca taacagacct    480

tccatcatgg tatatggtgg tactatcttg cccggtcatc caacatgtgg ttcttcgaag    540

atctctaaaa acatcgatat cgtctctgcg ttccaatcct acggtgaata tatttccaag    600

caattcactg aagaagaaag agaagatgtt gtggaacatg catgcccagg tcctggttct    660

tgtggtggta tgtatactgc caacacaatg gcttctgccg ctgaagtgct aggtttgacc    720

attccaaact cctcttcctt cccagccgtt tccaaggaga agttagctga gtgtgacaac    780

attggtgaat acatcaagaa gacaatggaa ttgggtattt tacctcgtga tatcctcaca    840

aaagaggctt ttgaaaacgc cattacttat gtcgttgcaa ccggtgggtc cactaatgct    900

gttttgcatt tggtggctgt tgctcactct gcgggtgtca agttgtcacc agatgatttc    960

caaagaatca gtgatactac accattgatc ggtgacttca aaccttctgg taaatacgtc   1020

atggccgatt tgattaacgt tggtggtacc caatctgtga ttaagtatct atatgaaaac   1080

aacatgttgc acggtaacac aatgactgtt accggtgaca ctttggcaga acgtgcaaag   1140

aaagcaccaa gcctacctga aggacaagag attattaagc cactctccca cccaatcaag   1200

gccaacggtc acttgcaaat tctgtacggt tcattggcac caggtggagc tgtgggtaaa   1260

attaccggta aggaaggtac ttacttcaag ggtagagcac gtgtgttcga agaggaaggt   1320

gcctttattg aagccttgga aagaggtgaa atcaagaagg gtgaaaaaac cgttgttgtt   1380

atcagatatg aaggtccaag aggtgcacca ggtatgcctg aaatgctaaa gccttcctct   1440

gctctgatgg gttacggttt gggtaaagat gttgcattgt tgactgatgg tagattctct   1500

ggtggttctc acgggttctt aatcggccac attgttcccg aagccgctga aggtggtcct   1560

atcgggttgg tcagagacgg cgatgagatt atcattgatg ctgataataa caagattgac   1620

ctattagtct ctgataagga aatggctcaa cgtaaacaaa gttgggttgc acctccacct   1680

cgttacacaa gaggtactct atccaagtat gctaagttgg tttccaacgc ttccaacggt   1740

tgtgttttag atgcttga                                                 1758
```

<210> SEQ ID NO 48
<211> LENGTH: 585
<212> TYPE: PRT
<213> ORGANISM: Saccharomyces cerevisiae

<400> SEQUENCE: 48

```
Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
            20                  25                  30

Pro Lys Gly Gln Gly Ala Ser Gln Ala Met Leu Tyr Ala Thr Gly Phe
        35                  40                  45

Lys Lys Glu Asp Phe Lys Lys Pro Gln Val Gly Val Gly Ser Cys Trp
    50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
```

```
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
    130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Glu Arg Glu
        195                 200                 205

Asp Val Val Glu His Ala Cys Pro Gly Pro Gly Ser Cys Gly Gly Met
    210                 215                 220

Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
        275                 280                 285

Thr Tyr Val Val Ala Thr Gly Gly Ser Thr Asn Ala Val Leu His Leu
    290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
        355                 360                 365

Thr Val Thr Gly Asp Thr Leu Ala Glu Arg Ala Lys Lys Ala Pro Ser
    370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Glu Gly Ala Phe Ile Glu Ala Leu Glu Arg
        435                 440                 445

Gly Glu Ile Lys Lys Gly Glu Lys Thr Val Val Val Ile Arg Tyr Glu
    450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
            500                 505                 510
```

-continued

```
Pro Glu Ala Ala Glu Gly Gly Pro Ile Gly Leu Val Arg Asp Gly Asp
        515                 520                 525

Glu Ile Ile Ile Asp Ala Asp Asn Asn Lys Ile Asp Leu Leu Val Ser
    530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585


<210> SEQ ID NO 49
<211> LENGTH: 8019
<212> TYPE: DNA
<213> ORGANISM: Saccharomyces cerevisiae

<400> SEQUENCE: 49

atgacagcta tcttaaactg ggaagatata tcccctgttt tagagaaagg cacccgcgaa      60

tcacacgtgt ctaaaagagt tcccttttg caagatatat cacaattagt tcgtcaagaa      120

acattggaaa aacctcaatt atctgaaatt gctttcgttt tattgaatac cttcacgatt      180

tacgaagaca ataggtctaa aagtttggta acttcaatat tgcttgacat cttaaatcta      240

gagccatgtc tcctagaaaa ctttatccga ttcatttccg acgtggtcat cagtaatccg      300

gctaccaaag cagtcgctga ttaccttaat ttgttagatt ggattaattc tttcttgatt      360

tttgtgtcgc ataattctaa tttatttgaa gagtacattc caaaattgtt ggtcgcccat      420

tcttatgcaa cgttcggtgt ggaaactatt cttgacaatc aagaagaagg caagaaatcc      480

caagataagc agaaccagca tagaaagaga attcgttatt gcattttcca aacaacggtc      540

aaagcattcc ttaagtgctt gaaggataat gacgacagta tttccttcat gaagatttca      600

attaaaactg tactggagag ctactctaag ctgaagataa ccagtgttgg agtagttatg      660

ataatgggtg cactaactca ggctgcactt cagttattat cgaggcaacc agctctgcac      720

tccgttttaa aggaaaattc tgcagagaaa tattgcgaat atttgggcaa agaagtgttt      780

ttaggcaaaa acccaccatc ttccttttgc ttagagattg gtttgaagcc atttttaaaa      840

gaatttgttt cacaagagtt attcattaag tttttcatcc ctaatattga aaaagcagtt      900

ttaagatctc ctgaggttgg tttttcgatt ttatctgagt tatatgctgg tgtttctcct      960

gaaaaagtaa atctcttaaa tgcctttgct tcctcgaaac tgattaatca atacttctcg     1020

tcatttaaaa gctcaaaaga ggtagttaga tccgtctcgc ttcagtctat gataatctta     1080

ttgagaaaaa tttccaatac tgacactacc ttggaagatt tgaccaagct tattgacgaa     1140

atatttaaga acatcaaatc gaacttaaat gcagattaca aatcacttat ttccaaaatt     1200

ctcatagaaa taccettaac gcactatgag gtttcagaaa aaatctgcaa agggctgtcc     1260

ccatatattg gtaaagaagg taatgaagca gccttgactc taatgcttaa cgcttttttt     1320

gttcattatt ttagtctggg caaacctatt gaagacttgg ataaaattat atcagctggt     1380

tttgcagata aaaaaacctgc tttgaaaaaa tgctggtttg ccgcattttt gaacaattcc     1440

aatgctgcct ctgaagaggt gattttaaac tttatagacg gttgtttgga atttgtgaaa     1500

gactccatca tacattatca gactcacggg catgcatgta ttctagcatc aattgaattt     1560

acaaacaaaa ttttggcatt ggacaatact gagctaaatg atcgtgttat gcagctcata     1620

gaaacccttc ctgaaaattc ttcgataggt gatgctatct taactgctgc attatcaaca     1680

gagctatcca tcgaaaaccg tattcatgct gttaatttac tacaagaatt gttctacaag     1740
```

aaacccgaat ttattgggtt tagcgtgatt gatgcaattg aaaggagaat gcgtgtccaa 1800
gaattaatac ctcaacaaaa tacatccttt aaatatgtca cttctgtact actggccatt 1860
acgtctgagt tacctgacaa ggaagcctcg ataaaggtat taatcaatgc tctggtcata 1920
gcgcaatgga atattttcaa cattaagaat ggctgggctg gtttagtttt acgtgcaagg 1980
cttgatccag ctgaagttgt caaagaacat gctagcgtta tcatggagaa gattcttgaa 2040
atcacaggta gttgtgaatg gatagataca atttatggtg catgcggttt gcaagcagct 2100
gcctatgcag catttattca gcctaatgag ttcacaccga tcctttgtaa gactatcgaa 2160
gcagatttaa ccgcggatga tttctcacgt ttatctgaag aggacttcga aatttttgca 2220
ggagaggaag gtgttctggt ggttgacgtc ctggaagaaa gcatgaataa gaaactttcc 2280
aataaaaatt ctaaagagta cgaaactcta atgtgggaac aaaaaataag gaaggagcaa 2340
gccaaaaaga atgtgaaaaa actttcaaaa gaggaacaag agctcgttaa tgaacagtta 2400
gcgaaagaat ctgcagttag atcacacgtt tcggaaattt ccactcgttt aaagcgtggt 2460
attagattgg tatctgaact ttccaaagct gcttgcttag tccaaaatgg catcgctact 2520
tggttcccct tggcagtcac aaagcttttg tacctatgct cggaaccaaa tatttcaaag 2580
ctaacagagg atgtaaataa tgtgttcttg cagctttctc aaaatgtctc cgagagatta 2640
ggtaatatca gacttttctt aggtttggcg actttgcgtg tgcacaatgc taatggcatc 2700
tcgcaagatt atttacaaga accactggtt gaattactta caagagttct ttttaggatc 2760
aagttcgtct ccaaccaagc agcaatagat tccatcagtt tgacatatat tttaccattg 2820
ttgattaatg ttttagaaaa gggtaaggcg attgcattaa agaatgcgga caagcctgtt 2880
gttaaggctg agtttgttga agaagatgaa gaagaagaac atctgttact ggccatggaa 2940
attatttctg tacacgctga agcttttgag gatccttcca ttccgagaat ttccattgtt 3000
gaagtgttac tatctcttct atctttaccc tcaaaagcga agattgctaa agattgtttc 3060
aacgctctgt gccaaagcat atctgttgca ccaaatcaag aagaccttga tatgatacta 3120
tcaaatttac tatcaccaaa tcaatttgtc cgttcaacaa tattagaaac tcttgataac 3180
gaattcgaat tagaaccttt tatgaaatat tcacctgaag ttttcatttg cagatttgat 3240
tcggatcctt ccaaccgcga gattgcagat ttcatttggg agttcaacaa atttgtagtc 3300
aacgatgaat tactaaaaag cttattccca ctattcaatc aggatgatag tggcttgaga 3360
ttatttgcgg caaacgcgta cgcatttggt gcggtaagtc tgtttacctc tgaagagaac 3420
tcctcgaaag attacttaaa tgatttgctg aacttttata aagaaaaggc aaagccattg 3480
gagccaattc ttgatcaatt tggcttggtt cttgtttctg cgagtgaaca aaaagatcca 3540
tggcaaggaa gaagtaccgt tgctattaca ttaaaaatca tggctaaggc tttttctgca 3600
gaggatgata ctgtcgttaa cattataaaa tttttggtcg atgatggagg tctagtagac 3660
agagagccta ttgttcgtca agaaatgaaa gaagctggtg ttgaattaat tacgttacat 3720
ggctcacaaa actcgaagga tttaattcct atatttgaag aagcattaag ctccagtacg 3780
gacagtgcct taaaagagaa cgttattatt ttgtatggta cattagcaag acatttacag 3840
caaagtgatg caaggattca cacgatcatt gaaagattgc tttcaacttt ggatactcct 3900
tctgcggata ttcaacaggc tgtgtcggct tgtatagcac cactagtttt ccagttcaaa 3960
caaaaagttg gtgattactt gggtatccta atggagaaac tgctgaatcc aactgttgct 4020
tcttctatgc ggaaaggtgc cgcttggggt atcgctggtt tagtgaaagg ttacggtatc 4080
tcggctctct cggagtttga cattattcgc aacctcatcg aagctgcaga agataaaaag 4140

```
gagccaaaaa gacgtgaatc tgttggcttc tgctttcaat atttgtctga atctctagga   4200
aagtttttg aaccatatgt gatagaaatt cttccaaata ttttaaagaa tttaggggat   4260
gctgttcctg aagttagaga tgcaaccgct cgtgccacta aggctataat ggcgcatact   4320
acaggttacg gtgttaaaaa gttaattcca gttgctgttt ctaatttgga tgaaattgct   4380
tggagaacta agaggggctc tgttcaattg ttgggtaata tggcttattt agatcctact   4440
caattgtcag cttctttgtc caccattgtc ccagaaattg ttggtgtatt gaacgactct   4500
cacaaagagg tgcgtaaggc cgctgatgaa tccttgaaaa gattcggtga agttatcaga   4560
aatccggaaa ttcagaaatt ggtgcccgta cttttgcaag ctatcggtga tccaacaaaa   4620
tacactgaag aggccttgga ttcgttaatt caaacacaat ttgtccatta tattgatggt   4680
ccttcactag cactaattat tcatattatt catcgtggta tgcatgatag atctgccaac   4740
attaagagga aagcatgtaa gatcgtgggc aatatggcca ttttggttga taccaaagat   4800
ctcatcccat atttacaaca gctgatagat gaagtggaga ttgctatggt ggatccagtt   4860
ccaaatacta gagccacagc agcacgtgct ttgggtgctt tggtagaaag gttaggtgaa   4920
gagcaattcc cagatttgat tcctcgtcta ctagatacct taagtgacga atcaaaatct   4980
ggtgatcgtc tcggttctgc tcaagctcta gctgaagtta ttagtggctt gggcttgacc   5040
aagttggatg agatgttacc aaccatttta gctggtgtaa ccaattttcg tgcttatatc   5100
agggaaggat tcatgccttt gctgcttttc cttcctgttt gttttggatc acaatttgct   5160
ccatacatta atcagattat tcagcctatt ctttccggat tggccgataa tgatgaaaat   5220
attcgcgata ctgctttgaa ggctggtaaa ttaattgtca aaaactacgc tacaaaggcc   5280
gttgatttgt tgttgcctga attagaaagg ggtatgttcg atgaaaatga cagaattcgc   5340
ttatcttctg ttcaattaac cggagaacta ttgttccaag ttactggtat ttcctccagg   5400
aacgaatttt ctgaggaaga tggtgatcat aatggtgaat tctctggtaa attggtcgat   5460
gtacttggcc aagaccgtcg tgatagaatt ttagccgcat tatttgtatg caggaacgac   5520
acttctggta tcgtacgtgc tacgacggtt gacatttgga aggcattggt tccaaatact   5580
ccaagagctg tgaaagagat ccttccaaca ttgactggta tgatagtcac tcacttggct   5640
tcatcatcca atgtattacg caacattgct gctcagacct taggtgatct tgtccgtcgt   5700
gtaggtggta atgctttgtc ccaactgtta ccaagtttgg aggaatcttt gatagaaaca   5760
tcaaactcag attcgagaca aggtgtttgt attgctcttt atgagttaat tgaatcggct   5820
tctacggaaa cgatatcaca gttccaatct accatcgtta acattattcg tacggcatta   5880
attgatgagt cggctactgt cagagaagcg gctgcattat cttttgatgt attccaagat   5940
gttgtaggaa aaactgctgt tgatgaagtt ttaccatatt tgttgcatat gcttgaatct   6000
tctgataatt ctgactttgc tttgttaggt ttacaagaaa ttatgtcgaa gaagtccgac   6060
gtaatcttcc caattttaat tccaacccta ttagcccctc caatagacgc cttcagggct   6120
tctgctttag gttctttggc ggaagttgct ggctcagcct tatacaagcg tttatcaatt   6180
ataatcaacg cactagtgga tgcaatcata ggtacttctg aagatgaatc gaccaagggt   6240
gcattagaac ttgcattaga cagggtattc ttatctgtga atgatgacga aggtcttcac   6300
ccattacttc aacagattat gtcactacta aagagtgata atatagagaa acgcatagct   6360
gttttagaac gtttgccaaa tttcttcgat aagactgttc ttgattttga tgtctatatt   6420
ccgaactttg tctctcacgc aattttatca ttagatgatg aagatcaaag ggttgttaat   6480
ggtaacttca atgctttgtc tactttgttg aagaaggttg ataagcccac cttagaaaaa   6540
```

-continued

```
ttagttaagc ctgctaaaca gtcattggca ttaacaggca ggcaaggtca agatgtcgct   6600

gcatttaagc ttccaagagg ccctaactgt gttttgccta ttttcttgca tggtttgatg   6660

tatggttcga atgatgaaag ggaagaatct gcattagcca ttgctgacgt tgtttcgaag   6720

acccctgccg ctaacttgaa gccatttgtg agcgtaatta ctggtccatt aattcgtgtc   6780

gtgggtgaaa gatttagtag tgatatcaaa gcagcaattt tatttgcact taatgtgcta   6840

ttcattaaga ttccaatgtt cttgaggcct tttatccctc aattacaaag aacatttgtt   6900

aaatccttgt ctgacgctac caatgaaacg ttacgtctcc gcgccgcaaa ggctcttggt   6960

gccctgattg aacatcagcc tcgtgttgac cctctagtca ttgaactggt gacaggtgcc   7020

aagcaagcca cagatgaagg tgtcaagact gcgatgctta aagctttact ggaagttatt   7080

atgaaggctg gttccaaatt aaacgaaaat tctaagacaa acattgtcaa tttagttgag   7140

gaagaaatgt tgggtagcaa tgacaaattg gcagttgctt acgctaaatt aatcggatcg   7200

ttatcagaga ttttgtcgaa cgacgaagcc cacaagatat tgcaagacaa ggttttgaat   7260

gcagatctag atggagaaac cggtaagttt gctattctga ctttgaattc ctttttgaaa   7320

gatgcaccaa cacatatatt caatacgggc ttgatagacg aatttgtaag ttacattttg   7380

aatgcaatcc gttcccctga tgtttacttc ggagaaaatg gtaccattgc tgctggtaaa   7440

ttacttttat tagaaggaga aaagaggtct ccatttgtta aaaaggatgc tgcagaacca   7500

ttcaaaattg gcgatgaaaa catcaatctg ttaattaatg agttgagcaa agctgtctta   7560

caaccagcca gtaattctac ggatgtaaga aggttggcct tggtggttat aagaacacta   7620

gccagattca aatttgacga gtgcattaag caatacttcg atgtagtagg accatctgta   7680

ttttcttgct tgcgtgatcc tgttatccca attaagctcg cagcagaaaa agcatattta   7740

gctttgttca aattggttga agaagatgac atgcatactt tcaacgagtg gtttgctaaa   7800

atttcagatc gcggtaacag catcgaaact gtcacaggta ctacaattca attacggtct   7860

gttggggact ataccaagag ggttggtaaa aggttagcaa atgtcgaaag agaaaggatt   7920

gctgccggag gagacgcgga aacaatgttt agtgacagat ttgaagatga aagagaaata   7980

tgggctgtcg gaggtgttga attaaccact gatatttga                          8019
```

<210> SEQ ID NO 50
<211> LENGTH: 2672
<212> TYPE: PRT
<213> ORGANISM: Saccharomyces cerevisiae

<400> SEQUENCE: 50

```
Met Thr Ala Ile Leu Asn Trp Glu Asp Ile Ser Pro Val Leu Glu Lys
1               5                   10                  15

Gly Thr Arg Glu Ser His Val Ser Lys Arg Val Pro Phe Leu Gln Asp
            20                  25                  30

Ile Ser Gln Leu Val Arg Gln Glu Thr Leu Glu Lys Pro Gln Leu Ser
        35                  40                  45

Glu Ile Ala Phe Val Leu Leu Asn Thr Phe Thr Ile Tyr Glu Asp Asn
    50                  55                  60

Arg Ser Lys Ser Leu Val Thr Ser Ile Leu Leu Asp Ile Leu Asn Leu
65                  70                  75                  80

Glu Pro Cys Leu Leu Glu Asn Phe Ile Arg Phe Ile Ser Asp Val Val
                85                  90                  95

Ile Ser Asn Pro Ala Thr Lys Ala Val Ala Asp Tyr Leu Asn Leu Leu
            100                 105                 110
```

-continued

```
Asp Trp Ile Asn Ser Phe Leu Ile Phe Val Ser His Asn Ser Asn Leu
        115                 120                 125

Phe Glu Glu Tyr Ile Pro Lys Leu Leu Val Ala His Ser Tyr Ala Thr
    130                 135                 140

Phe Gly Val Glu Thr Ile Leu Asp Asn Gln Glu Glu Gly Lys Lys Ser
145                 150                 155                 160

Gln Asp Lys Gln Asn Gln His Arg Lys Arg Ile Arg Tyr Cys Ile Phe
                165                 170                 175

Gln Thr Thr Val Lys Ala Phe Leu Lys Cys Leu Lys Asp Asn Asp Asp
            180                 185                 190

Ser Ile Ser Phe Met Lys Ile Ser Ile Lys Thr Val Leu Glu Ser Tyr
        195                 200                 205

Ser Lys Leu Lys Ile Thr Ser Val Gly Val Val Met Ile Met Gly Ala
    210                 215                 220

Leu Thr Gln Ala Ala Leu Gln Leu Leu Ser Arg Gln Pro Ala Leu His
225                 230                 235                 240

Ser Val Leu Lys Glu Asn Ser Ala Glu Lys Tyr Cys Glu Tyr Leu Gly
                245                 250                 255

Lys Glu Val Phe Leu Gly Lys Asn Pro Pro Ser Ser Phe Cys Leu Glu
            260                 265                 270

Ile Gly Leu Lys Pro Phe Leu Lys Glu Phe Val Ser Gln Glu Leu Phe
        275                 280                 285

Ile Lys Phe Phe Ile Pro Asn Ile Glu Lys Ala Val Leu Arg Ser Pro
    290                 295                 300

Glu Val Gly Phe Ser Ile Leu Ser Glu Leu Tyr Ala Gly Val Ser Pro
305                 310                 315                 320

Glu Lys Val Asn Leu Leu Asn Ala Phe Ala Ser Ser Lys Leu Ile Asn
                325                 330                 335

Gln Tyr Phe Ser Ser Phe Lys Ser Ser Lys Glu Val Val Arg Ser Val
            340                 345                 350

Ser Leu Gln Ser Met Ile Ile Leu Leu Arg Lys Ile Ser Asn Thr Asp
        355                 360                 365

Thr Thr Leu Glu Asp Leu Thr Lys Leu Ile Asp Glu Ile Phe Lys Asn
    370                 375                 380

Ile Lys Ser Asn Leu Asn Ala Asp Tyr Lys Ser Leu Ile Ser Lys Ile
385                 390                 395                 400

Leu Ile Glu Ile Pro Leu Thr His Tyr Glu Val Ser Glu Lys Ile Cys
                405                 410                 415

Lys Gly Leu Ser Pro Tyr Ile Gly Lys Glu Gly Asn Glu Ala Ala Leu
            420                 425                 430

Thr Leu Met Leu Asn Ala Phe Phe Val His Tyr Phe Ser Leu Gly Lys
        435                 440                 445

Pro Ile Glu Asp Leu Asp Lys Ile Ile Ser Ala Gly Phe Ala Asp Lys
    450                 455                 460

Lys Pro Ala Leu Lys Lys Cys Trp Phe Ala Ala Phe Leu Asn Asn Ser
465                 470                 475                 480

Asn Ala Ala Ser Glu Glu Val Ile Leu Asn Phe Ile Asp Gly Cys Leu
                485                 490                 495

Glu Phe Val Lys Asp Ser Ile Ile His Tyr Gln Thr His Gly His Ala
            500                 505                 510

Cys Ile Leu Ala Ser Ile Glu Phe Thr Asn Lys Ile Leu Ala Leu Asp
        515                 520                 525

Asn Thr Glu Leu Asn Asp Arg Val Met Gln Leu Ile Glu Thr Leu Pro
    530                 535                 540
```

-continued

```
Glu Asn Ser Ser Ile Gly Asp Ala Ile Leu Thr Ala Ala Leu Ser Thr
545                 550                 555                 560

Glu Leu Ser Ile Glu Asn Arg Ile His Ala Val Asn Leu Leu Gln Glu
                565                 570                 575

Leu Phe Tyr Lys Lys Pro Glu Phe Ile Gly Phe Ser Val Ile Asp Ala
            580                 585                 590

Ile Glu Arg Arg Met Arg Val Gln Glu Leu Ile Pro Gln Gln Asn Thr
        595                 600                 605

Ser Phe Lys Tyr Val Thr Ser Val Leu Leu Ala Ile Thr Ser Glu Leu
    610                 615                 620

Pro Asp Lys Glu Ala Ser Ile Lys Val Leu Ile Asn Ala Leu Val Ile
625                 630                 635                 640

Ala Gln Trp Asn Ile Phe Asn Ile Lys Asn Gly Trp Ala Gly Leu Val
                645                 650                 655

Leu Arg Ala Arg Leu Asp Pro Ala Glu Val Val Lys Glu His Ala Ser
            660                 665                 670

Val Ile Met Glu Lys Ile Leu Glu Ile Thr Gly Ser Cys Glu Trp Ile
        675                 680                 685

Asp Thr Ile Tyr Gly Ala Cys Gly Leu Gln Ala Ala Ala Tyr Ala Ala
    690                 695                 700

Phe Ile Gln Pro Asn Glu Phe Thr Pro Ile Leu Cys Lys Thr Ile Glu
705                 710                 715                 720

Ala Asp Leu Thr Ala Asp Asp Phe Ser Arg Leu Ser Glu Glu Asp Phe
                725                 730                 735

Glu Ile Phe Ala Gly Glu Glu Gly Val Leu Val Val Asp Val Leu Glu
            740                 745                 750

Glu Ser Met Asn Lys Lys Leu Ser Asn Lys Asn Ser Lys Glu Tyr Glu
        755                 760                 765

Thr Leu Met Trp Glu Gln Lys Ile Arg Lys Glu Gln Ala Lys Lys Asn
    770                 775                 780

Val Lys Lys Leu Ser Lys Glu Glu Gln Glu Leu Val Asn Glu Gln Leu
785                 790                 795                 800

Ala Lys Glu Ser Ala Val Arg Ser His Val Ser Glu Ile Ser Thr Arg
                805                 810                 815

Leu Lys Arg Gly Ile Arg Leu Val Ser Glu Leu Ser Lys Ala Ala Cys
            820                 825                 830

Leu Val Gln Asn Gly Ile Ala Thr Trp Phe Pro Leu Ala Val Thr Lys
        835                 840                 845

Leu Leu Tyr Leu Cys Ser Glu Pro Asn Ile Ser Lys Leu Thr Glu Asp
    850                 855                 860

Val Asn Asn Val Phe Leu Gln Leu Ser Gln Asn Val Ser Glu Arg Leu
865                 870                 875                 880

Gly Asn Ile Arg Leu Phe Leu Gly Leu Ala Thr Leu Arg Val His Asn
                885                 890                 895

Ala Asn Gly Ile Ser Gln Asp Tyr Leu Gln Glu Pro Leu Val Glu Leu
            900                 905                 910

Leu Thr Arg Val Leu Phe Arg Ile Lys Phe Val Ser Asn Gln Ala Ala
        915                 920                 925

Ile Asp Ser Ile Ser Leu Thr Tyr Ile Leu Pro Leu Leu Ile Asn Val
    930                 935                 940

Leu Glu Lys Gly Lys Ala Ile Ala Leu Lys Asn Ala Asp Lys Pro Val
945                 950                 955                 960

Val Lys Ala Glu Phe Val Glu Glu Asp Glu Glu Glu Glu His Leu Leu
```

```
                965                 970                 975

Leu Ala Met Glu Ile Ile Ser Val His Ala Glu Ala Phe Glu Asp Pro
            980                 985                 990

Ser Ile Pro Arg Ile Ser Ile Val  Glu Val Leu Leu Ser  Leu Leu Ser
        995                 1000                1005

Leu Pro  Ser Lys Ala Lys Ile  Ala Lys Asp Cys Phe  Asn Ala Leu
    1010                 1015                 1020

Cys Gln  Ser Ile Ser Val Ala  Pro Asn Gln Glu Asp  Leu Asp Met
    1025                 1030                 1035

Ile Leu  Ser Asn Leu Leu Ser  Pro Asn Gln Phe Val  Arg Ser Thr
    1040                 1045                 1050

Ile Leu  Glu Thr Leu Asp Asn  Glu Phe Glu Leu Glu  Pro Phe Met
    1055                 1060                 1065

Lys Tyr  Ser Pro Glu Val Phe  Ile Cys Arg Phe Asp  Ser Asp Pro
    1070                 1075                 1080

Ser Asn  Arg Glu Ile Ala Asp  Phe Ile Trp Glu Phe  Asn Lys Phe
    1085                 1090                 1095

Val Val  Asn Asp Glu Leu Leu  Lys Ser Leu Phe Pro  Leu Phe Asn
    1100                 1105                 1110

Gln Asp  Asp Ser Gly Leu Arg  Leu Phe Ala Ala Asn  Ala Tyr Ala
    1115                 1120                 1125

Phe Gly  Ala Val Ser Leu Phe  Thr Ser Glu Glu Asn  Ser Ser Lys
    1130                 1135                 1140

Asp Tyr  Leu Asn Asp Leu Leu  Asn Phe Tyr Lys Glu  Lys Ala Lys
    1145                 1150                 1155

Pro Leu  Glu Pro Ile Leu Asp  Gln Phe Gly Leu Val  Leu Val Ser
    1160                 1165                 1170

Ala Ser  Glu Gln Lys Asp Pro  Trp Gln Gly Arg Ser  Thr Val Ala
    1175                 1180                 1185

Ile Thr  Leu Lys Ile Met Ala  Lys Ala Phe Ser Ala  Glu Asp Asp
    1190                 1195                 1200

Thr Val  Val Asn Ile Ile Lys  Phe Leu Val Asp Asp  Gly Gly Leu
    1205                 1210                 1215

Val Asp  Arg Glu Pro Ile Val  Arg Gln Glu Met Lys  Glu Ala Gly
    1220                 1225                 1230

Val Glu  Leu Ile Thr Leu His  Gly Ser Gln Asn Ser  Lys Asp Leu
    1235                 1240                 1245

Ile Pro  Ile Phe Glu Glu Ala  Leu Ser Ser Ser Thr  Asp Ser Ala
    1250                 1255                 1260

Leu Lys  Glu Asn Val Ile Ile  Leu Tyr Gly Thr Leu  Ala Arg His
    1265                 1270                 1275

Leu Gln  Gln Ser Asp Ala Arg  Ile His Thr Ile Ile  Glu Arg Leu
    1280                 1285                 1290

Leu Ser  Thr Leu Asp Thr Pro  Ser Ala Asp Ile Gln  Gln Ala Val
    1295                 1300                 1305

Ser Ala  Cys Ile Ala Pro Leu  Val Phe Gln Phe Lys  Gln Lys Val
    1310                 1315                 1320

Gly Asp  Tyr Leu Gly Ile Leu  Met Glu Lys Leu Leu  Asn Pro Thr
    1325                 1330                 1335

Val Ala  Ser Ser Met Arg Lys  Gly Ala Ala Trp Gly  Ile Ala Gly
    1340                 1345                 1350

Leu Val  Lys Gly Tyr Gly Ile  Ser Ala Leu Ser Glu  Phe Asp Ile
    1355                 1360                 1365
```

```
Ile Arg  Asn Leu Ile Glu Ala  Ala Glu Asp Lys Lys  Glu Pro Lys
    1370                 1375                 1380

Arg Arg  Glu Ser Val Gly Phe  Cys Phe Gln Tyr Leu  Ser Glu Ser
    1385                 1390                 1395

Leu Gly  Lys Phe Phe Glu Pro  Tyr Val Ile Glu Ile  Leu Pro Asn
    1400                 1405                 1410

Ile Leu  Lys Asn Leu Gly Asp  Ala Val Pro Glu Val  Arg Asp Ala
    1415                 1420                 1425

Thr Ala  Arg Ala Thr Lys Ala  Ile Met Ala His Thr  Thr Gly Tyr
    1430                 1435                 1440

Gly Val  Lys Lys Leu Ile Pro  Val Ala Val Ser Asn  Leu Asp Glu
    1445                 1450                 1455

Ile Ala  Trp Arg Thr Lys Arg  Gly Ser Val Gln Leu  Leu Gly Asn
    1460                 1465                 1470

Met Ala  Tyr Leu Asp Pro Thr  Gln Leu Ser Ala Ser  Leu Ser Thr
    1475                 1480                 1485

Ile Val  Pro Glu Ile Val Gly  Val Leu Asn Asp Ser  His Lys Glu
    1490                 1495                 1500

Val Arg  Lys Ala Ala Asp Glu  Ser Leu Lys Arg Phe  Gly Glu Val
    1505                 1510                 1515

Ile Arg  Asn Pro Glu Ile Gln  Lys Leu Val Pro Val  Leu Leu Gln
    1520                 1525                 1530

Ala Ile  Gly Asp Pro Thr Lys  Tyr Thr Glu Glu Ala  Leu Asp Ser
    1535                 1540                 1545

Leu Ile  Gln Thr Gln Phe Val  His Tyr Ile Asp Gly  Pro Ser Leu
    1550                 1555                 1560

Ala Leu  Ile Ile His Ile Ile  His Arg Gly Met His  Asp Arg Ser
    1565                 1570                 1575

Ala Asn  Ile Lys Arg Lys Ala  Cys Lys Ile Val Gly  Asn Met Ala
    1580                 1585                 1590

Ile Leu  Val Asp Thr Lys Asp  Leu Ile Pro Tyr Leu  Gln Gln Leu
    1595                 1600                 1605

Ile Asp  Glu Val Glu Ile Ala  Met Val Asp Pro Val  Pro Asn Thr
    1610                 1615                 1620

Arg Ala  Thr Ala Ala Arg Ala  Leu Gly Ala Leu Val  Glu Arg Leu
    1625                 1630                 1635

Gly Glu  Glu Gln Phe Pro Asp  Leu Ile Pro Arg Leu  Leu Asp Thr
    1640                 1645                 1650

Leu Ser  Asp Glu Ser Lys Ser  Gly Asp Arg Leu Gly  Ser Ala Gln
    1655                 1660                 1665

Ala Leu  Ala Glu Val Ile Ser  Gly Leu Gly Leu Thr  Lys Leu Asp
    1670                 1675                 1680

Glu Met  Leu Pro Thr Ile Leu  Ala Gly Val Thr Asn  Phe Arg Ala
    1685                 1690                 1695

Tyr Ile  Arg Glu Gly Phe Met  Pro Leu Leu Leu Phe  Leu Pro Val
    1700                 1705                 1710

Cys Phe  Gly Ser Gln Phe Ala  Pro Tyr Ile Asn Gln  Ile Ile Gln
    1715                 1720                 1725

Pro Ile  Leu Ser Gly Leu Ala  Asp Asn Asp Glu Asn  Ile Arg Asp
    1730                 1735                 1740

Thr Ala  Leu Lys Ala Gly Lys  Leu Ile Val Lys Asn  Tyr Ala Thr
    1745                 1750                 1755

Lys Ala  Val Asp Leu Leu Leu  Pro Glu Leu Glu Arg  Gly Met Phe
    1760                 1765                 1770
```

```
Asp Glu  Asn Asp Arg Ile Arg  Leu Ser Ser Val Gln  Leu Thr Gly
    1775                 1780                 1785

Glu Leu  Leu Phe Gln Val Thr  Gly Ile Ser Ser Arg  Asn Glu Phe
    1790                 1795                 1800

Ser Glu  Glu Asp Gly Asp His  Asn Gly Glu Phe Ser  Gly Lys Leu
    1805                 1810                 1815

Val Asp  Val Leu Gly Gln Asp  Arg Arg Asp Arg Ile  Leu Ala Ala
    1820                 1825                 1830

Leu Phe  Val Cys Arg Asn Asp  Thr Ser Gly Ile Val  Arg Ala Thr
    1835                 1840                 1845

Thr Val  Asp Ile Trp Lys Ala  Leu Val Pro Asn Thr  Pro Arg Ala
    1850                 1855                 1860

Val Lys  Glu Ile Leu Pro Thr  Leu Thr Gly Met Ile  Val Thr His
    1865                 1870                 1875

Leu Ala  Ser Ser Ser Asn Val  Leu Arg Asn Ile Ala  Ala Gln Thr
    1880                 1885                 1890

Leu Gly  Asp Leu Val Arg Arg  Val Gly Gly Asn Ala  Leu Ser Gln
    1895                 1900                 1905

Leu Leu  Pro Ser Leu Glu Glu  Ser Leu Ile Glu Thr  Ser Asn Ser
    1910                 1915                 1920

Asp Ser  Arg Gln Gly Val Cys  Ile Ala Leu Tyr Glu  Leu Ile Glu
    1925                 1930                 1935

Ser Ala  Ser Thr Glu Thr Ile  Ser Gln Phe Gln Ser  Thr Ile Val
    1940                 1945                 1950

Asn Ile  Ile Arg Thr Ala Leu  Ile Asp Glu Ser Ala  Thr Val Arg
    1955                 1960                 1965

Glu Ala  Ala Ala Leu Ser Phe  Asp Val Phe Gln Asp  Val Val Gly
    1970                 1975                 1980

Lys Thr  Ala Val Asp Glu Val  Leu Pro Tyr Leu Leu  His Met Leu
    1985                 1990                 1995

Glu Ser  Ser Asp Asn Ser Asp  Phe Ala Leu Leu Gly  Leu Gln Glu
    2000                 2005                 2010

Ile Met  Ser Lys Lys Ser Asp  Val Ile Phe Pro Ile  Leu Ile Pro
    2015                 2020                 2025

Thr Leu  Leu Ala Pro Pro Ile  Asp Ala Phe Arg Ala  Ser Ala Leu
    2030                 2035                 2040

Gly Ser  Leu Ala Glu Val Ala  Gly Ser Ala Leu Tyr  Lys Arg Leu
    2045                 2050                 2055

Ser Ile  Ile Ile Asn Ala Leu  Val Asp Ala Ile Ile  Gly Thr Ser
    2060                 2065                 2070

Glu Asp  Glu Ser Thr Lys Gly  Ala Leu Glu Leu Ala  Leu Asp Arg
    2075                 2080                 2085

Val Phe  Leu Ser Val Asn Asp  Asp Glu Gly Leu His  Pro Leu Leu
    2090                 2095                 2100

Gln Gln  Ile Met Ser Leu Leu  Lys Ser Asp Asn Ile  Glu Lys Arg
    2105                 2110                 2115

Ile Ala  Val Leu Glu Arg Leu  Pro Asn Phe Phe Asp  Lys Thr Val
    2120                 2125                 2130

Leu Asp  Phe Asp Val Tyr Ile  Pro Asn Phe Val Ser  His Ala Ile
    2135                 2140                 2145

Leu Ser  Leu Asp Asp Glu Asp  Gln Arg Val Val Asn  Gly Asn Phe
    2150                 2155                 2160

Asn Ala  Leu Ser Thr Leu Leu  Lys Lys Val Asp Lys  Pro Thr Leu
```

```
    2165                2170                2175

Glu Lys  Leu Val Lys Pro Ala  Lys Gln Ser Leu Ala  Leu Thr Gly
    2180                2185                2190

Arg Gln  Gly Gln Asp Val Ala  Ala Phe Lys Leu Pro  Arg Gly Pro
    2195                2200                2205

Asn Cys  Val Leu Pro Ile Phe  Leu His Gly Leu Met  Tyr Gly Ser
    2210                2215                2220

Asn Asp  Glu Arg Glu Glu Ser  Ala Leu Ala Ile Ala  Asp Val Val
    2225                2230                2235

Ser Lys  Thr Pro Ala Ala Asn  Leu Lys Pro Phe Val  Ser Val Ile
    2240                2245                2250

Thr Gly  Pro Leu Ile Arg Val  Val Gly Glu Arg Phe  Ser Ser Asp
    2255                2260                2265

Ile Lys  Ala Ala Ile Leu Phe  Ala Leu Asn Val Leu  Phe Ile Lys
    2270                2275                2280

Ile Pro  Met Phe Leu Arg Pro  Phe Ile Pro Gln Leu  Gln Arg Thr
    2285                2290                2295

Phe Val  Lys Ser Leu Ser Asp  Ala Thr Asn Glu Thr  Leu Arg Leu
    2300                2305                2310

Arg Ala  Ala Lys Ala Leu Gly  Ala Leu Ile Glu His  Gln Pro Arg
    2315                2320                2325

Val Asp  Pro Leu Val Ile Glu  Leu Val Thr Gly Ala  Lys Gln Ala
    2330                2335                2340

Thr Asp  Glu Gly Val Lys Thr  Ala Met Leu Lys Ala  Leu Leu Glu
    2345                2350                2355

Val Ile  Met Lys Ala Gly Ser  Lys Leu Asn Glu Asn  Ser Lys Thr
    2360                2365                2370

Asn Ile  Val Asn Leu Val Glu  Glu Glu Met Leu Gly  Ser Asn Asp
    2375                2380                2385

Lys Leu  Ala Val Ala Tyr Ala  Lys Leu Ile Gly Ser  Leu Ser Glu
    2390                2395                2400

Ile Leu  Ser Asn Asp Glu Ala  His Lys Ile Leu Gln  Asp Lys Val
    2405                2410                2415

Leu Asn  Ala Asp Leu Asp Gly  Glu Thr Gly Lys Phe  Ala Ile Leu
    2420                2425                2430

Thr Leu  Asn Ser Phe Leu Lys  Asp Ala Pro Thr His  Ile Phe Asn
    2435                2440                2445

Thr Gly  Leu Ile Asp Glu Phe  Val Ser Tyr Ile Leu  Asn Ala Ile
    2450                2455                2460

Arg Ser  Pro Asp Val Tyr Phe  Gly Glu Asn Gly Thr  Ile Ala Ala
    2465                2470                2475

Gly Lys  Leu Leu Leu Leu Glu  Gly Glu Lys Arg Ser  Pro Phe Val
    2480                2485                2490

Lys Lys  Asp Ala Ala Glu Pro  Phe Lys Ile Gly Asp  Glu Asn Ile
    2495                2500                2505

Asn Leu  Leu Ile Asn Glu Leu  Ser Lys Ala Val Leu  Gln Pro Ala
    2510                2515                2520

Ser Asn  Ser Thr Asp Val Arg  Arg Leu Ala Leu Val  Val Ile Arg
    2525                2530                2535

Thr Leu  Ala Arg Phe Lys Phe  Asp Glu Cys Ile Lys  Gln Tyr Phe
    2540                2545                2550

Asp Val  Val Gly Pro Ser Val  Phe Ser Cys Leu Arg  Asp Pro Val
    2555                2560                2565
```

-continued

```
Ile Pro Ile Lys Leu Ala Ala Glu Lys Ala Tyr Leu Ala Leu Phe
    2570                2575                2580

Lys Leu Val Glu Glu Asp Asp Met His Thr Phe Asn Glu Trp Phe
    2585                2590                2595

Ala Lys Ile Ser Asp Arg Gly Asn Ser Ile Glu Thr Val Thr Gly
    2600                2605                2610

Thr Thr Ile Gln Leu Arg Ser Val Gly Asp Tyr Thr Lys Arg Val
    2615                2620                2625

Gly Lys Arg Leu Ala Asn Val Glu Arg Glu Arg Ile Ala Ala Gly
    2630                2635                2640

Gly Asp Ala Glu Thr Met Phe Ser Asp Arg Phe Glu Asp Glu Arg
    2645                2650                2655

Glu Ile Trp Ala Val Gly Gly Val Glu Leu Thr Thr Asp Ile
    2660                2665                2670
```

<210> SEQ ID NO 51
<211> LENGTH: 4980
<212> TYPE: DNA
<213> ORGANISM: Saccharomyces cerevisiae

<400> SEQUENCE: 51

```
atgtcattga gtcatctcac tttagatcaa tattatgaaa tacagtgcaa cgaacttgaa      60

gcgatacgtt ccatttatat ggatgacttt actgacttaa ctaaaagaaa gtctagctgg     120

gataagcagc cacagattat attcgaaatt acgcttcgat ctgttgacaa agagccggtt     180

gaatcttcta taacattaca ttttgcgatg accccaatgt atccttatac cgctccagaa     240

atagaattca aaaatgtaca aaatgtaatg gatagtcaat tgcaaatgct gaaaagtgaa     300

tttaagaaaa tccacaacac ctcccgaggc caagagatta tatttgaaat tacatctttt     360

actcaagaaa aactggacga atttcaaaat gtggtaaata cacagtcctt ggaagatgat     420

cgattacaaa gaatcaaaga aactaaagaa caattagaaa aggaagaaag agaaaaacaa     480

caggaaacaa taaaaaaaag atcagatgag cagcgaagga tagatgaaat tgttcaaaga     540

gagttggaga aaagacaaga tgatgatgat gatttgctat tcaacagaac aacccagtta     600

gatttacaac caccttcaga atgggttgca tcaggtgaag ctattgtctt ttcaaaaact     660

ataaaggcaa aattgcctaa taactcaatg ttcaagttta aagcagttgt aaatcctaag     720

ccaataaaac tgacatcaga tatatttagt ttttccaaac aatttcttgt gaagccttat     780

ataccaccag aatctccgtt ggcagatttt ttaatgtctt ctgaaatgat ggaaaatttc     840

tactatttgc tatctgaaat tgaattggat aatagctatt tcaacacaag taatggaaaa     900

aaagaaatag caaatttaga gaaagagtta gagacggtgt tgaaagctaa gcatgacaat     960

gtgaatcgat tgttcggtta tacggtggag cgcatgggga gaaataatgc aacgtttgtt    1020

tggaaaataa gactcttgac agagtactgt aactactatc cattgggaga tttgatacaa    1080

tctgttggat ttgttaactt agcaacagcg cgtatttgga tgattagatt gcttgaagga    1140

ttggaggcca tacacaaatt gggaattgtt cataaatgta tcaacttaga aaccgtgatc    1200

ctggtgaagg atgcagattt tggaagcact attcccaagt tagttcactc cacttatggc    1260

tacactgttt tgaatatgct atcgagatat ccaaataaaa atggttcttc ggttgagtta    1320

tctccaagta catggatagc ccctgagttg ttgaaattca ataacgccaa acctcaaaga    1380

ttaactgata tttggcaact tggtgttttg tttatccaga taatcagtgg atctgatata    1440

gtgatgaatt ttgaaacgcc tcaagaattc ctagattcaa caagtatgga tgaaacttta    1500

tatgatcttc tttcgaaaat gcttaataac gatccgaaga aaagattagg aacattagaa    1560
```

ctactgccca tgaaattctt aaggaccaat attgactcta caatcaatcg atttaactta 1620
gtttccgaaa gtgtcaattc taattccttg gagttaactc ctggagatac cataaccgtt 1680
cggggcaatg gaggtagaac actttcacaa tcgagtatac gaagaagatc atttaatgtt 1740
ggttccagat tctcttctat aaatcctgca acgcgatcac gatatgcttc tgactttgaa 1800
gagattgcag ttttaggcca gggcgcattt ggacaagttg tcaaggcacg taatgctctc 1860
gatagcagat actatgcgat caagaagatt agacatacag aagaaaagtt atctactata 1920
ttgagtgaag taatgctgtt agcaagctta aatcatcaat atgttgtgcg ttactatgct 1980
gcatggttag aagaagacag tatggatgaa aacgtttttg aatcaactga tgaagaaagt 2040
gacttgagcg aatcttcctc tgattttgag gaaaatgatt tattagatca aagcagtatt 2100
tttaaaaata gaacaaatca cgatttggat aatagtaact gggatttcat atcggggtca 2160
ggatatccgg atattgtctt tgaaaatagt tctcgtgatg atgaaaatga agatctagac 2220
catgatactt cctcgacttc ctcgagcgaa agtcaagatg atactgataa agaatcaaag 2280
agtatccaga acgttccaag aaggaggaat tttgtaaaac cgatgactgc tgttaagaag 2340
aaaagtacgc tttttattca aatggagtac tgtgaaaata gaacgctata tgatttgatc 2400
cattctgaaa atttaaatca acaacgtgat gaatattgga ggttatttcg acaaattttg 2460
gaagcactga gttatataca ttcccagggt atcattcata gggatctgaa gccaatgaat 2520
atttttatag atgaatcgag aaatgttaaa atcggtgatt ttgggttagc taagaacgtc 2580
catagatctc tggatatact taagctagat tcacagaatt tgccaggcag ctcagataat 2640
ttaacatccg ccattggtac agcaatgtat gttgctactg aagttttaga tggtacaggt 2700
cactataatg aaaagattga tatgtattca cttggaatca tttttttga aatgatctat 2760
cctttcagta caggtatgga gagagttaat attttgaaaa agttacgatc agtgtcgata 2820
gaatttcctc ctgatttcga cgataataag atgaaagttg aaaagaaaat tataaggtta 2880
ctcatagacc atgatcccaa taaaaggcct ggtgctagga cattattaaa tagtggttgg 2940
cttcctgtga agcatcagga tgaagtaatc aaagaggctt taaaaagttt gtcgaatcct 3000
tcatcccctt ggcaacagca agttcgagaa agtttattta accaatctta cagtctaaca 3060
aatgatattc tatttgataa ctcagttcca acatccactc ctttcgcaaa cattctcagg 3120
tcccaaatga cagaagaggt agttaaaatt ttcaggaaac atggaggaat tgaaaataat 3180
gctcctccga ggatttttcc aaaggccccc atatacggta cgcagaatgt atatgaagtg 3240
cttgacaagg gcggtaccgt cttgcagtta caatatgatt taacttatcc tatggctagg 3300
tatctatcta aaaatccaag tctgatttct aagcaatata ggatgcagca cgtttaccga 3360
cctcctgatc attcaaggtc aagtttggaa cctagaaagt ttggtgagat tgacttcgac 3420
ataatttcaa aatcttcctc agagtcagga ttttatgatg cagaaagctt gaaaattatc 3480
gatgaaatat taaccgtatt tcctgtattt gagaaaacaa acactttttt catattaaat 3540
catgctgata ttttggagag tgttttcaac tttacaaata ttgataaagc ccaaaggcct 3600
ctagtttcac gaatgttgtc gcaagtaggc tttgcaaggt ccttcaagga agtaaagaat 3660
gaactaaagg cgcaactgaa catatcttct acggcattga atgatttgga gttatttgat 3720
tttagactgg acttcgaagc agccaaaaaa cgcctgtata aattgatgat tgatagtccg 3780
catctaaaaa aaattgagga ctctttgtcc catatatcaa aggttctcag ttacctaaaa 3840
cccttagaag ttgcaagaaa tgttgtgata tctcctttga gtaactacaa tagcgctttt 3900
tacaaaggag gtatcatgtt tcatgcagtt tatgacgatg gatcctcacg taatatgata 3960

```
gctgctggag ggaggtatga cactttgata tcctttttg ccagaccatc aggaaaaaag   4020

agcagcaata ctcgtaaggc tgtaggtttc aacttagcgt gggaaacaat attcggtata   4080

gcccaaaact atttcaaact cgcttctgga aataggataa agaagagaaa taggtttttg   4140

aaagatacag ctgttgattg gaagccaagc aggtgtgatg tattgatatc gagtttttcg   4200

aactctttgt tggacacaat cggggttaca atactgaata cattgtggaa gcaaaacatt   4260

aaagcggata tgttaaggga ttgttcctcg gtggatgatg tcgttactgg cgctcaacag   4320

gatggtatag actggatttt gctgattaag caacaagcgt atccactaac caatcacaag   4380

agaaagtaca agccattaaa aataaaaaaa ttgagcacta atgttgacat agatttagat   4440

cttgatgagt ttttaacctt gtaccaacaa gaaactggta ataaatcttt gatcaacgat   4500

agtctcactt tgggcgataa ggctgatgaa tttaaaagat gggatgaaaa cagcagtgcc   4560

ggtagtagtc aagaaggtga catagatgat gttgttgctg gttcgactaa taatcaaaag   4620

gtaatttatg ttccaaacat ggctacaaga tctaagaaag ctaataaaag ggaaaagtgg   4680

gtttatgagg atgcagccag aaattcttcg aatatgatat tacacaattt atccaatgca   4740

ccaattatca ctgttgatgc cttaagagat gaaactttag aaataatctc aattacttct   4800

ttggctcaga aggaagaatg gctgagaaaa gtttttgggt caggtaataa ctcgactcct   4860

agaagctttg ccacgagcat ttataataac ctctccaaag aggctcataa agggaatagg   4920

tgggcaatat tatactgcca caaaaccgga aaatcatctg ttatcgattt acagaggtag   4980
```

<210> SEQ ID NO 52
<211> LENGTH: 1659
<212> TYPE: PRT
<213> ORGANISM: Saccharomyces cerevisiae

<400> SEQUENCE: 52

```
Met Ser Leu Ser His Leu Thr Leu Asp Gln Tyr Tyr Glu Ile Gln Cys
1               5                   10                  15

Asn Glu Leu Glu Ala Ile Arg Ser Ile Tyr Met Asp Asp Phe Thr Asp
            20                  25                  30

Leu Thr Lys Arg Lys Ser Ser Trp Asp Lys Gln Pro Gln Ile Ile Phe
        35                  40                  45

Glu Ile Thr Leu Arg Ser Val Asp Lys Glu Pro Val Glu Ser Ser Ile
    50                  55                  60

Thr Leu His Phe Ala Met Thr Pro Met Tyr Pro Tyr Thr Ala Pro Glu
65                  70                  75                  80

Ile Glu Phe Lys Asn Val Gln Asn Val Met Asp Ser Gln Leu Gln Met
                85                  90                  95

Leu Lys Ser Glu Phe Lys Lys Ile His Asn Thr Ser Arg Gly Gln Glu
            100                 105                 110

Ile Ile Phe Glu Ile Thr Ser Phe Thr Gln Glu Lys Leu Asp Glu Phe
        115                 120                 125

Gln Asn Val Val Asn Thr Gln Ser Leu Glu Asp Asp Arg Leu Gln Arg
    130                 135                 140

Ile Lys Glu Thr Lys Glu Gln Leu Glu Lys Glu Glu Arg Glu Lys Gln
145                 150                 155                 160

Gln Glu Thr Ile Lys Lys Arg Ser Asp Glu Gln Arg Arg Ile Asp Glu
                165                 170                 175

Ile Val Gln Arg Glu Leu Glu Lys Arg Gln Asp Asp Asp Asp Asp Leu
            180                 185                 190

Leu Phe Asn Arg Thr Thr Gln Leu Asp Leu Gln Pro Pro Ser Glu Trp
```

-continued

```
        195                 200                 205

Val Ala Ser Gly Glu Ala Ile Val Phe Ser Lys Thr Ile Lys Ala Lys
    210                 215                 220

Leu Pro Asn Asn Ser Met Phe Lys Phe Lys Ala Val Val Asn Pro Lys
225                 230                 235                 240

Pro Ile Lys Leu Thr Ser Asp Ile Phe Ser Phe Ser Lys Gln Phe Leu
                245                 250                 255

Val Lys Pro Tyr Ile Pro Pro Glu Ser Pro Leu Ala Asp Phe Leu Met
            260                 265                 270

Ser Ser Glu Met Met Glu Asn Phe Tyr Tyr Leu Leu Ser Glu Ile Glu
        275                 280                 285

Leu Asp Asn Ser Tyr Phe Asn Thr Ser Asn Gly Lys Lys Glu Ile Ala
    290                 295                 300

Asn Leu Glu Lys Glu Leu Glu Thr Val Leu Lys Ala Lys His Asp Asn
305                 310                 315                 320

Val Asn Arg Leu Phe Gly Tyr Thr Val Glu Arg Met Gly Arg Asn Asn
                325                 330                 335

Ala Thr Phe Val Trp Lys Ile Arg Leu Leu Thr Glu Tyr Cys Asn Tyr
            340                 345                 350

Tyr Pro Leu Gly Asp Leu Ile Gln Ser Val Gly Phe Val Asn Leu Ala
        355                 360                 365

Thr Ala Arg Ile Trp Met Ile Arg Leu Leu Glu Gly Leu Glu Ala Ile
    370                 375                 380

His Lys Leu Gly Ile Val His Lys Cys Ile Asn Leu Glu Thr Val Ile
385                 390                 395                 400

Leu Val Lys Asp Ala Asp Phe Gly Ser Thr Ile Pro Lys Leu Val His
                405                 410                 415

Ser Thr Tyr Gly Tyr Thr Val Leu Asn Met Leu Ser Arg Tyr Pro Asn
            420                 425                 430

Lys Asn Gly Ser Ser Val Glu Leu Ser Pro Ser Thr Trp Ile Ala Pro
        435                 440                 445

Glu Leu Leu Lys Phe Asn Asn Ala Lys Pro Gln Arg Leu Thr Asp Ile
    450                 455                 460

Trp Gln Leu Gly Val Leu Phe Ile Gln Ile Ile Ser Gly Ser Asp Ile
465                 470                 475                 480

Val Met Asn Phe Glu Thr Pro Gln Glu Phe Leu Asp Ser Thr Ser Met
                485                 490                 495

Asp Glu Thr Leu Tyr Asp Leu Leu Ser Lys Met Leu Asn Asn Asp Pro
            500                 505                 510

Lys Lys Arg Leu Gly Thr Leu Glu Leu Leu Pro Met Lys Phe Leu Arg
        515                 520                 525

Thr Asn Ile Asp Ser Thr Ile Asn Arg Phe Asn Leu Val Ser Glu Ser
    530                 535                 540

Val Asn Ser Asn Ser Leu Glu Leu Thr Pro Gly Asp Thr Ile Thr Val
545                 550                 555                 560

Arg Gly Asn Gly Gly Arg Thr Leu Ser Gln Ser Ser Ile Arg Arg Arg
                565                 570                 575

Ser Phe Asn Val Gly Ser Arg Phe Ser Ser Ile Asn Pro Ala Thr Arg
            580                 585                 590

Ser Arg Tyr Ala Ser Asp Phe Glu Glu Ile Ala Val Leu Gly Gln Gly
        595                 600                 605

Ala Phe Gly Gln Val Val Lys Ala Arg Asn Ala Leu Asp Ser Arg Tyr
    610                 615                 620
```

```
Tyr Ala Ile Lys Lys Ile Arg His Thr Glu Glu Lys Leu Ser Thr Ile
625                 630                 635                 640

Leu Ser Glu Val Met Leu Leu Ala Ser Leu Asn His Gln Tyr Val Val
                645                 650                 655

Arg Tyr Tyr Ala Ala Trp Leu Glu Glu Asp Ser Met Asp Glu Asn Val
            660                 665                 670

Phe Glu Ser Thr Asp Glu Glu Ser Asp Leu Ser Glu Ser Ser Ser Asp
        675                 680                 685

Phe Glu Glu Asn Asp Leu Leu Asp Gln Ser Ser Ile Phe Lys Asn Arg
    690                 695                 700

Thr Asn His Asp Leu Asp Asn Ser Asn Trp Asp Phe Ile Ser Gly Ser
705                 710                 715                 720

Gly Tyr Pro Asp Ile Val Phe Glu Asn Ser Ser Arg Asp Asp Glu Asn
                725                 730                 735

Glu Asp Leu Asp His Asp Thr Ser Ser Thr Ser Ser Ser Glu Ser Gln
            740                 745                 750

Asp Asp Thr Asp Lys Glu Ser Lys Ser Ile Gln Asn Val Pro Arg Arg
        755                 760                 765

Arg Asn Phe Val Lys Pro Met Thr Ala Val Lys Lys Lys Ser Thr Leu
    770                 775                 780

Phe Ile Gln Met Glu Tyr Cys Glu Asn Arg Thr Leu Tyr Asp Leu Ile
785                 790                 795                 800

His Ser Glu Asn Leu Asn Gln Gln Arg Asp Glu Tyr Trp Arg Leu Phe
                805                 810                 815

Arg Gln Ile Leu Glu Ala Leu Ser Tyr Ile His Ser Gln Gly Ile Ile
            820                 825                 830

His Arg Asp Leu Lys Pro Met Asn Ile Phe Ile Asp Glu Ser Arg Asn
        835                 840                 845

Val Lys Ile Gly Asp Phe Gly Leu Ala Lys Asn Val His Arg Ser Leu
    850                 855                 860

Asp Ile Leu Lys Leu Asp Ser Gln Asn Leu Pro Gly Ser Ser Asp Asn
865                 870                 875                 880

Leu Thr Ser Ala Ile Gly Thr Ala Met Tyr Val Ala Thr Glu Val Leu
                885                 890                 895

Asp Gly Thr Gly His Tyr Asn Glu Lys Ile Asp Met Tyr Ser Leu Gly
            900                 905                 910

Ile Ile Phe Phe Glu Met Ile Tyr Pro Phe Ser Thr Gly Met Glu Arg
        915                 920                 925

Val Asn Ile Leu Lys Lys Leu Arg Ser Val Ser Ile Glu Phe Pro Pro
    930                 935                 940

Asp Phe Asp Asp Asn Lys Met Lys Val Glu Lys Lys Ile Ile Arg Leu
945                 950                 955                 960

Leu Ile Asp His Asp Pro Asn Lys Arg Pro Gly Ala Arg Thr Leu Leu
                965                 970                 975

Asn Ser Gly Trp Leu Pro Val Lys His Gln Asp Glu Val Ile Lys Glu
            980                 985                 990

Ala Leu Lys Ser Leu Ser Asn Pro  Ser Ser Pro Trp Gln  Gln Gln Val
        995                 1000                1005

Arg Glu  Ser Leu Phe Asn Gln  Ser Tyr Ser Leu Thr  Asn Asp Ile
    1010                1015                1020

Leu Phe  Asp Asn Ser Val Pro  Thr Ser Thr Pro Phe  Ala Asn Ile
    1025                1030                1035

Leu Arg  Ser Gln Met Thr Glu  Glu Val Val Lys Ile  Phe Arg Lys
    1040                1045                1050
```

His Gly Gly Ile Glu Asn Asn Ala Pro Pro Arg Ile Phe Pro Lys
1055 1060 1065

Ala Pro Ile Tyr Gly Thr Gln Asn Val Tyr Glu Val Leu Asp Lys
1070 1075 1080

Gly Gly Thr Val Leu Gln Leu Gln Tyr Asp Leu Thr Tyr Pro Met
1085 1090 1095

Ala Arg Tyr Leu Ser Lys Asn Pro Ser Leu Ile Ser Lys Gln Tyr
1100 1105 1110

Arg Met Gln His Val Tyr Arg Pro Pro Asp His Ser Arg Ser Ser
1115 1120 1125

Leu Glu Pro Arg Lys Phe Gly Glu Ile Asp Phe Asp Ile Ile Ser
1130 1135 1140

Lys Ser Ser Ser Glu Ser Gly Phe Tyr Asp Ala Glu Ser Leu Lys
1145 1150 1155

Ile Ile Asp Glu Ile Leu Thr Val Phe Pro Val Phe Glu Lys Thr
1160 1165 1170

Asn Thr Phe Phe Ile Leu Asn His Ala Asp Ile Leu Glu Ser Val
1175 1180 1185

Phe Asn Phe Thr Asn Ile Asp Lys Ala Gln Arg Pro Leu Val Ser
1190 1195 1200

Arg Met Leu Ser Gln Val Gly Phe Ala Arg Ser Phe Lys Glu Val
1205 1210 1215

Lys Asn Glu Leu Lys Ala Gln Leu Asn Ile Ser Ser Thr Ala Leu
1220 1225 1230

Asn Asp Leu Glu Leu Phe Asp Phe Arg Leu Asp Phe Glu Ala Ala
1235 1240 1245

Lys Lys Arg Leu Tyr Lys Leu Met Ile Asp Ser Pro His Leu Lys
1250 1255 1260

Lys Ile Glu Asp Ser Leu Ser His Ile Ser Lys Val Leu Ser Tyr
1265 1270 1275

Leu Lys Pro Leu Glu Val Ala Arg Asn Val Val Ile Ser Pro Leu
1280 1285 1290

Ser Asn Tyr Asn Ser Ala Phe Tyr Lys Gly Gly Ile Met Phe His
1295 1300 1305

Ala Val Tyr Asp Asp Gly Ser Ser Arg Asn Met Ile Ala Ala Gly
1310 1315 1320

Gly Arg Tyr Asp Thr Leu Ile Ser Phe Phe Ala Arg Pro Ser Gly
1325 1330 1335

Lys Lys Ser Ser Asn Thr Arg Lys Ala Val Gly Phe Asn Leu Ala
1340 1345 1350

Trp Glu Thr Ile Phe Gly Ile Ala Gln Asn Tyr Phe Lys Leu Ala
1355 1360 1365

Ser Gly Asn Arg Ile Lys Lys Arg Asn Arg Phe Leu Lys Asp Thr
1370 1375 1380

Ala Val Asp Trp Lys Pro Ser Arg Cys Asp Val Leu Ile Ser Ser
1385 1390 1395

Phe Ser Asn Ser Leu Leu Asp Thr Ile Gly Val Thr Ile Leu Asn
1400 1405 1410

Thr Leu Trp Lys Gln Asn Ile Lys Ala Asp Met Leu Arg Asp Cys
1415 1420 1425

Ser Ser Val Asp Asp Val Val Thr Gly Ala Gln Gln Asp Gly Ile
1430 1435 1440

Asp Trp Ile Leu Leu Ile Lys Gln Gln Ala Tyr Pro Leu Thr Asn

-continued

```
    1445                1450                1455

His Lys  Arg Lys Tyr Lys Pro  Leu Lys Ile Lys Lys  Leu Ser Thr
    1460                1465                1470

Asn Val  Asp Ile Asp Leu Asp  Leu Asp Glu Phe Leu  Thr Leu Tyr
    1475                1480                1485

Gln Gln  Glu Thr Gly Asn Lys  Ser Leu Ile Asn Asp  Ser Leu Thr
    1490                1495                1500

Leu Gly  Asp Lys Ala Asp Glu  Phe Lys Arg Trp Asp  Glu Asn Ser
    1505                1510                1515

Ser Ala  Gly Ser Ser Gln Glu  Gly Asp Ile Asp Asp  Val Val Ala
    1520                1525                1530

Gly Ser  Thr Asn Asn Gln Lys  Val Ile Tyr Val Pro  Asn Met Ala
    1535                1540                1545

Thr Arg  Ser Lys Lys Ala Asn  Lys Arg Glu Lys Trp  Val Tyr Glu
    1550                1555                1560

Asp Ala  Ala Arg Asn Ser Ser  Asn Met Ile Leu His  Asn Leu Ser
    1565                1570                1575

Asn Ala  Pro Ile Ile Thr Val  Asp Ala Leu Arg Asp  Glu Thr Leu
    1580                1585                1590

Glu Ile  Ile Ser Ile Thr Ser  Leu Ala Gln Lys Glu  Glu Trp Leu
    1595                1600                1605

Arg Lys  Val Phe Gly Ser Gly  Asn Asn Ser Thr Pro  Arg Ser Phe
    1610                1615                1620

Ala Thr  Ser Ile Tyr Asn Asn  Leu Ser Lys Glu Ala  His Lys Gly
    1625                1630                1635

Asn Arg  Trp Ala Ile Leu Tyr  Cys His Lys Thr Gly  Lys Ser Ser
    1640                1645                1650

Val Ile  Asp Leu Gln Arg
    1655
```

<210> SEQ ID NO 53
<211> LENGTH: 918
<212> TYPE: DNA
<213> ORGANISM: Saccharomyces cerevisiae

<400> SEQUENCE: 53

```
atgtcggagt ttaatattac agaaacttat ctaaggtttt tagaagaaga tactgagatg     60

acaatgccga ttgctgccat tgaagcattg gtcacgctat taagaataaa aacaccagaa    120

acagcggcag aaatgattaa tacaataaaa agctccacgg aagaacttat taaatccatt    180

ccgaactcag tttccctgag agccggttgt gatattttca tgagatttgt cttaagaaat    240

cttcatttat acggtgattg ggaaaactgt aaacaacatt tgattgaaaa tggccagctt    300

tttgtatcga gagccaaaaa atcgcgtaac aagattgcag aaataggggt ggatttcata    360

gctgatgatg atatcatctt ggtacatggt tattcgagag cagtattttc tttattaaat    420

catgcagcaa ataagtttat taggttcaga tgtgtggtga cagaatcaag acctagcaaa    480

caagggaacc agctatatac tttacttgaa caaaagggca tacccgtgac tcttattgtc    540

gatagcgcgg ttggagcggt aatcgataag gttgacaaag tgttcgttgg tgctgagggt    600

gttgctgaat caggtggtat tataaatctc gtgggtacct attcagtggg tgttttagca    660

cataatgcaa gaaaaccatt ctatgtggtc actgaaagtc acaaatttgt tcgtatgttt    720

ccattgtctt cagatgatct acctatggcc ggccctcctt tggatttcac acgtcgtacg    780

gacgatctag aagatgcatt gcgtgggccc acgatcgact ataccgccca agaatacatt    840
```

-continued

```
actgcattga ttacagattt aggggtcctc actccaagtg ccgtttcaga agagttaatc     900

aagatgtggt atgattaa                                                    918


<210> SEQ ID NO 54
<211> LENGTH: 305
<212> TYPE: PRT
<213> ORGANISM: Saccharomyces cerevisiae

<400> SEQUENCE: 54

Met Ser Glu Phe Asn Ile Thr Glu Thr Tyr Leu Arg Phe Leu Glu Glu
1               5                   10                  15

Asp Thr Glu Met Thr Met Pro Ile Ala Ala Ile Glu Ala Leu Val Thr
            20                  25                  30

Leu Leu Arg Ile Lys Thr Pro Glu Thr Ala Ala Glu Met Ile Asn Thr
        35                  40                  45

Ile Lys Ser Ser Thr Glu Glu Leu Ile Lys Ser Ile Pro Asn Ser Val
    50                  55                  60

Ser Leu Arg Ala Gly Cys Asp Ile Phe Met Arg Phe Val Leu Arg Asn
65                  70                  75                  80

Leu His Leu Tyr Gly Asp Trp Glu Asn Cys Lys Gln His Leu Ile Glu
                85                  90                  95

Asn Gly Gln Leu Phe Val Ser Arg Ala Lys Lys Ser Arg Asn Lys Ile
            100                 105                 110

Ala Glu Ile Gly Val Asp Phe Ile Ala Asp Asp Asp Ile Ile Leu Val
        115                 120                 125

His Gly Tyr Ser Arg Ala Val Phe Ser Leu Leu Asn His Ala Ala Asn
    130                 135                 140

Lys Phe Ile Arg Phe Arg Cys Val Val Thr Glu Ser Arg Pro Ser Lys
145                 150                 155                 160

Gln Gly Asn Gln Leu Tyr Thr Leu Leu Glu Gln Lys Gly Ile Pro Val
                165                 170                 175

Thr Leu Ile Val Asp Ser Ala Val Gly Ala Val Ile Asp Lys Val Asp
            180                 185                 190

Lys Val Phe Val Gly Ala Glu Gly Val Ala Glu Ser Gly Gly Ile Ile
        195                 200                 205

Asn Leu Val Gly Thr Tyr Ser Val Gly Val Leu Ala His Asn Ala Arg
    210                 215                 220

Lys Pro Phe Tyr Val Val Thr Glu Ser His Lys Phe Val Arg Met Phe
225                 230                 235                 240

Pro Leu Ser Ser Asp Asp Leu Pro Met Ala Gly Pro Pro Leu Asp Phe
                245                 250                 255

Thr Arg Arg Thr Asp Asp Leu Glu Asp Ala Leu Arg Gly Pro Thr Ile
            260                 265                 270

Asp Tyr Thr Ala Gln Glu Tyr Ile Thr Ala Leu Ile Thr Asp Leu Gly
        275                 280                 285

Val Leu Thr Pro Ser Ala Val Ser Glu Glu Leu Ile Lys Met Trp Tyr
    290                 295                 300

Asp
305


<210> SEQ ID NO 55
<211> LENGTH: 846
<212> TYPE: DNA
<213> ORGANISM: Sacharomyces cerevisiae

<400> SEQUENCE: 55
```

-continued

```
atgtccgaat atcagccaag tttatttgct ttaaatccaa tgggtttctc accattggat     60

ggttctaaat caaccaacga aaatgtatct gcttccactt ctactgccaa accaatggtt    120

ggccaattga tttttgataa attcatcaag actgaagagg atccaattat caaacaggat    180

accccttcga accttgattt tgattttgct cttccacaaa cggcaactgc acctgatgcc    240

aagaccgttt tgccaattcc ggagctagat gacgctgtag tggaatcttt cttttcgtca    300

agcactgatt caactccaat gtttgagtat gaaaacctag aagacaactc taaagaatgg    360

acatccttgt ttgacaatga cattccagtt accactgacg atgtttcatt ggctgataag    420

gcaattgaat ccactgaaga agtttctctg gtaccatcca atctggaagt ctcgacaact    480

tcattcttac ccactcctgt tctagaagat gctaaactga ctcaaacaag aaaggttaag    540

aaaccaaatt cagtcgttaa gaagtcacat catgttggaa aggatgacga atcgagactg    600

gatcatctag gtgttgttgc ttacaaccgc aaacagcgtt cgattccact ttctccaatt    660

gtgcccgaat ccagtgatcc tgctgctcta aaacgtgcta gaaacactga agccgccagg    720

cgttctcgtg cgagaaagtt gcaaagaatg aaacaacttg aagacaaggt tgaagaattg    780

ctttcgaaaa attatcactt ggaaaatgag gttgccagat taaagaaatt agttggcgaa    840

cgctga                                                               846
```

<210> SEQ ID NO 56
<211> LENGTH: 281
<212> TYPE: PRT
<213> ORGANISM: Saccharomyces cerevisiae

<400> SEQUENCE: 56

```
Met Ser Glu Tyr Gln Pro Ser Leu Phe Ala Leu Asn Pro Met Gly Phe
1               5                   10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

Leu Asp Phe Asp Phe Ala Leu Pro Gln Thr Ala Thr Ala Pro Asp Ala
65                  70                  75                  80

Lys Thr Val Leu Pro Ile Pro Glu Leu Asp Asp Ala Val Val Glu Ser
                85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
        115                 120                 125

Pro Val Thr Thr Asp Asp Val Ser Leu Ala Asp Lys Ala Ile Glu Ser
    130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
    210                 215                 220
```

Ser Asp Pro Ala Ala Leu Lys Arg Ala Arg Asn Thr Glu Ala Ala Arg
225 230 235 240

Arg Ser Arg Ala Arg Lys Leu Gln Arg Met Lys Gln Leu Glu Asp Lys
245 250 255

Val Glu Glu Leu Leu Ser Lys Asn Tyr His Leu Glu Asn Glu Val Ala
260 265 270

Arg Leu Lys Lys Leu Val Gly Glu Arg
275 280

<210> SEQ ID NO 57
<211> LENGTH: 1320
<212> TYPE: DNA
<213> ORGANISM: Saccharomyces cerevisiae

<400> SEQUENCE: 57
atggtcacaa aacatcagat tgaagaggat cacttggatg gagctacgac ggatcccgaa 60
gttaaacggg taaaattaga aaacaacgtt gaagaaatac aacctgagca ggctgagacc 120
aataaacaag agggcaccga taaagagaat aaaggaaagt tcgagaaaga aactgagaga 180
ataggaggat ctgaagtggt tacagatgtg gaaaaaggaa ttgtcaaatt tgaatttgat 240
ggtgttgaat acacattcaa agagagaccc agtgtcgtag aggaaaatga aggtaaaatt 300
gagtttaggg tggtgaataa tgataatact aaagaaaaca tgatggtcct aactggatta 360
aaaaacattt ttcaaaagca attaccaaaa atgcccaaag aatacattgc caggttagtc 420
tatgatcgaa gtcatctttc catggctgtc attaggaagc cattgactgt cgtaggtggc 480
ataacatatc gacctttcga taagagagaa ttcgcagaaa ttgttttctg tgccatcagt 540
tcgacggaac aggtacgcgg ttatggtgcg catctaatga atcacttaaa agactatgtt 600
agaaatacct cgaacataaa atatttttg acatatgcag ataattacgc tattggatac 660
tttaaaaagc aaggcttcac taaagaaatc acgttggata aaagtatatg gatgggatat 720
attaaagatt atgaaggtgg tacgctgatg caatgttcta tgttaccaag aatacgatat 780
ttggacgcag gtaagattct attattacaa gaagcggccc tgcgaagaaa aataagaacg 840
atttcgaaat cgcatattgt aaggcctggt ttagagcaat tcaaagactt aaacaatatc 900
aaaccgattg atccaatgac tattcctggc ttgaaagaag ccggctggac tcccgagatg 960
gatgcgttgg cacaacgtcc caagcgtggt ccacacgatg cagcaataca gaatatactc 1020
acagagctac aaaatcatgc agcagcttgg cccttcttac aacccgttaa taaagaggag 1080
gtccccgact attatgattt tatcaaagag ccaatggact tgagcaccat ggaaataaaa 1140
ttagagagca acaaatatca gaagatggaa gacttcatat atgatgccag attggtgttt 1200
aacaattgcc gaatgtacaa tggcgagaat acgtcgtatt acaagtatgc taataggcta 1260
gagaaattct tcaataataa agtaaaagaa atacctgaat attctcacct tattgattaa 1320

<210> SEQ ID NO 58
<211> LENGTH: 439
<212> TYPE: PRT
<213> ORGANISM: Saccharomyces cerevisiae

<400> SEQUENCE: 58

Met Val Thr Lys His Gln Ile Glu Glu Asp His Leu Asp Gly Ala Thr
1 5 10 15

Thr Asp Pro Glu Val Lys Arg Val Lys Leu Glu Asn Asn Val Glu Glu
20 25 30

Ile Gln Pro Glu Gln Ala Glu Thr Asn Lys Gln Glu Gly Thr Asp Lys
35 40 45

```
Glu Asn Lys Gly Lys Phe Glu Lys Glu Thr Glu Arg Ile Gly Gly Ser
    50                  55                  60

Glu Val Val Thr Asp Val Glu Lys Gly Ile Val Lys Phe Glu Phe Asp
65                  70                  75                  80

Gly Val Glu Tyr Thr Phe Lys Glu Arg Pro Ser Val Val Glu Glu Asn
                85                  90                  95

Glu Gly Lys Ile Glu Phe Arg Val Val Asn Asn Asp Asn Thr Lys Glu
            100                 105                 110

Asn Met Met Val Leu Thr Gly Leu Lys Asn Ile Phe Gln Lys Gln Leu
        115                 120                 125

Pro Lys Met Pro Lys Glu Tyr Ile Ala Arg Leu Val Tyr Asp Arg Ser
    130                 135                 140

His Leu Ser Met Ala Val Ile Arg Lys Pro Leu Thr Val Val Gly Gly
145                 150                 155                 160

Ile Thr Tyr Arg Pro Phe Asp Lys Arg Glu Phe Ala Glu Ile Val Phe
                165                 170                 175

Cys Ala Ile Ser Ser Thr Glu Gln Val Arg Gly Tyr Gly Ala His Leu
            180                 185                 190

Met Asn His Leu Lys Asp Tyr Val Arg Asn Thr Ser Asn Ile Lys Tyr
        195                 200                 205

Phe Leu Thr Tyr Ala Asp Asn Tyr Ala Ile Gly Tyr Phe Lys Lys Gln
    210                 215                 220

Gly Phe Thr Lys Glu Ile Thr Leu Asp Lys Ser Ile Trp Met Gly Tyr
225                 230                 235                 240

Ile Lys Asp Tyr Glu Gly Gly Thr Leu Met Gln Cys Ser Met Leu Pro
                245                 250                 255

Arg Ile Arg Tyr Leu Asp Ala Gly Lys Ile Leu Leu Leu Gln Glu Ala
            260                 265                 270

Ala Leu Arg Arg Lys Ile Arg Thr Ile Ser Lys Ser His Ile Val Arg
        275                 280                 285

Pro Gly Leu Glu Gln Phe Lys Asp Leu Asn Asn Ile Lys Pro Ile Asp
    290                 295                 300

Pro Met Thr Ile Pro Gly Leu Lys Glu Ala Gly Trp Thr Pro Glu Met
305                 310                 315                 320

Asp Ala Leu Ala Gln Arg Pro Lys Arg Gly Pro His Asp Ala Ala Ile
                325                 330                 335

Gln Asn Ile Leu Thr Glu Leu Gln Asn His Ala Ala Ala Trp Pro Phe
            340                 345                 350

Leu Gln Pro Val Asn Lys Glu Glu Val Pro Asp Tyr Tyr Asp Phe Ile
        355                 360                 365

Lys Glu Pro Met Asp Leu Ser Thr Met Glu Ile Lys Leu Glu Ser Asn
    370                 375                 380

Lys Tyr Gln Lys Met Glu Asp Phe Ile Tyr Asp Ala Arg Leu Val Phe
385                 390                 395                 400

Asn Asn Cys Arg Met Tyr Asn Gly Glu Asn Thr Ser Tyr Tyr Lys Tyr
                405                 410                 415

Ala Asn Arg Leu Glu Lys Phe Phe Asn Asn Lys Val Lys Glu Ile Pro
            420                 425                 430

Glu Tyr Ser His Leu Ile Asp
        435

<210> SEQ ID NO 59
<211> LENGTH: 2259
<212> TYPE: DNA
```

<213> ORGANISM: Saccharomyces cerevisiae

<400> SEQUENCE: 59

```
atggcaagca tcggttcgca agtgagaaaa gctgcttcta gtattgaccc tatcgtcacg     60
gattacgcag tgggctactt taaccacttg tccggaataa cttttgatgc tgttcaaagt    120
aagcaggtag atttgtccac tgaagtgcaa tttgtgtccg atttattgat tgatgcgggt    180
gcgtcaaagg ctaaagttaa agaactatcg gaaagtattt tgaagcaatt gactactcaa    240
ctaaaggaga acgaagccaa attggaattg accggtgata cgtccaagag attacttgat    300
attaatgtct taaagagtca taacagtaaa tccgatatca acgtctcatt aagcatgctg    360
ggtgtgaacg gtgacatcga acatactggt agaaagatgg aaacaagagt tgatttgaaa    420
aaactggcca aggctgaaca aaagatcgca aagaaagtcg ccaagagaaa taacaaattt    480
gttaaatacg aggcttctaa attgatcaat gaccaaaagg aggaggatta cgattctttc    540
tttttgcaaa tcaacccttt agaattcggt tcatccgctg gtaaatccaa ggatatccat    600
attgacactt tcgacttgta cgttggtgac ggtcaaagaa ttttgtccaa cgcccaattg    660
actctaagtt ttggtcacag atatggtctt gtgggccaaa atggtattgg taaatctact    720
ttgttaaggg ctctatctag aagagagctg aacgtcccca aacatgtttc gattttacac    780
gtggaacaag agttaagagg tgatgataca aaggctttac aaagtgtgct ggatgcagac    840
gtttggagaa aacaactatt aagtgaagaa gccaagatca atgaaagatt aaaggaaatg    900
gatgtattaa gacaggaatt cgaagaagac agtttagaag ttaaaaaatt ggacaatgaa    960
agagaagact tggataacca tttgatacag atttctgaca aattagtcga tatggaatct   1020
gacaaggctg aagctagggc agcatcaatc ttatatggtt tggggttcag tacggaggca   1080
cagcaacaac ccactaattc cttttccggt ggttggagaa tgagattgtc cttggcaaga   1140
gccttattct gtcaaccaga tcttttgttg ttagatgaac cttccaatat gttggatgtg   1200
ccatccatcg cttatttagc agagtatttg aaaacatatc caaatacagt tttgacagtt   1260
tctcacgacc gtgcattctt gaatgaagtg gctacagata tcatttatca acacaacgaa   1320
agactagact attacagagg ccaagatttc gataccttttt acaccacaaa ggaggaacgt   1380
agaaagaatg ctcaacgtga gtatgataac caaatggttt acagaaagca cttgcaagag   1440
tttattgaca aatacagata caatgctgcc aaatcacagg aagctcaatc aagaattaag   1500
aaattggaaa aattgcccgt tttggagcca cctgaacaag acaaaaccat tgatttcaaa   1560
ttccctgaat gtgataaatt gtctccacca attatccaat tgcaagacgt ttcctttggt   1620
tatgatgaaa acaacctatt attgaaagat gttaacctgg acgttcaaat ggattccaga   1680
attgcccttg taggtgccaa tggttgtggt aagactacac tgttgaagat tatgatggag   1740
cagttaagac cactaaaagg ctttgtatca agaaacccaa gattacgtat aggctacttc   1800
actcaacatc atgtggattc tatggatttg accacgtctg cagtggactg gatgtccaaa   1860
tccttcccag gtaaaactga tgaagagtat agacgtcatc taggttcatt tggtatcact   1920
ggtaccctgg gtctacaaaa gatgcaatta ttatccggtg gtcaaaaatc tcgtgtagca   1980
ttcgctgcat tgtgtttaaa taatccacac attttggttc tggatgaacc ttctaaccat   2040
ttggatacca ctggtctaga cgctttggta gaagccttga aaaatttcaa cggtggtgtc   2100
ttaatggttt cccatgatat ctctgttatt gactctgttt gtaaagagat ttgggtttca   2160
gagcaaggta ctgtcaagag gttcgaaggt acaatttacg actatagaga ttacatcttg   2220
cagtctgctg atgctgcagg tgtggttaaa aagcattga                          2259
```

<210> SEQ ID NO 60
<211> LENGTH: 752
<212> TYPE: PRT
<213> ORGANISM: Saccharomyces cerevisiae

<400> SEQUENCE: 60

Met Ala Ser Ile Gly Ser Gln Val Arg Lys Ala Ala Ser Ser Ile Asp
1               5                   10                  15

Pro Ile Val Thr Asp Tyr Ala Val Gly Tyr Phe Asn His Leu Ser Gly
            20                  25                  30

Ile Thr Phe Asp Ala Val Gln Ser Lys Gln Val Asp Leu Ser Thr Glu
        35                  40                  45

Val Gln Phe Val Ser Asp Leu Leu Ile Asp Ala Gly Ala Ser Lys Ala
    50                  55                  60

Lys Val Lys Glu Leu Ser Glu Ser Ile Leu Lys Gln Leu Thr Thr Gln
65                  70                  75                  80

Leu Lys Glu Asn Glu Ala Lys Leu Glu Leu Thr Gly Asp Thr Ser Lys
                85                  90                  95

Arg Leu Leu Asp Ile Asn Val Leu Lys Ser His Asn Ser Lys Ser Asp
            100                 105                 110

Ile Asn Val Ser Leu Ser Met Leu Gly Val Asn Gly Asp Ile Glu His
        115                 120                 125

Thr Gly Arg Lys Met Glu Thr Arg Val Asp Leu Lys Lys Leu Ala Lys
    130                 135                 140

Ala Glu Gln Lys Ile Ala Lys Lys Val Ala Lys Arg Asn Asn Lys Phe
145                 150                 155                 160

Val Lys Tyr Glu Ala Ser Lys Leu Ile Asn Asp Gln Lys Glu Glu Asp
                165                 170                 175

Tyr Asp Ser Phe Phe Leu Gln Ile Asn Pro Leu Glu Phe Gly Ser Ser
            180                 185                 190

Ala Gly Lys Ser Lys Asp Ile His Ile Asp Thr Phe Asp Leu Tyr Val
        195                 200                 205

Gly Asp Gly Gln Arg Ile Leu Ser Asn Ala Gln Leu Thr Leu Ser Phe
    210                 215                 220

Gly His Arg Tyr Gly Leu Val Gly Gln Asn Gly Ile Gly Lys Ser Thr
225                 230                 235                 240

Leu Leu Arg Ala Leu Ser Arg Arg Glu Leu Asn Val Pro Lys His Val
                245                 250                 255

Ser Ile Leu His Val Glu Gln Glu Leu Arg Gly Asp Asp Thr Lys Ala
            260                 265                 270

Leu Gln Ser Val Leu Asp Ala Asp Val Trp Arg Lys Gln Leu Leu Ser
        275                 280                 285

Glu Glu Ala Lys Ile Asn Glu Arg Leu Lys Glu Met Asp Val Leu Arg
    290                 295                 300

Gln Glu Phe Glu Glu Asp Ser Leu Glu Val Lys Lys Leu Asp Asn Glu
305                 310                 315                 320

Arg Glu Asp Leu Asp Asn His Leu Ile Gln Ile Ser Asp Lys Leu Val
                325                 330                 335

Asp Met Glu Ser Asp Lys Ala Glu Ala Arg Ala Ala Ser Ile Leu Tyr
            340                 345                 350

Gly Leu Gly Phe Ser Thr Glu Ala Gln Gln Gln Pro Thr Asn Ser Phe
        355                 360                 365

Ser Gly Gly Trp Arg Met Arg Leu Ser Leu Ala Arg Ala Leu Phe Cys
    370                 375                 380

```
Gln Pro Asp Leu Leu Leu Leu Asp Glu Pro Ser Asn Met Leu Asp Val
385                 390                 395                 400

Pro Ser Ile Ala Tyr Leu Ala Glu Tyr Leu Lys Thr Tyr Pro Asn Thr
                405                 410                 415

Val Leu Thr Val Ser His Asp Arg Ala Phe Leu Asn Glu Val Ala Thr
            420                 425                 430

Asp Ile Ile Tyr Gln His Asn Glu Arg Leu Asp Tyr Tyr Arg Gly Gln
        435                 440                 445

Asp Phe Asp Thr Phe Tyr Thr Thr Lys Glu Glu Arg Arg Lys Asn Ala
    450                 455                 460

Gln Arg Glu Tyr Asp Asn Gln Met Val Tyr Arg Lys His Leu Gln Glu
465                 470                 475                 480

Phe Ile Asp Lys Tyr Arg Tyr Asn Ala Ala Lys Ser Gln Glu Ala Gln
                485                 490                 495

Ser Arg Ile Lys Lys Leu Glu Lys Leu Pro Val Leu Glu Pro Pro Glu
            500                 505                 510

Gln Asp Lys Thr Ile Asp Phe Lys Phe Pro Glu Cys Asp Lys Leu Ser
        515                 520                 525

Pro Pro Ile Ile Gln Leu Gln Asp Val Ser Phe Gly Tyr Asp Glu Asn
    530                 535                 540

Asn Leu Leu Leu Lys Asp Val Asn Leu Asp Val Gln Met Asp Ser Arg
545                 550                 555                 560

Ile Ala Leu Val Gly Ala Asn Gly Cys Gly Lys Thr Thr Leu Leu Lys
                565                 570                 575

Ile Met Met Glu Gln Leu Arg Pro Leu Lys Gly Phe Val Ser Arg Asn
            580                 585                 590

Pro Arg Leu Arg Ile Gly Tyr Phe Thr Gln His His Val Asp Ser Met
        595                 600                 605

Asp Leu Thr Thr Ser Ala Val Asp Trp Met Ser Lys Ser Phe Pro Gly
    610                 615                 620

Lys Thr Asp Glu Glu Tyr Arg Arg His Leu Gly Ser Phe Gly Ile Thr
625                 630                 635                 640

Gly Thr Leu Gly Leu Gln Lys Met Gln Leu Leu Ser Gly Gly Gln Lys
                645                 650                 655

Ser Arg Val Ala Phe Ala Ala Leu Cys Leu Asn Asn Pro His Ile Leu
            660                 665                 670

Val Leu Asp Glu Pro Ser Asn His Leu Asp Thr Thr Gly Leu Asp Ala
        675                 680                 685

Leu Val Glu Ala Leu Lys Asn Phe Asn Gly Gly Val Leu Met Val Ser
    690                 695                 700

His Asp Ile Ser Val Ile Asp Ser Val Cys Lys Glu Ile Trp Val Ser
705                 710                 715                 720

Glu Gln Gly Thr Val Lys Arg Phe Glu Gly Thr Ile Tyr Asp Tyr Arg
                725                 730                 735

Asp Tyr Ile Leu Gln Ser Ala Asp Ala Ala Gly Val Val Lys Lys His
            740                 745                 750
```

<210> SEQ ID NO 61
<211> LENGTH: 7575
<212> TYPE: DNA
<213> ORGANISM: Yarrowia lipolytica

<400> SEQUENCE: 61

```
atgatacgcg gtgtgatcag gctggatcgt gatctacttc cgtgtccatt atcacatcat      60

gtcatcgtct tctcatctgg atcaatgtca tccaccaaag accggctgga gttttggaag     120
```

-continued

```
gaacagcaaa tgctcctgtc ctctcccgac tcccttccgt ctatcctcag tgctcttttt    180
cagactattc cacactactc cgaccacgta tcgagggacg tggtagtcga cacgtggaaa    240
ctgctgctaa aggaacaccc tgccgccctt caaaaggttg tgcccgtgct cgccaagcag    300
tttgccatct acaaaaagtc ctccacaaac aacctcatgg tgctgctgga gtggaccaac    360
tactttgtgt ccttctccct gaccaacgcc gggtccgagc tcaacgactt tgtcttcaag    420
gacctcattt ccatgcaggc cgagctcgtg gacctgtgct cagcatgcaa ccgggagcga    480
atggccaaga gcgctctgag gcagacccga gccgcgtttg cagcctgcat cacagctaac    540
ggagctctga ccaaactgct gaacgtatgc cttccaggca cccccacgtc tacggctctg    600
ctgggctgtc tagcatctgc atgcgctgaa aatgctcctc aaacttttga gcagctggat    660
ctttcagcct actcgcagtt ttacggcgcc aacgtgcttg gcgccaaggt tctgccctgc    720
aaaaacgcca ccaaacagtt ttgcacggga tactttggca acctgtctcg tgaccaaaag    780
tccaaggtcg cggctgatat ctttgatgcc accaagaagt cgattctgag gtctcccgag    840
tctgttctcg agtacgcaat tcccctgttg ctagagagtc tcgataaaga cgatgagtca    900
gcaaagaagc tggttgacgg catttccgct tccctggtca catgtctcaa gtcttccaat    960
cagctcactc gagatggagc tgtcacatgc atcggagtgg cctgtgctat ctctcacgag   1020
accctctact ccgagttggc caagactgtg tctaaggtga ctgtgttgga gcaaaaagtg   1080
gcctatggaa acgctattgc tggctgtcac gtgaccgatc cttctctgtc tgccgccctt   1140
gctcctgtgg ttaccaagga gaagaacgag attgccctga ctgctctgtc gcgtgccttt   1200
ttggtccact tttcccctga tcaggctaag actctctctt ctggactgtc tgactccaac   1260
gctggcgtcg tcaagacctg ggttctacag ctggtcaact tcccccaaca cgctgagcac   1320
gtgacaggtg agctggagaa gattctcgct tcttccacca tcgtcaaggg tgcgatttct   1380
ggtcttggag ctgtttacct gctcaccaag gctggaaaag ctgtaaaatc tgacaaggct   1440
ctggaactgg ctctatctcc tcgagtgtac accaaactca gtgcaggcga atttgtcact   1500
ggtttcaagg ctctggagtc gctgttcaag gaggttaacc ctgacaatgc ccccgacttt   1560
ggtaagacca tcttcttcta tgcttatggc gactccgagg tcaaggtgga cgttgactgc   1620
tctagattgg ttggtcccgc tctgaggagc aattactcgg atggtctggc tggggctgtc   1680
atttctggaa tttctgacac ccacgtcagc gagagaaagt actccaagtt gctttactcg   1740
ctgtttagtg ccgagaacaa ctgcgacaag gctcttgtcg atgggctaga ggtactgtgt   1800
ggcgtcggac tgtggattga gtccgttctg ggagcatctc gagatccccg aaagttgttg   1860
ttggacaatg agaagcatgt caagtcgatt ctgtcttcgg ctacctcctc caacctctat   1920
cctaccatcg ctacagtctg tttcattgct cctgacgtct ttgctggtga ggttgccgag   1980
cagttcactg tttcgaacct ctcctgtgtc accactgagg ccgtgaccat cttcaacact   2040
cccgctgacg aactggcttt cgatatcaag cgaacggagc gtgtggctca caaaaactcc   2100
aaggaatacc aggacaagct gtgggaagaa aacctcaaga aggagctcca aaagaagaag   2160
ggtgttgtcg aaaagccaaa gtacaccaag gaggaacaaa tcaaggtaga cgaacagatg   2220
aagaaggagg cagaaattag aacggaggtc accgcagtcg cagatcacgt gacccggctc   2280
atgggcatca tttccgccct ctccaaggag gccatgacgg ttgataacgg caaagaaacg   2340
tggtttggac cggccatgac gctcatgctc gagctcctca gacaccccaa cgtggatgtg   2400
ctttgttcca gtcacgtgac caagactctc acggacatgt cttggatcac caacgacaag   2460
ctgggttcca ttagaccctt cctggccgtc tgcctgctca gaatgtatgg taatcacgtg   2520
```

-continued

```
agcgaggacc tccagaagga gtcacgtgac tctctcatca cgcgggtgct gtacaagatt   2580
cattctgtgg ccatgtcttc tcctcttgac gctatttctc tgattttcgt gcttcccatt   2640
gtcttgtttg tgctcaagaa ccagtctcgt gacaaggacg tggctgagga gcaaacgcat   2700
cttgccattg agattgtcac ttgtcacacc tctgcttttg ccgacgtgat tactcctcga   2760
tctgaaatca tgagcgccct cattcagctc atgaagagca ctcccaccaa ggccaagctt   2820
gctcgtgagt gtctgtactc tgtggttgag cacgtggctc tgacaattac gaaacccgaa   2880
gagcacgtgt tgctgagtaa cctgttcact ggagacactg gtgttcgtca tgctattctg   2940
gaggctgttg acgctcatct cactcttgat gactcctctc ctgaactcta cgtgacctgt   3000
ttcgatgtgg acgacgtgaa ccgagaactt gccgagcaga tttactccga gaacaagctc   3060
tgcaagccct cttcttctgt tcttctcccc ttcctggctg ctgagtcgtc ttctctgcgc   3120
ctgtcttcgg cacgtgccta tgctgccact gccgaagctg actcctacaa ccagctcatg   3180
gcctacatta tcgaggcttc tgtgcccatt cctcctaccc tggaccagta cggaaagccc   3240
aagaagggcg agtctgcacg tgaccagtgg gaagctcgat gcggagctgg tctagctgtt   3300
cacgagatgg cacctggcat gtctcccgag catgtgattt cgttcattga gttccttgtc   3360
gaaaccggct actctgatgt caactctgac gtccgacagg agttcaatga tgccggtctg   3420
gctcttgttg atcagcatgg cctcaagaac gttgaggagc tgatgaagat cattcagaac   3480
cgactcaaca aggcgtctaa cggctccgag agcgatgacc acgtgatttc gtcttgtgtt   3540
gttctgtatg gtgctctggc ccgccacctg gaatcttcag attcccgtct gcctgtcatc   3600
tacgaccgaa tgttggttgc tctagatact ccttctgagt ctgtgcagtt ccgagtctcc   3660
gaatgtcttt ctggactggt cagcaagatg gacaagaagg ctagagatgg ctacttggac   3720
cagctcaccg agaagcttct ttctgactct tctctcgcca ttcgacgagg agcagcatat   3780
ggtattgctg gtctcgttag aggaggcgga attgcttcca ttggagagac tgatctcatg   3840
cgaaccctga cagatgctat ggagaacaag aagtcgtctg ccgcccgtca gagtgcccag   3900
tttgtggtcg agactctgtc gatggcactc cagcgacact ttgagcccta tgccctgcag   3960
ctcatgcctc tggtgcttgc tgctcttggt gatcccgttt tcgaggtccg agaagctacc   4020
aacgatgctt ctcgtcaggt tatgaagcac accactgcct acggagtgac caaactcatt   4080
cccatggcca ttgaaaacct caacctcact gcttggcgat ctaagagagg agctgtggaa   4140
ttgctcggta acatggccta cctgtccccc catgaactgt ccaccaacct gtcgctaatt   4200
gtccccgaga ttgtggcggt gctcaacgat acgcacaagg aggtgcgggc cgcggctaac   4260
agctctctca accggtttgg tcacgtgatt tccaaccccg agattcaggc tcttgttccc   4320
aagctcattg gtgccattgc cgagcctgag aagaccgagg ttgctctgga cggtctgctc   4380
aagacccagt ttgtgcatta cattgacgct ccctccctcg ctctcattag tcacgtgctc   4440
cagcgtggtc ttggagaccg atccgccgca gtcaagaaga aggcttgtca gattgttggc   4500
aacatggcca ttttgacttc ggctcaggac attgcacctt acttgcccga gctgactgtt   4560
tccctggaga ccgccatggt cgatcccgta cctggcactc gtgctactgc tgcccgggct   4620
ctgggttctc ttgtcgagaa gctgggcgag cctgcgttcc ctgatctggt ccctcgactt   4680
ctttccactc tcagagacga gtctcgagct ggagaccacc ttggtgctgc ccagggtctg   4740
tctgaggttg tgtgcggtct gggtcttcga aagctggaag aaattctgcc tcaggtgatc   4800
aaatcctgcg cttcccccaa gaatcacatt cgagctgctt tcatgccgct gatgatcttc   4860
ctgcctgcca cctttggcaa ctcgctgacc ccttacctgt cccagatcat tcctgtgatt   4920
```

-continued

```
ctttctggac ttgccgatga tgttgattcc gtcagagacg cttccctcaa ggctggtcgg   4980
ctcctggtgt ccaacttctc cagcaagtct gttgacctgc tgttgcccga gcttctcgtc   5040
ggcatgtctg actccaacca ccgaattcga cttgcctcgg ttgaactcat gggagaccta   5100
ctcttccagc tcactggtct caccaagaac gagcttgatg agtctgatga tgtcaacgca   5160
ggccaggccc tgctctcgtt gctgggacaa cagactcgag acactgttct ggccaacttg   5220
tttgtttgtc gagcagatac ctctggacag gtgcgacttg cgtcgatcga aatctggaaa   5280
gcgctggtgg ccaacacccc tcgaactgtc aaggagattc ttcccgagct caccaaccag   5340
gtggttaccc ggctggcttc tcgggaccac gagcagcgag aaatcgccgc ctccaccctc   5400
ggagaactcg tccgacgagt ctcggactcc ctgcagcagc ttctccctac tctgcagacc   5460
aacctcgaca actccgactc tgaccagaaa cagggtatct gcattgctct caaggagctc   5520
atcgtctcct cctctagaga ccagctggac gcccataaga cgaccgttgt tcacattctg   5580
cacgagactc tgaccgactc gtcacgcgat gtgcgttccg ctgccgcctc tgcgttcgat   5640
gcctacaacg agattatggg aaactcggct gtcgacgaca ttctccccaa gctgctgttg   5700
ctgctcaagg agcgtcccga ggctgctctg gcggctctca aggacatcat gcaatcgcga   5760
gccaactcga ttttccccgt tgtgctgccc aagctgctgt ctcagcctat ttccgtcttc   5820
aacgccgagg ccctcgcttc tctggctcct gttgctggcc agaccctgct gcgacgactt   5880
ccccaggtgg ttggcaacct tgtgtccgcc attatcagcg cgcgtgatca gaaggacgac   5940
gaacgagcgt ctgctttgtt tgactctctt gtctccattt tcctgtcggt gtctgacgaa   6000
ggaatccatt cactcatgca gcagctcaag tccatggcca aggacgagga ctcggccgtg   6060
cgaacactgc tgttcgagac cctcacaccc tttttcaagg acacccagtt ggatctttct   6120
gcttactaca ttgactgggc tgagctgtgt atctatggtc ttgacgacga gtctgtttct   6180
tctgctgcca agagcgctct ggagactctg gtcaagaatc tgtccaagga ggagttggaa   6240
accctctcca agcctgctta ttccgctctc gccaacacct ccatcccccct ggccggtatc   6300
aatgtgccca agggacccgc ctgtattctc cccatcttcg tgcagggtct catgtacggt   6360
acttcggacc agcgagaggc ctctgccaac ggtatgggat gcattgtaga gcgagttgac   6420
gcgtcgctgc tcaagttgca cgttacccag atcacaggtc ccctcattcg aaccattgga   6480
gaacggttcc cggcctctgt caaggtggct atcgttacaa ctctcaacct gctcctcaag   6540
aactgctctg ctttcctcaa gcctttcctg ccccagcttc agagaacctt tgccaagtgt   6600
ctcagtgata ccggctctga gcgactgcga aacgaggctg ccgaggccct gggtaccctg   6660
attaccctgc agtcccgagt ggatcctctg gtcagcgagc tcgttaccgg agtcaaaaac   6720
tccaccgacg agggcgtcac caacgcaatg ttcaaggctc tgcagggcgt cgtgtccaag   6780
gccggcggcc agatgagcca acagtcacgg gatctcgttt ttaacctcgc cgatgaggtc   6840
acgggactcg acaagcatgt gttggccaag atgcttggag gtctagctaa ggtcggagac   6900
gcttctgtgg tctatgaggt gtcccagaag gtcaacaaca gcgagtttgg cgcctatgtg   6960
ctgaatgagc tgcttgtggc ccaggctggc gatgaacgtg tgtctacacg tgacctcccc   7020
gatgattcgc ctgattacgt cacttctacg ctcgagttga tgaagtccga gacacctgca   7080
gtttccgatg ctgccactct agcctgtgga aagctgctgc tggctttcgg tggcctgccg   7140
tttgagatca caaagattct gttgactcag ctggctcaga acatcactgc accggcctct   7200
tcgtcttccg acactcgacg tctggcactg gtggtgcttc gtactgttgc tagacagcag   7260
catgcgctta ccaagcccca cgtgactctt cttgctactt ccacgtttgc gtgtgtgcga   7320
```

-continued gaaatggtca ttcctatcaa gcttgctgct gagaaggcgt ggttggctct gttcgacctg 7380
gttactggtt ccacagagtt tgacaagtgg tttggagagg tgcagtcgga gctgcccaac 7440
aacggacggt ctattggcga ctacactaag cgtgttgcca tgagactggc ccaggctgag 7500
cgagagcgac tggaggaggg aggagacgac atggagagtg ataagcggga ggacgaggcg 7560
gagatttggg agtag 7575

<210> SEQ ID NO 62
<211> LENGTH: 2524
<212> TYPE: PRT
<213> ORGANISM: Yarrowia lipolytica

<400> SEQUENCE: 62

Met Ile Arg Gly Val Ile Arg Leu Asp Arg Asp Leu Leu Pro Cys Pro
1 5 10 15

Leu Ser His His Val Ile Val Phe Ser Ser Gly Ser Met Ser Ser Thr
20 25 30

Lys Asp Arg Leu Glu Phe Trp Lys Glu Gln Gln Met Leu Leu Ser Ser
35 40 45

Pro Asp Ser Leu Pro Ser Ile Leu Ser Ala Leu Phe Gln Thr Ile Pro
50 55 60

His Tyr Ser Asp His Val Ser Arg Asp Val Val Val Asp Thr Trp Lys
65 70 75 80

Leu Leu Leu Lys Glu His Pro Ala Ala Leu Gln Lys Val Val Pro Val
85 90 95

Leu Ala Lys Gln Phe Ala Ile Tyr Lys Lys Ser Ser Thr Asn Asn Leu
100 105 110

Met Val Leu Leu Glu Trp Thr Asn Tyr Phe Val Ser Phe Ser Leu Thr
115 120 125

Asn Ala Gly Ser Glu Leu Asn Asp Phe Val Phe Lys Asp Leu Ile Ser
130 135 140

Met Gln Ala Glu Leu Val Asp Leu Cys Ser Ala Cys Asn Arg Glu Arg
145 150 155 160

Met Ala Lys Ser Ala Leu Arg Gln Thr Arg Ala Ala Phe Ala Ala Cys
165 170 175

Ile Thr Ala Asn Gly Ala Leu Thr Lys Leu Leu Asn Val Cys Leu Pro
180 185 190

Gly Thr Pro Thr Ser Thr Ala Leu Leu Gly Cys Leu Ala Ser Ala Cys
195 200 205

Ala Glu Asn Ala Pro Gln Thr Phe Glu Gln Leu Asp Leu Ser Ala Tyr
210 215 220

Ser Gln Phe Tyr Gly Ala Asn Val Leu Gly Ala Lys Val Leu Pro Cys
225 230 235 240

Lys Asn Ala Thr Lys Gln Phe Cys Thr Gly Tyr Phe Gly Asn Leu Ser
245 250 255

Arg Asp Gln Lys Ser Lys Val Ala Ala Asp Ile Phe Asp Ala Thr Lys
260 265 270

Lys Ser Ile Leu Arg Ser Pro Glu Ser Val Leu Glu Tyr Ala Ile Pro
275 280 285

Leu Leu Leu Glu Ser Leu Asp Lys Asp Asp Glu Ser Ala Lys Lys Leu
290 295 300

Val Asp Gly Ile Ser Ala Ser Leu Val Thr Cys Leu Lys Ser Ser Asn
305 310 315 320

Gln Leu Thr Arg Asp Gly Ala Val Thr Cys Ile Gly Val Ala Cys Ala

```
                325                 330                 335

Ile Ser His Glu Thr Leu Tyr Ser Glu Leu Ala Lys Thr Val Ser Lys
            340                 345                 350

Val Thr Val Leu Glu Gln Lys Val Ala Tyr Gly Asn Ala Ile Ala Gly
        355                 360                 365

Cys His Val Thr Asp Pro Ser Leu Ser Ala Ala Leu Ala Pro Val Val
    370                 375                 380

Thr Lys Glu Lys Asn Glu Ile Ala Leu Thr Ala Leu Ser Arg Ala Phe
385                 390                 395                 400

Leu Val His Phe Ser Pro Asp Gln Ala Lys Thr Leu Ser Ser Gly Leu
                405                 410                 415

Ser Asp Ser Asn Ala Gly Val Val Lys Thr Trp Val Leu Gln Leu Val
            420                 425                 430

Asn Phe Pro Gln His Ala Glu His Val Thr Gly Glu Leu Glu Lys Ile
        435                 440                 445

Leu Ala Ser Ser Thr Ile Val Lys Gly Ala Ile Ser Gly Leu Gly Ala
    450                 455                 460

Val Tyr Leu Leu Thr Lys Ala Gly Lys Ala Val Lys Ser Asp Lys Ala
465                 470                 475                 480

Leu Glu Leu Ala Leu Ser Pro Arg Val Tyr Thr Lys Leu Ser Ala Gly
                485                 490                 495

Glu Phe Val Thr Gly Phe Lys Ala Leu Glu Ser Leu Phe Lys Glu Val
            500                 505                 510

Asn Pro Asp Asn Ala Pro Asp Phe Gly Lys Thr Ile Phe Phe Tyr Ala
        515                 520                 525

Tyr Gly Asp Ser Glu Val Lys Val Asp Val Asp Cys Ser Arg Leu Val
    530                 535                 540

Gly Pro Ala Leu Arg Ser Asn Tyr Ser Asp Gly Leu Ala Gly Ala Val
545                 550                 555                 560

Ile Ser Gly Ile Ser Asp Thr His Val Ser Glu Arg Lys Tyr Ser Lys
                565                 570                 575

Leu Leu Tyr Ser Leu Phe Ser Ala Glu Asn Asn Cys Asp Lys Ala Leu
            580                 585                 590

Val Asp Gly Leu Glu Val Leu Cys Gly Val Gly Leu Trp Ile Glu Ser
        595                 600                 605

Val Leu Gly Ala Ser Arg Asp Pro Arg Lys Leu Leu Leu Asp Asn Glu
    610                 615                 620

Lys His Val Lys Ser Ile Leu Ser Ser Ala Thr Ser Ser Asn Leu Tyr
625                 630                 635                 640

Pro Thr Ile Ala Thr Val Cys Phe Ile Ala Pro Asp Val Phe Ala Gly
                645                 650                 655

Glu Val Ala Glu Gln Phe Thr Val Ser Asn Leu Ser Cys Val Thr Thr
            660                 665                 670

Glu Ala Val Thr Ile Phe Asn Thr Pro Ala Asp Glu Leu Ala Phe Asp
        675                 680                 685

Ile Lys Arg Thr Glu Arg Val Ala His Lys Asn Ser Lys Glu Tyr Gln
    690                 695                 700

Asp Lys Leu Trp Glu Glu Asn Leu Lys Lys Glu Leu Gln Lys Lys Lys
705                 710                 715                 720

Gly Val Val Glu Lys Pro Lys Tyr Thr Lys Glu Glu Gln Ile Lys Val
                725                 730                 735

Asp Glu Gln Met Lys Lys Glu Ala Glu Ile Arg Thr Glu Val Thr Ala
            740                 745                 750
```

```
Val Ala Asp His Val Thr Arg Leu Met Gly Ile Ile Ser Ala Leu Ser
        755                 760                 765

Lys Glu Ala Met Thr Val Asp Asn Gly Lys Glu Thr Trp Phe Gly Pro
    770                 775                 780

Ala Met Thr Leu Met Leu Glu Leu Leu Arg His Pro Asn Val Asp Val
785                 790                 795                 800

Leu Cys Ser Ser His Val Thr Lys Thr Leu Thr Asp Met Ser Trp Ile
                805                 810                 815

Thr Asn Asp Lys Leu Gly Ser Ile Arg Pro Phe Leu Ala Val Cys Leu
            820                 825                 830

Leu Arg Met Tyr Gly Asn His Val Ser Glu Asp Leu Gln Lys Glu Ser
        835                 840                 845

Arg Asp Ser Leu Ile Thr Arg Val Leu Tyr Lys Ile His Ser Val Ala
    850                 855                 860

Met Ser Ser Pro Leu Asp Ala Ile Ser Leu Ile Phe Val Leu Pro Ile
865                 870                 875                 880

Val Leu Phe Val Leu Lys Asn Gln Ser Arg Asp Lys Asp Val Ala Glu
                885                 890                 895

Glu Gln Thr His Leu Ala Ile Glu Ile Val Thr Cys His Thr Ser Ala
            900                 905                 910

Phe Ala Asp Val Ile Thr Pro Arg Ser Glu Ile Met Ser Ala Leu Ile
        915                 920                 925

Gln Leu Met Lys Ser Thr Pro Thr Lys Ala Lys Leu Ala Arg Glu Cys
    930                 935                 940

Leu Tyr Ser Val Val Glu His Val Ala Leu Thr Ile Thr Lys Pro Glu
945                 950                 955                 960

Glu His Val Leu Leu Ser Asn Leu Phe Thr Gly Asp Thr Gly Val Arg
                965                 970                 975

His Ala Ile Leu Glu Ala Val Asp Ala His Leu Thr Leu Asp Asp Ser
            980                 985                 990

Ser Pro Glu Leu Tyr Val Thr Cys  Phe Asp Val Asp Asp  Val Asn Arg
        995                 1000                1005

Glu Leu  Ala Glu Gln Ile Tyr  Ser Glu Asn Lys Leu  Cys Lys Pro
    1010                1015                1020

Ser Ser  Ser Val Leu Leu Pro  Phe Leu Ala Ala Glu  Ser Ser Ser
    1025                1030                1035

Leu Arg  Leu Ser Ser Ala Arg  Ala Tyr Ala Ala Thr  Ala Glu Ala
    1040                1045                1050

Asp Ser  Tyr Asn Gln Leu Met  Ala Tyr Ile Ile Glu  Ala Ser Val
    1055                1060                1065

Pro Ile  Pro Pro Thr Leu Asp  Gln Tyr Gly Lys Pro  Lys Lys Gly
    1070                1075                1080

Glu Ser  Ala Arg Asp Gln Trp  Glu Ala Arg Cys Gly  Ala Gly Leu
    1085                1090                1095

Ala Val  His Glu Met Ala Pro  Gly Met Ser Pro Glu  His Val Ile
    1100                1105                1110

Ser Phe  Ile Glu Phe Leu Val  Glu Thr Gly Tyr Ser  Asp Val Asn
    1115                1120                1125

Ser Asp  Val Arg Gln Glu Phe  Asn Asp Ala Gly Leu  Ala Leu Val
    1130                1135                1140

Asp Gln  His Gly Leu Lys Asn  Val Glu Glu Leu Met  Lys Ile Ile
    1145                1150                1155

Gln Asn  Arg Leu Asn Lys Ala  Ser Asn Gly Ser Glu  Ser Asp Asp
    1160                1165                1170
```

-continued

His Val Ile Ser Ser Cys Val Val Leu Tyr Gly Ala Leu Ala Arg
1175 1180 1185

His Leu Glu Ser Ser Asp Ser Arg Leu Pro Val Ile Tyr Asp Arg
1190 1195 1200

Met Leu Val Ala Leu Asp Thr Pro Ser Glu Ser Val Gln Phe Arg
1205 1210 1215

Val Ser Glu Cys Leu Ser Gly Leu Val Ser Lys Met Asp Lys Lys
1220 1225 1230

Ala Arg Asp Gly Tyr Leu Asp Gln Leu Thr Glu Lys Leu Leu Ser
1235 1240 1245

Asp Ser Ser Leu Ala Ile Arg Arg Gly Ala Ala Tyr Gly Ile Ala
1250 1255 1260

Gly Leu Val Arg Gly Gly Gly Ile Ala Ser Ile Gly Glu Thr Asp
1265 1270 1275

Leu Met Arg Thr Leu Thr Asp Ala Met Glu Asn Lys Lys Ser Ser
1280 1285 1290

Ala Ala Arg Gln Ser Ala Gln Phe Val Val Glu Thr Leu Ser Met
1295 1300 1305

Ala Leu Gln Arg His Phe Glu Pro Tyr Ala Leu Gln Leu Met Pro
1310 1315 1320

Leu Val Leu Ala Ala Leu Gly Asp Pro Val Phe Glu Val Arg Glu
1325 1330 1335

Ala Thr Asn Asp Ala Ser Arg Gln Val Met Lys His Thr Thr Ala
1340 1345 1350

Tyr Gly Val Thr Lys Leu Ile Pro Met Ala Ile Glu Asn Leu Asn
1355 1360 1365

Leu Thr Ala Trp Arg Ser Lys Arg Gly Ala Val Glu Leu Leu Gly
1370 1375 1380

Asn Met Ala Tyr Leu Ser Pro His Glu Leu Ser Thr Asn Leu Ser
1385 1390 1395

Leu Ile Val Pro Glu Ile Val Ala Val Leu Asn Asp Thr His Lys
1400 1405 1410

Glu Val Arg Ala Ala Ala Asn Ser Ser Leu Asn Arg Phe Gly His
1415 1420 1425

Val Ile Ser Asn Pro Glu Ile Gln Ala Leu Val Pro Lys Leu Ile
1430 1435 1440

Gly Ala Ile Ala Glu Pro Glu Lys Thr Glu Val Ala Leu Asp Gly
1445 1450 1455

Leu Leu Lys Thr Gln Phe Val His Tyr Ile Asp Ala Pro Ser Leu
1460 1465 1470

Ala Leu Ile Ser His Val Leu Gln Arg Gly Leu Gly Asp Arg Ser
1475 1480 1485

Ala Ala Val Lys Lys Lys Ala Cys Gln Ile Val Gly Asn Met Ala
1490 1495 1500

Ile Leu Thr Ser Ala Gln Asp Ile Ala Pro Tyr Leu Pro Glu Leu
1505 1510 1515

Thr Val Ser Leu Glu Thr Ala Met Val Asp Pro Val Pro Gly Thr
1520 1525 1530

Arg Ala Thr Ala Ala Arg Ala Leu Gly Ser Leu Val Glu Lys Leu
1535 1540 1545

Gly Glu Pro Ala Phe Pro Asp Leu Val Pro Arg Leu Leu Ser Thr
1550 1555 1560

Leu Arg Asp Glu Ser Arg Ala Gly Asp His Leu Gly Ala Ala Gln 1565 1570 1575

Gly Leu Ser Glu Val Val Cys Gly Leu Gly Leu Arg Lys Leu Glu
1580 1585 1590

Glu Ile Leu Pro Gln Val Ile Lys Ser Cys Ala Ser Pro Lys Asn
1595 1600 1605

His Ile Arg Ala Ala Phe Met Pro Leu Met Ile Phe Leu Pro Ala
1610 1615 1620

Thr Phe Gly Asn Ser Leu Thr Pro Tyr Leu Ser Gln Ile Ile Pro
1625 1630 1635

Val Ile Leu Ser Gly Leu Ala Asp Asp Val Asp Ser Val Arg Asp
1640 1645 1650

Ala Ser Leu Lys Ala Gly Arg Leu Leu Val Ser Asn Phe Ser Ser
1655 1660 1665

Lys Ser Val Asp Leu Leu Leu Pro Glu Leu Leu Val Gly Met Ser
1670 1675 1680

Asp Ser Asn His Arg Ile Arg Leu Ala Ser Val Glu Leu Met Gly
1685 1690 1695

Asp Leu Leu Phe Gln Leu Thr Gly Leu Thr Lys Asn Glu Leu Asp
1700 1705 1710

Glu Ser Asp Asp Val Asn Ala Gly Gln Ala Leu Leu Ser Leu Leu
1715 1720 1725

Gly Gln Gln Thr Arg Asp Thr Val Leu Ala Asn Leu Phe Val Cys
1730 1735 1740

Arg Ala Asp Thr Ser Gly Gln Val Arg Leu Ala Ser Ile Glu Ile
1745 1750 1755

Trp Lys Ala Leu Val Ala Asn Thr Pro Arg Thr Val Lys Glu Ile
1760 1765 1770

Leu Pro Glu Leu Thr Asn Gln Val Val Thr Arg Leu Ala Ser Arg
1775 1780 1785

Asp His Glu Gln Arg Glu Ile Ala Ala Ser Thr Leu Gly Glu Leu
1790 1795 1800

Val Arg Arg Val Ser Asp Ser Leu Gln Gln Leu Leu Pro Thr Leu
1805 1810 1815

Gln Thr Asn Leu Asp Asn Ser Asp Ser Asp Gln Lys Gln Gly Ile
1820 1825 1830

Cys Ile Ala Leu Lys Glu Leu Ile Val Ser Ser Ser Arg Asp Gln
1835 1840 1845

Leu Asp Ala His Lys Thr Thr Val Val His Ile Leu His Glu Thr
1850 1855 1860

Leu Thr Asp Ser Ser Arg Asp Val Arg Ser Ala Ala Ala Ser Ala
1865 1870 1875

Phe Asp Ala Tyr Asn Glu Ile Met Gly Asn Ser Ala Val Asp Asp
1880 1885 1890

Ile Leu Pro Lys Leu Leu Leu Leu Leu Lys Glu Arg Pro Glu Ala
1895 1900 1905

Ala Leu Ala Ala Leu Lys Asp Ile Met Gln Ser Arg Ala Asn Ser
1910 1915 1920

Ile Phe Pro Val Val Leu Pro Lys Leu Leu Ser Gln Pro Ile Ser
1925 1930 1935

Val Phe Asn Ala Glu Ala Leu Ala Ser Leu Ala Pro Val Ala Gly
1940 1945 1950

Gln Thr Leu Leu Arg Arg Leu Pro Gln Val Val Gly Asn Leu Val
1955 1960 1965

-continued

```
Ser Ala  Ile Ile Ser Ala Arg  Asp Gln Lys Asp Asp  Glu Arg Ala
    1970                 1975                 1980

Ser Ala  Leu Phe Asp Ser Leu  Val Ser Ile Phe Leu  Ser Val Ser
    1985                 1990                 1995

Asp Glu  Gly Ile His Ser Leu  Met Gln Gln Leu Lys  Ser Met Ala
    2000                 2005                 2010

Lys Asp  Glu Asp Ser Ala Val  Arg Thr Leu Leu Phe  Glu Thr Leu
    2015                 2020                 2025

Thr Pro  Phe Phe Lys Asp Thr  Gln Leu Asp Leu Ser  Ala Tyr Tyr
    2030                 2035                 2040

Ile Asp  Trp Ala Glu Leu Cys  Ile Tyr Gly Leu Asp  Asp Glu Ser
    2045                 2050                 2055

Val Ser  Ser Ala Ala Lys Ser  Ala Leu Glu Thr Leu  Val Lys Asn
    2060                 2065                 2070

Leu Ser  Lys Glu Glu Leu Glu  Thr Leu Ser Lys Pro  Ala Tyr Ser
    2075                 2080                 2085

Ala Leu  Ala Asn Thr Ser Ile  Pro Leu Ala Gly Ile  Asn Val Pro
    2090                 2095                 2100

Lys Gly  Pro Ala Cys Ile Leu  Pro Ile Phe Val Gln  Gly Leu Met
    2105                 2110                 2115

Tyr Gly  Thr Ser Asp Gln Arg  Glu Ala Ser Ala Asn  Gly Met Gly
    2120                 2125                 2130

Cys Ile  Val Glu Arg Val Asp  Ala Ser Leu Leu Lys  Leu His Val
    2135                 2140                 2145

Thr Gln  Ile Thr Gly Pro Leu  Ile Arg Thr Ile Gly  Glu Arg Phe
    2150                 2155                 2160

Pro Ala  Ser Val Lys Val Ala  Ile Val Thr Thr Leu  Asn Leu Leu
    2165                 2170                 2175

Leu Lys  Asn Cys Ser Ala Phe  Leu Lys Pro Phe Leu  Pro Gln Leu
    2180                 2185                 2190

Gln Arg  Thr Phe Ala Lys Cys  Leu Ser Asp Thr Gly  Ser Glu Arg
    2195                 2200                 2205

Leu Arg  Asn Glu Ala Ala Glu  Ala Leu Gly Thr Leu  Ile Thr Leu
    2210                 2215                 2220

Gln Ser  Arg Val Asp Pro Leu  Val Ser Glu Leu Val  Thr Gly Val
    2225                 2230                 2235

Lys Asn  Ser Thr Asp Glu Gly  Val Thr Asn Ala Met  Phe Lys Ala
    2240                 2245                 2250

Leu Gln  Gly Val Val Ser Lys  Ala Gly Gly Gln Met  Ser Gln Gln
    2255                 2260                 2265

Ser Arg  Asp Leu Val Phe Asn  Leu Ala Asp Glu Val  Thr Gly Leu
    2270                 2275                 2280

Asp Lys  His Val Leu Ala Lys  Met Leu Gly Gly Leu  Ala Lys Val
    2285                 2290                 2295

Gly Asp  Ala Ser Val Val Tyr  Glu Val Ser Gln Lys  Val Asn Asn
    2300                 2305                 2310

Ser Glu  Phe Gly Ala Tyr Val  Leu Asn Glu Leu Leu  Val Ala Gln
    2315                 2320                 2325

Ala Gly  Asp Glu Arg Val Ser  Thr Arg Asp Leu Pro  Asp Asp Ser
    2330                 2335                 2340

Pro Asp  Tyr Val Thr Ser Thr  Leu Glu Leu Met Lys  Ser Glu Thr
    2345                 2350                 2355

Pro Ala  Val Ser Asp Ala Ala  Thr Leu Ala Cys Gly  Lys Leu Leu
    2360                 2365                 2370
```

Leu Ala Phe Gly Gly Leu Pro Phe Glu Ile Thr Lys Ile Leu Leu
    2375                2380                2385

Thr Gln Leu Ala Gln Asn Ile Thr Ala Pro Ala Ser Ser Ser Ser
    2390                2395                2400

Asp Thr Arg Arg Leu Ala Leu Val Val Leu Arg Thr Val Ala Arg
    2405                2410                2415

Gln Gln His Ala Leu Thr Lys Pro His Val Thr Leu Leu Ala Thr
    2420                2425                2430

Ser Thr Phe Ala Cys Val Arg Glu Met Val Ile Pro Ile Lys Leu
    2435                2440                2445

Ala Ala Glu Lys Ala Trp Leu Ala Leu Phe Asp Leu Val Thr Gly
    2450                2455                2460

Ser Thr Glu Phe Asp Lys Trp Phe Gly Glu Val Gln Ser Glu Leu
    2465                2470                2475

Pro Asn Asn Gly Arg Ser Ile Gly Asp Tyr Thr Lys Arg Val Ala
    2480                2485                2490

Met Arg Leu Ala Gln Ala Glu Arg Glu Arg Leu Glu Glu Gly Gly
    2495                2500                2505

Asp Asp Met Glu Ser Asp Lys Arg Glu Asp Glu Ala Glu Ile Trp
    2510                2515                2520

Glu

<210> SEQ ID NO 63
<211> LENGTH: 4926
<212> TYPE: DNA
<213> ORGANISM: Yarrowia lipolytica

<400> SEQUENCE: 63
atggagttac aggaactgca agaaaacgag gcggaggctt tgaaggccat ctacatggac 60
gattttgttg acaccacaaa gtcatctgca tggaacaaaa cgccttcgcc atcatttgag 120
attcacatgc gatcgaccga cccggacgcc gaagatgccc tatccagttt aacgctccag 180
gtcgagctca cgagtaccta ccccaaaacg gtccctgtta ttcgcatcaa aaaccccaaa 240
aacattttag catcacaggt ggccaagtta gagaagtgga tcgccgccac ctgcaaggag 300
ctcattggcg cagagatgat cttcgaggtc acctcgtata tccaggagcg actggaggat 360
tttcaacaga aggtgtccac cgccagtctg gaggaggagc ggcagatgaa gatcgagaag 420
caacaggagc agctacgaaa gcaaaagagc gacgaggcca aaaagcggga acaggaaaac 480
gcggaggaag acagagtgct agagatgatg gttgtggagg agctcaagcg acgcaaacag 540
cgggatgatg aagcgcaaaa ggcgcttact gcggagcgac aattgtcaaa cggcggccca 600
gtcatggccg attgcattga gtttgacaga ataacaacaa tctcgcgagc aggacaccca 660
gcaatcagtt tcagaagagt aggaggacaa atacccgtgc gagggtactc ttttggtaac 720
aattttttgg tgcggcccgt gacagaccca ccaaccgaca tatccctgct tctcacagaa 780
gttagacttc agggcacata ctggatccag gcagagggaa agaagatgat tcaactactc 840
gagtctgact tggacaactt gagaaagttt cgacacgaaa acgtcatcag tctctacgac 900
cacaagttcc aacgatgtcc agatacttcc ggatggacgc tatacctact ttccgaatat 960
tctcctggag gaactgtgtc tgatctgctt gataccgtgg gtaccgtgag tctcaaagtg 1020
acacgagtat gggctattca actactcgaa gccctggagg ctatccacaa ggctggattg 1080
gttcacaaga gtgtcaatgt ggacactgtg gtcctttttc gaaacgcaga aattggagaa 1140
acagtggtca agttgggata cactgttttt ggtcaacgtc ttaacgaaat gaattcggcg 1200

-continued

```
tgcacatttg atatgactgc ctctgtttca tcgatacaac acgacagtga tgcttggtca   1260
cctcctgagc tagtgcagca gagtggaaac aagcagacgc gtaagacaga cgtgtgggct   1320
ctgggtgtga tgcttcttca gaccttcatg ggtaagcagg tgacgtcaga gtattacgga   1380
cctacagatg tgatcaacag tctggatctg ggagattccc tggaagagtt ccttcgaaaa   1440
atgttcatgc cttctcccaa gaaacgtctt tctgcatttg agctcttgcc ttgtgaattc   1500
cttcgaactg gtgtcgactc gccagtgaag ttggcgtgtg cttccagcag tggtggaaaa   1560
cgaggtcgag gaagaagcat gtctacggat ggacgacctc accgggattc catgagtggt   1620
ctttccatgt ctcgatatgc tcaggacttc gaggaaacgg ttttgttagg acgaggtggc   1680
tatggtgtcg ttgtgaaggc tcgcaacaag ttggatggcc gtttctacgc catcaagcga   1740
gttcaacata cagcagacaa gttgacttcc attctaacag aggtcatgct gctgtctcgt   1800
ctcaataatc agtacgtggt tcgatacttt gctgcgtggt tggaagagtc ctacgactat   1860
caggatgagt ctgccatcga ggactacgat tcagaggagg agtggagcga aagtgtttct   1920
agagttgaaa catctgtcag cgcgtttcct gcccgtctca acggctcata cgaccaagat   1980
acgtttgacg agctctccat gaacgcctcg gtggacttca tctccaactc cctgcatcga   2040
gagtatcctg agattgaatt cggagtcagt tcagaggatg atgaagaccg cgagagtgac   2100
gatagcgaca gcgaagacga gacttcttcg gggagcgtat caacatcttc tcccatcaac   2160
agcagacaca aaactaccgt caagactctc gttggaaagg ctgctctggc tgagctgcgt   2220
gactctcctc gacacaagca agacaagtct ctggtaaaat ccaccctatt cattcaaatg   2280
gaatattgtg agaagcacac tttggcggat ttgatcaagc agaacctctc atctaaacct   2340
gaagactgct ggcgattgtt tggccagatt cttgatgctc tgagccacat tcattctcag   2400
ggcatcatcc atcgagatct caagcctatg aacattttca ttgactcatc tggtaatgtc   2460
aaggtcggag attttggact ggccaagaat atccatactg gaacttctct ggttggtgcc   2520
ggtgcaggaa ctggtgggag ctcgtctcag tacacaggtg aggatatgac aggcgacatc   2580
ggtactacgc tgtacgtcgc caatgaggta ttagccacag gcggggaggc caattacaac   2640
gagaaagttg acatgtactc tttgggtatc atctttttcg agatggtgtt ccccatgaac   2700
actgcgatgg agcgtgtcta cattcttcga gacttgcgca accctaaggt catcttccct   2760
ccagcgtttg aggcttctaa gtacaacgaa cctcgtaaga tcattcgaag cttgctcgac   2820
catgacccca gcaagagacc ttctgcccaa caactcttgg cctcaggcat tttgccgatt   2880
cctaataagg acaagactat caaggaggtg attcgaagct tggtagaccc ctcgcccagt   2940
tcgccatggc tttctcaagt gtgtcgggct ctgttctcac gacctctcaa gacagcgcag   3000
gtgtttcttt acgaccgtgc aatcgctggt gagggcagta aatcggactc tcgcgattct   3060
cttctccagg ctcagatgat tgagcaaatc gaggcaactt tcagaaacca cggtgccatc   3120
aaggtcaaca atcgaccatt gctatttccg aagtctctca tatacaagtc cccaaatgtg   3180
gtgtcagtac tcgatcaagc gggtacaatt cttcagttgc ccttcgacct gacactccct   3240
catgctcgaa tgcttgccaa gggtcagact tactaccata agtctttctg ctgtgattat   3300
gtctatcgag cagatgagaa caatgtcgtt agccatcccc gccggtttgg agagattgac   3360
tttgacattg taacccagga ttctacggac ttgcctctgt atgacgccga ggctatccga   3420
gtactcgacc aggtgatcca gttgttccca tcttttaaaa acaacaacgt cgtcatttac   3480
attaaccatt gggatatcct gcagactatt ttggattcat gtcgtattgg gcaagcccag   3540
agagctgttg ctcttcggct tctggacgag accggacagg cccctgctcg ccaggttgtc   3600
```

aaggaagagc ttcgaaccaa gtactctgtc ggtgccaccg ctttggatga tttggaatca 3660
tttggattcc gagacgacat cgacaaggcc gaacaacgtc ttcgtaagat gatcgagggc 3720
agcgagcata ccactcggct gacagagtca ttcttgtgga ttcgaaaggt ttctacctat 3780
ctgaaacgtt ttggctgtac ccgtcgtgtc tacgttgctc cattgagtaa ttacaacgag 3840
gacttctacc gcagcggtct gatgtttcag gctgtcgttg aggataccgc tccacagaag 3900
cgcacgtcca ttctagctgt tggtggacga tatgaccgac tgattactcg gttcagacac 3960
gagtcattgg atcgaggagt tccccgcacg catgctgtcg gcttcaacct tgcttgggaa 4020
tcaatcttcg actccatgaa ggcctacaga gatgccttga tgaaaaagca aaagaagaag 4080
ggcacggttc aggttctcag cacatccact tcgtcatctg ctctcgagtt gcaacgttgg 4140
tacccctctc gttgtgatgc tctcgttacg tccttcaata gtaacacatt gcgcactgtt 4200
tgtctagatg ttttgaagga cttgtgggga gcaggtattc gagctgactt gtgccgagat 4260
tgttcatcat cggaggaact tgttgcgcgg gctcagagtg aaggtatcaa ttggatcatc 4320
atcgtcaagc agcatagtgg ctactcttct gctgcggccg cgtacaagcc ccttcgtgtc 4380
aagaatgttg cgcggaacga cgacactgat attgatagag atggaatcgt cggtcatatg 4440
atgactgagt tgaatgagcg gggtggatct tacagcaaca caaacgccct ggcacccccct 4500 tctctgtctg tgcctcacga cccatcgcct ccagcttcca ttgtggatac tagcgatatc 4560
tatgccacca acaaggtgtc tgtgatcacg aatgagtgga acaagagtaa gtcctccaag 4620
agaaccaacc agtggaacga cgaggaggaa cgtgcgttga gacacacgcg ttcgctggta 4680
cacgacatcc aggaggctcc cattttcaca atcgatgtca aggaagatat acttgacgcc 4740
atttctgtga cttctctggc atcgtttgat gaatggcgtc gaaaggtgat tggtatccag 4800
ccttcacata agccttacct ggcaaagatc tacaaccagc tggtcaagct gaaggaaaca 4860
cgatctacgg ctttactgta ttcacctaaa gcagacaagt tgattcttta caatctgagg 4920
aagtga 4926

<210> SEQ ID NO 64
<211> LENGTH: 1641
<212> TYPE: PRT
<213> ORGANISM: Yarrowia lipolytica

<400> SEQUENCE: 64

Met Glu Leu Gln Glu Leu Gln Glu Asn Glu Ala Glu Ala Leu Lys Ala
1 5 10 15

Ile Tyr Met Asp Asp Phe Val Asp Thr Thr Lys Ser Ser Ala Trp Asn
20 25 30

Lys Thr Pro Ser Pro Ser Phe Glu Ile His Met Arg Ser Thr Asp Pro
35 40 45

Asp Ala Glu Asp Ala Leu Ser Ser Leu Thr Leu Gln Val Glu Leu Thr
50 55 60

Ser Thr Tyr Pro Lys Thr Val Pro Val Ile Arg Ile Lys Asn Pro Lys
65 70 75 80

Asn Ile Leu Ala Ser Gln Val Ala Lys Leu Glu Lys Trp Ile Ala Ala
85 90 95

Thr Cys Lys Glu Leu Ile Gly Ala Glu Met Ile Phe Glu Val Thr Ser
100 105 110

Tyr Ile Gln Glu Arg Leu Glu Asp Phe Gln Gln Lys Val Ser Thr Ala
115 120 125

Ser Leu Glu Glu Glu Arg Gln Met Lys Ile Glu Lys Gln Gln Glu Gln

-continued

```
    130                 135                 140

Leu Arg Lys Gln Lys Ser Asp Glu Ala Lys Lys Arg Glu Gln Glu Asn
145                 150                 155                 160

Ala Glu Glu Asp Arg Val Leu Glu Met Met Val Val Glu Glu Leu Lys
                165                 170                 175

Arg Arg Lys Gln Arg Asp Asp Glu Ala Gln Lys Ala Leu Thr Ala Glu
            180                 185                 190

Arg Gln Leu Ser Asn Gly Gly Pro Val Met Ala Asp Cys Ile Glu Phe
        195                 200                 205

Asp Arg Ile Thr Thr Ile Ser Arg Ala Gly His Pro Ala Ile Ser Phe
    210                 215                 220

Arg Arg Val Gly Gly Gln Ile Pro Val Arg Gly Tyr Ser Phe Gly Asn
225                 230                 235                 240

Asn Phe Leu Val Arg Pro Val Thr Asp Pro Pro Thr Asp Ile Ser Leu
                245                 250                 255

Leu Leu Thr Glu Val Arg Leu Gln Gly Thr Tyr Trp Ile Gln Ala Glu
            260                 265                 270

Gly Lys Lys Met Ile Gln Leu Leu Glu Ser Asp Leu Asp Asn Leu Arg
        275                 280                 285

Lys Phe Arg His Glu Asn Val Ile Ser Leu Tyr Asp His Lys Phe Gln
    290                 295                 300

Arg Cys Pro Asp Thr Ser Gly Trp Thr Leu Tyr Leu Leu Ser Glu Tyr
305                 310                 315                 320

Ser Pro Gly Gly Thr Val Ser Asp Leu Leu Asp Thr Val Gly Thr Val
                325                 330                 335

Ser Leu Lys Val Thr Arg Val Trp Ala Ile Gln Leu Leu Glu Ala Leu
            340                 345                 350

Glu Ala Ile His Lys Ala Gly Leu Val His Lys Ser Val Asn Val Asp
        355                 360                 365

Thr Val Val Leu Phe Arg Asn Ala Glu Ile Gly Glu Thr Val Val Lys
    370                 375                 380

Leu Gly Tyr Thr Val Phe Gly Gln Arg Leu Asn Glu Met Asn Ser Ala
385                 390                 395                 400

Cys Thr Phe Asp Met Thr Ala Ser Val Ser Ser Ile Gln His Asp Ser
                405                 410                 415

Asp Ala Trp Ser Pro Pro Glu Leu Val Gln Gln Ser Gly Asn Lys Gln
            420                 425                 430

Thr Arg Lys Thr Asp Val Trp Ala Leu Gly Val Met Leu Leu Gln Thr
        435                 440                 445

Phe Met Gly Lys Gln Val Thr Ser Glu Tyr Tyr Gly Pro Thr Asp Val
    450                 455                 460

Ile Asn Ser Leu Asp Leu Gly Asp Ser Leu Glu Glu Phe Leu Arg Lys
465                 470                 475                 480

Met Phe Met Pro Ser Pro Lys Lys Arg Leu Ser Ala Phe Glu Leu Leu
                485                 490                 495

Pro Cys Glu Phe Leu Arg Thr Gly Val Asp Ser Pro Val Lys Leu Ala
            500                 505                 510

Cys Ala Ser Ser Ser Gly Gly Lys Arg Gly Arg Gly Arg Ser Met Ser
        515                 520                 525

Thr Asp Gly Arg Pro His Arg Asp Ser Met Ser Gly Leu Ser Met Ser
    530                 535                 540

Arg Tyr Ala Gln Asp Phe Glu Glu Thr Val Leu Leu Gly Arg Gly Gly
545                 550                 555                 560
```

```
Tyr Gly Val Val Val Lys Ala Arg Asn Lys Leu Asp Gly Arg Phe Tyr
                565                 570                 575

Ala Ile Lys Arg Val Gln His Thr Ala Asp Lys Leu Thr Ser Ile Leu
            580                 585                 590

Thr Glu Val Met Leu Leu Ser Arg Leu Asn Asn Gln Tyr Val Val Arg
        595                 600                 605

Tyr Phe Ala Ala Trp Leu Glu Glu Ser Tyr Asp Tyr Gln Asp Glu Ser
    610                 615                 620

Ala Ile Glu Asp Tyr Asp Ser Glu Glu Glu Trp Ser Glu Ser Val Ser
625                 630                 635                 640

Arg Val Glu Thr Ser Val Ser Ala Phe Pro Ala Arg Leu Asn Gly Ser
                645                 650                 655

Tyr Asp Gln Asp Thr Phe Asp Glu Leu Ser Met Asn Ala Ser Val Asp
            660                 665                 670

Phe Ile Ser Asn Ser Leu His Arg Glu Tyr Pro Glu Ile Glu Phe Gly
        675                 680                 685

Val Ser Ser Glu Asp Asp Glu Asp Arg Glu Ser Asp Asp Ser Asp Ser
    690                 695                 700

Glu Asp Glu Thr Ser Ser Gly Ser Val Ser Thr Ser Ser Pro Ile Asn
705                 710                 715                 720

Ser Arg His Lys Thr Thr Val Lys Thr Leu Val Gly Lys Ala Ala Leu
                725                 730                 735

Ala Glu Leu Arg Asp Ser Pro Arg His Lys Gln Asp Lys Ser Leu Val
            740                 745                 750

Lys Ser Thr Leu Phe Ile Gln Met Glu Tyr Cys Glu Lys His Thr Leu
        755                 760                 765

Ala Asp Leu Ile Lys Gln Asn Leu Ser Ser Lys Pro Glu Asp Cys Trp
    770                 775                 780

Arg Leu Phe Gly Gln Ile Leu Asp Ala Leu Ser His Ile His Ser Gln
785                 790                 795                 800

Gly Ile Ile His Arg Asp Leu Lys Pro Met Asn Ile Phe Ile Asp Ser
                805                 810                 815

Ser Gly Asn Val Lys Val Gly Asp Phe Gly Leu Ala Lys Asn Ile His
            820                 825                 830

Thr Gly Thr Ser Leu Val Gly Ala Gly Ala Gly Thr Gly Gly Ser Ser
        835                 840                 845

Ser Gln Tyr Thr Gly Glu Asp Met Thr Gly Asp Ile Gly Thr Thr Leu
    850                 855                 860

Tyr Val Ala Asn Glu Val Leu Ala Thr Gly Gly Glu Ala Asn Tyr Asn
865                 870                 875                 880

Glu Lys Val Asp Met Tyr Ser Leu Gly Ile Ile Phe Phe Glu Met Val
                885                 890                 895

Phe Pro Met Asn Thr Ala Met Glu Arg Val Tyr Ile Leu Arg Asp Leu
            900                 905                 910

Arg Asn Pro Lys Val Ile Phe Pro Pro Ala Phe Glu Ala Ser Lys Tyr
        915                 920                 925

Asn Glu Pro Arg Lys Ile Ile Arg Ser Leu Leu Asp His Asp Pro Ser
    930                 935                 940

Lys Arg Pro Ser Ala Gln Gln Leu Leu Ala Ser Gly Ile Leu Pro Ile
945                 950                 955                 960

Pro Asn Lys Asp Lys Thr Ile Lys Glu Val Ile Arg Ser Leu Val Asp
                965                 970                 975

Pro Ser Pro Ser Ser Pro Trp Leu Ser Gln Val Cys Arg Ala Leu Phe
            980                 985                 990
```

```
Ser Arg Pro Leu Lys Thr Ala Gln  Val Phe Leu Tyr Asp  Arg Ala Ile
        995                 1000                 1005

Ala Gly  Glu Gly Ser Lys Ser  Asp Ser Arg Asp Ser  Leu Leu Gln
    1010                 1015                 1020

Ala Gln  Met Ile Glu Gln Ile  Glu Ala Thr Phe Arg  Asn His Gly
    1025                 1030                 1035

Ala Ile  Lys Val Asn Asn Arg  Pro Leu Leu Phe Pro  Lys Ser Leu
    1040                 1045                 1050

Ile Tyr  Lys Ser Pro Asn Val  Val Ser Val Leu Asp  Gln Ala Gly
    1055                 1060                 1065

Thr Ile  Leu Gln Leu Pro Phe  Asp Leu Thr Leu Pro  His Ala Arg
    1070                 1075                 1080

Met Leu  Ala Lys Gly Gln Thr  Tyr Tyr His Lys Ser  Phe Cys Cys
    1085                 1090                 1095

Asp Tyr  Val Tyr Arg Ala Asp  Glu Asn Asn Val Val  Ser His Pro
    1100                 1105                 1110

Arg Arg  Phe Gly Glu Ile Asp  Phe Asp Ile Val Thr  Gln Asp Ser
    1115                 1120                 1125

Thr Asp  Leu Pro Leu Tyr Asp  Ala Glu Ala Ile Arg  Val Leu Asp
    1130                 1135                 1140

Gln Val  Ile Gln Leu Phe Pro  Ser Phe Lys Asn Asn  Asn Val Val
    1145                 1150                 1155

Ile Tyr  Ile Asn His Trp Asp  Ile Leu Gln Thr Ile  Leu Asp Ser
    1160                 1165                 1170

Cys Arg  Ile Gly Gln Ala Gln  Arg Ala Val Ala Leu  Arg Leu Leu
    1175                 1180                 1185

Asp Glu  Thr Gly Gln Ala Pro  Ala Arg Gln Val Val  Lys Glu Glu
    1190                 1195                 1200

Leu Arg  Thr Lys Tyr Ser Val  Gly Ala Thr Ala Leu  Asp Asp Leu
    1205                 1210                 1215

Glu Ser  Phe Gly Phe Arg Asp  Asp Ile Asp Lys Ala  Glu Gln Arg
    1220                 1225                 1230

Leu Arg  Lys Met Ile Glu Gly  Ser Glu His Thr Thr  Arg Leu Thr
    1235                 1240                 1245

Glu Ser  Phe Leu Trp Ile Arg  Lys Val Ser Thr Tyr  Leu Lys Arg
    1250                 1255                 1260

Phe Gly  Cys Thr Arg Arg Val  Tyr Val Ala Pro Leu  Ser Asn Tyr
    1265                 1270                 1275

Asn Glu  Asp Phe Tyr Arg Ser  Gly Leu Met Phe Gln  Ala Val Val
    1280                 1285                 1290

Glu Asp  Thr Ala Pro Gln Lys  Arg Thr Ser Ile Leu  Ala Val Gly
    1295                 1300                 1305

Gly Arg  Tyr Asp Arg Leu Ile  Thr Arg Phe Arg His  Glu Ser Leu
    1310                 1315                 1320

Asp Arg  Gly Val Pro Arg Thr  His Ala Val Gly Phe  Asn Leu Ala
    1325                 1330                 1335

Trp Glu  Ser Ile Phe Asp Ser  Met Lys Ala Tyr Arg  Asp Ala Leu
    1340                 1345                 1350

Met Lys  Lys Gln Lys Lys Lys  Gly Thr Val Gln Val  Leu Ser Thr
    1355                 1360                 1365

Ser Thr  Ser Ser Ser Ala Leu  Glu Leu Gln Arg Trp  Tyr Pro Ser
    1370                 1375                 1380

Arg Cys  Asp Ala Leu Val Thr  Ser Phe Asn Ser Asn  Thr Leu Arg
```

```
    1385                1390                1395

Thr Val  Cys Leu Asp Val Leu  Lys Asp Leu Trp Gly  Ala Gly Ile
    1400                1405                1410

Arg Ala  Asp Leu Cys Arg Asp  Cys Ser Ser Ser Glu  Glu Leu Val
    1415                1420                1425

Ala Arg  Ala Gln Ser Glu Gly  Ile Asn Trp Ile Ile  Ile Val Lys
    1430                1435                1440

Gln His  Ser Gly Tyr Ser Ser  Ala Ala Ala Ala Tyr  Lys Pro Leu
    1445                1450                1455

Arg Val  Lys Asn Val Ala Arg  Asn Asp Asp Thr Asp  Ile Asp Arg
    1460                1465                1470

Asp Gly  Ile Val Gly His Met  Met Thr Glu Leu Asn  Glu Arg Gly
    1475                1480                1485

Gly Ser  Tyr Ser Asn Thr Asn  Ala Leu Ala Pro Pro  Ser Leu Ser
    1490                1495                1500

Val Pro  His Asp Pro Ser Pro  Pro Ala Ser Ile Val  Asp Thr Ser
    1505                1510                1515

Asp Ile  Tyr Ala Thr Asn Lys  Val Ser Val Ile Thr  Asn Glu Trp
    1520                1525                1530

Asn Lys  Ser Lys Ser Ser Lys  Arg Thr Asn Gln Trp  Asn Asp Glu
    1535                1540                1545

Glu Glu  Arg Ala Leu Arg His  Thr Arg Ser Leu Val  His Asp Ile
    1550                1555                1560

Gln Glu  Ala Pro Ile Phe Thr  Ile Asp Val Lys Glu  Asp Ile Leu
    1565                1570                1575

Asp Ala  Ile Ser Val Thr Ser  Leu Ala Ser Phe Asp  Glu Trp Arg
    1580                1585                1590

Arg Lys  Val Ile Gly Ile Gln  Pro Ser His Lys Pro  Tyr Leu Ala
    1595                1600                1605

Lys Ile  Tyr Asn Gln Leu Val  Lys Leu Lys Glu Thr  Arg Ser Thr
    1610                1615                1620

Ala Leu  Leu Tyr Ser Pro Lys  Ala Asp Lys Leu Ile  Leu Tyr Asn
    1625                1630                1635

Leu Arg  Lys
    1640
```

<210> SEQ ID NO 65
<211> LENGTH: 924
<212> TYPE: DNA
<213> ORGANISM: Yarrowia lipolytica

<400> SEQUENCE: 65

```
atggccaaat tcgacatcaa agagacatat ctgcgctttc tgcgggacga ccccgacatc     60

accatgcctg tcgcggccat tgaggccctg gtccagctgc tcagtgagac cgaaaccagc    120

acatcagccg agctgattca gactctcaag gaggcgagcg cggagctcaa gacgtctgtg    180

gacaactcta tgtcgctttc tgcaggctgt gatctgttta tgcgatttgt gttgcgaaat    240

atccgggaat atggcgactg ggaggcctgc aagggccatt tggtaaagaa cggaaggctg    300

tttgccgagc gaagtaaggc tgctcgaaag accatttcgg aaaagggtct agcatttgtg    360

cgggatgacg atgtcattct ggtccactct ttctcgcgaa cggtactggc ccttctggaa    420

catgctgcta agaacttggt gcgtttcaga gtgtttgtca cagaggctgc tcctagtgat    480

cagggtaagc gaatggccaa ggcattgagg gagagaggca ttcccgtgag tctaattgtg    540

gacaacgccg tcggatctgt gattgacgag gtgtccaagg tgttttgtgg tgccgaggga    600
```

```
gtggcggagt ctggaggagt catcaaccac gtcggatcat atcagattgc cgtgctagcc    660

aagaacgcaa ataagccctt ctacgtggtc accgagagtc acaagtttgt gcgaatcttc    720

cctctggccc aggccgatct gccagacacc aaaaagatgt tccacttcac tgttgaggag    780

cccgaggagc agaatgccga caagggtctg tcgccagtcg tcgactttac gcctcacgat    840

tacatcactg cacttatcac agatctggga gttctcactc caagtggcgt ttctgaggag    900

ctgattaaaa tgtggtatga gtaa                                           924


<210> SEQ ID NO 66
<211> LENGTH: 307
<212> TYPE: PRT
<213> ORGANISM: Yarrowia lipolytica

<400> SEQUENCE: 66

Met Ala Lys Phe Asp Ile Lys Glu Thr Tyr Leu Arg Phe Leu Arg Asp
1               5                   10                  15

Asp Pro Asp Ile Thr Met Pro Val Ala Ala Ile Glu Ala Leu Val Gln
            20                  25                  30

Leu Leu Ser Glu Thr Glu Thr Ser Thr Ser Ala Glu Leu Ile Gln Thr
        35                  40                  45

Leu Lys Glu Ala Ser Ala Glu Leu Lys Thr Ser Val Asp Asn Ser Met
    50                  55                  60

Ser Leu Ser Ala Gly Cys Asp Leu Phe Met Arg Phe Val Leu Arg Asn
65                  70                  75                  80

Ile Arg Glu Tyr Gly Asp Trp Glu Ala Cys Lys Gly His Leu Val Lys
                85                  90                  95

Asn Gly Arg Leu Phe Ala Glu Arg Ser Lys Ala Ala Arg Lys Thr Ile
            100                 105                 110

Ser Glu Lys Gly Leu Ala Phe Val Arg Asp Asp Asp Val Ile Leu Val
        115                 120                 125

His Ser Phe Ser Arg Thr Val Leu Ala Leu Leu Glu His Ala Ala Lys
    130                 135                 140

Asn Leu Val Arg Phe Arg Val Phe Val Thr Glu Ala Ala Pro Ser Asp
145                 150                 155                 160

Gln Gly Lys Arg Met Ala Lys Ala Leu Arg Glu Arg Gly Ile Pro Val
                165                 170                 175

Ser Leu Ile Val Asp Asn Ala Val Gly Ser Val Ile Asp Glu Val Ser
            180                 185                 190

Lys Val Phe Cys Gly Ala Glu Gly Val Ala Glu Ser Gly Gly Val Ile
        195                 200                 205

Asn His Val Gly Ser Tyr Gln Ile Ala Val Leu Ala Lys Asn Ala Asn
    210                 215                 220

Lys Pro Phe Tyr Val Val Thr Glu Ser His Lys Phe Val Arg Ile Phe
225                 230                 235                 240

Pro Leu Ala Gln Ala Asp Leu Pro Asp Thr Lys Lys Met Phe His Phe
                245                 250                 255

Thr Val Glu Glu Pro Glu Glu Gln Asn Ala Asp Lys Gly Leu Ser Pro
            260                 265                 270

Val Val Asp Phe Thr Pro His Asp Tyr Ile Thr Ala Leu Ile Thr Asp
        275                 280                 285

Leu Gly Val Leu Thr Pro Ser Gly Val Ser Glu Glu Leu Ile Lys Met
    290                 295                 300

Trp Tyr Glu
305
```

<210> SEQ ID NO 67
<211> LENGTH: 1395
<212> TYPE: DNA
<213> ORGANISM: Yarrowia lipolytica

<400> SEQUENCE: 67
atggattcgg atactgagtc agtgaaacga agaaagtcct ccgggtccga aagcgagtcg 60
agcgtgcgag atccgaaacg aaccaagatt gaagatgagg atttccagga gaacggcata 120
gacgatgagg atgaggagga ggaagaggag gaagctaagg acgaagggga tgaagacgac 180
gaagaaaaag gagaggacga cgaggaggac gatgaagaaa aagaaggcga ggatggagaa 240
ggagaggaag aagacgaaga ggaggatgag gagaagaagc gagaggagga ggagaagtac 300
gttaccagct tcaactttga tggtgtggaa tacaagtaca aagagcgacc agcagtgatt 360
gaggagcgtg aaggaaagat tgaatttcgt gttgtcaaca acgataactc caaggaaaac 420
ctcatgatcc tgacaggtct caagaacatt ttccagaaac agctgcccaa aatgcctcga 480
gagtacattg cccgactagt gtacgacaga agtcatgtgt caatggcagt tgttagaaag 540
cctctcacgg tggtcggagg aattacattt cggccgttcg atacccggaa gtttgctgaa 600
atcgtcttct gtgccatcag tagtacagag caggtccgag gatacggagc gcacttgatg 660
aaccatttga aggactacgt taaggctaca tcgcctgtga tgtactttct gacatacgcc 720
gataactatg ccattggata cttcaagaag cagggtttct ccaaggagat ctccctcgac 780
agatcggtgt ggatgggata catcaaggat tacgagggag gtactctcat gcagtgctcc 840
atgctgccac gaatcagata ccttgacgtc aacaagattc ttctgctaca gaaggcactg 900
attcacaaga agatccgggc catctccaag agtcatgttg tgcgaaaagg cctcgaccac 960
tttcgtgatt cgaccacgcc agtggacccc atgacgatcc cgggcttgaa ggaggctgga 1020
tggacacctg agatggacga gttggctaga cgaccaaagc gaggtcctca ttttgcagtc 1080
atgcagcacg tgctgtcaga gttgcagaac cacgcttctg cttggccgtt tgcccaggct 1140
gttaaccgag acgaggtgcc cgactactat gaggtcatta aggagcccat ggatctctca 1200
acgatggagc aacgtctcga agctgactct tacaagacca tggaggagtt tgtgtatgac 1260
gctcggttgg tgttcaataa ctgtcgtgct tacaacaacg agacgacgac ttactataag 1320
aatgccaaca agctagagaa gttcatggtg gccaaaatca aagagatccc tgagtactct 1380
catttggtgg agtaa 1395

<210> SEQ ID NO 68
<211> LENGTH: 464
<212> TYPE: PRT
<213> ORGANISM: Yarrowia lipolytica

<400> SEQUENCE: 68

Met Asp Ser Asp Thr Glu Ser Val Lys Arg Arg Lys Ser Ser Gly Ser
1 5 10 15

Glu Ser Glu Ser Ser Val Arg Asp Pro Lys Arg Thr Lys Ile Glu Asp
20 25 30

Glu Asp Phe Gln Glu Asn Gly Ile Asp Asp Glu Asp Glu Glu Glu Glu
35 40 45

Glu Glu Glu Ala Lys Asp Glu Gly Asp Glu Asp Asp Glu Glu Lys Gly
50 55 60

Glu Asp Asp Glu Glu Asp Asp Glu Glu Lys Glu Gly Glu Asp Gly Glu
65 70 75 80

```
Gly Glu Glu Glu Asp Glu Glu Glu Asp Glu Glu Lys Lys Arg Glu Glu
                85                  90                  95

Glu Glu Lys Tyr Val Thr Ser Phe Asn Phe Asp Gly Val Glu Tyr Lys
            100                 105                 110

Tyr Lys Glu Arg Pro Ala Val Ile Glu Glu Arg Glu Gly Lys Ile Glu
        115                 120                 125

Phe Arg Val Val Asn Asn Asp Asn Ser Lys Glu Asn Leu Met Ile Leu
    130                 135                 140

Thr Gly Leu Lys Asn Ile Phe Gln Lys Gln Leu Pro Lys Met Pro Arg
145                 150                 155                 160

Glu Tyr Ile Ala Arg Leu Val Tyr Asp Arg Ser His Val Ser Met Ala
                165                 170                 175

Val Val Arg Lys Pro Leu Thr Val Val Gly Gly Ile Thr Phe Arg Pro
            180                 185                 190

Phe Asp Thr Arg Lys Phe Ala Glu Ile Val Phe Cys Ala Ile Ser Ser
        195                 200                 205

Thr Glu Gln Val Arg Gly Tyr Gly Ala His Leu Met Asn His Leu Lys
    210                 215                 220

Asp Tyr Val Lys Ala Thr Ser Pro Val Met Tyr Phe Leu Thr Tyr Ala
225                 230                 235                 240

Asp Asn Tyr Ala Ile Gly Tyr Phe Lys Lys Gln Gly Phe Ser Lys Glu
                245                 250                 255

Ile Ser Leu Asp Arg Ser Val Trp Met Gly Tyr Ile Lys Asp Tyr Glu
            260                 265                 270

Gly Gly Thr Leu Met Gln Cys Ser Met Leu Pro Arg Ile Arg Tyr Leu
        275                 280                 285

Asp Val Asn Lys Ile Leu Leu Leu Gln Lys Ala Leu Ile His Lys Lys
    290                 295                 300

Ile Arg Ala Ile Ser Lys Ser His Val Val Arg Lys Gly Leu Asp His
305                 310                 315                 320

Phe Arg Asp Ser Thr Thr Pro Val Asp Pro Met Thr Ile Pro Gly Leu
                325                 330                 335

Lys Glu Ala Gly Trp Thr Pro Glu Met Asp Glu Leu Ala Arg Arg Pro
            340                 345                 350

Lys Arg Gly Pro His Phe Ala Val Met Gln His Val Leu Ser Glu Leu
        355                 360                 365

Gln Asn His Ala Ser Ala Trp Pro Phe Ala Gln Ala Val Asn Arg Asp
    370                 375                 380

Glu Val Pro Asp Tyr Tyr Glu Val Ile Lys Glu Pro Met Asp Leu Ser
385                 390                 395                 400

Thr Met Glu Gln Arg Leu Glu Ala Asp Ser Tyr Lys Thr Met Glu Glu
                405                 410                 415

Phe Val Tyr Asp Ala Arg Leu Val Phe Asn Asn Cys Arg Ala Tyr Asn
            420                 425                 430

Asn Glu Thr Thr Thr Tyr Tyr Lys Asn Ala Asn Lys Leu Glu Lys Phe
        435                 440                 445

Met Val Ala Lys Ile Lys Glu Ile Pro Glu Tyr Ser His Leu Val Glu
    450                 455                 460
```

<210> SEQ ID NO 69
<211> LENGTH: 5295
<212> TYPE: DNA
<213> ORGANISM: Candida albicans

<400> SEQUENCE: 69

-continued

```
atgccagaaa catcaattac tctggattta gaacatagac aacaagatga aattagtagt     60
atatcatcaa tttatggtga tatctttaaa gatattactc caacgggttt agtttggaat    120
aaaaaaccca gtccgcattt ccaagtattt ttatcatcgt caaataatcc tgatcgaccg    180
actgtttcca ttacattaga tatagaattc actcctactt atcctttatc acctccaaaa    240
gtaaaactac taaatgctcg taatttattg aaaattaata ttgctaaatt agaaaagaaa    300
tgtaaagatt taatcaaaga atatcccgaa caagaagttt ctttcacgat aatttccgaa    360
ttgattttca tgttagatga aatacaaaca acaactgaaa aagtattatc attagaagaa    420
gaaagagaat taagattaag aaatgaaaga agggcattag aagaaaaaga ggcgaaacag    480
aagaaggatg aagaattggc tcgaaagaaa caaaataaag aattgaatga acaaattcaa    540
aaaattcaag gtgaatttga tgatgatttt actgatgatc aagatttaga tatgtcaact    600
actaatgata ataataattc attaatccca cttgataaag atcaattttt catttttgaa    660
aatgccatgg aagcaaccat tcctaataca agacggaaat ttaagtttcg agcaatactg    720
ggattcataa gatataatca aaagggggtt ttcaattcaa ttggatccca atatattgtt    780
aaaccattta ttgataatga aatccggaat aaaattgaaa ataaaggttc tgatttggca    840
ttcttattaa cagtgattga tttaaccaat gaatattggc aaactgacaa ggggaagcga    900
gaaattcaag atttagaatc ggaattacaa tcaattatga gtataaatca tagtaatata    960
ttaaaattaa ttggatttca aatagataaa acaaatgttt ggagagtaag attgttaacg   1020
gaattttctc cagttagtga aacattatat gatattctcc ctactgccga atttattaat   1080
tgggcattag caagaacttg gcttattcaa ttattaccag caatggaata tcttcataat   1140
gccggattca tccataaact tatatgtccc atgaccatag ttatatttca agagaaggac   1200
caattgtatt atcaaaattc aactaatgaa ttattaagta atagtattgg tggtggtggt   1260
ggtggtgggg aagactcatt aaccatcagt gctaaaaaag tgttgaaatt atgtcatcct   1320
tcatatgggt atcgtttatt agagatgatt ctgttacatc caaatgaggg agaaacatta   1380
gatcgatctc cacaagtaaa tccaccagca tggttagcac cagaattgaa aacttctggg   1440
tatcattaca aatctgatat ttgggattta ggagtacttt tcttaagagt aatgttagga   1500
tttgatattt taaacaccac ataccataca cctagtgatt ttataaataa attttccgtt   1560
aaagattttg ttggagcaga agaatatgct tcattagtgt atgatgtatt atcgaaaatg   1620
ttacaagtta aattatcaaa acgaccatct cctttggaat taaatgccgt aaaattttta   1680
cgagatggtc ccataatttc aaaattacaa tcggaaacta acttatcacg aatgaaaaaa   1740
aatgtcgaaa ctgatttggt atcatcaacc aatacaagac atgttcaaat acaaggacat   1800
gaacaggatt cgactgcaac aacaaaacat ttgaatattt atcatcaaaa tatttcacgc   1860
agacggttat ctaaccagaa tactcaacat ccatattttg gtgaaaattc tagtcttatc   1920
atgccttcag ggtcacaacg aaatatgggg agatacgcca gagattttga agaaattggg   1980
aaattgggtc gtggtggatt tggtgaagtt gttaaagcta gaagtagaat ggaagggata   2040
ttttatgctg tgaaaaaaat taaacatcga gctgataaat tggattcttt attaagtgaa   2100
gttttatctt tagctagatt gaaccatcaa tatattgttc gttattatgg tacttgggtt   2160
gaagaattag aagatacatc tgcgattcca tccaatagca catctgctat tgcgagcgat   2220
gacgaagagg aggaagagga ggaagatgac acagaaggcg actttggtga tgatgatctt   2280
gaactgacat tttcaagtcg tgttggtcgt tcatcatctg tgttacctag ttatgataac   2340
tcatttcaag tcgattacat ttcaacatct tttgacccta ggatagaatt tgatgaaagt   2400
```

tcagaagaag atgaccaaaa tgaagatgat gatccgtttg tgtttgccaa ttcaactgat 2460
gatatctcaa ataatgaaac agaagatcgt tccaaaagtg attcgaaaga agtttctgtt 2520
aaaaaaccaa aagatgttgt taactcctct aaaaatgcat caccgaaatc aatattatat 2580
atacaaatgg agttttgtga aaataatacc cttctcaatc ttattgaaca aggattacct 2640
aataaccctg atgaatattg gagacttttc cgacaattac ttgaagcagt ttcatatatt 2700
catcgtgaag gatttattca tcgtgattta aaaccaatga atattttcat tgatagatcc 2760
aataatatta aagttgggga tttcggatta gctaaaaatt cacaattttc ttcagttgtt 2820
ctgacgaata atcaagtgga agctaaagat aatgaattat ctaccgtggt gggaacatta 2880
ttttatactg ccaatgaagt ggccacgggt caatacgatg aaaaagttga tatgtattca 2940
cttggaataa ttttctttga aatgtgttat cctcttgcca cgggtatgca aagagctaaa 3000
acattaaatg atttacgatt gaaatcagtt gaattcccta caaatttcat tgctagtaaa 3060
tataaaactg aaaaaaaaat tattcgatta ttattagatc atgatcctaa aattcgtcct 3120
agtgcagcac aacttttaca aagtggttgg ttacccgttg aacatcaaga tcaagttatt 3180
caagaagcat taaaatcttt agctgatcca gcatctcctt ggcaacaaca agttcgtgaa 3240
gcattgttca atcaaccgta tctgcttgct aaagatttaa tgtttgataa acaaaatgaa 3300
cataattccc ataataagca tgttgaattg gatacttcga atgattattt attatttgat 3360
aaaatcatga aagaattgac caagattttc actaatcatg gagccattga gaatttaaat 3420
acaaatttag ttttaccaaa ggcaccttca caatcaagag aattagttta tgatttttg 3480
gatagaagtg gtgcagtttt aactttacct tatgatttga ctttaccaac agcaagattt 3540
ttaagtaaaa ccgatatgac aattcctaaa acttttcgac acgaatttgt ctatcgacct 3600
aatgttcgag gtattggtat acctgatcgt tatagtgccg ttaattttga tatagccggt 3660
ggactggaag ttaacaaggc aacacttttc gctcatgatg ctgaatgttt aaaagtgatt 3720
gatgaaattg tcaatacttt accatgtttt aaaaatacca ttattgttat taatcattat 3780
gatattttgg atgctgttgt ttcatttttct tttggtaata ttggaattga tgataagaaa 3840
aaattagata tttttggagt attatcacaa ttgggaattg ataaatcacc cgatgaaata 3900
aaacgttact tgagggaaga ttttcaagta ccacatactg ttactaaaga tcttgttgaa 3960
aatttcaatt ttacatgtga agtggaacgg gcaagacaaa aattacaaaa attaatggtt 4020
gattctcccc cattattaaa agttgaacga gcatatactt atttaattga agtggttaaa 4080
attttgaaac acacgaatat taaaacatca atgattttca atccattgag taattataat 4140
agtaaatatt atatccatgg aataatgttt caagcagttt ttaaacctga tagatccaaa 4200
cgttatacta gagtagttac tggtggacga tatgattcat taattgaatc tttttcaaat 4260
gtcaccacaa caactaaaca aatcactcct catggtgttg gattttcatt gactactagt 4320
ttacttttca ttcttatgaa aacattaatt tctcgaggga aatctaaatt ggatcttgta 4380
aataaatgga agggcaatcg atgtaaagta cttataagtt ctactcaaca acaattttta 4440
agtcaagtgg gatatcaatt agtttctaaa ttttggaata aaaacataag tgctgatata 4500
acatcagttg cagcaaagac tcaagatgaa atattccaaa atggtaattc agaaggggct 4560
atatggatag ttataatacg actgttacct acaacaattg ggaattcatt ctcatctttg 4620
aatggtggta gtggtggtag tagtagtagt actactacta ctagcactag cattagaaga 4680
agtaaaaaat ctggatctgg atttaaacct ttgaaattga gaaatataat tactggtaaa 4740
gatattgatt tagattatga tgaagtgata gattatttgg tgactgaatt attagaagat 4800

```
tcagaacatg aagaaaatga tcaagataat ggtacgatga caaactcaac aacattactt   4860

acatcatcat cattatcttc taaaacaaat caagaagaag aattattaaa tggaccaatt   4920

gattcagttg aaattgatca aaaaatcatt gttgttaaaa atgatgctcc tcgtagtagg   4980

aaaaataaac gagataaatg ggaatcagaa aatgatgcta aattagctgg acaacaatgt   5040

ataaaaaatt taagtggtgg acctgttgtt gttattgatg ctagagatga aatattagat   5100

atgattagta ttacttcaat tcatcaacaa gatgaatgga ttagaaaagt ggtttataca   5160

actaataatt tcccaaaaag ttttgctatg aatatttata atactttgat taaagaattt   5220

aataaaggtt caatttggtg tattttggtg tcttcaagaa ctcaacatac aactattgtt   5280

gatctacgtc gataa                                                    5295
```

```
<210> SEQ ID NO 70
<211> LENGTH: 1764
<212> TYPE: PRT
<213> ORGANISM: Candida albicans

<400> SEQUENCE: 70

Met Pro Glu Thr Ser Ile Thr Ser Asp Leu Glu His Arg Gln Gln Asp
1               5                   10                  15

Glu Ile Ser Ser Ile Ser Ser Ile Tyr Gly Asp Ile Phe Lys Asp Ile
            20                  25                  30

Thr Pro Thr Gly Leu Val Trp Asn Lys Lys Pro Ser Pro His Phe Gln
        35                  40                  45

Val Phe Leu Ser Ser Ser Asn Asn Pro Asp Arg Pro Thr Val Ser Ile
    50                  55                  60

Thr Leu Asp Ile Glu Phe Thr Pro Thr Tyr Pro Leu Ser Pro Pro Lys
65                  70                  75                  80

Val Lys Leu Leu Asn Ala Arg Asn Leu Leu Lys Ile Asn Ile Ala Lys
                85                  90                  95

Leu Glu Lys Lys Cys Lys Asp Leu Ile Lys Glu Tyr Pro Glu Gln Glu
            100                 105                 110

Val Ser Phe Thr Ile Ile Ser Glu Leu Ile Phe Met Leu Asp Glu Ile
        115                 120                 125

Gln Thr Thr Thr Glu Lys Val Leu Ser Leu Glu Glu Glu Arg Glu Leu
    130                 135                 140

Arg Leu Arg Asn Glu Arg Arg Ala Leu Glu Glu Lys Glu Ala Lys Gln
145                 150                 155                 160

Lys Lys Asp Glu Glu Leu Ala Arg Lys Lys Gln Asn Lys Glu Leu Asn
                165                 170                 175

Glu Gln Ile Gln Lys Ile Gln Gly Glu Phe Asp Asp Asp Phe Thr Asp
            180                 185                 190

Asp Gln Asp Leu Asp Met Ser Thr Thr Asn Asp Asn Asn Asn Ser Leu
        195                 200                 205

Ile Pro Leu Asp Lys Asp Gln Phe Phe Ile Phe Glu Asn Ala Met Glu
    210                 215                 220

Ala Thr Ile Pro Asn Thr Arg Arg Lys Phe Lys Phe Arg Ala Ile Ser
225                 230                 235                 240

Gly Phe Ile Arg Tyr Asn Gln Lys Gly Val Phe Asn Ser Ile Gly Ser
                245                 250                 255

Gln Tyr Ile Val Lys Pro Phe Ile Asp Asn Glu Ile Arg Asn Lys Ile
            260                 265                 270

Glu Asn Lys Gly Ser Asp Leu Ala Phe Leu Leu Thr Val Ile Asp Leu
        275                 280                 285
```

```
Thr Asn Glu Tyr Trp Gln Thr Asp Lys Gly Lys Arg Glu Ile Gln Asp
    290                 295                 300

Leu Glu Ser Glu Leu Gln Ser Ile Met Ser Ile Asn His Ser Asn Ile
305                 310                 315                 320

Leu Lys Leu Ile Gly Phe Gln Ile Asp Lys Thr Asn Val Trp Arg Val
                325                 330                 335

Arg Leu Leu Thr Glu Phe Ser Pro Val Ser Glu Thr Leu Tyr Asp Ile
            340                 345                 350

Leu Pro Thr Ala Glu Phe Ile Asn Trp Ala Leu Ala Arg Thr Trp Leu
        355                 360                 365

Ile Gln Leu Leu Pro Ala Met Glu Tyr Leu His Asn Ala Gly Phe Ile
    370                 375                 380

His Lys Leu Ile Cys Pro Met Thr Ile Val Ile Phe Gln Glu Lys Asp
385                 390                 395                 400

Gln Leu Tyr Tyr Gln Asn Ser Thr Asn Glu Leu Leu Ser Asn Ser Ile
                405                 410                 415

Gly Gly Gly Gly Gly Gly Gly Glu Asp Ser Leu Thr Ile Ser Ala Lys
            420                 425                 430

Lys Val Leu Lys Leu Cys His Pro Ser Tyr Gly Tyr Arg Leu Leu Glu
        435                 440                 445

Met Ile Ser Leu His Pro Asn Glu Gly Glu Thr Leu Asp Arg Ser Pro
    450                 455                 460

Gln Val Asn Pro Pro Ala Trp Leu Ala Pro Glu Leu Lys Thr Ser Gly
465                 470                 475                 480

Tyr His Tyr Lys Ser Asp Ile Trp Asp Leu Gly Val Leu Phe Leu Arg
                485                 490                 495

Val Met Leu Gly Phe Asp Ile Leu Asn Thr Thr Tyr His Thr Pro Ser
            500                 505                 510

Asp Phe Ile Asn Lys Phe Ser Val Lys Asp Phe Val Gly Ala Glu Glu
        515                 520                 525

Tyr Ala Ser Leu Val Tyr Asp Val Leu Ser Lys Met Leu Gln Val Lys
    530                 535                 540

Leu Ser Lys Arg Pro Ser Pro Leu Glu Leu Asn Ala Val Lys Phe Leu
545                 550                 555                 560

Arg Asp Gly Pro Ile Ile Ser Lys Leu Gln Ser Glu Thr Asn Leu Ser
                565                 570                 575

Arg Met Lys Lys Asn Val Glu Thr Asp Leu Val Ser Ser Thr Asn Thr
            580                 585                 590

Arg His Val Gln Ile Gln Gly His Glu Gln Asp Ser Thr Ala Thr Thr
        595                 600                 605

Lys His Leu Asn Ile Tyr His Gln Asn Ile Ser Arg Arg Arg Leu Ser
    610                 615                 620

Asn Gln Asn Thr Gln His Pro Tyr Phe Gly Glu Asn Ser Ser Leu Ile
625                 630                 635                 640

Met Pro Ser Gly Ser Gln Arg Asn Met Gly Arg Tyr Ala Arg Asp Phe
                645                 650                 655

Glu Glu Ile Gly Lys Leu Gly Arg Gly Gly Phe Gly Glu Val Val Lys
            660                 665                 670

Ala Arg Ser Arg Met Glu Gly Ile Phe Tyr Ala Val Lys Lys Ile Lys
        675                 680                 685

His Arg Ala Asp Lys Leu Asp Ser Leu Leu Ser Glu Val Leu Ser Leu
    690                 695                 700

Ala Arg Leu Asn His Gln Tyr Ile Val Arg Tyr Tyr Gly Thr Trp Val
705                 710                 715                 720
```

```
Glu Glu Leu Glu Asp Thr Ser Ala Ile Pro Ser Asn Ser Thr Ser Ala
                725                 730                 735

Ile Ala Ser Asp Asp Glu Glu Glu Glu Glu Glu Glu Asp Asp Thr Glu
            740                 745                 750

Gly Asp Phe Gly Asp Asp Asp Leu Glu Ser Thr Phe Ser Ser Arg Val
        755                 760                 765

Gly Arg Ser Ser Ser Val Leu Pro Ser Tyr Asp Asn Ser Phe Gln Val
    770                 775                 780

Asp Tyr Ile Ser Thr Ser Phe Asp Pro Arg Ile Glu Phe Asp Glu Ser
785                 790                 795                 800

Ser Glu Glu Asp Asp Gln Asn Glu Asp Asp Asp Pro Phe Val Phe Ala
                805                 810                 815

Asn Ser Thr Asp Asp Ile Ser Asn Asn Glu Thr Glu Asp Arg Ser Lys
            820                 825                 830

Ser Asp Ser Lys Glu Val Ser Val Lys Lys Pro Lys Asp Val Val Asn
        835                 840                 845

Ser Ser Lys Asn Ala Ser Pro Lys Ser Ile Leu Tyr Ile Gln Met Glu
    850                 855                 860

Phe Cys Glu Asn Asn Thr Leu Leu Asn Leu Ile Glu Gln Gly Leu Pro
865                 870                 875                 880

Asn Asn Pro Asp Glu Tyr Trp Arg Leu Phe Arg Gln Leu Leu Glu Ala
                885                 890                 895

Val Ser Tyr Ile His Arg Glu Gly Phe Ile His Arg Asp Leu Lys Pro
            900                 905                 910

Met Asn Ile Phe Ile Asp Arg Ser Asn Asn Ile Lys Val Gly Asp Phe
        915                 920                 925

Gly Leu Ala Lys Asn Ser Gln Phe Ser Ser Val Val Ser Thr Asn Asn
    930                 935                 940

Gln Val Glu Ala Lys Asp Asn Glu Leu Ser Thr Val Val Gly Thr Leu
945                 950                 955                 960

Phe Tyr Thr Ala Asn Glu Val Ala Thr Gly Gln Tyr Asp Glu Lys Val
                965                 970                 975

Asp Met Tyr Ser Leu Gly Ile Ile Phe Phe Glu Met Cys Tyr Pro Leu
            980                 985                 990

Ala Thr Gly Met Gln Arg Ala Lys  Thr Leu Asn Asp Leu  Arg Leu Lys
        995                 1000                1005

Ser Val  Glu Phe Pro Thr Asn  Phe Ile Ala Ser Lys  Tyr Lys Thr
    1010                 1015                 1020

Glu Lys  Lys Ile Ile Arg Leu  Leu Leu Asp His Asp  Pro Lys Ile
    1025                 1030                 1035

Arg Pro  Ser Ala Ala Gln Leu  Leu Gln Ser Gly Trp  Leu Pro Val
    1040                 1045                 1050

Glu His  Gln Asp Gln Val Ile  Gln Glu Ala Leu Lys  Ser Leu Ala
    1055                 1060                 1065

Asp Pro  Ala Ser Pro Trp Gln  Gln Gln Val Arg Glu  Ala Leu Phe
    1070                 1075                 1080

Asn Gln  Pro Tyr Ser Leu Ala  Lys Asp Leu Met Phe  Asp Lys Gln
    1085                 1090                 1095

Asn Glu  His Asn Ser His Asn  Lys His Val Glu Leu  Asp Thr Ser
    1100                 1105                 1110

Asn Asp  Tyr Leu Leu Phe Asp  Lys Ile Met Lys Glu  Leu Thr Lys
    1115                 1120                 1125

Ile Phe  Thr Asn His Gly Ala  Ile Glu Asn Leu Asn  Thr Asn Leu
```

-continued

```
    1130                1135                1140

Val Leu  Pro Lys Ala Pro Ser  Gln Ser Arg Glu Leu  Val Tyr Asp
    1145                1150                1155

Phe Leu  Asp Arg Ser Gly Ala  Val Leu Thr Leu Pro  Tyr Asp Leu
    1160                1165                1170

Thr Leu  Pro Thr Ala Arg Phe  Leu Ser Lys Thr Asp  Met Thr Ile
    1175                1180                1185

Pro Lys  Thr Phe Arg His Glu  Phe Val Tyr Arg Pro  Asn Val Arg
    1190                1195                1200

Gly Ile  Gly Ile Pro Asp Arg  Tyr Ser Ala Val Asn  Phe Asp Ile
    1205                1210                1215

Ala Gly  Gly Ser Glu Val Asn  Lys Ala Thr Leu Phe  Ala His Asp
    1220                1225                1230

Ala Glu  Cys Leu Lys Val Ile  Asp Glu Ile Val Asn  Thr Leu Pro
    1235                1240                1245

Cys Phe  Lys Asn Thr Ile Ile  Val Ile Asn His Tyr  Asp Ile Leu
    1250                1255                1260

Asp Ala  Val Val Ser Phe Ser  Phe Gly Asn Ile Gly  Ile Asp Asp
    1265                1270                1275

Lys Lys  Lys Leu Asp Ile Phe  Gly Val Leu Ser Gln  Leu Gly Ile
    1280                1285                1290

Asp Lys  Ser Pro Asp Glu Ile  Lys Arg Tyr Leu Arg  Glu Asp Phe
    1295                1300                1305

Gln Val  Pro His Thr Val Thr  Lys Asp Leu Val Glu  Asn Phe Asn
    1310                1315                1320

Phe Thr  Cys Glu Val Glu Arg  Ala Arg Gln Lys Leu  Gln Lys Leu
    1325                1330                1335

Met Val  Asp Ser Pro Pro Leu  Leu Lys Val Glu Arg  Ala Tyr Thr
    1340                1345                1350

Tyr Leu  Ile Glu Val Val Lys  Ile Leu Lys His Thr  Asn Ile Lys
    1355                1360                1365

Thr Ser  Met Ile Phe Asn Pro  Leu Ser Asn Tyr Asn  Ser Lys Tyr
    1370                1375                1380

Tyr Ile  His Gly Ile Met Phe  Gln Ala Val Phe Lys  Pro Asp Arg
    1385                1390                1395

Ser Lys  Arg Tyr Thr Arg Val  Val Thr Gly Gly Arg  Tyr Asp Ser
    1400                1405                1410

Leu Ile  Glu Ser Phe Ser Asn  Val Thr Thr Thr Thr  Lys Gln Ile
    1415                1420                1425

Thr Pro  His Gly Val Gly Phe  Ser Leu Thr Thr Ser  Leu Leu Phe
    1430                1435                1440

Ile Leu  Met Lys Thr Leu Ile  Ser Arg Gly Lys Ser  Lys Leu Asp
    1445                1450                1455

Leu Val  Asn Lys Trp Lys Gly  Asn Arg Cys Lys Val  Leu Ile Ser
    1460                1465                1470

Ser Thr  Gln Gln Gln Phe Leu  Ser Gln Val Gly Tyr  Gln Leu Val
    1475                1480                1485

Ser Lys  Phe Trp Asn Lys Asn  Ile Ser Ala Asp Ile  Thr Ser Val
    1490                1495                1500

Ala Ala  Lys Thr Gln Asp Glu  Ile Phe Gln Asn Gly  Asn Ser Glu
    1505                1510                1515

Gly Ala  Ile Trp Ile Val Ile  Ile Arg Ser Leu Pro  Thr Thr Ile
    1520                1525                1530
```

```
Gly Asn  Ser Phe Ser Ser Leu  Asn Gly Gly Ser Gly  Gly Ser Ser
    1535                 1540                 1545

Ser Ser  Thr Thr Thr Thr Ser  Thr Ser Ile Arg Arg  Ser Lys Lys
    1550                 1555                 1560

Ser Gly  Ser Gly Phe Lys Pro  Leu Lys Leu Arg Asn  Ile Ile Thr
    1565                 1570                 1575

Gly Lys  Asp Ile Asp Leu Asp  Tyr Asp Glu Val Ile  Asp Tyr Leu
    1580                 1585                 1590

Val Thr  Glu Leu Leu Glu Asp  Ser Glu His Glu Glu  Asn Asp Gln
    1595                 1600                 1605

Asp Asn  Gly Thr Met Thr Asn  Ser Thr Thr Leu Leu  Thr Ser Ser
    1610                 1615                 1620

Ser Leu  Ser Ser Lys Thr Asn  Gln Glu Glu Glu Leu  Leu Asn Gly
    1625                 1630                 1635

Pro Ile  Asp Ser Val Glu Ile  Asp Gln Lys Ile Ile  Val Val Lys
    1640                 1645                 1650

Asn Asp  Ala Pro Arg Ser Arg  Lys Asn Lys Arg Asp  Lys Trp Glu
    1655                 1660                 1665

Ser Glu  Asn Asp Ala Lys Leu  Ala Gly Gln Gln Cys  Ile Lys Asn
    1670                 1675                 1680

Leu Ser  Gly Gly Pro Val Val  Val Ile Asp Ala Arg  Asp Glu Ile
    1685                 1690                 1695

Leu Asp  Met Ile Ser Ile Thr  Ser Ile His Gln Gln  Asp Glu Trp
    1700                 1705                 1710

Ile Arg  Lys Val Val Tyr Thr  Thr Asn Asn Phe Pro  Lys Ser Phe
    1715                 1720                 1725

Ala Met  Asn Ile Tyr Asn Thr  Leu Ile Lys Glu Phe  Asn Lys Gly
    1730                 1735                 1740

Ser Ile  Trp Cys Ile Leu Val  Ser Ser Arg Thr Gln  His Thr Thr
    1745                 1750                 1755

Ile Val  Asp Leu Arg Arg
    1760
```

<210> SEQ ID NO 71
<211> LENGTH: 936
<212> TYPE: DNA
<213> ORGANISM: Candida albicans

<400> SEQUENCE: 71

```
atggctgatt ttgacattaa ggaaacgtat cttaagtttt tagaagaaga caaagatatg     60

actatgccta tcgcggcaat tgagtcactt gtgtcaatgt taaaagcaaa gtcaccatca    120

acttcctccg aattaatcaa tttagtttcg aaaaatattg atttattaaa gtcttcaatt    180

cccaacaata tttctctttc tgctgggtgt gatttattta tgagatttgt gttgagaaac    240

actaatgtat attctgattg ggagtcattt tcacagaatc ttgttgagaa tggagaattg    300

tttgttcaac gtgctaagga atcaagactt aaactggcag aatacggtgt tccatttatc    360

aaggatgacg atgtaatatt agttcattca tattcacgtg tcgtttacag tctattgttg    420

aaggctaaac aggagaagct aattcgattc aaagttttgg ttaccgagag tagaccaaca    480

ggaaatggat actacatggc taggaaattg aaagaggcag acataccggt tgaggttatt    540

gtagataacg cagtgggata tgttttgcat aaagtagaca aaatcttggt tggtgccgaa    600

ggggtcgctg aaagtggtgg agtaataaat cacattggaa cgtatcaaat tggctgttta    660

gctaaagtca acaataagcc tttctatgtc gtgaccgagt ctcacaaatt tgtcagattg    720
```

```
tttcccttgg cacctaatga cctacctaac agcattagtc atttcgatta tgacgaaaac    780

agaaccgaag agctcaacca cagtggacaa gaacttttcg aaaccaggtt tgttgatttc    840

acacctcatg aatacattac tgctttgata acagatttgg gagtattgac tccatctgca    900

gtcagtgaag agttgataaa aatatggtac gattga                              936
```

<210> SEQ ID NO 72
<211> LENGTH: 311
<212> TYPE: PRT
<213> ORGANISM: Candida albicans

<400> SEQUENCE: 72

```
Met Ala Asp Phe Asp Ile Lys Glu Thr Tyr Leu Lys Phe Leu Glu Glu
1               5                   10                  15

Asp Lys Asp Met Thr Met Pro Ile Ala Ala Ile Glu Ser Leu Val Ser
            20                  25                  30

Met Leu Lys Ala Lys Ser Pro Ser Thr Ser Ser Glu Leu Ile Asn Leu
        35                  40                  45

Val Ser Lys Asn Ile Asp Leu Leu Lys Ser Ser Ile Pro Asn Asn Ile
    50                  55                  60

Ser Leu Ser Ala Gly Cys Asp Leu Phe Met Arg Phe Val Leu Arg Asn
65                  70                  75                  80

Thr Asn Val Tyr Ser Asp Trp Glu Ser Phe Ser Gln Asn Leu Val Glu
                85                  90                  95

Asn Gly Glu Leu Phe Val Gln Arg Ala Lys Glu Ser Arg Leu Lys Ser
            100                 105                 110

Ala Glu Tyr Gly Val Pro Phe Ile Lys Asp Asp Asp Val Ile Leu Val
        115                 120                 125

His Ser Tyr Ser Arg Val Val Tyr Ser Leu Leu Leu Lys Ala Lys Gln
    130                 135                 140

Glu Lys Leu Ile Arg Phe Lys Val Leu Val Thr Glu Ser Arg Pro Thr
145                 150                 155                 160

Gly Asn Gly Tyr Tyr Met Ala Arg Lys Leu Lys Glu Ala Asp Ile Pro
                165                 170                 175

Val Glu Val Ile Val Asp Asn Ala Val Gly Tyr Val Leu His Lys Val
            180                 185                 190

Asp Lys Ile Leu Val Gly Ala Glu Gly Val Ala Glu Ser Gly Gly Val
        195                 200                 205

Ile Asn His Ile Gly Thr Tyr Gln Ile Gly Cys Leu Ala Lys Val Asn
    210                 215                 220

Asn Lys Pro Phe Tyr Val Val Thr Glu Ser His Lys Phe Val Arg Leu
225                 230                 235                 240

Phe Pro Leu Ala Pro Asn Asp Leu Pro Asn Ser Ile Ser His Phe Asp
                245                 250                 255

Tyr Asp Glu Asn Arg Thr Glu Glu Leu Asn His Ser Gly Gln Glu Leu
            260                 265                 270

Phe Glu Thr Arg Phe Val Asp Phe Thr Pro His Glu Tyr Ile Thr Ala
        275                 280                 285

Leu Ile Thr Asp Leu Gly Val Leu Thr Pro Ser Ala Val Ser Glu Glu
    290                 295                 300

Leu Ile Lys Ile Trp Tyr Asp
305                 310
```

<210> SEQ ID NO 73
<211> LENGTH: 1350
<212> TYPE: DNA

<213> ORGANISM: Candida albicans

<400> SEQUENCE: 73
atggttgaca gaaaaagaac tgcagcaata cgtgccgagg atgatgatga agaaaatgac 60
aatgttcctt tacagaaaaa agtgaaaata gaagcaaagc agaaagaaga agaggaagat 120
ggtgataagt caggagccac ggaaaccaaa tctgaggtga aacaagaatc aaaagaagaa 180
actactcaaa aggaaaataa tgaagaggac gaggaagagg aagaagagga agatgacgaa 240
gaagccgaag aagagaagaa aagaataacc aatttcaatt ttgatggcga aatttacaca 300
ttcaaggaaa gaccttcggt aattgaagaa aaagaaggca aaatagagtt tcgtgtggtg 360
aataatgaca atagtcgaga aaacttgatt gtgctaaccg ggttaaagaa tattttccaa 420
aagcaactac ccaagatgcc tcgtgaatat atctcgcgtt tggtgtatga tcgatcacat 480
ttgtcaatgg cagttgtgag aaagccatta actgtggtag gtgggatcac ataccgtcca 540
tttaacaacc gtggatttgc cgaaattgtg ttttgtgcta tctcgtcaac tgaacaagtg 600
cgtgggtatg gtgcacattt gatgaatcat ttgaaagact atgtgagggc aacatctcca 660
atcaaatatt tcttgacgta tgcagataac tatgctattg ggtatttcaa aaagcagggt 720
ttcacgaagg aaatatcatt agataaatcg gtgtggatgg ggtacatcaa ggattacgaa 780
ggtggtacat tgatgcagtg ctcgatgtta ccgtcaatat taaggtacct tgatctgggt 840
aaaatattac ttttgcaaaa agctgctatt gaaagaaaaa tacggtctag atctaaatca 900
aaaatagtga gaccgggttt gcaagttttt aaaaccaata agaatgtgac attagacccc 960
aaagatatcc ctggattagc agaggcaggg tggctggaag aaatggataa attagcacaa 1020
aaaccgaaaa gaggaccaca ttataacttt atggttacgc tattcagtga aattcagaac 1080 caccccttctg cttggccatt tgcagtggca gtcaacaaag aagaagtacc agattattat 1140
cgagttattg aacatccaat tgatttggca acaatagaac aaaaattgga aaacaacttg 1200
tatttaaaat ttactgattt tgtggatgat ctaaaactaa tgttcaacaa ttgtcgagct 1260
tataattcgg aaaccacaac atattataaa aacgcaaata aactagaaaa gtttatgaat 1320
aataaattga aagactgtag ttttgtatag 1350

<210> SEQ ID NO 74
<211> LENGTH: 449
<212> TYPE: PRT
<213> ORGANISM: Candida albicans

<400> SEQUENCE: 74

Met Val Asp Arg Lys Arg Thr Ala Ala Ile Arg Ala Glu Asp Asp Asp
1 5 10 15

Glu Glu Asn Asp Asn Val Pro Leu Gln Lys Lys Val Lys Ile Glu Ala
20 25 30

Lys Gln Lys Glu Glu Glu Glu Asp Gly Asp Lys Ser Gly Ala Thr Glu
35 40 45

Thr Lys Ser Glu Val Lys Gln Glu Ser Lys Glu Glu Thr Thr Gln Lys
50 55 60

Glu Asn Asn Glu Glu Asp Glu Glu Glu Glu Glu Glu Glu Asp Asp Glu
65 70 75 80

Glu Ala Glu Glu Glu Lys Lys Arg Ile Thr Asn Phe Asn Phe Asp Gly
85 90 95

Glu Ile Tyr Thr Phe Lys Glu Arg Pro Ser Val Ile Glu Glu Lys Glu
100 105 110

Gly Lys Ile Glu Phe Arg Val Val Asn Asn Asp Asn Ser Arg Glu Asn

```
        115                 120                 125

Leu Ile Val Leu Thr Gly Leu Lys Asn Ile Phe Gln Lys Gln Leu Pro
    130                 135                 140

Lys Met Pro Arg Glu Tyr Ile Ser Arg Leu Val Tyr Asp Arg Ser His
145                 150                 155                 160

Leu Ser Met Ala Val Val Arg Lys Pro Leu Thr Val Val Gly Gly Ile
                165                 170                 175

Thr Tyr Arg Pro Phe Asn Asn Arg Gly Phe Ala Glu Ile Val Phe Cys
            180                 185                 190

Ala Ile Ser Ser Thr Glu Gln Val Arg Gly Tyr Gly Ala His Leu Met
        195                 200                 205

Asn His Leu Lys Asp Tyr Val Arg Ala Thr Ser Pro Ile Lys Tyr Phe
    210                 215                 220

Leu Thr Tyr Ala Asp Asn Tyr Ala Ile Gly Tyr Phe Lys Lys Gln Gly
225                 230                 235                 240

Phe Thr Lys Glu Ile Ser Leu Asp Lys Ser Val Trp Met Gly Tyr Ile
                245                 250                 255

Lys Asp Tyr Glu Gly Gly Thr Leu Met Gln Cys Ser Met Leu Pro Ser
            260                 265                 270

Ile Leu Arg Tyr Leu Asp Ser Gly Lys Ile Leu Leu Leu Gln Lys Ala
        275                 280                 285

Ala Ile Glu Arg Lys Ile Arg Ser Arg Ser Lys Ser Lys Ile Val Arg
    290                 295                 300

Pro Gly Leu Gln Val Phe Lys Thr Asn Lys Asn Val Thr Leu Asp Pro
305                 310                 315                 320

Lys Asp Ile Pro Gly Leu Ala Glu Ala Gly Trp Ser Glu Glu Met Asp
                325                 330                 335

Lys Leu Ala Gln Lys Pro Lys Arg Gly Pro His Tyr Asn Phe Met Val
            340                 345                 350

Thr Leu Phe Ser Glu Ile Gln Asn His Pro Ser Ala Trp Pro Phe Ala
        355                 360                 365

Val Ala Val Asn Lys Glu Glu Val Pro Asp Tyr Tyr Arg Val Ile Glu
    370                 375                 380

His Pro Ile Asp Leu Ala Thr Ile Glu Gln Lys Leu Glu Asn Asn Leu
385                 390                 395                 400

Tyr Leu Lys Phe Thr Asp Phe Val Asp Asp Leu Lys Leu Met Phe Asn
                405                 410                 415

Asn Cys Arg Ala Tyr Asn Ser Glu Thr Thr Thr Tyr Tyr Lys Asn Ala
            420                 425                 430

Asn Lys Leu Glu Lys Phe Met Asn Asn Lys Leu Lys Asp Cys Ser Phe
        435                 440                 445

Val
```

<210> SEQ ID NO 75
<211> LENGTH: 1350
<212> TYPE: DNA
<213> ORGANISM: Candida albicans

<400> SEQUENCE: 75

```
atggttgaca gaaaaagaac tgcagcaata cgtgccgagg atgatgatga agaaaatgac      60

aatgttcctt tacagaaaaa agtgaaaata gaagcaaagc agaaagaaga agaggaagat     120

ggtgataagt caggagccac ggaaaccaaa tctgaggtga aacaagaatc aaaagaagaa     180

actactcaaa aggaaaataa tgaagaggac gaggaagagg aagaagagga agatgacgaa     240
```

gaagccgaag aagagaagaa aagaataacc aatttcaatt ttgatggcga aatttacaca 300
ttcaaggaaa gaccttcggt aattgaagaa aaagaaggca aaatagagtt tcgtgtggtg 360
aataatgaca atagtcgaga aaacttgatt gtgctaaccg ggttaaagaa tattttccaa 420
aagcaactac ccaagatgcc tcgtgaatat atctcgcgtt tggtgtatga tcgatcacat 480
ttgtcaatgg cagttgtgag aaagccatta actgtggtag gtgggatcac ataccgtcca 540
tttaacaacc gtggatttgc cgaaattgtg ttttgtgcta tctcgtcaac tgaacaagtg 600
cgtgggtatg gtgcacattt gatgaatcat ttgaaagact atgtgagggc aacatctcca 660
atcaaatatt tcttgacgta tgcagataac tatgctattg ggtatttcaa aaagcagggt 720
ttcacgaagg aaatatcatt agataaatcg gtgtggatgg ggtacatcaa ggattacgaa 780
ggtggtacat tgatgcagtg ctcgatgtta ccgtcaatat taaggtacct tgatctgggt 840
aaaatattac ttttgcaaaa agctgctatt gaaagaaaaa tacggtctag atctaaatca 900
aaaatagtga gaccgggttt gcaagttttt aaaaccaata agaatgtgac attagacccc 960
aaagatatcc ctggattagc agaggcaggg tggctggaag aaatggataa attagcacaa 1020
aaaccgaaaa gaggaccaca ttataacttt atggttacgc tattcagtga aattcagaac 1080 caccccttctg cttggccatt tgcagtggca gtcaacaaag aagaagtacc agattattat 1140
cgagttattg aacatccaat tgatttggca acaatagaac aaaaattgga aaacaacttg 1200
tatttaaaat ttactgattt tgtggatgat ctaaaactaa tgttcaacaa ttgtcgagct 1260
tataattcgg aaaccacaac atattataaa aacgcaaata aactagaaaa gtttatgaat 1320
aataaattga aagactgtag ttttgtatag 1350

<210> SEQ ID NO 76
<211> LENGTH: 672
<212> TYPE: DNA
<213> ORGANISM: Saccharomyces cerevisiae

<400> SEQUENCE: 76
agttcgagtt tatcattatc aatactgcca tttcaaagaa tacgtaaata attaatagta 60
gtgattttcc taactttatt tagtcaaaaa attagccttt taattctgct gtaacccgta 120
catgcccaaa ataggggggcg ggttacacag aatatataac atcgtaggtg tctgggtgaa 180
cagtttattc ctggcatcca ctaaatataa tggagcccgc tttttaagct ggcatccaga 240
aaaaaaaaga atcccagcac caaaatattg ttttcttcac caaccatcag ttcataggtc 300
cattctctta gcgcaactac agagaacagg ggcacaaaca ggcaaaaaac gggcacaacc 360
tcaatggagt gatgcaacct gcctggagta aatgatgaca caaggcaatt gacccacgca 420
tgtatctatc tcattttctt acaccttcta ttaccttctg ctctctctga tttggaaaaa 480
gctgaaaaaa aaggttgaaa ccagttccct gaaattattc ccctacttga ctaataagta 540
tataaagacg gtaggtattg attgtaattc tgtaaatcta tttcttaaac ttcttaaatt 600
ctacttttat agttagtctt ttttttagtt ttaaaacacc aagaacttag tttcgaataa 660
acacacataa ac 672

<210> SEQ ID NO 77
<211> LENGTH: 270
<212> TYPE: DNA
<213> ORGANISM: Saccharomyces cerevisiae

<400> SEQUENCE: 77
gacctcgagt catgtaatta gttatgtcac gcttacattc acgccctccc cccacatccg 60

-continued

```
ctctaaccga aaaggaagga gttagacaac ctgaagtcta ggtccctatt tattttttta    120

tagttatgtt agtattaaga acgttattta tatttcaaat ttttcttttt tttctgtaca    180

gacgcgtgta cgcatgtaac attatactga aaaccttgct tgagaaggtt ttgggacgct    240

cgaaggcttt aatttgcggc cggtacccaa                                     270
```

<210> SEQ ID NO 78
<211> LENGTH: 643
<212> TYPE: DNA
<213> ORGANISM: Saccharomyces cerevisiae

<400> SEQUENCE: 78

```
gaaatgaata acaatactga cagtactaaa taattgccta cttggcttca catacgttgc     60

atacgtcgat atagataata atgataatga cagcaggatt atcgtaatac gtaatagttg    120

aaaatctcaa aaatgtgtgg gtcattacgt aaataatgat aggaatggga ttcttctatt    180

tttccttttt ccattctagc agccgtcggg aaaacgtggc atcctctctt tcgggctcaa    240

ttggagtcac gctgccgtga gcatcctctc tttccatatc taacaactga gcacgtaacc    300

aatggaaaag catgagctta gcgttgctcc aaaaaagtat tggatggtta ataccatttg    360

tctgttctct tctgactttg actcctcaaa aaaaaaaaat ctacaatcaa cagatcgctt    420

caattacgcc ctcacaaaaa ctttttttcct tcttcttcgc ccacgttaaa ttttatccct    480

catgttgtct aacggatttc tgcacttgat ttattataaa aagacaaaga cataatactt    540

ctctatcaat ttcagttatt gttcttcctt gcgttattct tctgttcttc tttttctttt    600

gtcatatata accataacca agtaatacat attcaaatct aga                      643
```

<210> SEQ ID NO 79
<211> LENGTH: 760
<212> TYPE: DNA
<213> ORGANISM: Saccharomyces cerevisiae

<400> SEQUENCE: 79

```
tcttttccga tttttttcta aaccgtggaa tatttcggat atccttttgt tgtttccggg     60

tgtacaatat ggacttcctc ttttctggca accaaaccca tacatcggga ttcctataat    120

accttcgttg gtctccctaa catgtaggtg gcggagggga gatatacaat agaacagata    180

ccagacaaga cataatgggc taaacaagac tacaccaatt acactgcctc attgatggtg    240

gtacataacg aactaatact gtagccctag acttgatagc catcatcata tcgaagtttc    300

actacccttt ttccatttgc catctattga agtaataata ggcgcatgca acttcttttc    360

tttttttttc ttttctctct cccccgttgt tgtctcacca tatccgcaat gacaaaaaaa    420

tgatggaaga cactaaagga aaaaattaac gacaaagaca gcaccaacag atgtcgttgt    480

tccagagctg atgaggggta tctcgaagca cacgaaactt tttccttcct tcattcacgc    540

acactactct ctaatgagca acggtatacg gccttccttc cagttacttg aatttgaaat    600

aaaaaaaagt ttgctgtctt gctatcaagt ataaatagac ctgcaattat taatcttttg    660

tttcctcgtc attgttctcg ttccctttct tccttgtttc tttttctgca caatatttca    720

agctatacca agcatacaat caactatctc atatacaatg                          760
```

<210> SEQ ID NO 80
<211> LENGTH: 316
<212> TYPE: DNA
<213> ORGANISM: Saccharomyces cerevisiae

<400> SEQUENCE: 80

-continued

```
gagtaagcga atttcttatg atttatgatt tttattatta aataagttat aaaaaaaata     60

agtgtataca aattttaaag tgactcttag gttttaaaac gaaaattctt attcttgagt    120

aactctttcc tgtaggtcag gttgctttct caggtatagc atgaggtcgc tcttattgac    180

cacacctcta ccggcatgcc gagcaaatgc ctgcaaatcg ctccccattt cacccaattg    240

tagatatgct aactccagca atgagttgat gaatctcggt gtgtatttta tgtcctcaga    300

ggacaacacc tgtggt                                                     316
```

<210> SEQ ID NO 81
<211> LENGTH: 753
<212> TYPE: DNA
<213> ORGANISM: Saccharomyces cerevisiae

<400> SEQUENCE: 81

```
gcatgcttgc atttagtcgt gcaatgtatg actttaagat ttgtgagcag gaagaaaagg     60

gagaatcttc taacgataaa cccttgaaaa actgggtaga ctacgctatg ttgagttgct    120

acgcaggctg cacaattaca cgagaatgct cccgcctagg atttaaggct aagggacgtg    180

caatgcagac gacagatcta aatgaccgtg tcggtgaagt gttcgccaaa cttttcggtt    240

aacacatgca gtgatgcacg cgcgatggtg ctaagttaca tatatatata tatagccata    300

gtgatgtcta agtaaccttt atggtatatt tcttaatgtg gaaagatact agcgcgcgca    360

cccacacaca agcttcgtct tttcttgaag aaaagaggaa gctcgctaaa tgggattcca    420

ctttccgttc cctgccagct gatggaaaaa ggttagtgga acgatgaaga ataaaaagag    480

agatccactg aggtgaaatt tcagctgaca gcgagtttca tgatcgtgat gaacaatggt    540

aacgagttgt ggctgttgcc agggagggtg gttctcaact tttaatgtat ggccaaatcg    600

ctacttgggt ttgttatata acaaagaaga aataatgaac tgattctctt cctccttctt    660

gtcctttctt aattctgttg taattacctt cctttgtaat tttttttgta attattcttc    720

ttaataatcc aaacaaacac acatattaca ata                                  753
```

<210> SEQ ID NO 82
<211> LENGTH: 20
<212> TYPE: DNA
<213> ORGANISM: Artificial Sequence
<220> FEATURE:
<223> OTHER INFORMATION: Primer N98SeqF1

<400> SEQUENCE: 82

```
cgtgttagtc acatcaggac                                                  20
```

<210> SEQ ID NO 83
<211> LENGTH: 24
<212> TYPE: DNA
<213> ORGANISM: Artificial Sequence
<220> FEATURE:
<223> OTHER INFORMATION: Primer N98SeqF2

<400> SEQUENCE: 83

```
ggccatagca aaaatccaaa cagc                                             24
```

<210> SEQ ID NO 84
<211> LENGTH: 24
<212> TYPE: DNA
<213> ORGANISM: Artificial Sequence
<220> FEATURE:
<223> OTHER INFORMATION: Primer N98SeqF3

<400> SEQUENCE: 84
ccacgatcaa tcatatcgaa cacg 24

<210> SEQ ID NO 85
<211> LENGTH: 20
<212> TYPE: DNA
<213> ORGANISM: Artificial Sequence
<220> FEATURE:
<223> OTHER INFORMATION: Primer N98SeqF4

<400> SEQUENCE: 85
ggtttctgtc tctggtgacg 20

<210> SEQ ID NO 86
<211> LENGTH: 22
<212> TYPE: DNA
<213> ORGANISM: Artificial Sequence
<220> FEATURE:
<223> OTHER INFORMATION: Primer N99SeqR1

<400> SEQUENCE: 86
gtctggtgat tctacgcgca ag 22

<210> SEQ ID NO 87
<211> LENGTH: 22
<212> TYPE: DNA
<213> ORGANISM: Artificial Sequence
<220> FEATURE:
<223> OTHER INFORMATION: Primer N99SeqR2

<400> SEQUENCE: 87
catcgactgc attacgcaac tc 22

<210> SEQ ID NO 88
<211> LENGTH: 22
<212> TYPE: DNA
<213> ORGANISM: Artificial Sequence
<220> FEATURE:
<223> OTHER INFORMATION: Primer N99SeqR3

<400> SEQUENCE: 88
cgatcgtcag aacaacatct gc 22

<210> SEQ ID NO 89
<211> LENGTH: 20
<212> TYPE: DNA
<213> ORGANISM: Artificial Sequence
<220> FEATURE:
<223> OTHER INFORMATION: Primer N99SeqR4

<400> SEQUENCE: 89
ccttcagtgt tcgctgtcag 20

<210> SEQ ID NO 90
<211> LENGTH: 36
<212> TYPE: DNA
<213> ORGANISM: Artificial Sequence
<220> FEATURE:
<223> OTHER INFORMATION: Primer N136

<400> SEQUENCE: 90
ccgcggatag atctgaaatg aataacaata ctgaca 36

<210> SEQ ID NO 91
<211> LENGTH: 65
<212> TYPE: DNA
<213> ORGANISM: Artificial Sequence
<220> FEATURE:

<223> OTHER INFORMATION: Primer N137

<400> SEQUENCE: 91
taccaccgaa gttgatttgc ttcaacatcc tcagctctag atttgaatat gtattacttg 60
gttat 65

<210> SEQ ID NO 92
<211> LENGTH: 28
<212> TYPE: DNA
<213> ORGANISM: Artificial Sequence
<220> FEATURE:
<223> OTHER INFORMATION: Primer N138

<400> SEQUENCE: 92
atgttgaagc aaatcaactt cggtggta 28

<210> SEQ ID NO 93
<211> LENGTH: 22
<212> TYPE: DNA
<213> ORGANISM: Artificial Sequence
<220> FEATURE:
<223> OTHER INFORMATION: Primer N139

<400> SEQUENCE: 93
ttattggttt tctggtctca ac 22

<210> SEQ ID NO 94
<211> LENGTH: 57
<212> TYPE: DNA
<213> ORGANISM: Artificial Sequence
<220> FEATURE:
<223> OTHER INFORMATION: Primer N140

<400> SEQUENCE: 94
aagttgagac cagaaaacca ataattaatt aatcatgtaa ttagttatgt cacgctt 57

<210> SEQ ID NO 95
<211> LENGTH: 30
<212> TYPE: DNA
<213> ORGANISM: Artificial Sequence
<220> FEATURE:
<223> OTHER INFORMATION: Primer N141

<400> SEQUENCE: 95
gcggccgccc gcaaattaaa gccttcgagc 30

<210> SEQ ID NO 96
<211> LENGTH: 28
<212> TYPE: DNA
<213> ORGANISM: Artificial Sequence
<220> FEATURE:
<223> OTHER INFORMATION: Primer N142

<400> SEQUENCE: 96
ggatccgcat gcttgcattt agtcgtgc 28

<210> SEQ ID NO 97
<211> LENGTH: 56
<212> TYPE: DNA
<213> ORGANISM: Artificial Sequence
<220> FEATURE:
<223> OTHER INFORMATION: N143

<400> SEQUENCE: 97
caggtaatcc cccacagtat acatcctcag ctattgtaat atgtgtgttt gtttgg 56

<210> SEQ ID NO 98
<211> LENGTH: 22
<212> TYPE: DNA
<213> ORGANISM: Artificial Sequence
<220> FEATURE:
<223> OTHER INFORMATION: Primer N144

<400> SEQUENCE: 98
atgtatactg tgggggatta cc 22

<210> SEQ ID NO 99
<211> LENGTH: 22
<212> TYPE: DNA
<213> ORGANISM: Artificial Sequence
<220> FEATURE:
<223> OTHER INFORMATION: Primer N145

<400> SEQUENCE: 99
ttagctttta ttttgctccg ca 22

<210> SEQ ID NO 100
<211> LENGTH: 57
<212> TYPE: DNA
<213> ORGANISM: Artificial Sequence
<220> FEATURE:
<223> OTHER INFORMATION: Primer N146

<400> SEQUENCE: 100
tttgcggagc aaaataaaag ctaattaatt aagagtaagc gaatttctta tgattta 57

<210> SEQ ID NO 101
<211> LENGTH: 28
<212> TYPE: DNA
<213> ORGANISM: Artificial Sequence
<220> FEATURE:
<223> OTHER INFORMATION: Primer N147

<400> SEQUENCE: 101
actagtacca caggtgttgt cctctgag 28

<210> SEQ ID NO 102
<211> LENGTH: 22
<212> TYPE: DNA
<213> ORGANISM: Artificial Sequence
<220> FEATURE:
<223> OTHER INFORMATION: Primer N151

<400> SEQUENCE: 102
ctagagagct ttcgttttca tg 22

<210> SEQ ID NO 103
<211> LENGTH: 57
<212> TYPE: DNA
<213> ORGANISM: Artificial Sequence
<220> FEATURE:
<223> OTHER INFORMATION: Primer N152

<400> SEQUENCE: 103
ctcatgaaaa cgaaagctct ctagttaatt aatcatgtaa ttagttatgt cacgctt 57

<210> SEQ ID NO 104
<211> LENGTH: 25
<212> TYPE: DNA
<213> ORGANISM: Artificial Sequence
<220> FEATURE:
<223> OTHER INFORMATION: Primer N155

<400> SEQUENCE: 104
atggcaaaga agctcaacaa gtact 25

<210> SEQ ID NO 105
<211> LENGTH: 22
<212> TYPE: DNA
<213> ORGANISM: Artificial Sequence
<220> FEATURE:
<223> OTHER INFORMATION: Primer N156

<400> SEQUENCE: 105
tcaagcatct aaaacacaac cg 22

<210> SEQ ID NO 106
<211> LENGTH: 57
<212> TYPE: DNA
<213> ORGANISM: Artificial Sequence
<220> FEATURE:
<223> OTHER INFORMATION: Primer N157

<400> SEQUENCE: 106
aacggttgtg ttttagatgc ttgattaatt aagagtaagc gaatttctta tgattta 57

<210> SEQ ID NO 107
<211> LENGTH: 28
<212> TYPE: DNA
<213> ORGANISM: Artificial Sequence
<220> FEATURE:
<223> OTHER INFORMATION: Primer N158

<400> SEQUENCE: 107
ggatcctttt ctggcaacca aacccata 28

<210> SEQ ID NO 108
<211> LENGTH: 56
<212> TYPE: DNA
<213> ORGANISM: Artificial Sequence
<220> FEATURE:
<223> OTHER INFORMATION: Primer N159

<400> SEQUENCE: 108
cgagtacttg ttgagcttct ttgccatcct cagcgagata gttgattgta tgcttg 56

<210> SEQ ID NO 109
<211> LENGTH: 19
<212> TYPE: DNA
<213> ORGANISM: Artificial Sequence
<220> FEATURE:
<223> OTHER INFORMATION: Primer N160SeqF1

<400> SEQUENCE: 109
gaaaacgtgg catcctctc 19

<210> SEQ ID NO 110
<211> LENGTH: 19
<212> TYPE: DNA
<213> ORGANISM: Artificial Sequence
<220> FEATURE:
<223> OTHER INFORMATION: Primer N160SeqF2

<400> SEQUENCE: 110
gctgactggc caagagaaa 19

<210> SEQ ID NO 111
<211> LENGTH: 20
<212> TYPE: DNA

<213> ORGANISM: Artificial Sequence
<220> FEATURE:
<223> OTHER INFORMATION: Primer N160SeqF3

<400> SEQUENCE: 111
tgtacttctc ccacggtttc 20

<210> SEQ ID NO 112
<211> LENGTH: 22
<212> TYPE: DNA
<213> ORGANISM: Artificial Sequence
<220> FEATURE:
<223> OTHER INFORMATION: Primer N160SeqF4

<400> SEQUENCE: 112
agctacccaa tctctatacc ca 22

<210> SEQ ID NO 113
<211> LENGTH: 22
<212> TYPE: DNA
<213> ORGANISM: Artificial Sequence
<220> FEATURE:
<223> OTHER INFORMATION: Primer N160SeqF5

<400> SEQUENCE: 113
cctgaagtct aggtccctat tt 22

<210> SEQ ID NO 114
<211> LENGTH: 19
<212> TYPE: DNA
<213> ORGANISM: Artificial Sequence
<220> FEATURE:
<223> OTHER INFORMATION: N160SeqR1

<400> SEQUENCE: 114
gcgtgaatgt aagcgtgac 19

<210> SEQ ID NO 115
<211> LENGTH: 20
<212> TYPE: DNA
<213> ORGANISM: Artificial Sequence
<220> FEATURE:
<223> OTHER INFORMATION: Primer N160SeqR2

<400> SEQUENCE: 115
cgtcgtattg agccaagaac 20

<210> SEQ ID NO 116
<211> LENGTH: 20
<212> TYPE: DNA
<213> ORGANISM: Artificial Sequence
<220> FEATURE:
<223> OTHER INFORMATION: Primer N160SeqR3

<400> SEQUENCE: 116
gcatcggaca acaagttcat 20

<210> SEQ ID NO 117
<211> LENGTH: 22
<212> TYPE: DNA
<213> ORGANISM: Artificial Sequence
<220> FEATURE:
<223> OTHER INFORMATION: Primer N160SeqR4

<400> SEQUENCE: 117
tcgttcttga agtagtccaa ca 22

<210> SEQ ID NO 118
<211> LENGTH: 19
<212> TYPE: DNA
<213> ORGANISM: Artificial Sequence
<220> FEATURE:
<223> OTHER INFORMATION: Primer N160SeqR5

<400> SEQUENCE: 118
tgagcccgaa agagaggat 19

<210> SEQ ID NO 119
<211> LENGTH: 19
<212> TYPE: DNA
<213> ORGANISM: Artificial Sequence
<220> FEATURE:
<223> OTHER INFORMATION: Primer N161SeqF1

<400> SEQUENCE: 119
acggtatacg gccttcctt 19

<210> SEQ ID NO 120
<211> LENGTH: 20
<212> TYPE: DNA
<213> ORGANISM: Artificial Sequence
<220> FEATURE:
<223> OTHER INFORMATION: Primer N161SeqF2

<400> SEQUENCE: 120
gggtttgaaa gctatgcagt 20

<210> SEQ ID NO 121
<211> LENGTH: 22
<212> TYPE: DNA
<213> ORGANISM: Artificial Sequence
<220> FEATURE:
<223> OTHER INFORMATION: Primer N161SeqF3

<400> SEQUENCE: 121
ggtggtatgt atactgccaa ca 22

<210> SEQ ID NO 122
<211> LENGTH: 22
<212> TYPE: DNA
<213> ORGANISM: Artificial Sequence
<220> FEATURE:
<223> OTHER INFORMATION: Primer N161SeqF4

<400> SEQUENCE: 122
ggtggtaccc aatctgtgat ta 22

<210> SEQ ID NO 123
<211> LENGTH: 20
<212> TYPE: DNA
<213> ORGANISM: Artificial Sequence
<220> FEATURE:
<223> OTHER INFORMATION: Primer N161SeqF5

<400> SEQUENCE: 123
cggtttgggt aaagatgttg 20

<210> SEQ ID NO 124
<211> LENGTH: 22
<212> TYPE: DNA
<213> ORGANISM: Artificial Sequence
<220> FEATURE:
<223> OTHER INFORMATION: Primer N161SeqF6

<400> SEQUENCE: 124
aaacgaaaat tcttattctt ga 22

<210> SEQ ID NO 125
<211> LENGTH: 22
<212> TYPE: DNA
<213> ORGANISM: Artificial Sequence
<220> FEATURE:
<223> OTHER INFORMATION: Primer N161SeqR1

<400> SEQUENCE: 125
tcgttttaaa acctaagagt ca 22

<210> SEQ ID NO 126
<211> LENGTH: 19
<212> TYPE: DNA
<213> ORGANISM: Artificial Sequence
<220> FEATURE:
<223> OTHER INFORMATION: Primer N161SeqR2

<400> SEQUENCE: 126
ccaaaccgta acccatcag 19

<210> SEQ ID NO 127
<211> LENGTH: 19
<212> TYPE: DNA
<213> ORGANISM: Artificial Sequence
<220> FEATURE:
<223> OTHER INFORMATION: Primer N161SeqR3

<400> SEQUENCE: 127
cacagattgg gtaccacca 19

<210> SEQ ID NO 128
<211> LENGTH: 20
<212> TYPE: DNA
<213> ORGANISM: Artificial Sequence
<220> FEATURE:
<223> OTHER INFORMATION: Primer N161Seqr4

<400> SEQUENCE: 128
accacaagaa ccaggacctg 20

<210> SEQ ID NO 129
<211> LENGTH: 19
<212> TYPE: DNA
<213> ORGANISM: Artificial Sequence
<220> FEATURE:
<223> OTHER INFORMATION: Primer N161SeqR5

<400> SEQUENCE: 129
catagctttc aaacccgct 19

<210> SEQ ID NO 130
<211> LENGTH: 22
<212> TYPE: DNA
<213> ORGANISM: Artificial Sequence
<220> FEATURE:
<223> OTHER INFORMATION: Primer N161SeqR6

<400> SEQUENCE: 130
cgtataccgt tgctcattag ag 22

<210> SEQ ID NO 131
<211> LENGTH: 23
<212> TYPE: DNA

<213> ORGANISM: Artificial Sequence
<220> FEATURE:
<223> OTHER INFORMATION: Primer N162

<400> SEQUENCE: 131
atgttgacaa aagcaacaaa aga 23

<210> SEQ ID NO 132
<211> LENGTH: 38
<212> TYPE: DNA
<213> ORGANISM: Artificial Sequence
<220> FEATURE:
<223> OTHER INFORMATION: Primer N189

<400> SEQUENCE: 132
atccgcggat agatctagtt cgagtttatc attatcaa 38

<210> SEQ ID NO 133
<211> LENGTH: 53
<212> TYPE: DNA
<213> ORGANISM: Artificial Sequemce
<220> FEATURE:
<223> OTHER INFORMATION: Primer N190.1

<400> SEQUENCE: 133
ttcttttgtt gcttttgtca acatcctcag cgtttatgtg tgtttattcg aaa 53

<210> SEQ ID NO 134
<211> LENGTH: 38
<212> TYPE: DNA
<213> ORGANISM: Artificial Sequence
<220> FEATURE:
<223> OTHER INFORMATION: Primer N176

<400> SEQUENCE: 134
atccgcggat agatctatta gaagccgccg agcgggcg 38

<210> SEQ ID NO 135
<211> LENGTH: 31
<212> TYPE: DNA
<213> ORGANISM: Artificial Sequence
<220> FEATURE:
<223> OTHER INFORMATION: Primer N177

<400> SEQUENCE: 135
atcctcagct tttctccttg acgttaaagt a 31

<210> SEQ ID NO 136
<211> LENGTH: 38
<212> TYPE: DNA
<213> ORGANISM: Artificial Sequence
<220> FEATURE:
<223> OTHER INFORMATION: Primer N191

<400> SEQUENCE: 136
atccgcggat agatctccca ttaccgacat ttgggcgc 38

<210> SEQ ID NO 137
<211> LENGTH: 31
<212> TYPE: DNA
<213> ORGANISM: Artificial Sequence
<220> FEATURE:
<223> OTHER INFORMATION: Primer N192

<400> SEQUENCE: 137
atcctcagcg atgattgatt gattgattgt a 31

<210> SEQ ID NO 138
<211> LENGTH: 1474
<212> TYPE: DNA
<213> ORGANISM: artificial sequence
<220> FEATURE:
<223> OTHER INFORMATION: constructed URA3 gene bounded by repeats

<400> SEQUENCE: 138
gcattgcgga ttacgtattc taatgttcag cccgcggaac gccagcaaat caccacccat 60
gcgcatgata ctgagtcttg tacacgctgg gcttccagtg tactgagagt gcaccatacc 120
acagcttttc aattcaattc atcatttttt ttttattctt ttttttgatt tcggtttctt 180
tgaaattttt ttgattcggt aatctccgaa cagaaggaag aacgaaggaa ggagcacaga 240
cttagattgg tatatatacg catatgtagt gttgaagaaa catgaaattg cccagtattc 300
ttaacccaac tgcacagaac aaaaacctgc aggaaacgaa gataaatcat gtcgaaagct 360
acatataagg aacgtgctgc tactcatcct agtcctgttg ctgccaagct atttaatatc 420
atgcacgaaa agcaaacaaa cttgtgtgct tcattggatg ttcgtaccac caaggaatta 480
ctggagttag ttgaagcatt aggtcccaaa atttgtttac taaaaacaca tgtggatatc 540
ttgactgatt tttccatgga gggcacagtt aagccgctaa aggcattatc cgccaagtac 600 aatttttac tcttcgaaga cagaaaattt gctgacattg gtaatacagt caaattgcag 660
tactctgcgg gtgtatacag aatagcagaa tgggcagaca ttacgaatgc acacggtgtg 720
gtgggcccag gtattgttag cggtttgaag caggcggcag aagaagtaac aaaggaacct 780
agaggccttt tgatgttagc agaattgtca tgcaagggct ccctatctac tggagaatat 840
actaagggta ctgttgacat tgcgaagagc gacaaagatt ttgttatcgg ctttattgct 900
caaagagaca tgggtggaag agatgaaggt tacgattggt tgattatgac acccggtgtg 960
ggtttagatg acaagggaga cgcattgggt caacagtata gaaccgtgga tgatgtggtc 1020
tctacaggat ctgacattat tattgttgga agaggactat ttgcaaaggg aagggatgct 1080
aaggtagagg gtgaacgtta cagaaaagca ggctgggaag catatttgag aagatgcggc 1140
cagcaaaact aaaaaactgt attataagta aatgcatgta tactaaactc acaaattaga 1200
gcttcaattt aattatatca gttattaccc tatgcggtgt gaaataccgc acagatgcgt 1260
aaggagaaaa taccgcatca ggaaattgta aacgttaata ttttgttaaa attcgcgtta 1320
aatttttgtt aaatcagctc atttttaac caataggccg aaatcggcaa aatcttcagc 1380
ccgcggaacg ccagcaaatc accacccatg cgcatgatac tgagtcttgt acacgctggg 1440
cttccagtga tgatacaacg agttagccaa ggtg 1474

<210> SEQ ID NO 139
<211> LENGTH: 75
<212> TYPE: DNA
<213> ORGANISM: artificial sequence
<220> FEATURE:
<223> OTHER INFORMATION: synthetic primer

<400> SEQUENCE: 139
ctttacattg ttggaaagcc tcgttgtctt ttaagatttt ataagcattg gcattgcgga 60
ttacgtattc taatg 75

<210> SEQ ID NO 140
<211> LENGTH: 76
<212> TYPE: DNA
<213> ORGANISM: artificial sequence
<220> FEATURE:

<223> OTHER INFORMATION: synthetic primer

<400> SEQUENCE: 140
tgaattagat gaatcagcta gcctaaatat agtatctaag acattgtata caccttggct 60
aactcgttgt atcatc 76

<210> SEQ ID NO 141
<211> LENGTH: 75
<212> TYPE: DNA
<213> ORGANISM: artificial sequence
<220> FEATURE:
<223> OTHER INFORMATION: synthetic primer

<400> SEQUENCE: 141
ataaaaattt ccctatacta tcattaatta aatcattatt attactaaag gcattgcgga 60
ttacgtattc taatg 75

<210> SEQ ID NO 142
<211> LENGTH: 76
<212> TYPE: DNA
<213> ORGANISM: artificial sequence
<220> FEATURE:
<223> OTHER INFORMATION: synthetic primer

<400> SEQUENCE: 142
aaattggcat aaaaaagatt aaattcttat ctaagtgaat gtatctattt caccttggct 60
aactcgttgt atcatc 76

<210> SEQ ID NO 143
<211> LENGTH: 25
<212> TYPE: DNA
<213> ORGANISM: artificial sequence
<220> FEATURE:
<223> OTHER INFORMATION: primer binding sequence

<400> SEQUENCE: 143
gcattgcgga ttacgtattc taatg 25

<210> SEQ ID NO 144
<211> LENGTH: 26
<212> TYPE: DNA
<213> ORGANISM: artificial sequence
<220> FEATURE:
<223> OTHER INFORMATION: primer binding sequence

<400> SEQUENCE: 144
gatgatacaa cgagttagcc aaggtg 26

<210> SEQ ID NO 145
<211> LENGTH: 75
<212> TYPE: DNA
<213> ORGANISM: artificial sequence
<220> FEATURE:
<223> OTHER INFORMATION: direct repeat sequence

<400> SEQUENCE: 145
ttcagcccgc ggaacgccag caaatcacca cccatgcgca tgatactgag tcttgtacac 60
gctgggcttc cagtg 75

<210> SEQ ID NO 146
<211> LENGTH: 75
<212> TYPE: DNA
<213> ORGANISM: artificial sequence
<220> FEATURE:

-continued

```
<223> OTHER INFORMATION: direct repeat sequence

<400> SEQUENCE: 146

ttcagcccgc ggaacgccag caaatcacca cccatgcgca tgatactgag tcttgtacac      60

gctgggcttc cagtg                                                        75


<210> SEQ ID NO 147
<211> LENGTH: 200
<212> TYPE: DNA
<213> ORGANISM: artificial sequence
<220> FEATURE:
<223> OTHER INFORMATION: promoter to express URA3

<400> SEQUENCE: 147

ttttttattc ttttttttga tttcggtttc tttgaaattt ttttgattcg gtaatctccg      60

aacagaagga agaacgaagg aaggagcaca gacttagatt ggtatatata cgcatatgta     120

gtgttgaaga aacatgaaat tgcccagtat tcttaaccca actgcacaga acaaaaacct     180

gcaggaaacg aagataaatc                                                  200


<210> SEQ ID NO 148
<211> LENGTH: 804
<212> TYPE: DNA
<213> ORGANISM: artificial sequence
<220> FEATURE:
<223> OTHER INFORMATION: coding region for URA3

<400> SEQUENCE: 148

atgtcgaaag ctacatataa ggaacgtgct gctactcatc ctagtcctgt tgctgccaag      60

ctatttaata tcatgcacga aaagcaaaca aacttgtgtg cttcattgga tgttcgtacc     120

accaaggaat tactggagtt agttgaagca ttaggtccca aaatttgttt actaaaaaca     180

catgtggata tcttgactga tttttccatg gagggcacag ttaagccgct aaaggcatta     240

tccgccaagt acaatttttt actcttcgaa gacagaaaat ttgctgacat tggtaataca     300

gtcaaattgc agtactctgc gggtgtatac agaatagcag aatgggcaga cattacgaat     360

gcacacggtg tggtgggccc aggtattgtt agcggtttga agcaggcggc agaagaagta     420

acaaaggaac ctagaggcct tttgatgtta gcagaattgt catgcaaggg ctccctatct     480

actggagaat atactaaggg tactgttgac attgcgaaga gcgacaaaga ttttgttatc     540

ggctttattg ctcaaagaga catgggtgga agagatgaag gttacgattg gttgattatg     600

acacccggtg tgggtttaga tgacaaggga gacgcattgg gtcaacagta tagaaccgtg     660

gatgatgtgg tctctacagg atctgacatt attattgttg gaagaggact atttgcaaag     720

ggaagggatg ctaaggtaga gggtgaacgt tacagaaaag caggctggga agcatatttg     780

agaagatgcg gccagcaaaa ctaa                                             804
```